United States Patent
Echeverria Larraza et al.

(10) Patent No.: US 12,384,844 B2
(45) Date of Patent: Aug. 12, 2025

(54) AGONISTS OF TREM2

(71) Applicant: Genentech Inc., South San Francisco, CA (US)

(72) Inventors: Ainhoa Echeverria Larraza, South San Francisco, CA (US); David Verne Hansen, Mapleton, UT (US); Isidro Hotzel, Brisbane, CA (US); Yi-Chun Hsiao, San Mateo, CA (US); Zhonghua Lin, San Francisco, CA (US); Dhaya Seshasayee, Cupertino, CA (US); Benny Chih, Millbrae, CA (US)

(73) Assignee: Genentech, Inc., South San Francisco, CA (US)

( * ) Notice: Subject to any disclaimer, the term of this patent is extended or adjusted under 35 U.S.C. 154(b) by 560 days.

(21) Appl. No.: 17/742,686

(22) Filed: May 12, 2022

(65) Prior Publication Data

US 2022/0389097 A1    Dec. 8, 2022

Related U.S. Application Data

(60) Provisional application No. 63/188,800, filed on May 14, 2021.

(51) Int. Cl.
| | |
|---|---|
| *C07K 16/28* | (2006.01) |
| *A61K 39/00* | (2006.01) |
| *A61K 47/68* | (2017.01) |
| *A61P 25/28* | (2006.01) |

(52) U.S. Cl.
CPC ...... *C07K 16/2803* (2013.01); *A61K 47/6849* (2017.08); *A61P 25/28* (2018.01); *A61K 2039/505* (2013.01); *C07K 2317/24* (2013.01); *C07K 2317/33* (2013.01); *C07K 2317/34* (2013.01); *C07K 2317/52* (2013.01); *C07K 2317/55* (2013.01); *C07K 2317/565* (2013.01); *C07K 2317/71* (2013.01); *C07K 2317/92* (2013.01)

(58) Field of Classification Search
CPC combination set(s) only.
See application file for complete search history.

(56) References Cited

U.S. PATENT DOCUMENTS

| | | | |
|---|---|---|---|
| 11,390,670 B2 * | 7/2022 | Seoane Suarez | A61P 35/02 |
| 12,060,572 B2 * | 8/2024 | Barzel | A61K 39/4632 |
| 2020/0140545 A1 | 5/2020 | Brand et al. | |
| 2020/0277373 A1 | 9/2020 | Chen et al. | |

FOREIGN PATENT DOCUMENTS

| | | |
|---|---|---|
| WO | 2018015573 A2 | 1/2018 |
| WO | 2020172450 A1 | 8/2020 |

OTHER PUBLICATIONS

Deczkowska, Aleksandra et al., "The Physiology, Pathology, and Potential Therapeutic Applications of the TREM2 Signaling Pathway", Cell, vol. 181, No. 6, Jun. 11, 2020.
PCT International Search Report from PCT/US2022/028920 mailed on Sep. 15, 2022, 5 pages.
Price, Brittani R. et al., "Therapeutic Trem2 activation ameliorates amyloid-beta deposition and improves cognition in the 5XFAD model of amyloid deposition", Journal of Neuroinflammation, vol. 17, No. 1, Dec. 1, 2020.
Schlepckow, Kai et al., "Enhancing protective microglial activities with a dual function TREM2 antibody to the stalk region", EMBO Molecular Medicine, vol. 12, No. 4, Mar. 10, 2020.
Written Opinion from PCT/US2022/028920 mailed on Sep. 15, 2022, 7 pages.

* cited by examiner

*Primary Examiner* — Adam Weidner
*Assistant Examiner* — Laura Ann Essex
(74) *Attorney, Agent, or Firm* — McNeill PLLC

(57) ABSTRACT

This application discloses, inter alia, certain antibodies that specifically bind to human TREM2 (triggering receptor expressed on myeloid cells 2). In some embodiments, the antibodies act as TREM2 agonists. In some embodiments, antibodies herein specifically bind to the stalk region of intact, human TREM2, without binding to soluble TREM2, which is the product of TREM2 cleavage between residues H157 and S158. In some embodiments, the antibodies act as TREM2 agonists, specifically bind to the stalk region of TREM2 with dissociation constants ranging from 10 nM to as low as 100-500 pM, 10-50 pM, or 1-10 pM, specifically bind to a TREM2 epitope spanning the H157-S158 cleavage site, and do not bind to soluble TREM2. In some embodiments, antibodies herein also inhibit shedding of soluble TREM2 in a human microglia cell model and in vivo in a mouse model, decrease levels of soluble TREM2 in plasma, CSF and/or the brain, enhance survival of human microglia cells, and increase Aβ plaque formation and compaction in a human microglia model (for example, as measured by increased Aβ plaque intensity and/or increased X04 plaque intensity in human microglia), and thus, may provide a number of neuroprotective activities.

42 Claims, 41 Drawing Sheets
Specification includes a Sequence Listing.

| Campaign | Species | Immunogen and method | Animals fused | Human TREM2 ELISA positives | Human TREM2 FACS positives | Unique clones |
|---|---|---|---|---|---|---|
| 1 | SD rats | Human TREM2 pDNA genegun | 3 | 88 | 71 | 15 |
| 3 | SD rats | Human TREM2 ECD protein | 3 | 900 | 346 | 174 |
| 5 | SD rats | Human TREM2 EV | 2 | 366 | 270 | 5 |
| 6 | TREM2 KO mice | Human TREM2 ECD TREM2 | 5 | 18 | 18 | 5 |
| 8 | TREM2 KO mice | Human TREM2 pDNA HTV | 6 | 278 | 242 | 30 |

Fig. 1

| Peptide | 129-175 sequence |
|---|---|
| Stalk | L A D P L D H R D A G D L W F P G E S E S F E D A H V E H S I S R S L L E G E I P F P P T S I |
| 129-148 | L A D P L D H R D A G D L W F P G E S E |
| 139-158 | G D L W F P G E S E S F E D A H V E H S |
| 149-168 | S F E D A H V E H S I S R S L L E G E I |
| 159-175 | I S R S L L E G E I P F P P T S I |
| 146-169 | E S E S F E D A H V E H S I S R S L L E G E I P |
| 146-161 | E S E S F E D A H V E H S I S R |
| 151-165 | E D A H V E H S I S R S L L E |
| 155-169 | V E H S I S R S L L E G E I P |
| 152-161 | D A H V E H S I S R |
| 154-164 | H V E H S I S R S L L |

*Fig. 2A*

| Peptide | 3.10C2 | 3.18E5 | 3.50G1 |
|---|---|---|---|
| Stalk | 1.91 | 1.88 | 2.13 |
| 129-148 | 0.19 | 0.28 | 0.19 |
| 139-158 | 0.37 | 0.51 | 0.43 |
| 149-168 | 2.16 | | 1.28 |
| 159-175 | 0.07 | 0.07 | 0.08 |
| 146-169 | 1.66 | 1.6 | 1.68 |
| 146-161 | 2.95 | 2.89 | 2.52 |
| 151-165 | 2.52 | 2.42 | 2.32 |
| 155-169 | 0.13 | 0.14 | 0.13 |
| 152-161 | 0.12 | 0.15 | 0.14 |
| 154-164 | 0.39 | 0.40 | 0.26 |
| 151 to 161 | | | |

| Fab fragment | TREM2 residue | | | | | | | | | | | | |
|---|---|---|---|---|---|---|---|---|---|---|---|---|---|
| | S 149 | F 150 | E 151 | D 152 | A 153 | H 154 | V 155 | E 156 | H 157 | S 158 | I 159 | S 160 | R 161 |
| 3.10C2 | | | | ▓ | | ▓ | | | ▓ | ▓ | | | |
| 3.50G1 | | | | ▓ | | | | ▓ | ▓ | ▓ | ▓ | | |
| Para.09-L27H7 | | | | ▓ | | | | | ▓ | | ▓ | | |
| 3.47B1 | | | | | | | | | ▓ | ▓ | | | |
| 9F5 | | ▓ | ▓ | ▓ | | | | ▓ | | | | | |
| AL2p-31 | | ▓ | ▓ | | | ▓ | | ▓ | | | | | |
| 14D3 | | | | | ▓ | ▓ | | ▓ | | ▓ | | | |
| 14D8 | | | | | ▓ | ▓ | | ▓ | ▓ | | | | |

| | | | | | | | | | | | | | |
|---|---|---|---|---|---|---|---|---|---|---|---|---|---|
| 149 | A | F | E | D | A | H | V | E | H | S | I | S | R |
| 150 | S | A | E | D | A | H | V | E | H | S | I | S | R |
| 151 | S | F | A | D | A | H | V | E | H | S | I | S | R |
| 152 | S | F | E | A | A | H | V | E | H | S | I | S | R |
| 153 | S | F | E | D | G | H | V | E | H | S | I | S | R |
| 154 | S | F | E | D | A | A | V | E | H | S | I | S | R |
| 155 | S | F | E | D | A | H | A | E | H | S | I | S | R |
| 156 | S | F | E | D | A | H | V | A | H | S | I | S | R |
| 157 | S | F | E | D | A | H | V | E | A | S | I | S | R |
| 158 | S | F | E | D | A | H | V | E | H | A | I | S | R |
| 159 | S | F | E | D | A | H | V | E | H | S | A | S | R |
| 160 | S | F | E | D | A | H | V | E | H | S | I | A | R |
| 161 | S | F | E | D | A | H | V | E | H | S | I | S | A |

*Fig. 5*

| Kabat number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 27a | 27b | 27c | 27d | 27e | 28 | 29 | 30 | 31 | 32 | 33 | 34 | 35 | 36 | 37 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | | | | | | | CDR L1 - Chothia | | | | | | CDR L1 - Kabat | | | | | | | | | |
| IGKV2-28*01 | D | I | V | M | T | Q | S | P | L | S | L | P | V | T | P | G | E | P | A | S | – | S | C | R | S | S | Q | S | L | L | H | S | N | G | Y | N | Y | L | D | W | Y | L |
| 3.10C2 | D | T | V | L | T | Q | A | P | L | S | L | S | V | T | P | G | E | S | A | S | – | S | C | R | S | S | K | S | L | L | G | V | R | D | I | T | S | L | Y | W | Y | L |
| 3.10C2-L1 | D | T | V | L | T | Q | S | P | L | S | L | P | V | T | P | G | E | P | A | S | – | S | C | R | S | S | K | S | L | L | G | V | R | D | I | T | S | L | Y | W | Y | L |
| 3.10C2-L5 | D | T | V | M | T | Q | S | P | L | S | L | P | V | T | P | G | E | P | A | S | – | S | C | R | S | S | K | S | L | L | G | V | R | D | I | T | S | L | Y | W | Y | L |

| Kabat number | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | CDR L2 - Chothia / CDR L2 - Kabat | | | | | | | | | | | | | | | | | | | | | | | | | | | | | |
| IGKV2-28*01 | Q | K | P | G | Q | S | P | Q | L | L | – | Y | L | G | S | N | R | A | S | G | V | P | D | R | F | S | G | S | G | S | G | T | D | F | T | L | K | I | S | R | V | E |
| 3.10C2 | Q | K | P | G | K | S | P | Q | L | L | – | Y | R | M | S | N | L | A | S | G | V | P | D | R | F | S | G | S | G | S | E | T | D | F | T | L | K | I | S | E | V | E |
| 3.10C2-L1 | Q | K | P | G | Q | S | P | Q | L | L | – | Y | R | M | S | N | L | A | S | G | V | P | D | R | F | S | G | S | G | S | G | T | D | F | T | L | K | I | S | R | V | E |
| 3.10C2-L5 | Q | K | P | G | Q | S | P | Q | L | L | – | Y | R | M | S | N | L | A | S | G | V | P | D | R | F | S | G | S | G | S | G | T | D | F | T | L | K | I | S | R | V | E |

| Kabat number | 80 | 81 | 82 | 83 | 84 | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 |
|---|---|---|---|---|---|---|---|---|---|---|---|---|---|---|---|---|---|---|---|---|---|---|---|---|---|---|---|---|
| | | | | | | | | | | CDR L3 - Chothia / CDR L3 - Kabat | | | | | | | | | | | | | | | | | | |
| IGKV2-28*01 | A | E | D | V | G | V | Y | Y | C | M | Q | A | L | Q | T | P | W | T | F | G | Q | G | T | K | V | E | I | K |
| 3.10C2 | A | T | D | V | G | V | Y | Y | C | A | Q | F | L | R | Y | P | Y | T | F | G | Q | G | P | K | V | E | L | K |
| 3.10C2-L1 | A | E | D | V | G | V | Y | Y | C | A | Q | F | L | R | Y | P | Y | T | F | G | Q | G | T | K | V | E | I | K |
| 3.10C2-L5 | A | E | D | V | G | V | Y | Y | C | A | Q | F | L | R | Y | P | Y | T | F | G | Q | G | T | K | V | E | I | K |

Sequence alignment (Kabat numbering), positions 1–42:

| Kabat number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| IGHV3-73*01 | E | V | Q | L | V | E | S | G | G | G | L | V | Q | P | G | G | S | L | K | L | S | C | A | A | S | G | F | T | F | S | G | S | A | M | H | W | V | R | Q | A | S | G |
| Para.09 | E | V | Q | L | V | E | T | G | G | S | L | V | Q | P | G | K | S | L | R | L | T | C | C | A | S | G | F | P | F | S | N | V | W | L | H | W | V | R | Q | S | P | E |
| Para.09-H1 | E | V | Q | L | V | E | S | G | G | G | L | V | Q | P | G | G | S | L | K | L | S | C | A | T | S | G | F | P | F | S | N | V | W | L | H | W | V | R | Q | A | S | G |
| Para.09-H5 | E | V | Q | L | V | E | S | G | G | G | L | V | Q | P | G | G | S | L | K | L | S | C | A | T | S | G | F | P | F | S | N | V | W | L | H | W | V | R | Q | A | S | G |
| Para.09-H7 | E | V | Q | L | V | E | S | G | G | G | L | V | Q | P | G | G | S | L | K | L | S | C | A | T | S | G | F | P | F | S | N | V | W | L | H | W | V | R | Q | A | S | G |

CDRH1-Contact: 30–35; CDRH1-Kabat: 31–35

Positions 43–81:

| Kabat number | 43 | 44 | 45 | 46 | 47 | 48 | 49 | 50 | 51 | 52 | 52a | 52b | 52c | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| IGHV3-73*01 | K | G | L | E | W | V | G | R | I | R | S | K | A | N | S | Y | A | T | A | Y | A | A | S | V | K | G | R | F | T | I | S | R | D | D | S | K | N | T | A | Y | L | Q |
| Para.09 | K | H | P | E | W | V | A | H | I | K | A | K | - | S | D | N | Y | A | T | Y | Y | A | E | S | V | K | G | R | F | T | I | S | R | D | D | S | K | S | S | V | F | L | Q |
| Para.09-H1 | K | G | P | E | W | V | A | H | I | K | A | K | - | S | D | N | Y | A | T | Y | Y | A | E | S | V | K | G | R | F | T | I | S | R | D | D | S | K | S | T | V | Y | L | Q |
| Para.09-H5 | K | G | P | E | W | V | A | H | I | K | A | K | - | S | D | N | Y | A | T | Y | Y | A | E | S | V | K | G | R | F | T | I | S | R | D | D | S | K | N | T | V | Y | L | Q |
| Para.09-H7 | K | G | L | E | W | V | A | H | I | K | A | K | - | S | D | N | Y | A | T | Y | Y | A | E | S | V | K | G | R | F | T | I | S | R | D | D | S | K | N | T | V | Y | L | Q |

CDRH2-Contact: 47–52c; CDRH2-Kabat: 50–58

Positions 82–113:

| Kabat number | 82 | 82a | 82b | 82c | 83 | 84 | 85 | 86 | 87 | 88 | 89 | 90 | 91 | 92 | 93 | 94 | 95 | 96 | 101 | 102 | 103 | 104 | 105 | 106 | 107 | 108 | 109 | 110 | 111 | 112 | 113 |
|---|---|---|---|---|---|---|---|---|---|---|---|---|---|---|---|---|---|---|---|---|---|---|---|---|---|---|---|---|---|---|---|
| IGHV3-73*01 | M | N | S | L | K | T | E | D | T | A | V | Y | Y | C | T | R |  |  |  |  |  |  |  |  |  |  |  |  |  |  |  |
| Para.09 | M | N | S | L | K | E | E | D | T | A | I | Y | Y | C | T | R | D | I | L | E | Y | M | D | V | W | G | Q | G | T | L | V | T | V | S | S |
| Para.09-H1 | M | N | S | L | K | T | E | D | T | A | V | Y | Y | C | T | R | D | I | L | E | Y | … | W | G | Q | G | T | T | V | T | V | S | S |
| Para.09-H5 | M | N | S | L | K | T | E | D | T | A | V | Y | Y | C | T | R | D | I | L | E | Y | … | W | G | Q | G | T | T | V | T | V | S | S |
| Para.09-H7 | M | N | S | L | K | T | E | D | T | A | V | Y | Y | C | T | R | D | I | L | E | Y | … | W | G | Q | G | T | T | V | T | V | S | S |

CDRH3-Contact: 93–101; CDRH3-Kabat: 95–102

Fig. 9A h3.10C2.v1 light chain (Kabat numbering):

| Kabat # | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 27a | 27b | 27c | 27d | 27e | 28 | 29 | 30 | 31 | 32 | 33 | 34 | 35 | 36 | 37 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| h3.10C2.v1 | D | V | V | M | T | Q | S | P | L | S | L | P | V | T | P | G | E | P | A | S | I | S | C | R | S | S | R | S | L | L | T | S | K | G | I | T | S | L | Y | W | Y | L |

CDR L1 - Kabat: positions 24–34

| Kabat # | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| h3.10C2.v1 | Q | K | P | G | Q | S | P | Q | L | L | I | Y | R | M | S | N | L | A | S | G | I | P | D | R | F | S | G | S | G | S | G | T | D | F | T | L | K | I | S | R | V | E |

CDR L2 - Kabat: positions 50–56

| Kabat # | 80 | 81 | 82 | 83 | 84 | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 |
|---|---|---|---|---|---|---|---|---|---|---|---|---|---|---|---|---|---|---|---|---|---|---|---|---|---|---|---|---|
| h3.10C2.v1 | A | E | D | V | G | V | Y | Y | C | A | Q | F | L | V | Y | P | Y | T | F | G | Q | G | T | K | V | E | I | K |

CDR L3 - Kabat: positions 89–97

Fig. 9B h3.10C2.v1 heavy chain (Kabat numbering):

| Kabat # | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| h3.10C2.v1 | E | V | Q | L | V | E | S | G | G | G | L | V | Q | P | G | G | S | L | K | L | S | C | A | T | S | G | F | P | F | S | N | V | W | M | H | W | V | R | Q | A | S | G |

CDRH1 - Kabat: positions 31–35

| Kabat # | 43 | 44 | 45 | 46 | 47 | 48 | 49 | 50 | 51 | 52 | 52a | 52b | 52c | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| h3.10C2.v1 | K | G | L | E | W | I | A | H | I | K | A | K | S | D | N | Y | A | T | Y | Y | A | E | S | V | K | G | R | F | T | I | S | R | D | D | S | K | T | T | I | Y | L | Q |

CDRH2 - Kabat

| Kabat # | 82 | 82a | 82b | 82c | 83 | 84 | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 | 108 | 109 | 110 | 111 | 112 | 113 |
|---|---|---|---|---|---|---|---|---|---|---|---|---|---|---|---|---|---|---|---|---|---|---|---|---|---|---|---|---|---|---|---|---|---|---|---|
| h3.10C2.v1 | M | N | S | L | K | T | E | D | T | A | V | Y | Y | C | T | G | L | D | Y | W | G | Q | G | T | T | V | T | V | S | S | | | | | |

CDRH3 - Kabat

| Kabat number | hPara.09.v2 |
|---|---|
| 1 | D |
| 2 | V |
| 3 | V |
| 4 | M |
| 5 | T |
| 6 | Q |
| 7 | S |
| 8 | P |
| 9 | L |
| 10 | S |
| 11 | L |
| 12 | P |
| 13 | V |
| 14 | T |
| 15 | P |
| 16 | G |
| 17 | E |
| 18 | P |
| 19 | A |
| 20 | S |
| 21 | I |
| 22 | S |
| 23 | C |
| 24 | R |
| 25 | S |
| 26 | S |
| 27 | R |
| 27a | S |
| 27b | L |
| 27c | L |
| 27d | T |
| 27e | S |
| 28 | K |
| 29 | G |
| 30 | I |
| 31 | T |
| 32 | S |
| 33 | L |
| 34 | Y |
| 35 | W |
| 36 | Y |
| 37 | L |

(CDR L1 – Kabat: positions 24–34)

| Kabat number | hPara.09.v2 |
|---|---|
| 38 | Q |
| 39 | K |
| 40 | P |
| 41 | G |
| 42 | Q |
| 43 | S |
| 44 | P |
| 45 | Q |
| 46 | L |
| 47 | L |
| 48 | I |
| 49 | Y |
| 50 | R |
| 51 | M |
| 52 | S |
| 53 | N |
| 54 | L |
| 55 | A |
| 56 | S |
| 57 | G |
| 58 | I |
| 59 | P |
| 60 | D |
| 61 | R |
| 62 | F |
| 63 | S |
| 64 | G |
| 65 | S |
| 66 | G |
| 67 | S |
| 68 | G |
| 69 | T |
| 70 | D |
| 71 | F |
| 72 | T |
| 73 | L |
| 74 | K |
| 75 | I |
| 76 | S |
| 77 | R |
| 78 | V |
| 79 | E |

(CDR L2 – Kabat: positions 50–56)

| Kabat number | hPara.09.v2 |
|---|---|
| 80 | A |
| 81 | E |
| 82 | D |
| 83 | V |
| 84 | G |
| 85 | V |
| 86 | Y |
| 87 | Y |
| 88 | C |
| 89 | A |
| 90 | Q |
| 91 | F |
| 92 | L |
| 93 | V |
| 94 | Y |
| 95 | P |
| 96 | Y |
| 97 | T |
| 98 | F |
| 99 | G |
| 100 | Q |
| 101 | G |
| 102 | T |
| 103 | K |
| 104 | V |
| 105 | E |
| 106 | I |
| 107 | K |

(CDR L3 – Kabat: positions 89–97)

Fig. 12A

| Kabat number | hPara.09.v2 |
|---|---|
| 1 | E |
| 2 | V |
| 3 | Q |
| 4 | L |
| 5 | V |
| 6 | E |
| 7 | S |
| 8 | G |
| 9 | G |
| 10 | G |
| 11 | L |
| 12 | V |
| 13 | Q |
| 14 | P |
| 15 | G |
| 16 | G |
| 17 | S |
| 18 | L |
| 19 | K |
| 20 | L |
| 21 | S |
| 22 | C |
| 23 | A |
| 24 | T |
| 25 | S |
| 26 | G |
| 27 | F |
| 28 | P |
| 29 | F |
| 30 | S |
| 31 | N |
| 32 | V |
| 33 | W |
| 34 | L |
| 35 | H |
| 36 | W |
| 37 | V |
| 38 | R |
| 39 | Q |
| 40 | A |
| 41 | S |
| 42 | G |

(CDR H1 – Kabat: positions 31–35)

| Kabat number | hPara.09.v2 |
|---|---|
| 43 | K |
| 44 | G |
| 45 | P |
| 46 | E |
| 47 | W |
| 48 | V |
| 49 | A |
| 50 | H |
| 51 | I |
| 52 | K |
| 52a | A |
| 52b | K |
| 52c | S |
| 53 | D |
| 54 | N |
| 55 | Y |
| 56 | A |
| 57 | T |
| 58 | Y |
| 59 | Y |
| 60 | A |
| 61 | E |
| 62 | S |
| 63 | V |
| 64 | K |
| 65 | G |
| 66 | R |
| 67 | F |
| 68 | T |
| 69 | I |
| 70 | S |
| 71 | R |
| 72 | D |
| 73 | D |
| 74 | D |
| 75 | S |
| 76 | K |
| 77 | N |
| 78 | T |
| 79 | V |
| 80 | Y |
| 81 | L |
| 82 | Q |

(CDR H2 – Kabat: positions 50–65)

| Kabat number | hPara.09.v2 |
|---|---|
| 82a | M |
| 82b | N |
| 82c | S |
| 83 | L |
| 84 | K |
| 85 | T |
| 86 | E |
| 87 | D |
| 88 | T |
| 89 | A |
| 90 | V |
| 91 | Y |
| 92 | Y |
| 93 | C |
| 94 | T |
| 95 | D |
| 96 | I |
| 97 | L |
| 98 | E |
| 99 | Y |
| 100 | W |
| 101 | G |
| 102 | Q |
| 103 | G |
| 104 | T |
| 105 | L |
| 106 | V |
| 107 | T |
| 108 | V |
| 109 | S |
| 110 | S |

(CDR H3 – Kabat)

Sequence alignment (Kabat numbering) of heavy chain variants:

- hPara.09.v2
- hPara.09.v2 I58V/Q100P
- hPara.09.v2 Q100P
- hPara.09.v2 Q100P/V104L
- hPara.09.H5-3.10C2.L10

CDRH1 – Kabat, CDRH2 – Kabat, and CDRH3 – Kabat regions are indicated.

Region 1 (FR1–CDRH1–FR2), positions ~1–35:

E V Q L V E S G G G L V Q P G G S L K L S C A T S G F P F S N V W L H W V R Q A S G

Region 2 (FR2–CDRH2–FR3), positions ~36–66:

K G P E W V A H I K A K S D N Y A T Y Y A E S V K G R F T I S R D D S K N T V Y L Q
(I58V variant: V in place of I at position 58)

Region 3 (FR3–CDRH3–FR4), positions ~93–113:

M N S L K T E D T A V Y Y C T D I L E Y W G Q G T L V T V S S
(Q100P variants: P in place of Q at position 100; V104L variant: L in place of V at position 104)

| Kabat number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | CDR L1 - Kabat | | | | | | | | | | 34 | 35 | 36 | 37 |
|---|---|---|---|---|---|---|---|---|---|---|---|---|---|---|---|---|---|---|---|---|---|---|---|---|---|---|---|---|---|---|---|---|---|---|---|---|
| h3.10C2.v1 | D | V | V | M | T | Q | S | P | L | S | L | P | V | T | P | G | E | P | A | S | I | S | C | R | S | S | R | S | L | L | T | S | K | G | R | R |
| h3.10C2.v1 Q100P | D | V | V | M | T | Q | S | P | L | S | L | P | V | T | P | G | E | P | A | S | I | S | C | R | S | S | R | S | L | L | T | S | K | G | R | R |
| h3.10C2.v1 I58V/Q100P | D | V | V | M | T | Q | S | P | L | S | L | P | V | T | P | G | E | P | A | S | I | S | C | R | S | S | R | S | L | L | T | S | K | G | R | R |
| h3.10C2.v1 Q100P/V104L | D | V | V | M | T | Q | S | P | L | S | L | P | V | T | P | G | E | P | A | S | I | S | C | R | S | S | R | S | L | L | T | S | K | G | R | R |
| h3.10C2.H1-3.10C2.L10 | D | T | V | M | T | Q | S | P | L | S | L | P | V | T | P | G | E | P | A | S | I | S | C | R | S | S | K | S | L | L | G | V | R | D | R | R |

| Kabat number | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 |
|---|---|---|---|---|---|---|---|---|---|---|---|---|---|---|---|---|---|---|---|---|---|---|---|---|---|---|---|---|---|---|---|---|---|---|---|---|---|---|---|---|---|
| h3.10C2.v1 | I | T | S | L | Y | W | Y | L | R | R | K | P | G | Q | S | P | Q | L | L | I | Y | R | M | S | N | L | A | S | G | I | P | D | R | F | S | G | S | G | S | G | T |
| h3.10C2.v1 Q100P | I | T | S | L | Y | W | Y | L | R | R | K | P | G | Q | S | P | Q | L | L | I | Y | R | M | S | N | L | A | S | G | I | P | D | R | F | S | G | S | G | S | G | T |
| h3.10C2.v1 I58V/Q100P | I | T | S | L | Y | W | Y | L | R | R | K | P | G | Q | S | P | Q | L | L | I | Y | R | M | S | N | L | A | S | G | V | P | D | R | F | S | G | S | G | S | G | T |
| h3.10C2.v1 Q100P/V104L | I | T | S | L | Y | W | Y | L | R | R | K | P | G | Q | S | P | Q | L | L | I | Y | R | M | S | N | L | A | S | G | V | P | D | R | F | S | G | S | G | S | G | T |
| h3.10C2.H1-3.10C2.L10 | I | T | S | L | Y | W | Y | L | R | R | K | P | G | Q | S | P | Q | L | L | I | Y | R | M | S | N | L | A | S | G | I | P | D | R | F | S | G | S | G | S | G | T |

| Kabat number | 79 | 80 | 81 | 82 | 83 | 84 | 85 | 86 | 87 | 88 | 89 | 90 | 91 | 92 | 93 | 94 | 95 | 96 | 97 | 98 | CDR L3 - Kabat | | | 100 | 101 | 102 | 103 | 104 | 105 | 106 | 107 |
|---|---|---|---|---|---|---|---|---|---|---|---|---|---|---|---|---|---|---|---|---|---|---|---|---|---|---|---|---|---|---|---|
| h3.10C2.v1 | L | K | I | S | R | V | E | A | E | D | V | G | V | Y | Y | C | A | Q | F | L | V | Y | P | Q | G | T | K | V | E | I | K |
| h3.10C2.v1 Q100P | L | K | I | S | R | V | E | A | E | D | V | G | V | Y | Y | C | A | Q | F | L | V | Y | P | P | G | T | K | V | E | I | K |
| h3.10C2.v1 I58V/Q100P | L | K | I | S | R | V | E | A | E | D | V | G | V | Y | Y | C | A | Q | F | L | V | Y | P | P | G | T | K | V | E | I | K |
| h3.10C2.v1 Q100P/V104L | L | K | I | S | R | V | E | A | E | D | V | G | V | Y | Y | C | A | Q | F | L | V | Y | P | P | G | T | K | L | E | I | K |
| h3.10C2.H1-3.10C2.L10 | L | K | I | S | R | V | E | A | E | D | V | G | V | Y | Y | C | A | Q | F | L | R | Y | P | P | G | T | K | V | E | I | K |

*Fig. 14A*

| Kabat number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| h3.10C2.v1 | E | V | Q | L | V | E | S | G | G | G | L | V | Q | P | G | G | S | L | K | L | S | C | A | T | S | G | F | P | F | S | N | V | W | M | H | W | V | R | Q | A | S | G |
| h3.10C2.v1 Q100P | E | V | Q | L | V | E | S | G | G | G | L | V | Q | P | G | G | S | L | K | L | S | C | A | T | S | G | F | P | F | S | N | V | W | M | H | W | V | R | Q | A | S | G |
| h3.10C2.v1 I58V/Q100P | E | V | Q | L | V | E | S | G | G | G | L | V | Q | P | G | G | S | L | K | L | S | C | A | T | S | G | F | P | F | S | N | V | W | M | H | W | V | R | Q | A | S | G |
| h3.10C2.v1 Q100P/V104L | E | V | Q | L | V | E | S | G | G | G | L | V | Q | P | G | G | S | L | K | L | S | C | A | T | S | G | F | P | F | S | N | V | W | M | H | W | V | R | Q | A | S | G |
| h3.10C2.H1-3.10C2.L10 | E | V | Q | L | V | E | S | G | G | G | L | V | Q | P | G | G | S | L | K | L | S | C | A | T | S | G | F | P | F | S | N | V | W | M | H | W | V | R | Q | A | S | G |

CDRH1 - Kabat

| Kabat number | 43 | 44 | 45 | 46 | 47 | 48 | 49 | 50 | 51 | 52 | 52a | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 |
|---|---|---|---|---|---|---|---|---|---|---|---|---|---|---|---|---|---|---|---|---|---|---|---|---|---|---|---|---|---|---|---|---|---|---|---|---|---|---|---|---|
| h3.10C2.v1 | K | G | L | E | W | I | A | H | I | K | A | K | S | D | N | Y | A | T | Y | Y | A | E | S | V | K | G | R | F | T | I | S | R | D | D | S | K | T | T | I | Y |
| h3.10C2.v1 Q100P | K | G | L | E | W | I | A | H | I | K | A | K | S | D | N | Y | A | T | Y | Y | A | E | S | V | K | G | R | F | T | I | S | R | D | D | S | K | T | T | I | Y |
| h3.10C2.v1 I58V/Q100P | K | G | L | E | W | I | A | H | I | K | A | K | S | D | N | Y | V | T | Y | Y | A | E | S | V | K | G | R | F | T | I | S | R | D | D | S | K | T | T | I | Y |
| h3.10C2.v1 Q100P/V104L | K | G | L | E | W | I | A | H | I | K | A | K | S | D | N | Y | A | T | Y | Y | A | E | S | V | K | G | R | F | T | I | S | R | D | D | S | K | T | T | I | Y |
| h3.10C2.H1-3.10C2.L10 | K | G | L | E | W | I | A | H | I | K | A | K | S | D | N | Y | A | T | Y | Y | A | E | S | V | K | G | R | F | T | I | S | R | D | D | S | K | T | T | I | Y |

CDRH2 - Kabat

| Kabat number | 82a | 82b | 82c | 83 | 84 | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 | 108 | 109 | 110 | 111 | 112 | 113 |
|---|---|---|---|---|---|---|---|---|---|---|---|---|---|---|---|---|---|---|---|---|---|---|---|---|---|---|---|---|---|---|---|---|---|---|
| h3.10C2.v1 | M | N | S | L | K | T | E | D | T | A | V | Y | Y | C | T | G | L | D | Y | W | G | Q | G | T | T | V | T | V | S | S | | | | |
| h3.10C2.v1 Q100P | M | N | S | L | K | T | E | D | T | A | V | Y | Y | C | T | G | L | D | Y | W | G | Q | G | T | T | V | T | V | S | S | | | | |
| h3.10C2.v1 I58V/Q100P | M | N | S | L | K | T | E | D | T | A | V | Y | Y | C | T | G | L | D | Y | W | G | Q | G | T | T | V | T | V | S | S | | | | |
| h3.10C2.v1 Q100P/V104L | M | N | S | L | K | T | E | D | T | A | V | Y | Y | C | T | G | L | D | Y | W | G | Q | G | T | T | V | T | V | S | S | | | | |
| h3.10C2.H1-3.10C2.L10 | M | N | S | L | K | T | E | D | T | A | V | Y | Y | C | T | G | L | D | Y | W | G | Q | G | T | T | V | T | V | S | S | | | | |

CDRH3 - Kabat

*Fig. 14B*

SEQUENCE LISTING

<160> NUMBER OF SEQ ID NOS: 177

<210> SEQ ID NO 1
<211> LENGTH: 5
<212> TYPE: PRT
<213> ORGANISM: Artificial Sequence
<220> FEATURE:
<223> OTHER INFORMATION: Synthetic: 3.10C2.v1 heavy chain CDR1

<400> SEQUENCE: 1

Asn Val Trp Met His
1               5

<210> SEQ ID NO 2
<211> LENGTH: 19
<212> TYPE: PRT
<213> ORGANISM: Artificial Sequence
<220> FEATURE:
<223> OTHER INFORMATION: Synthetic: 3.10C2.v1 heavy chain CDR2

<400> SEQUENCE: 2

His Ile Lys Ala Lys Ser Asp Asn Tyr Ala Thr Tyr Tyr Ala Glu Ser
1               5                   10                  15

Val Lys Gly

<210> SEQ ID NO 3
<211> LENGTH: 3
<212> TYPE: PRT
<213> ORGANISM: Artificial Sequence
<220> FEATURE:
<223> OTHER INFORMATION: Synthetic: 3.10C2.v1 heavy chain CDR3

<400> SEQUENCE: 3

Leu Asp Tyr
1

<210> SEQ ID NO 4
<211> LENGTH: 16
<212> TYPE: PRT
<213> ORGANISM: Artificial Sequence
<220> FEATURE:
<223> OTHER INFORMATION: Synthetic: 3.10C2.v1 light chain CDR1

<400> SEQUENCE: 4

Arg Ser Ser Arg Ser Leu Leu Thr Ser Lys Gly Ile Thr Ser Leu Tyr
1               5                   10                  15

```
<210> SEQ ID NO 5
<211> LENGTH: 7
<212> TYPE: PRT
<213> ORGANISM: Artificial Sequence
<220> FEATURE:
<223> OTHER INFORMATION: Synthetic: 3.10C2.v1 light chain CDR2

<400> SEQUENCE: 5

Arg Met Ser Asn Leu Ala Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic: 3.10C2.v1 light chain CDR3

<400> SEQUENCE: 6

Ala Gln Phe Leu Val Tyr Pro Tyr Thr
1               5

<210> SEQ ID NO 7
<211> LENGTH: 114
<212> TYPE: PRT
<213> ORGANISM: Artificial Sequence
<220> FEATURE:
<223> OTHER INFORMATION: Synthetic: h3.10C2.V1 heavy chain variable
      region

<400> SEQUENCE: 7

Glu Val Gln Leu Val Glu Ser Gly Gly Gly Leu Val Gln Pro Gly Gly
1               5                   10                  15

Ser Leu Lys Leu Ser Cys Ala Thr Ser Gly Phe Pro Phe Ser Asn Val
            20                  25                  30

Trp Met His Trp Val Arg Gln Ala Ser Gly Lys Gly Leu Glu Trp Ile
        35                  40                  45

Ala His Ile Lys Ala Lys Ser Asp Asn Tyr Ala Thr Tyr Tyr Ala Glu
    50                  55                  60

Ser Val Lys Gly Arg Phe Thr Ile Ser Arg Asp Asp Ser Lys Thr Thr
65                  70                  75                  80

Ile Tyr Leu Gln Met Asn Ser Leu Lys Thr Glu Asp Thr Ala Val Tyr
                85                  90                  95

Tyr Cys Thr Gly Leu Asp Tyr Trp Gly Gln Gly Thr Thr Val Thr Val
            100                 105                 110

Ser Ser

<210> SEQ ID NO 8
<211> LENGTH: 112
<212> TYPE: PRT
<213> ORGANISM: Artificial Sequence
<220> FEATURE:
<223> OTHER INFORMATION: Synthetic: h3.10C2.V1 light chain variable
      region

<400> SEQUENCE: 8

Asp Val Val Met Thr Gln Ser Pro Leu Ser Leu Pro Val Thr Pro Gly
1               5                   10                  15

Glu Pro Ala Ser Ile Ser Cys Arg Ser Ser Arg Ser Leu Leu Thr Ser
            20                  25                  30

Lys Gly Ile Thr Ser Leu Tyr Trp Tyr Leu Gln Lys Pro Gly Gln Ser
        35                  40                  45
```

```
Pro Gln Leu Leu Ile Tyr Arg Met Ser Asn Leu Ala Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ala Gln Phe
                 85                  90                  95

Leu Val Tyr Pro Tyr Thr Phe Gly Gln Gly Thr Lys Val Glu Ile Lys
            100                 105                 110

<210> SEQ ID NO 9
<211> LENGTH: 7
<212> TYPE: PRT
<213> ORGANISM: Artificial Sequence
<220> FEATURE:
<223> OTHER INFORMATION: Synthetic: 3.10C2.v1 heavy chain CDR1 (Chothia)

<400> SEQUENCE: 9

Gly Phe Pro Phe Ser Asn Val
 1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic: 3.10C2.v1 heavy chain CDR2 (Chothia)

<400> SEQUENCE: 10

Lys Ala Lys Ser Asp Asn Tyr Ala
 1               5

<210> SEQ ID NO 11
<211> LENGTH: 5
<212> TYPE: PRT
<213> ORGANISM: Artificial Sequence
<220> FEATURE:
<223> OTHER INFORMATION: Synthetic: PARA.09 heavy chain CDR1

<400> SEQUENCE: 11

Asn Val Trp Leu His
 1               5

<210> SEQ ID NO 12
<211> LENGTH: 19
<212> TYPE: PRT
<213> ORGANISM: Artificial Sequence
<220> FEATURE:
<223> OTHER INFORMATION: Synthetic: PARA.09 heavy chain CDR2

<400> SEQUENCE: 12

His Ile Lys Ala Lys Ser Asp Asn Tyr Ala Thr Tyr Tyr Ala Glu Ser
 1               5                  10                  15

Val Lys Gly

<210> SEQ ID NO 13
<211> LENGTH: 4
<212> TYPE: PRT
<213> ORGANISM: Artificial Sequence
<220> FEATURE:
<223> OTHER INFORMATION: Synthetic: PARA.09 heavy chain CDR1

<400> SEQUENCE: 13

Ile Leu Glu Tyr
 1
```

```
<210> SEQ ID NO 14
<211> LENGTH: 16
<212> TYPE: PRT
<213> ORGANISM: Artificial Sequence
<220> FEATURE:
<223> OTHER INFORMATION: Synthetic: PARA.09 light chain CDR1

<400> SEQUENCE: 14

Arg Ser Ser Arg Ser Leu Leu Thr Ser Lys Gly Ile Thr Ser Leu Tyr
1               5                   10                  15

<210> SEQ ID NO 15
<211> LENGTH: 7
<212> TYPE: PRT
<213> ORGANISM: Artificial Sequence
<220> FEATURE:
<223> OTHER INFORMATION: Synthetic: PARA.09 light chain CDR1

<400> SEQUENCE: 15

Arg Met Ser Asn Leu Ala Ser
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic: PARA.09 light chain CDR1

<400> SEQUENCE: 16

Ala Gln Phe Leu Val Tyr Pro Tyr Thr
1               5

<210> SEQ ID NO 17
<211> LENGTH: 115
<212> TYPE: PRT
<213> ORGANISM: Artificial Sequence
<220> FEATURE:
<223> OTHER INFORMATION: Synthetic: hPARA.09.V2 heavy chain variable
      region

<400> SEQUENCE: 17

Glu Val Gln Leu Val Glu Ser Gly Gly Gly Leu Val Gln Pro Gly Gly
1               5                   10                  15

Ser Leu Lys Leu Ser Cys Ala Thr Ser Gly Phe Pro Phe Ser Asn Val
            20                  25                  30

Trp Leu His Trp Val Arg Gln Ala Ser Gly Lys Gly Pro Glu Trp Val
        35                  40                  45

Ala His Ile Lys Ala Lys Ser Asp Asn Tyr Ala Thr Tyr Tyr Ala Glu
    50                  55                  60

Ser Val Lys Gly Arg Phe Thr Ile Ser Arg Asp Asp Ser Lys Asn Thr
65                  70                  75                  80

Val Tyr Leu Gln Met Asn Ser Leu Lys Thr Glu Asp Thr Ala Val Tyr
                85                  90                  95

Tyr Cys Thr Asp Ile Leu Glu Tyr Trp Gly Gln Gly Thr Leu Val Thr
            100                 105                 110

Val Ser Ser
        115

<210> SEQ ID NO 18
<211> LENGTH: 112
<212> TYPE: PRT
```

```
<213> ORGANISM: Artificial Sequence
<220> FEATURE:
<223> OTHER INFORMATION: Synthetic: hPARA.09.V2 light chain variable
      region

<400> SEQUENCE: 18

Asp Val Val Met Thr Gln Ser Pro Leu Ser Leu Pro Val Thr Pro Gly
1               5                   10                  15

Glu Pro Ala Ser Ile Ser Cys Arg Ser Ser Arg Ser Leu Leu Thr Ser
            20                  25                  30

Lys Gly Ile Thr Ser Leu Tyr Trp Tyr Leu Gln Lys Pro Gly Gln Ser
        35                  40                  45

Pro Gln Leu Leu Ile Tyr Arg Met Ser Asn Leu Ala Ser Gly Ile Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Val Gly Val Tyr Tyr Cys Ala Gln Phe
                85                  90                  95

Leu Val Tyr Pro Tyr Thr Phe Gly Gln Gly Thr Lys Val Glu Ile Lys
            100                 105                 110

<210> SEQ ID NO 19
<211> LENGTH: 7
<212> TYPE: PRT
<213> ORGANISM: Artificial Sequence
<220> FEATURE:
<223> OTHER INFORMATION: Synthetic: PARA.09 heavy chain CDR1 (Chothia)

<400> SEQUENCE: 19

Gly Phe Pro Phe Ser Asn Val
1               5

<210> SEQ ID NO 20
<211> LENGTH: 8
<212> TYPE: PRT
<213> ORGANISM: Artificial Sequence
<220> FEATURE:
<223> OTHER INFORMATION: Synthetic: PARA.09 heavy chain CDR2 (Chothia)

<400> SEQUENCE: 20

Lys Ala Lys Ser Asp Asn Tyr Ala
1               5

<210> SEQ ID NO 21
<211> LENGTH: 230
<212> TYPE: PRT
<213> ORGANISM: Homo sapiens
<220> FEATURE:
<221> NAME/KEY: SITE
<222> LOCATION: (1)..(230)
<223> OTHER INFORMATION: Human TREM2 NP_061838.1(including signal
      sequence)

<400> SEQUENCE: 21

Met Glu Pro Leu Arg Leu Leu Ile Leu Leu Phe Val Thr Glu Leu Ser
1               5                   10                  15

Gly Ala His Asn Thr Thr Val Phe Gln Gly Val Ala Gly Gln Ser Leu
            20                  25                  30

Gln Val Ser Cys Pro Tyr Asp Ser Met Lys His Trp Gly Arg Arg Lys
        35                  40                  45

Ala Trp Cys Arg Gln Leu Gly Glu Lys Gly Pro Cys Gln Arg Val Val
    50                  55                  60
```

-continued

```
Ser Thr His Asn Leu Trp Leu Leu Ser Phe Leu Arg Arg Trp Asn Gly
 65                  70                  75                  80

Ser Thr Ala Ile Thr Asp Asp Thr Leu Gly Gly Thr Leu Thr Ile Thr
                 85                  90                  95

Leu Arg Asn Leu Gln Pro His Asp Ala Gly Leu Tyr Gln Cys Gln Ser
            100                 105                 110

Leu His Gly Ser Glu Ala Asp Thr Leu Arg Lys Val Leu Val Glu Val
        115                 120                 125

Leu Ala Asp Pro Leu Asp His Arg Asp Ala Gly Asp Leu Trp Phe Pro
    130                 135                 140

Gly Glu Ser Glu Ser Phe Glu Asp Ala His Val Glu His Ser Ile Ser
145                 150                 155                 160

Arg Ser Leu Leu Glu Gly Glu Ile Pro Phe Pro Pro Thr Ser Ile Leu
                165                 170                 175

Leu Leu Leu Ala Cys Ile Phe Leu Ile Lys Ile Leu Ala Ala Ser Ala
            180                 185                 190

Leu Trp Ala Ala Ala Trp His Gly Gln Lys Pro Gly Thr His Pro Pro
        195                 200                 205

Ser Glu Leu Asp Cys Gly His Asp Pro Gly Tyr Gln Leu Gln Thr Leu
    210                 215                 220

Pro Gly Leu Arg Asp Thr
225                 230
```

<210> SEQ ID NO 22
<211> LENGTH: 212
<212> TYPE: PRT
<213> ORGANISM: Homo sapiens
<220> FEATURE:
<221> NAME/KEY: SITE
<222> LOCATION: (1)..(212)
<223> OTHER INFORMATION: Human TREM2 (without signal sequence)

<400> SEQUENCE: 22

```
His Asn Thr Thr Val Phe Gln Gly Val Ala Gly Gln Ser Leu Gln Val
  1               5                  10                  15

Ser Cys Pro Tyr Asp Ser Met Lys His Trp Gly Arg Arg Lys Ala Trp
                 20                  25                  30

Cys Arg Gln Leu Gly Glu Lys Gly Pro Cys Gln Arg Val Val Ser Thr
            35                  40                  45

His Asn Leu Trp Leu Leu Ser Phe Leu Arg Arg Trp Asn Gly Ser Thr
        50                  55                  60

Ala Ile Thr Asp Asp Thr Leu Gly Gly Thr Leu Thr Ile Thr Leu Arg
 65                  70                  75                  80

Asn Leu Gln Pro His Asp Ala Gly Leu Tyr Gln Cys Gln Ser Leu His
                 85                  90                  95

Gly Ser Glu Ala Asp Thr Leu Arg Lys Val Leu Val Glu Val Leu Ala
            100                 105                 110

Asp Pro Leu Asp His Arg Asp Ala Gly Asp Leu Trp Phe Pro Gly Glu
        115                 120                 125

Ser Glu Ser Phe Glu Asp Ala His Val Glu His Ser Ile Ser Arg Ser
    130                 135                 140

Leu Leu Glu Gly Glu Ile Pro Phe Pro Pro Thr Ser Ile Leu Leu Leu
145                 150                 155                 160

Leu Ala Cys Ile Phe Leu Ile Lys Ile Leu Ala Ala Ser Ala Leu Trp
                165                 170                 175
```

Ala Ala Ala Trp His Gly Gln Lys Pro Gly Thr His Pro Ser Glu
            180                 185                 190

Leu Asp Cys Gly His Asp Pro Gly Tyr Gln Leu Gln Thr Leu Pro Gly
        195                 200                 205

Leu Arg Asp Thr
    210

<210> SEQ ID NO 23
<211> LENGTH: 139
<212> TYPE: PRT
<213> ORGANISM: Homo sapiens
<220> FEATURE:
<221> NAME/KEY: SITE
<222> LOCATION: (1)..(139)
<223> OTHER INFORMATION: Soluble human TREM2 (TREM2 ectodomain)

<400> SEQUENCE: 23

His Asn Thr Thr Val Phe Gln Gly Val Ala Gly Gln Ser Leu Gln Val
1               5                   10                  15

Ser Cys Pro Tyr Asp Ser Met Lys His Trp Gly Arg Arg Lys Ala Trp
            20                  25                  30

Cys Arg Gln Leu Gly Glu Lys Gly Pro Cys Gln Arg Val Val Ser Thr
        35                  40                  45

His Asn Leu Trp Leu Leu Ser Phe Leu Arg Arg Trp Asn Gly Ser Thr
    50                  55                  60

Ala Ile Thr Asp Asp Thr Leu Gly Gly Thr Leu Thr Ile Thr Leu Arg
65                  70                  75                  80

Asn Leu Gln Pro His Asp Ala Gly Leu Tyr Gln Cys Gln Ser Leu His
                85                  90                  95

Gly Ser Glu Ala Asp Thr Leu Arg Lys Val Leu Val Glu Val Leu Ala
            100                 105                 110

Asp Pro Leu Asp His Arg Asp Ala Gly Asp Leu Trp Phe Pro Gly Glu
        115                 120                 125

Ser Glu Ser Phe Glu Asp Ala His Val Glu His
    130                 135

<210> SEQ ID NO 24
<211> LENGTH: 5
<212> TYPE: PRT
<213> ORGANISM: Artificial Sequence
<220> FEATURE:
<223> OTHER INFORMATION: Synthetic: 3.10C2 heavy chain CDR1

<400> SEQUENCE: 24

Asn Val Trp Met His
1               5

<210> SEQ ID NO 25
<211> LENGTH: 19
<212> TYPE: PRT
<213> ORGANISM: Artificial Sequence
<220> FEATURE:
<223> OTHER INFORMATION: Synthetic: 3.10C2  heavy chain CDR2

<400> SEQUENCE: 25

His Ile Lys Ala Lys Ser Asp Asn Tyr Ala Thr Tyr Tyr Ala Glu Ser
1               5                   10                  15

Val Lys Gly

<210> SEQ ID NO 26

```
<211> LENGTH: 3
<212> TYPE: PRT
<213> ORGANISM: Artificial Sequence
<220> FEATURE:
<223> OTHER INFORMATION: Synthetic: 3.10C2 heavy chain CDR3

<400> SEQUENCE: 26

Leu Asp Tyr
1

<210> SEQ ID NO 27
<211> LENGTH: 16
<212> TYPE: PRT
<213> ORGANISM: Artificial Sequence
<220> FEATURE:
<223> OTHER INFORMATION: Synthetic: 3.10C2 light chain CDR1

<400> SEQUENCE: 27

Arg Ser Ser Lys Ser Leu Leu Gly Val Arg Asp Ile Thr Ser Leu Tyr
1               5                   10                  15

<210> SEQ ID NO 28
<211> LENGTH: 7
<212> TYPE: PRT
<213> ORGANISM: Artificial Sequence
<220> FEATURE:
<223> OTHER INFORMATION: Synthetic: 3.10C2 light chain CDR2

<400> SEQUENCE: 28

Arg Met Ser Asn Leu Ala Ser
1               5

<210> SEQ ID NO 29
<211> LENGTH: 9
<212> TYPE: PRT
<213> ORGANISM: Artificial Sequence
<220> FEATURE:
<223> OTHER INFORMATION: Synthetic: 3.10C2 light chain CDR3

<400> SEQUENCE: 29

Ala Gln Phe Leu Arg Tyr Pro Tyr Thr
1               5

<210> SEQ ID NO 30
<211> LENGTH: 114
<212> TYPE: PRT
<213> ORGANISM: Artificial Sequence
<220> FEATURE:
<223> OTHER INFORMATION: Synthetic: 3.10C2 heavy chain variable region

<400> SEQUENCE: 30

Glu Val Gln Leu Val Glu Thr Gly Gly Ser Leu Val Gln Pro Gly Lys
1               5                   10                  15

Ser Leu Lys Leu Thr Cys Ala Thr Ser Gly Phe Pro Phe Ser Asn Val
            20                  25                  30

Trp Met His Trp Val Arg Gln Ser Pro Glu Lys Gln Leu Glu Trp Ile
        35                  40                  45

Ala His Ile Lys Ala Lys Ser Asp Asn Tyr Ala Thr Tyr Tyr Ala Glu
    50                  55                  60

Ser Val Lys Gly Arg Phe Thr Ile Ser Arg Asp Asp Ser Lys Thr Ser
65                  70                  75                  80

Ile Tyr Leu Gln Met Asn Ser Leu Lys Glu Asp Thr Ala Ile Tyr
                85                  90                  95
```

```
Tyr Cys Thr Gly Leu Asp Tyr Trp Gly Gln Gly Val Met Val Thr Val
            100                 105                 110

Ser Ser

<210> SEQ ID NO 31
<211> LENGTH: 112
<212> TYPE: PRT
<213> ORGANISM: Artificial Sequence
<220> FEATURE:
<223> OTHER INFORMATION: Synthetic: 3.10C2 light chain variable region

<400> SEQUENCE: 31

Asp Thr Val Leu Thr Gln Ala Pro Leu Ser Leu Ser Val Thr Pro Gly
1               5                   10                  15

Glu Ser Ala Ser Ile Ser Cys Arg Ser Ser Lys Ser Leu Leu Gly Val
            20                  25                  30

Arg Asp Ile Thr Ser Leu Tyr Trp Tyr Leu Gln Lys Pro Gly Lys Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Glu Thr Asp Phe Thr Leu Lys Ile
65                  70                  75                  80

Ser Glu Val Glu Thr Glu Asp Val Gly Val Tyr Tyr Cys Ala Gln Phe
                85                  90                  95

Leu Arg Tyr Pro Tyr Thr Phe Gly Pro Gly Thr Lys Leu Glu Leu Lys
            100                 105                 110

<210> SEQ ID NO 32
<211> LENGTH: 7
<212> TYPE: PRT
<213> ORGANISM: Artificial Sequence
<220> FEATURE:
<223> OTHER INFORMATION: Synthetic: 3.10C2  heavy chain CDR1 (Chothia)

<400> SEQUENCE: 32

Gly Phe Pro Phe Ser Asn Val
1               5

<210> SEQ ID NO 33
<211> LENGTH: 8
<212> TYPE: PRT
<213> ORGANISM: Artificial Sequence
<220> FEATURE:
<223> OTHER INFORMATION: Synthetic: 3.10C2  heavy chain CDR2 (Chothia)

<400> SEQUENCE: 33

Lys Ala Lys Ser Asp Asn Tyr Ala
1               5

<210> SEQ ID NO 34
<211> LENGTH: 5
<212> TYPE: PRT
<213> ORGANISM: Artificial Sequence
<220> FEATURE:
<223> OTHER INFORMATION: Synthetic: 3.50G1 heavy chain CDR1

<400> SEQUENCE: 34

Asn Val Trp Met His
1               5

<210> SEQ ID NO 35
<211> LENGTH: 19
```

```
<212> TYPE: PRT
<213> ORGANISM: Artificial Sequence
<220> FEATURE:
<223> OTHER INFORMATION: Synthetic: 3.50G1 heavy chain CDR2

<400> SEQUENCE: 35

His Ile Lys Ala Lys Ser Asp Asn Tyr Ala Thr Tyr Tyr Ala Glu Ser
1               5                   10                  15

Val Lys Gly

<210> SEQ ID NO 36
<211> LENGTH: 3
<212> TYPE: PRT
<213> ORGANISM: Artificial Sequence
<220> FEATURE:
<223> OTHER INFORMATION: Synthetic: 3.50G1 heavy chain CDR3

<400> SEQUENCE: 36

Leu Asp Tyr
1

<210> SEQ ID NO 37
<211> LENGTH: 16
<212> TYPE: PRT
<213> ORGANISM: Artificial Sequence
<220> FEATURE:
<223> OTHER INFORMATION: Synthetic: 3.50G1 light chain CDR1

<400> SEQUENCE: 37

Arg Ser Asn Lys Ser Leu Leu Gly Ile Arg Asp Ile Thr Ser Leu Tyr
1               5                   10                  15

<210> SEQ ID NO 38
<211> LENGTH: 7
<212> TYPE: PRT
<213> ORGANISM: Artificial Sequence
<220> FEATURE:
<223> OTHER INFORMATION: Synthetic: 3.50G1 light chain CDR2

<400> SEQUENCE: 38

Arg Met Ser Asn Leu Ala Ser
1               5

<210> SEQ ID NO 39
<211> LENGTH: 9
<212> TYPE: PRT
<213> ORGANISM: Artificial Sequence
<220> FEATURE:
<223> OTHER INFORMATION: Synthetic: 3.50G1 light chain CDR3

<400> SEQUENCE: 39

Ala Gln Phe Leu Arg Tyr Pro Tyr Thr
1               5

<210> SEQ ID NO 40
<211> LENGTH: 114
<212> TYPE: PRT
<213> ORGANISM: Artificial Sequence
<220> FEATURE:
<223> OTHER INFORMATION: Synthetic: 3.50G1 heavy chain variable region

<400> SEQUENCE: 40

Glu Val Gln Leu Val Glu Thr Gly Gly Ser Leu Val Gln Pro Gly Lys
1               5                   10                  15

Ser Leu Lys Leu Thr Cys Ala Thr Ser Gly Phe Pro Phe Ser Asn Val
            20                  25                  30
```

```
Trp Met His Trp Val Arg Gln Ser Pro Glu Lys Gln Leu Glu Trp Ile
            35                  40                  45

Ala His Ile Lys Ala Lys Ser Asp Asn Tyr Ala Thr Tyr Tyr Ala Glu
 50                  55                  60

Ser Val Lys Gly Arg Phe Thr Ile Ser Arg Asp Asp Ser Lys Thr Ser
 65                  70                  75                  80

Ile Tyr Leu Gln Met Asn Ser Leu Lys Asp Asp Thr Ala Ile Tyr
                 85                  90                  95

Tyr Cys Thr Gly Leu Asp Tyr Trp Gly Gln Gly Val Met Val Thr Val
            100                 105                 110

Ser Ser

<210> SEQ ID NO 41
<211> LENGTH: 112
<212> TYPE: PRT
<213> ORGANISM: Artificial Sequence
<220> FEATURE:
<223> OTHER INFORMATION: Synthetic: 3.50G1 light chain variable region

<400> SEQUENCE: 41

Asp Thr Val Leu Thr Gln Ala Pro Leu Ser Val Ser Val Thr Pro Gly
 1               5                  10                  15

Glu Ser Ala Ser Ile Ser Cys Arg Ser Asn Lys Ser Leu Leu Gly Ile
            20                  25                  30

Arg Asp Ile Thr Ser Leu Tyr Trp Phe Leu Gln Lys Pro Gly Lys Ser
            35                  40                  45

Pro Gln Leu Leu Ile Tyr Arg Met Ser Asn Leu Ala Ser Gly Val Pro
 50                  55                  60

Asp Arg Phe Ser Gly Ser Gly Ser Glu Thr Asp Phe Thr Leu Lys Ile
 65                  70                  75                  80

Ser Glu Val Glu Thr Glu Asp Val Gly Val Tyr Tyr Cys Ala Gln Phe
                 85                  90                  95

Leu Arg Tyr Pro Tyr Thr Phe Gly Pro Gly Thr Lys Leu Glu Leu Gln
            100                 105                 110

<210> SEQ ID NO 42
<211> LENGTH: 7
<212> TYPE: PRT
<213> ORGANISM: Artificial Sequence
<220> FEATURE:
<223> OTHER INFORMATION: Synthetic: 3.50G1 heavy chain CDR1 (Chothia)

<400> SEQUENCE: 42

Gly Phe Pro Phe Ser Asn Val
 1               5

<210> SEQ ID NO 43
<211> LENGTH: 8
<212> TYPE: PRT
<213> ORGANISM: Artificial Sequence
<220> FEATURE:
<223> OTHER INFORMATION: Synthetic: 3.50G1 heavy chain CDR2 (Chothia)

<400> SEQUENCE: 43

Lys Ala Lys Ser Asp Asn Tyr Ala
 1               5

<210> SEQ ID NO 44
<211> LENGTH: 5
<212> TYPE: PRT
```

```
<213> ORGANISM: Artificial Sequence
<220> FEATURE:
<223> OTHER INFORMATION: Synthetic: 3.18E5 heavy chain CDR1

<400> SEQUENCE: 44

Asn Val Trp Met His
1               5

<210> SEQ ID NO 45
<211> LENGTH: 19
<212> TYPE: PRT
<213> ORGANISM: Artificial Sequence
<220> FEATURE:
<223> OTHER INFORMATION: Synthetic: 3.18E5 heavy chain CDR2

<400> SEQUENCE: 45

His Ile Lys Ala Lys Ser Asp Asn Tyr Ala Thr Tyr Tyr Ala Glu Ser
1               5                   10                  15

Val Lys Gly

<210> SEQ ID NO 46
<211> LENGTH: 3
<212> TYPE: PRT
<213> ORGANISM: Artificial Sequence
<220> FEATURE:
<223> OTHER INFORMATION: Synthetic: 3.18E5 heavy chain CDR3

<400> SEQUENCE: 46

Leu Asp Tyr
1

<210> SEQ ID NO 47
<211> LENGTH: 16
<212> TYPE: PRT
<213> ORGANISM: Artificial Sequence
<220> FEATURE:
<223> OTHER INFORMATION: Synthetic: 3.18E5 light chain CDR1

<400> SEQUENCE: 47

Arg Ser Asn Lys Ser Leu Leu Gly Ile Arg Asp Ile Thr Ser Leu Tyr
1               5                   10                  15

<210> SEQ ID NO 48
<211> LENGTH: 7
<212> TYPE: PRT
<213> ORGANISM: Artificial Sequence
<220> FEATURE:
<223> OTHER INFORMATION: Synthetic: 3.18E5 light chain CDR2

<400> SEQUENCE: 48

Arg Met Ser Asn Leu Ala Ser
1               5

<210> SEQ ID NO 49
<211> LENGTH: 9
<212> TYPE: PRT
<213> ORGANISM: Artificial Sequence
<220> FEATURE:
<223> OTHER INFORMATION: Synthetic: 3.18E5 light chain CDR3

<400> SEQUENCE: 49

Ala Gln Phe Leu Arg Tyr Pro Tyr Thr
1               5

<210> SEQ ID NO 50
<211> LENGTH: 114
```

```
<212> TYPE: PRT
<213> ORGANISM: Artificial Sequence
<220> FEATURE:
<223> OTHER INFORMATION: Synthetic: 3.18E5 heavy chain variable region

<400> SEQUENCE: 50

Glu Val Gln Leu Val Glu Thr Gly Gly Ser Leu Val Gln Pro Gly Lys
1               5                   10                  15

Ser Leu Lys Leu Thr Cys Ala Thr Ser Gly Phe Pro Phe Ser Asn Val
            20                  25                  30

Trp Met His Trp Val Arg Gln Ser Pro Glu Lys Gln Leu Glu Trp Ile
        35                  40                  45

Ala His Ile Lys Ala Lys Ser Asp Asn Tyr Ala Thr Tyr Tyr Ala Glu
    50                  55                  60

Ser Val Lys Gly Arg Phe Thr Ile Ser Arg Asp Asp Ser Lys Thr Thr
65                  70                  75                  80

Ile Tyr Leu Gln Met Asn Ser Leu Lys Glu Asp Thr Ala Ile Tyr
                85                  90                  95

Tyr Cys Thr Gly Leu Asp Tyr Trp Gly Gln Gly Val Met Val Thr Val
            100                 105                 110

Ser Ser

<210> SEQ ID NO 51
<211> LENGTH: 112
<212> TYPE: PRT
<213> ORGANISM: Artificial Sequence
<220> FEATURE:
<223> OTHER INFORMATION: Synthetic: 3.18E5 light chain variable region

<400> SEQUENCE: 51

Asp Thr Val Leu Thr Gln Ala Pro Leu Ser Val Ser Val Thr Pro Gly
1               5                   10                  15

Glu Ser Ala Ser Ile Ser Cys Arg Ser Asn Lys Ser Leu Leu Gly Ile
            20                  25                  30

Arg Asp Ile Thr Ser Leu Tyr Trp Tyr Leu Gln Lys Pro Gly Lys Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Glu Thr Asp Phe Thr Leu Lys Ile
65                  70                  75                  80

Ser Glu Val Glu Thr Glu Asp Val Gly Val Tyr Tyr Cys Ala Gln Phe
                85                  90                  95

Leu Arg Tyr Pro Tyr Thr Phe Gly Pro Gly Thr Lys Leu Glu Leu Lys
            100                 105                 110

<210> SEQ ID NO 52
<211> LENGTH: 7
<212> TYPE: PRT
<213> ORGANISM: Artificial Sequence
<220> FEATURE:
<223> OTHER INFORMATION: Synthetic: 3.18E5 heavy chain CDR1 (Chothia)

<400> SEQUENCE: 52

Gly Phe Pro Phe Ser Asn Val
1               5

<210> SEQ ID NO 53
<211> LENGTH: 8
<212> TYPE: PRT
<213> ORGANISM: Artificial Sequence
```

```
<220> FEATURE:
<223> OTHER INFORMATION: Synthetic: 3.18E5 heavy chain CDR2 (Chothia)

<400> SEQUENCE: 53

Lys Ala Lys Ser Asp Asn Tyr Ala
1               5

<210> SEQ ID NO 54
<211> LENGTH: 5
<212> TYPE: PRT
<213> ORGANISM: Artificial Sequence
<220> FEATURE:
<223> OTHER INFORMATION: Synthetic: 3.36F5 heavy chain CDR1

<400> SEQUENCE: 54

Asn Val Trp Met His
1               5

<210> SEQ ID NO 55
<211> LENGTH: 19
<212> TYPE: PRT
<213> ORGANISM: Artificial Sequence
<220> FEATURE:
<223> OTHER INFORMATION: Synthetic: 3.36F5 heavy chain CDR2

<400> SEQUENCE: 55

Gln Ile Lys Gly Lys Ser Asp Asn Tyr Ala Thr Tyr Tyr Ala Glu Ser
1               5                   10                  15

Leu Gln Gly

<210> SEQ ID NO 56
<211> LENGTH: 3
<212> TYPE: PRT
<213> ORGANISM: Artificial Sequence
<220> FEATURE:
<223> OTHER INFORMATION: Synthetic: 3.36F5 heavy chain CDR3

<400> SEQUENCE: 56

Leu Asp Tyr
1

<210> SEQ ID NO 57
<211> LENGTH: 16
<212> TYPE: PRT
<213> ORGANISM: Artificial Sequence
<220> FEATURE:
<223> OTHER INFORMATION: Synthetic: 3.36F5 light chain CDR1

<400> SEQUENCE: 57

Arg Ser Asn Lys Ser Leu Leu Ser Ser Lys Gly Ile Thr Ser Leu Tyr
1               5                   10                  15

<210> SEQ ID NO 58
<211> LENGTH: 7
<212> TYPE: PRT
<213> ORGANISM: Artificial Sequence
<220> FEATURE:
<223> OTHER INFORMATION: Synthetic: 3.36F5 light chain CDR2

<400> SEQUENCE: 58

Arg Met Ser Asn Leu Ala Ser
1               5

<210> SEQ ID NO 59
<211> LENGTH: 9
<212> TYPE: PRT
```

```
<213> ORGANISM: Artificial Sequence
<220> FEATURE:
<223> OTHER INFORMATION: Synthetic: 3.36F5 light chain CDR3

<400> SEQUENCE: 59

Ala Gln Phe Leu Gln Tyr Pro Tyr Thr
1               5

<210> SEQ ID NO 60
<211> LENGTH: 114
<212> TYPE: PRT
<213> ORGANISM: Artificial Sequence
<220> FEATURE:
<223> OTHER INFORMATION: Synthetic: 3.36F5 heavy chain variable region

<400> SEQUENCE: 60

Glu Val Gln Leu Val Glu Thr Gly Gly Ser Leu Val Gln Pro Gly Arg
1               5                   10                  15

Ser Leu Lys Leu Thr Cys Ala Thr Ser Gly Phe Thr Phe Thr Asn Val
            20                  25                  30

Trp Leu His Trp Ile Arg Arg Ser Pro Glu Asn Gln Leu Glu Trp Val
        35                  40                  45

Gly Gln Ile Lys Gly Lys Ser Asp Asn Tyr Ala Thr Tyr Tyr Ala Glu
    50                  55                  60

Ser Leu Gln Gly Arg Phe Thr Ile Ser Arg Asp Asp Ser Glu Arg Ser
65                  70                  75                  80

Ile Tyr Leu Gln Met Asn Asn Leu Lys Glu Glu Asp Thr Ala Ile Tyr
                85                  90                  95

Tyr Cys Thr Gly Leu Asp Tyr Trp Gly Gln Gly Val Met Val Thr Val
            100                 105                 110

Ser Ser

<210> SEQ ID NO 61
<211> LENGTH: 112
<212> TYPE: PRT
<213> ORGANISM: Artificial Sequence
<220> FEATURE:
<223> OTHER INFORMATION: Synthetic: 3.36F5 light chain variable region

<400> SEQUENCE: 61

Asp Thr Val Leu Thr Gln Gly Pro Leu Ser Val Ser Val Thr Pro Gly
1               5                   10                  15

Glu Ser Ala Ser Ile Ser Cys Arg Ser Lys Ser Leu Leu Ser Ser
            20                  25                  30

Lys Gly Ile Thr Ser Leu Tyr Trp Tyr Leu Gln Lys Pro Gly Lys Ser
        35                  40                  45

Pro Gln Leu Leu Ile Tyr Arg Met Ser Asn Leu Ala Ser Gly Val Pro
    50                  55                  60

Asp Arg Phe Ser Gly Gly Gly Ser Glu Thr Asp Phe Thr Leu Lys Ile
65                  70                  75                  80

Ser Lys Val Glu Thr Glu Asp Val Gly Val Tyr Tyr Cys Ala Gln Phe
                85                  90                  95

Leu Gln Tyr Pro Tyr Thr Phe Gly Ala Gly Thr Lys Leu Glu Leu Lys
            100                 105                 110

<210> SEQ ID NO 62
<211> LENGTH: 7
<212> TYPE: PRT
<213> ORGANISM: Artificial Sequence
<220> FEATURE:
```

```
<223> OTHER INFORMATION: Synthetic: 3.36F5 heavy chain CDR1 (Chothia)

<400> SEQUENCE: 62

Gly Phe Thr Phe Thr Asn Val
1               5

<210> SEQ ID NO 63
<211> LENGTH: 8
<212> TYPE: PRT
<213> ORGANISM: Artificial Sequence
<220> FEATURE:
<223> OTHER INFORMATION: Synthetic: 3.36F5 heavy chain CDR2 (Chothia)

<400> SEQUENCE: 63

Lys Gly Lys Ser Asp Asn Tyr Ala
1               5

<210> SEQ ID NO 64
<211> LENGTH: 5
<212> TYPE: PRT
<213> ORGANISM: Artificial Sequence
<220> FEATURE:
<223> OTHER INFORMATION: Synthetic: 3.27H7 heavy chain CDR1

<400> SEQUENCE: 64

Asn Val Trp Leu His
1               5

<210> SEQ ID NO 65
<211> LENGTH: 19
<212> TYPE: PRT
<213> ORGANISM: Artificial Sequence
<220> FEATURE:
<223> OTHER INFORMATION: Synthetic: 3.27H7 heavy chain CDR2

<400> SEQUENCE: 65

Gln Ile Lys Ala Arg Ser Asp Asn Tyr Ala Thr Tyr Tyr Ala Glu Ser
1               5                   10                  15

Val Lys Gly

<210> SEQ ID NO 66
<211> LENGTH: 3
<212> TYPE: PRT
<213> ORGANISM: Artificial Sequence
<220> FEATURE:
<223> OTHER INFORMATION: Synthetic: 3.27H7 heavy chain CDR3

<400> SEQUENCE: 66

Leu Asp Tyr
1

<210> SEQ ID NO 67
<211> LENGTH: 16
<212> TYPE: PRT
<213> ORGANISM: Artificial Sequence
<220> FEATURE:
<223> OTHER INFORMATION: Synthetic: 3.27H7 light chain CDR1

<400> SEQUENCE: 67

Arg Ser Ser Arg Ser Leu Leu Thr Ser Lys Gly Ile Thr Ser Leu Tyr
1               5                   10                  15

<210> SEQ ID NO 68
<211> LENGTH: 7
<212> TYPE: PRT
<213> ORGANISM: Artificial Sequence
```

```
<220> FEATURE:
<223> OTHER INFORMATION: Synthetic: 3.27H7 light chain CDR2

<400> SEQUENCE: 68

Arg Met Ser Asn Leu Ala Ser
1               5

<210> SEQ ID NO 69
<211> LENGTH: 9
<212> TYPE: PRT
<213> ORGANISM: Artificial Sequence
<220> FEATURE:
<223> OTHER INFORMATION: Synthetic: 3.27H7 light chain CDR3

<400> SEQUENCE: 69

Ala Gln Phe Leu Val Tyr Pro Tyr Thr
1               5

<210> SEQ ID NO 70
<211> LENGTH: 114
<212> TYPE: PRT
<213> ORGANISM: Artificial Sequence
<220> FEATURE:
<223> OTHER INFORMATION: Synthetic: 3.27H7 heavy chain variable region

<400> SEQUENCE: 70

Glu Val Gln Leu Val Glu Thr Gly Gly Ser Leu Val Gln Pro Gly Gly
1               5                   10                  15

Ser Leu Lys Leu Thr Cys Ala Thr Ser Gly Phe Pro Phe Ser Asn Val
            20                  25                  30

Trp Leu His Trp Ile Arg Arg Ser Pro Glu Lys Gln Leu Glu Trp Val
        35                  40                  45

Ala Gln Ile Lys Ala Arg Ser Asp Asn Tyr Ala Thr Tyr Tyr Ala Glu
    50                  55                  60

Ser Val Lys Gly Arg Phe Ile Val Ser Arg Asp Asp Ser Lys Thr Thr
65                  70                  75                  80

Ile Tyr Leu Gln Met Asn Asn Leu Lys Glu Glu Asp Thr Ala Ile Tyr
                85                  90                  95

Tyr Cys Thr Gly Leu Asp Tyr Trp Gly Gln Gly Val Met Val Thr Val
            100                 105                 110

Ser Ser

<210> SEQ ID NO 71
<211> LENGTH: 112
<212> TYPE: PRT
<213> ORGANISM: Artificial Sequence
<220> FEATURE:
<223> OTHER INFORMATION: Synthetic: 3.27H7 light chain variable region

<400> SEQUENCE: 71

Asp Val Val Leu Thr Gln Ala Pro Leu Ser Val Ser Val Thr Pro Gly
1               5                   10                  15

Glu Ser Ala Ser Ile Ser Cys Arg Ser Arg Ser Leu Leu Thr Ser
            20                  25                  30

Lys Gly Ile Thr Ser Leu Tyr Trp Tyr Leu Gln Lys Pro Gly Met Ser
        35                  40                  45

Pro His Leu Leu Ile Tyr Arg Met Ser Asn Leu Ala Ser Gly Ile Pro
    50                  55                  60

Asp Arg Phe Ser Gly Ser Gly Ser Glu Thr Asp Phe Thr Leu Lys Ile
65                  70                  75                  80
```

```
Ser Glu Val Glu Pro Glu Asp Val Gly Val Tyr Tyr Cys Ala Gln Phe
            85                  90                  95

Leu Val Tyr Pro Tyr Thr Phe Gly Ala Gly Thr Lys Leu Glu Leu Lys
            100                 105                 110

<210> SEQ ID NO 72
<211> LENGTH: 7
<212> TYPE: PRT
<213> ORGANISM: Artificial Sequence
<220> FEATURE:
<223> OTHER INFORMATION: Synthetic: 3.27H7 heavy chain CDR1 (Chothia)

<400> SEQUENCE: 72

Gly Phe Pro Phe Ser Asn Val
1               5

<210> SEQ ID NO 73
<211> LENGTH: 8
<212> TYPE: PRT
<213> ORGANISM: Artificial Sequence
<220> FEATURE:
<223> OTHER INFORMATION: Synthetic: 3.27H7 heavy chain CDR2 (Chothia)

<400> SEQUENCE: 73

Lys Ala Arg Ser Asp Asn Tyr Ala
1               5

<210> SEQ ID NO 74
<211> LENGTH: 114
<212> TYPE: PRT
<213> ORGANISM: Artificial Sequence
<220> FEATURE:
<223> OTHER INFORMATION: Synthetic: IGHV3-73*01 germline heavy chain

<400> SEQUENCE: 74

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
            20                  25                  30

Ala Met His Trp Val Arg Gln Ala Ser Gly Lys Gly Leu Glu Trp Val
        35                  40                  45

Gly Arg Ile Arg Ser Lys Ala Asn Ser Tyr Ala Thr Ala Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Arg Met Asp Val Trp Gly Gln Gly Thr Thr Val Thr Val
            100                 105                 110

Ser Ser

<210> SEQ ID NO 75
<211> LENGTH: 112
<212> TYPE: PRT
<213> ORGANISM: Artificial Sequence
<220> FEATURE:
<223> OTHER INFORMATION: Synthetic: IGKV2-28*01 germline light chain

<400> SEQUENCE: 75

Asp Ile Val Met Thr Gln Ser Pro Leu Ser Leu Pro Val Thr Pro Gly
1               5                   10                  15
```

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Tyr Thr Phe Gly Gln Gly Thr Lys Leu Glu Ile Lys
            100                 105                 110

<210> SEQ ID NO 76
<211> LENGTH: 114
<212> TYPE: PRT
<213> ORGANISM: Artificial Sequence
<220> FEATURE:
<223> OTHER INFORMATION: Synthetic: 3.10C2-H1 heavy chain variable
      region

<400> SEQUENCE: 76

Glu Val Gln Leu Val Glu Thr Gly Gly Ser Leu Val Gln Pro Gly Lys
1               5                   10                  15

Ser Leu Lys Leu Thr Cys Ala Thr Ser Gly Phe Pro Phe Ser Asn Val
                20                  25                  30

Trp Met His Trp Val Arg Gln Ser Pro Glu Lys Gln Leu Glu Trp Ile
            35                  40                  45

Ala His Ile Lys Ala Lys Ser Asp Asn Tyr Ala Thr Tyr Tyr Ala Glu
        50                  55                  60

Ser Val Lys Gly Arg Phe Thr Ile Ser Arg Asp Asp Ser Lys Thr Ser
65                  70                  75                  80

Ile Tyr Leu Gln Met Asn Ser Leu Lys Glu Asp Asp Thr Ala Ile Tyr
                85                  90                  95

Tyr Cys Thr Gly Leu Asp Tyr Trp Gly Gln Gly Val Met Val Thr Val
            100                 105                 110

Ser Ser

<210> SEQ ID NO 77
<211> LENGTH: 114
<212> TYPE: PRT
<213> ORGANISM: Artificial Sequence
<220> FEATURE:
<223> OTHER INFORMATION: Synthetic: 3.10C2-H3 heavy chain variable
      region

<400> SEQUENCE: 77

Glu Val Gln Leu Val Glu Thr Gly Gly Ser Leu Val Gln Pro Gly Lys
1               5                   10                  15

Ser Leu Lys Leu Thr Cys Ala Thr Ser Gly Phe Pro Phe Ser Asn Val
                20                  25                  30

Trp Met His Trp Val Arg Gln Ser Pro Glu Lys Gln Leu Glu Trp Ile
            35                  40                  45

Ala His Ile Lys Ala Lys Ser Asp Asn Tyr Ala Thr Tyr Tyr Ala Glu
        50                  55                  60

Ser Val Lys Gly Arg Phe Thr Ile Ser Arg Asp Asp Ser Lys Thr Ser
65                  70                  75                  80

Ile Tyr Leu Gln Met Asn Ser Leu Lys Glu Asp Asp Thr Ala Ile Tyr
                85                  90                  95

Tyr Cys Thr Gly Leu Asp Tyr Trp Gly Gln Gly Val Met Val Thr Val
            100                 105                 110

Ser Ser

<210> SEQ ID NO 78
<211> LENGTH: 114
<212> TYPE: PRT
<213> ORGANISM: Artificial Sequence
<220> FEATURE:
<223> OTHER INFORMATION: Synthetic: 3.10C2-H5 heavy chain variable
      region

<400> SEQUENCE: 78

Glu Val Gln Leu Val Glu Thr Gly Gly Ser Leu Val Gln Pro Gly Lys
1               5                   10                  15

Ser Leu Lys Leu Thr Cys Ala Thr Ser Gly Phe Pro Phe Ser Asn Val
            20                  25                  30

Trp Met His Trp Val Arg Gln Ser Pro Glu Lys Gln Leu Glu Trp Ile
        35                  40                  45

Ala His Ile Lys Ala Lys Ser Asp Asn Tyr Ala Thr Tyr Tyr Ala Glu
    50                  55                  60

Ser Val Lys Gly Arg Phe Thr Ile Ser Arg Asp Asp Ser Lys Thr Ser
65                  70                  75                  80

Ile Tyr Leu Gln Met Asn Ser Leu Lys Glu Asp Asp Thr Ala Ile Tyr
                85                  90                  95

Tyr Cys Thr Gly Leu Asp Tyr Trp Gly Gln Gly Val Met Val Thr Val
            100                 105                 110

Ser Ser

<210> SEQ ID NO 79
<211> LENGTH: 112
<212> TYPE: PRT
<213> ORGANISM: Artificial Sequence
<220> FEATURE:
<223> OTHER INFORMATION: Synthetic: 3.10C2-L1 light chain variable
      region

<400> SEQUENCE: 79

Asp Thr Val Leu Thr Gln Ala Pro Leu Ser Leu Ser Val Thr Pro Gly
1               5                   10                  15

Glu Ser Ala Ser Ile Ser Cys Arg Ser Ser Lys Ser Leu Leu Gly Val
            20                  25                  30

Arg Asp Ile Thr Ser Leu Tyr Trp Tyr Leu Gln Lys Pro Gly Lys Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Glu Thr Asp Phe Thr Leu Lys Ile
65                  70                  75                  80

Ser Glu Val Glu Thr Glu Asp Val Gly Val Tyr Tyr Cys Ala Gln Phe
                85                  90                  95

Leu Arg Tyr Pro Tyr Thr Phe Gly Pro Gly Thr Lys Leu Glu Leu Lys
            100                 105                 110

<210> SEQ ID NO 80
<211> LENGTH: 112
<212> TYPE: PRT
<213> ORGANISM: Artificial Sequence

```
<220> FEATURE:
<223> OTHER INFORMATION: Synthetic: 3.10C2-L5 light chain variable
      region

<400> SEQUENCE: 80

Asp Thr Val Leu Thr Gln Ala Pro Leu Ser Leu Ser Val Thr Pro Gly
1               5                   10                  15

Glu Ser Ala Ser Ile Ser Cys Arg Ser Lys Ser Leu Leu Gly Val
            20                  25                  30

Arg Asp Ile Thr Ser Leu Tyr Trp Tyr Leu Gln Lys Pro Gly Lys Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Glu Thr Asp Phe Thr Leu Lys Ile
65                  70                  75                  80

Ser Glu Val Glu Thr Glu Asp Val Gly Val Tyr Tyr Cys Ala Gln Phe
                85                  90                  95

Leu Arg Tyr Pro Tyr Thr Phe Gly Pro Gly Thr Lys Leu Glu Leu Lys
            100                 105                 110

<210> SEQ ID NO 81
<211> LENGTH: 115
<212> TYPE: PRT
<213> ORGANISM: Artificial Sequence
<220> FEATURE:
<223> OTHER INFORMATION: Synthetic: Para.09-H1 heavy chain variable
      region

<400> SEQUENCE: 81

Glu Val Gln Leu Val Glu Thr Gly Gly Ser Leu Val Gln Pro Gly Lys
1               5                   10                  15

Ser Leu Arg Leu Thr Cys Ala Thr Ser Gly Phe Pro Phe Ser Asn Val
            20                  25                  30

Trp Leu His Trp Val Arg Gln Ser Pro Glu Lys His Pro Glu Trp Val
        35                  40                  45

Ala His Ile Lys Ala Lys Ser Asp Asn Tyr Ala Thr Tyr Tyr Ala Glu
    50                  55                  60

Ser Val Lys Gly Arg Phe Thr Ile Ser Arg Asp Asp Ser Lys Ser Ser
65                  70                  75                  80

Val Phe Leu Gln Met Asn Ser Leu Lys Glu Glu Asp Thr Ala Ile Tyr
                85                  90                  95

Tyr Cys Thr Asp Ile Leu Glu Tyr Trp Gly Gln Gly Thr Leu Val Thr
            100                 105                 110

Val Ser Ser
        115

<210> SEQ ID NO 82
<211> LENGTH: 115
<212> TYPE: PRT
<213> ORGANISM: Artificial Sequence
<220> FEATURE:
<223> OTHER INFORMATION: Synthetic: Para.09-H5 heavy chain variable
      region

<400> SEQUENCE: 82

Glu Val Gln Leu Val Glu Thr Gly Gly Ser Leu Val Gln Pro Gly Lys
1               5                   10                  15

Ser Leu Arg Leu Thr Cys Ala Thr Ser Gly Phe Pro Phe Ser Asn Val
            20                  25                  30
```

```
Trp Leu His Trp Val Arg Gln Ser Pro Glu Lys His Pro Glu Trp Val
            35                  40                  45

Ala His Ile Lys Ala Lys Ser Asp Asn Tyr Ala Thr Tyr Tyr Ala Glu
 50                  55                  60

Ser Val Lys Gly Arg Phe Thr Ile Ser Arg Asp Asp Ser Lys Ser Ser
 65                  70                  75                  80

Val Phe Leu Gln Met Asn Ser Leu Lys Glu Glu Asp Thr Ala Ile Tyr
                 85                  90                  95

Tyr Cys Thr Asp Ile Leu Glu Tyr Trp Gly Gln Gly Thr Leu Val Thr
                100                 105                 110

Val Ser Ser
        115

<210> SEQ ID NO 83
<211> LENGTH: 115
<212> TYPE: PRT
<213> ORGANISM: Artificial Sequence
<220> FEATURE:
<223> OTHER INFORMATION: Synthetic: Para.09-H7 heavy chain variable
      region

<400> SEQUENCE: 83

Glu Val Gln Leu Val Glu Thr Gly Gly Ser Leu Val Gln Pro Gly Lys
 1               5                  10                  15

Ser Leu Arg Leu Thr Cys Ala Thr Ser Gly Phe Pro Phe Ser Asn Val
                20                  25                  30

Trp Leu His Trp Val Arg Gln Ser Pro Glu Lys His Pro Glu Trp Val
            35                  40                  45

Ala His Ile Lys Ala Lys Ser Asp Asn Tyr Ala Thr Tyr Tyr Ala Glu
 50                  55                  60

Ser Val Lys Gly Arg Phe Thr Ile Ser Arg Asp Asp Ser Lys Ser Ser
 65                  70                  75                  80

Val Phe Leu Gln Met Asn Ser Leu Lys Glu Glu Asp Thr Ala Ile Tyr
                 85                  90                  95

Tyr Cys Thr Asp Ile Leu Glu Tyr Trp Gly Gln Gly Thr Leu Val Thr
                100                 105                 110

Val Ser Ser
        115

<210> SEQ ID NO 84
<211> LENGTH: 112
<212> TYPE: PRT
<213> ORGANISM: Artificial Sequence
<220> FEATURE:
<223> OTHER INFORMATION: Synthetic: 3.27H7-L1 light chain variable
      region

<400> SEQUENCE: 84

Asp Val Val Leu Thr Gln Ala Pro Leu Ser Val Ser Val Thr Pro Gly
 1               5                  10                  15

Glu Ser Ala Ser Ile Ser Cys Arg Ser Ser Arg Ser Leu Leu Thr Ser
                20                  25                  30

Lys Gly Ile Thr Ser Leu Tyr Trp Tyr Leu Gln Lys Pro Gly Met Ser
            35                  40                  45

Pro His Leu Leu Ile Tyr Arg Met Ser Asn Leu Ala Ser Gly Ile Pro
 50                  55                  60

Asp Arg Phe Ser Gly Ser Gly Ser Glu Thr Asp Phe Thr Leu Lys Ile
 65                  70                  75                  80
```

```
Ser Glu Val Glu Pro Glu Asp Val Gly Val Tyr Tyr Cys Ala Gln Phe
            85                  90                  95

Leu Val Tyr Pro Tyr Thr Phe Gly Ala Gly Thr Lys Leu Glu Leu Lys
            100                 105                 110

<210> SEQ ID NO 85
<211> LENGTH: 112
<212> TYPE: PRT
<213> ORGANISM: Artificial Sequence
<220> FEATURE:
<223> OTHER INFORMATION: Synthetic: 3.27H7-L6 light chain variable
      region

<400> SEQUENCE: 85

Asp Val Val Leu Thr Gln Ala Pro Leu Ser Val Ser Val Thr Pro Gly
1               5                   10                  15

Glu Ser Ala Ser Ile Ser Cys Arg Ser Ser Arg Ser Leu Leu Thr Ser
            20                  25                  30

Lys Gly Ile Thr Ser Leu Tyr Trp Tyr Leu Gln Lys Pro Gly Met Ser
            35                  40                  45

Pro His Leu Leu Ile Tyr Arg Met Ser Asn Leu Ala Ser Gly Ile Pro
        50                  55                  60

Asp Arg Phe Ser Gly Ser Gly Ser Glu Thr Asp Phe Thr Leu Lys Ile
65                  70                  75                  80

Ser Glu Val Glu Pro Glu Asp Val Gly Val Tyr Tyr Cys Ala Gln Phe
            85                  90                  95

Leu Val Tyr Pro Tyr Thr Phe Gly Ala Gly Thr Lys Leu Glu Leu Lys
            100                 105                 110

<210> SEQ ID NO 86
<211> LENGTH: 232
<212> TYPE: PRT
<213> ORGANISM: Homo sapiens
<220> FEATURE:
<221> NAME/KEY: SITE
<222> LOCATION: (1)..(232)
<223> OTHER INFORMATION: Human IgG1 Fc region

<400> SEQUENCE: 86

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
        50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
            85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
        130                 135                 140

Lys Asn Gln Val Ser Leu Thr Cys Leu Val Lys Gly Phe Tyr Pro Ser
145                 150                 155                 160
```

```
Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 87
<211> LENGTH: 232
<212> TYPE: PRT
<213> ORGANISM: Homo sapiens
<220> FEATURE:
<221> NAME/KEY: SITE
<222> LOCATION: (1)..(232)
<223> OTHER INFORMATION: Human IgG1 N297G Fc region

<400> SEQUENCE: 87

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Gly Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 88
<211> LENGTH: 330
<212> TYPE: PRT
<213> ORGANISM: Mus musculus
<220> FEATURE:
```

<221> NAME/KEY: SITE
<222> LOCATION: (1)..(330)
<223> OTHER INFORMATION: Murine IgG2 Fc region

<400> SEQUENCE: 88

```
Ala Lys Thr Thr Ala Pro Ser Val Tyr Pro Leu Ala Pro Val Cys Gly
1               5                   10                  15
Asp Thr Thr Gly Ser Ser Val Thr Leu Gly Cys Leu Val Lys Gly Tyr
                20                  25                  30
Phe Pro Glu Pro Val Thr Leu Thr Trp Asn Ser Gly Ser Leu Ser Ser
            35                  40                  45
Gly Val His Thr Phe Pro Ala Val Leu Gln Ser Asp Leu Tyr Thr Leu
        50                  55                  60
Ser Ser Ser Val Thr Val Thr Ser Ser Thr Trp Pro Ser Gln Ser Ile
65                  70                  75                  80
Thr Cys Asn Val Ala His Pro Ala Ser Ser Thr Lys Val Asp Lys Lys
                85                  90                  95
Ile Glu Pro Arg Gly Pro Thr Ile Lys Pro Cys Pro Pro Cys Lys Cys
            100                 105                 110
Pro Ala Pro Asn Leu Leu Gly Gly Pro Ser Val Phe Ile Phe Pro Pro
        115                 120                 125
Lys Ile Lys Asp Val Leu Met Ile Ser Leu Ser Pro Ile Val Thr Cys
130                 135                 140
Val Val Val Asp Val Ser Glu Asp Asp Pro Asp Val Gln Ile Ser Trp
145                 150                 155                 160
Phe Val Asn Asn Val Glu Val His Thr Ala Gln Thr Gln Thr His Arg
                165                 170                 175
Glu Asp Tyr Asn Ser Thr Leu Arg Val Val Ser Ala Leu Pro Ile Gln
            180                 185                 190
His Gln Asp Trp Met Ser Gly Lys Glu Phe Lys Cys Lys Val Asn Asn
        195                 200                 205
Lys Asp Leu Pro Ala Pro Ile Glu Arg Thr Ile Ser Lys Pro Lys Gly
    210                 215                 220
Ser Val Arg Ala Pro Gln Val Tyr Val Leu Pro Pro Pro Glu Glu Glu
225                 230                 235                 240
Met Thr Lys Lys Gln Val Thr Leu Thr Cys Met Val Thr Asp Phe Met
                245                 250                 255
Pro Glu Asp Ile Tyr Val Glu Trp Thr Asn Asn Gly Lys Thr Glu Leu
            260                 265                 270
Asn Tyr Lys Asn Thr Glu Pro Val Leu Asp Ser Asp Gly Ser Tyr Phe
        275                 280                 285
Met Tyr Ser Lys Leu Arg Val Glu Lys Lys Asn Trp Val Glu Arg Asn
    290                 295                 300
Ser Tyr Ser Cys Ser Val Val His Glu Gly Leu His Asn His His Thr
305                 310                 315                 320
Thr Lys Ser Phe Ser Arg Thr Pro Gly Lys
                325                 330
```

<210> SEQ ID NO 89
<211> LENGTH: 330
<212> TYPE: PRT
<213> ORGANISM: Mus musculus
<220> FEATURE:
<221> NAME/KEY: SITE
<222> LOCATION: (1)..(330)
<223> OTHER INFORMATION: Murine IgG2 LALAPG Fc region

<400> SEQUENCE: 89

```
Ala Lys Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
            20                  25                  30

Phe Pro Glu Pro Val Thr Leu Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                85                  90                  95

Ile Glu Pro Arg Gly Pro Thr Ile Lys Pro Cys Pro Pro Cys Lys Cys
            100                 105                 110

Pro Ala Pro Asn Ala Ala Gly Gly Pro Ser Val Phe Ile Phe Pro Pro
        115                 120                 125

Lys Ile Lys Asp Val Leu Met Ile Ser Leu Ser Pro Ile Val Thr Cys
    130                 135                 140

Val Val Val Asp Val Ser Glu Asp Asp Pro Asp Val Gln Ile Ser Trp
145                 150                 155                 160

Phe Val Asn Asn Val Glu Val His Thr Ala Gln Thr Gln Thr His Arg
                165                 170                 175

Glu Asp Tyr Asn Ser Thr Leu Arg Val Val Ser Ala Leu Pro Ile Gln
            180                 185                 190

His Gln Asp Trp Met Ser Gly Lys Glu Phe Lys Cys Lys Val Asn Asn
        195                 200                 205

Lys Asp Leu Gly Ala Pro Ile Glu Arg Thr Ile Ser Lys Pro Lys Gly
    210                 215                 220

Ser Val Arg Ala Pro Gln Val Tyr Val Leu Pro Pro Glu Glu Glu
225                 230                 235                 240

Met Thr Lys Lys Gln Val Thr Leu Thr Cys Met Val Thr Asp Phe Met
                245                 250                 255

Pro Glu Asp Ile Tyr Val Glu Trp Thr Asn Asn Gly Lys Thr Glu Leu
            260                 265                 270

Asn Tyr Lys Asn Thr Glu Pro Val Leu Asp Ser Asp Gly Ser Tyr Phe
        275                 280                 285

Met Tyr Ser Lys Leu Arg Val Glu Lys Lys Asn Trp Val Glu Arg Asn
    290                 295                 300

Ser Tyr Ser Cys Ser Val Val His Glu Gly Leu His Asn His His Thr
305                 310                 315                 320

Thr Lys Ser Phe Ser Arg Thr Pro Gly Lys
                325                 330

<210> SEQ ID NO 90
<211> LENGTH: 46
<212> TYPE: PRT
<213> ORGANISM: Artificial Sequence
<220> FEATURE:
<223> OTHER INFORMATION: Synthetic: hTREM2 stalk 129-174

<400> SEQUENCE: 90

Leu Ala Asp Pro Leu Asp His Arg Asp Ala Gly Asp Leu Trp Phe Pro
1               5                   10                  15
```

```
Gly Glu Ser Glu Ser Phe Glu Asp Ala His Val Glu His Ser Ile Ser
            20                  25                  30
Arg Ser Leu Leu Glu Gly Glu Ile Pro Phe Pro Pro Thr Ser
        35                  40                  45

<210> SEQ ID NO 91
<211> LENGTH: 20
<212> TYPE: PRT
<213> ORGANISM: Artificial Sequence
<220> FEATURE:
<223> OTHER INFORMATION: Synthetic: hTREM2 stalk 129-148

<400> SEQUENCE: 91

Leu Ala Asp Pro Leu Asp His Arg Asp Ala Gly Asp Leu Trp Phe Pro
1               5                   10                  15
Gly Glu Ser Glu
            20

<210> SEQ ID NO 92
<211> LENGTH: 20
<212> TYPE: PRT
<213> ORGANISM: Artificial Sequence
<220> FEATURE:
<223> OTHER INFORMATION: Synthetic: hTREM2 stalk 139-158

<400> SEQUENCE: 92

Gly Asp Leu Trp Phe Pro Gly Glu Ser Glu Ser Phe Glu Asp Ala His
1               5                   10                  15
Val Glu His Ser
            20

<210> SEQ ID NO 93
<211> LENGTH: 20
<212> TYPE: PRT
<213> ORGANISM: Artificial Sequence
<220> FEATURE:
<223> OTHER INFORMATION: Synthetic: hTREM2 stalk 149-168

<400> SEQUENCE: 93

Ser Phe Glu Asp Ala His Val Glu His Ser Ile Ser Arg Ser Leu Leu
1               5                   10                  15
Glu Gly Glu Ile
            20

<210> SEQ ID NO 94
<211> LENGTH: 17
<212> TYPE: PRT
<213> ORGANISM: Artificial Sequence
<220> FEATURE:
<223> OTHER INFORMATION: Synthetic: hTREM2 stalk 159-175

<400> SEQUENCE: 94

Ile Ser Arg Ser Leu Leu Glu Gly Glu Ile Pro Phe Pro Pro Thr Ser
1               5                   10                  15
Ile

<210> SEQ ID NO 95
<211> LENGTH: 24
<212> TYPE: PRT
<213> ORGANISM: Artificial Sequence
<220> FEATURE:
<223> OTHER INFORMATION: Synthetic: hTREM2 stalk 146-169
```

-continued

<400> SEQUENCE: 95

Glu Ser Glu Ser Phe Glu Asp Ala His Val Glu His Ser Ile Ser Arg
1               5                   10                  15

Ser Leu Leu Glu Gly Glu Ile Pro
            20

<210> SEQ ID NO 96
<211> LENGTH: 16
<212> TYPE: PRT
<213> ORGANISM: Artificial Sequence
<220> FEATURE:
<223> OTHER INFORMATION: Synthetic: hTREM2 stalk 146-161

<400> SEQUENCE: 96

Glu Ser Glu Ser Phe Glu Asp Ala His Val Glu His Ser Ile Ser Arg
1               5                   10                  15

<210> SEQ ID NO 97
<211> LENGTH: 15
<212> TYPE: PRT
<213> ORGANISM: Artificial Sequence
<220> FEATURE:
<223> OTHER INFORMATION: Synthetic: hTREM2 stalk 151-165

<400> SEQUENCE: 97

Glu Asp Ala His Val Glu His Ser Ile Ser Arg Ser Leu Leu Glu
1               5                   10                  15

<210> SEQ ID NO 98
<211> LENGTH: 15
<212> TYPE: PRT
<213> ORGANISM: Artificial Sequence
<220> FEATURE:
<223> OTHER INFORMATION: Synthetic: hTREM2 stalk 155-169

<400> SEQUENCE: 98

Val Glu His Ser Ile Ser Arg Ser Leu Leu Glu Gly Glu Ile Pro
1               5                   10                  15

<210> SEQ ID NO 99
<211> LENGTH: 10
<212> TYPE: PRT
<213> ORGANISM: Artificial Sequence
<220> FEATURE:
<223> OTHER INFORMATION: Synthetic: hTREM2 stalk 152-161

<400> SEQUENCE: 99

Asp Ala His Val Glu His Ser Ile Ser Arg
1               5                   10

<210> SEQ ID NO 100
<211> LENGTH: 11
<212> TYPE: PRT
<213> ORGANISM: Artificial Sequence
<220> FEATURE:
<223> OTHER INFORMATION: Synthetic: hTREM2 stalk 154-164

<400> SEQUENCE: 100

His Val Glu His Ser Ile Ser Arg Ser Leu Leu
1               5                   10

<210> SEQ ID NO 101
<211> LENGTH: 11
<212> TYPE: PRT
<213> ORGANISM: Artificial Sequence

```
<220> FEATURE:
<223> OTHER INFORMATION: Synthetic: hTREM2 stalk 151-161

<400> SEQUENCE: 101

Glu Asp Ala His Val Glu His Ser Ile Ser Arg
1               5                   10

<210> SEQ ID NO 102
<211> LENGTH: 5
<212> TYPE: PRT
<213> ORGANISM: Artificial Sequence
<220> FEATURE:
<223> OTHER INFORMATION: Synthetic: 3.10C2 HC CDR3 (IMGT)

<400> SEQUENCE: 102

Thr Gly Leu Asp Tyr
1               5

<210> SEQ ID NO 103
<211> LENGTH: 5
<212> TYPE: PRT
<213> ORGANISM: Artificial Sequence
<220> FEATURE:
<223> OTHER INFORMATION: Synthetic: Para.01 HC CDR3 (IMGT)

<400> SEQUENCE: 103

Ile Leu Ala Tyr Ser
1               5

<210> SEQ ID NO 104
<211> LENGTH: 5
<212> TYPE: PRT
<213> ORGANISM: Artificial Sequence
<220> FEATURE:
<223> OTHER INFORMATION: Synthetic: Para.02 HC CDR3 (IMGT)

<400> SEQUENCE: 104

Thr Leu Gly Ala Tyr
1               5

<210> SEQ ID NO 105
<211> LENGTH: 5
<212> TYPE: PRT
<213> ORGANISM: Artificial Sequence
<220> FEATURE:
<223> OTHER INFORMATION: Synthetic: Para.03 HC CDR3 (IMGT)

<400> SEQUENCE: 105

Thr Pro Gly Val Tyr
1               5

<210> SEQ ID NO 106
<211> LENGTH: 5
<212> TYPE: PRT
<213> ORGANISM: Artificial Sequence
<220> FEATURE:
<223> OTHER INFORMATION: Synthetic: Para.04 HC CDR3 (IMGT)

<400> SEQUENCE: 106

Thr Arg Phe Asp Tyr
1               5

<210> SEQ ID NO 107
<211> LENGTH: 6
<212> TYPE: PRT
<213> ORGANISM: Artificial Sequence
<220> FEATURE:
```

<223> OTHER INFORMATION: Synthetic: Para.05 HC CDR3 (IMGT)

<400> SEQUENCE: 107

Arg Glu Gly Phe Asp Tyr
1               5

<210> SEQ ID NO 108
<211> LENGTH: 6
<212> TYPE: PRT
<213> ORGANISM: Artificial Sequence
<220> FEATURE:
<223> OTHER INFORMATION: Synthetic: Para.06 HC CDR3 (IMGT)

<400> SEQUENCE: 108

Arg Gly Arg Leu Val Asp
1               5

<210> SEQ ID NO 109
<211> LENGTH: 6
<212> TYPE: PRT
<213> ORGANISM: Artificial Sequence
<220> FEATURE:
<223> OTHER INFORMATION: Synthetic: Para.07 HC CDR3 (IMGT)

<400> SEQUENCE: 109

Arg Asn Tyr Phe Asp Tyr
1               5

<210> SEQ ID NO 110
<211> LENGTH: 6
<212> TYPE: PRT
<213> ORGANISM: Artificial Sequence
<220> FEATURE:
<223> OTHER INFORMATION: Synthetic: Para.08 HC CDR3 (IMGT)

<400> SEQUENCE: 110

Arg Ser Gly Pro Ser Tyr
1               5

<210> SEQ ID NO 111
<211> LENGTH: 6
<212> TYPE: PRT
<213> ORGANISM: Artificial Sequence
<220> FEATURE:
<223> OTHER INFORMATION: Synthetic: Para.09 HC CDR3 (IMGT)

<400> SEQUENCE: 111

Thr Asp Ile Leu Glu Tyr
1               5

<210> SEQ ID NO 112
<211> LENGTH: 6
<212> TYPE: PRT
<213> ORGANISM: Artificial Sequence
<220> FEATURE:
<223> OTHER INFORMATION: Synthetic: Para.10 HC CDR3 (IMGT)

<400> SEQUENCE: 112

Thr Gly Leu Gly Asp Tyr
1               5

<210> SEQ ID NO 113
<211> LENGTH: 6
<212> TYPE: PRT
<213> ORGANISM: Artificial Sequence
<220> FEATURE:
<223> OTHER INFORMATION: Synthetic: Para.11 HC CDR3 (IMGT)

```
<400> SEQUENCE: 113

Thr Pro Ala Phe Asp Tyr
1               5

<210> SEQ ID NO 114
<211> LENGTH: 6
<212> TYPE: PRT
<213> ORGANISM: Artificial Sequence
<220> FEATURE:
<223> OTHER INFORMATION: Synthetic: Para.12 HC CDR3 (IMGT)

<400> SEQUENCE: 114

Thr Arg Leu Gly Asp Tyr
1               5

<210> SEQ ID NO 115
<211> LENGTH: 6
<212> TYPE: PRT
<213> ORGANISM: Artificial Sequence
<220> FEATURE:
<223> OTHER INFORMATION: Synthetic: Para.13 HC CDR3 (IMGT)

<400> SEQUENCE: 115

Thr Arg Gln Leu Gly Gly
1               5

<210> SEQ ID NO 116
<211> LENGTH: 6
<212> TYPE: PRT
<213> ORGANISM: Artificial Sequence
<220> FEATURE:
<223> OTHER INFORMATION: Synthetic: Para.14 HC CDR3 (IMGT)

<400> SEQUENCE: 116

Thr Ser Gly Ser Leu Tyr
1               5

<210> SEQ ID NO 117
<211> LENGTH: 6
<212> TYPE: PRT
<213> ORGANISM: Artificial Sequence
<220> FEATURE:
<223> OTHER INFORMATION: Synthetic: Para.15 HC CDR3 (IMGT)

<400> SEQUENCE: 117

Thr Ser Pro Pro Asp Tyr
1               5

<210> SEQ ID NO 118
<211> LENGTH: 7
<212> TYPE: PRT
<213> ORGANISM: Artificial Sequence
<220> FEATURE:
<223> OTHER INFORMATION: Synthetic: Para.16 HC CDR3 (IMGT)

<400> SEQUENCE: 118

Leu Pro Lys Gly Phe Ala Tyr
1               5

<210> SEQ ID NO 119
<211> LENGTH: 7
<212> TYPE: PRT
<213> ORGANISM: Artificial Sequence
<220> FEATURE:
<223> OTHER INFORMATION: Synthetic: Para.17 HC CDR3 (IMGT)
```

```
<400> SEQUENCE: 119

Pro Arg Asp Leu Gly Asp Tyr
1               5

<210> SEQ ID NO 120
<211> LENGTH: 7
<212> TYPE: PRT
<213> ORGANISM: Artificial Sequence
<220> FEATURE:
<223> OTHER INFORMATION: Synthetic: Para.18 HC CDR3 (IMGT)

<400> SEQUENCE: 120

Ser Leu Phe Phe Asn Tyr His
1               5

<210> SEQ ID NO 121
<211> LENGTH: 7
<212> TYPE: PRT
<213> ORGANISM: Artificial Sequence
<220> FEATURE:
<223> OTHER INFORMATION: Synthetic: Para.19 HC CDR3 (IMGT)

<400> SEQUENCE: 121

Ser Pro Arg Gly Phe Ala Tyr
1               5

<210> SEQ ID NO 122
<211> LENGTH: 7
<212> TYPE: PRT
<213> ORGANISM: Artificial Sequence
<220> FEATURE:
<223> OTHER INFORMATION: Synthetic: Para.20 HC CDR3 (IMGT)

<400> SEQUENCE: 122

Ser Thr Ala Pro Phe Ala Tyr
1               5

<210> SEQ ID NO 123
<211> LENGTH: 7
<212> TYPE: PRT
<213> ORGANISM: Artificial Sequence
<220> FEATURE:
<223> OTHER INFORMATION: Synthetic: Para.21 HC CDR3 (IMGT)

<400> SEQUENCE: 123

Thr Phe Asn Asn Phe Asp Ser
1               5

<210> SEQ ID NO 124
<211> LENGTH: 7
<212> TYPE: PRT
<213> ORGANISM: Artificial Sequence
<220> FEATURE:
<223> OTHER INFORMATION: Synthetic: Para.22 HC CDR3 (IMGT)

<400> SEQUENCE: 124

Thr Gly Ser Tyr Phe Asp Tyr
1               5

<210> SEQ ID NO 125
<211> LENGTH: 7
<212> TYPE: PRT
<213> ORGANISM: Artificial Sequence
<220> FEATURE:
<223> OTHER INFORMATION: Synthetic: Para.23 HC CDR3 (IMGT)
```

-continued

```
<400> SEQUENCE: 125

Thr Leu Phe Phe Asn Tyr His
1               5

<210> SEQ ID NO 126
<211> LENGTH: 7
<212> TYPE: PRT
<213> ORGANISM: Artificial Sequence
<220> FEATURE:
<223> OTHER INFORMATION: Synthetic: Para.24 HC CDR3 (IMGT)

<400> SEQUENCE: 126

Thr Leu Gly Gly Tyr Asn Tyr
1               5

<210> SEQ ID NO 127
<211> LENGTH: 7
<212> TYPE: PRT
<213> ORGANISM: Artificial Sequence
<220> FEATURE:
<223> OTHER INFORMATION: Synthetic: Para.25 HC CDR3 (IMGT)

<400> SEQUENCE: 127

Thr Pro Gly Asn Phe Asn Tyr
1               5

<210> SEQ ID NO 128
<211> LENGTH: 7
<212> TYPE: PRT
<213> ORGANISM: Artificial Sequence
<220> FEATURE:
<223> OTHER INFORMATION: Synthetic: Para.26 HC CDR3 (IMGT)

<400> SEQUENCE: 128

Thr Ser Gly Gly Phe Asp Tyr
1               5

<210> SEQ ID NO 129
<211> LENGTH: 7
<212> TYPE: PRT
<213> ORGANISM: Artificial Sequence
<220> FEATURE:
<223> OTHER INFORMATION: Synthetic: Para.27 HC CDR3 (IMGT)

<400> SEQUENCE: 129

Thr Ser Gly Tyr Phe Asp Tyr
1               5

<210> SEQ ID NO 130
<211> LENGTH: 7
<212> TYPE: PRT
<213> ORGANISM: Artificial Sequence
<220> FEATURE:
<223> OTHER INFORMATION: Synthetic: Para.28 HC CDR3 (IMGT)

<400> SEQUENCE: 130

Thr Val Thr Leu Gly Ala Tyr
1               5

<210> SEQ ID NO 131
<211> LENGTH: 7
<212> TYPE: PRT
<213> ORGANISM: Artificial Sequence
<220> FEATURE:
<223> OTHER INFORMATION: Synthetic: Para.29 HC CDR3 (IMGT)
```

```
<400> SEQUENCE: 131

Thr Tyr Arg Gly Phe Asp Phe
1               5

<210> SEQ ID NO 132
<211> LENGTH: 112
<212> TYPE: PRT
<213> ORGANISM: Artificial Sequence
<220> FEATURE:
<223> OTHER INFORMATION: Synthetic: hPara.09.v2 Q100P Light Chain
      Variable Region

<400> SEQUENCE: 132

Asp Val Val Met Thr Gln Ser Pro Leu Ser Leu Pro Val Thr Pro Gly
1               5                   10                  15

Glu Pro Ala Ser Ile Ser Cys Arg Ser Arg Ser Leu Leu Thr Ser
            20                  25                  30

Lys Gly Ile Thr Ser Leu Tyr Trp Tyr Leu Gln Lys Pro Gly Gln Ser
        35                  40                  45

Pro Gln Leu Leu Ile Tyr Arg Met Ser Asn Leu Ala Ser Gly Ile Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Phe
                85                  90                  95

Leu Val Tyr Pro Tyr Thr Phe Gly Pro Gly Thr Lys Val Glu Ile Lys
            100                 105                 110

<210> SEQ ID NO 133
<211> LENGTH: 115
<212> TYPE: PRT
<213> ORGANISM: Artificial Sequence
<220> FEATURE:
<223> OTHER INFORMATION: Synthetic: hPara.09.v2 Q100P Heavy Chain
      Variable Region

<400> SEQUENCE: 133

Glu Val Gln Leu Val Glu Ser Gly Gly Gly Leu Val Gln Pro Gly Gly
1               5                   10                  15

Ser Leu Lys Leu Ser Cys Ala Thr Ser Gly Phe Pro Phe Ser Asn Val
            20                  25                  30

Trp Leu His Trp Val Arg Gln Ala Ser Gly Lys Gly Pro Glu Trp Val
        35                  40                  45

Ala His Ile Lys Ala Lys Ser Asp Asn Tyr Ala Thr Tyr Tyr Ala Glu
    50                  55                  60

Ser Val Lys Gly Arg Phe Thr Ile Ser Arg Asp Asp Ser Lys Asn Thr
65                  70                  75                  80

Val Tyr Leu Gln Met Asn Ser Leu Lys Thr Glu Asp Thr Ala Val Tyr
                85                  90                  95

Tyr Cys Thr Asp Ile Leu Glu Tyr Trp Gly Gln Gly Thr Leu Val Thr
            100                 105                 110

Val Ser Ser
        115

<210> SEQ ID NO 134
<211> LENGTH: 112
<212> TYPE: PRT
```

<213> ORGANISM: Artificial Sequence
<220> FEATURE:
<223> OTHER INFORMATION: Synthetic: hPara.09.v2 I58V/Q100P Light Chain
      Variable Region

<400> SEQUENCE: 134

Asp Val Val Met Thr Gln Ser Pro Leu Ser Leu Pro Val Thr Pro Gly
1               5                   10                  15

Glu Pro Ala Ser Ile Ser Cys Arg Ser Ser Arg Ser Leu Leu Thr Ser
            20                  25                  30

Lys Gly Ile Thr Ser Leu Tyr Trp Tyr Leu Gln Lys Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Phe
                85                  90                  95

Leu Val Tyr Pro Tyr Thr Phe Gly Pro Gly Thr Lys Val Glu Ile Lys
            100                 105                 110

<210> SEQ ID NO 135
<211> LENGTH: 115
<212> TYPE: PRT
<213> ORGANISM: Artificial Sequence
<220> FEATURE:
<223> OTHER INFORMATION: Synthetic: hPara.09.v2 I58V/Q100P Heavy Chain
      Variable Region

<400> SEQUENCE: 135

Glu Val Gln Leu Val Glu Ser Gly Gly Gly Leu Val Gln Pro Gly Gly
1               5                   10                  15

Ser Leu Lys Leu Ser Cys Ala Thr Ser Gly Phe Pro Phe Ser Asn Val
            20                  25                  30

Trp Leu His Trp Val Arg Gln Ala Ser Gly Lys Gly Pro Glu Trp Val
        35                  40                  45

Ala His Ile Lys Ala Lys Ser Asp Asn Tyr Ala Thr Tyr Tyr Ala Glu
    50                  55                  60

Ser Val Lys Gly Arg Phe Thr Ile Ser Arg Asp Asp Ser Lys Asn Thr
65                  70                  75                  80

Val Tyr Leu Gln Met Asn Ser Leu Lys Thr Glu Asp Thr Ala Val Tyr
                85                  90                  95

Tyr Cys Thr Asp Ile Leu Glu Tyr Trp Gly Gln Gly Thr Leu Val Thr
            100                 105                 110

Val Ser Ser
        115

<210> SEQ ID NO 136
<211> LENGTH: 112
<212> TYPE: PRT
<213> ORGANISM: Artificial Sequence
<220> FEATURE:
<223> OTHER INFORMATION: Synthetic: hPara.09.v2 Q100P/V104L Light Chain
      Variable Region

<400> SEQUENCE: 136

Asp Val Val Met Thr Gln Ser Pro Leu Ser Leu Pro Val Thr Pro Gly
1               5                   10                  15

Glu Pro Ala Ser Ile Ser Cys Arg Ser Ser Arg Ser Leu Leu Thr Ser
            20                  25                  30

```
Lys Gly Ile Thr Ser Leu Tyr Trp Tyr Leu Gln Lys Pro Gly Gln Ser
        35                  40                  45

Pro Gln Leu Leu Ile Tyr Arg Met Ser Asn Leu Ala Ser Gly Ile Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ala Gln Phe
                 85                  90                  95

Leu Val Tyr Pro Tyr Thr Phe Gly Pro Gly Thr Lys Leu Glu Ile Lys
                100                 105                 110

<210> SEQ ID NO 137
<211> LENGTH: 115
<212> TYPE: PRT
<213> ORGANISM: Artificial Sequence
<220> FEATURE:
<223> OTHER INFORMATION: Synthetic: hPara.09.v2 Q100P/V104L Heavy Chain
      Variable Region

<400> SEQUENCE: 137

Glu Val Gln Leu Val Glu Ser Gly Gly Gly Leu Val Gln Pro Gly Gly
1               5                   10                  15

Ser Leu Lys Leu Ser Cys Ala Thr Ser Gly Phe Pro Phe Ser Asn Val
             20                  25                  30

Trp Leu His Trp Val Arg Gln Ala Ser Gly Lys Gly Pro Glu Trp Val
         35                  40                  45

Ala His Ile Lys Ala Lys Ser Asp Asn Tyr Ala Thr Tyr Tyr Ala Glu
     50                  55                  60

Ser Val Lys Gly Arg Phe Thr Ile Ser Arg Asp Asp Ser Lys Asn Thr
 65                  70                  75                  80

Val Tyr Leu Gln Met Asn Ser Leu Lys Thr Glu Asp Thr Ala Val Tyr
                 85                  90                  95

Tyr Cys Thr Asp Ile Leu Glu Tyr Trp Gly Gly Thr Leu Val Thr
                100                 105                 110

Val Ser Ser
        115

<210> SEQ ID NO 138
<211> LENGTH: 112
<212> TYPE: PRT
<213> ORGANISM: Artificial Sequence
<220> FEATURE:
<223> OTHER INFORMATION: Synthetic: hPara.09.H5-3.10C2.L10 Light Chain
      Variable Region

<400> SEQUENCE: 138

Asp Thr Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu Gly Val
             20                  25                  30

Arg Asp Ile Thr Ser Leu Tyr Trp Tyr Leu Gln Lys Pro Gly Gln Ser
         35                  40                  45

Pro Gln Leu Leu Ile Tyr Arg Met Ser Asn Leu Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ala Gln Phe
                 85                  90                  95
```

```
Leu Arg Tyr Pro Tyr Thr Phe Gly Pro Gly Thr Lys Val Glu Ile Lys
            100                 105                 110
```

<210> SEQ ID NO 139
<211> LENGTH: 115
<212> TYPE: PRT
<213> ORGANISM: Artificial Sequence
<220> FEATURE:
<223> OTHER INFORMATION: Synthetic: hPara.09.H5-3.10C2.L10 Heavy Chain
      Variable Region

<400> SEQUENCE: 139

```
Glu Val Gln Leu Val Glu Ser Gly Gly Gly Leu Val Gln Pro Gly Gly
1               5                   10                  15

Ser Leu Lys Leu Ser Cys Ala Thr Ser Gly Phe Pro Phe Ser Asn Val
            20                  25                  30

Trp Leu His Trp Val Arg Gln Ala Ser Gly Lys Gly Pro Glu Trp Val
        35                  40                  45

Ala His Ile Lys Ala Lys Ser Asp Asn Tyr Ala Thr Tyr Tyr Ala Glu
    50                  55                  60

Ser Val Lys Gly Arg Phe Thr Ile Ser Arg Asp Asp Ser Lys Asn Thr
65                  70                  75                  80

Val Tyr Leu Gln Met Asn Ser Leu Lys Thr Glu Asp Thr Ala Val Tyr
                85                  90                  95

Tyr Cys Thr Asp Ile Leu Glu Tyr Trp Gly Gln Gly Thr Leu Val Thr
            100                 105                 110

Val Ser Ser
        115
```

<210> SEQ ID NO 140
<211> LENGTH: 20
<212> TYPE: DNA
<213> ORGANISM: Artificial Sequence
<220> FEATURE:
<223> OTHER INFORMATION: Synthetic: Alt-R CRISPR-Cas9 crRNA 1

<400> SEQUENCE: 140
ttgtagattc cgcagcgtaa                                              20

<210> SEQ ID NO 141
<211> LENGTH: 20
<212> TYPE: DNA
<213> ORGANISM: Artificial Sequence
<220> FEATURE:
<223> OTHER INFORMATION: Synthetic: Alt-R CRISPR-Cas9 crRNA 2

<400> SEQUENCE: 141
aatggtgaga gtgccaccca                                              20

<210> SEQ ID NO 142
<211> LENGTH: 20
<212> TYPE: DNA
<213> ORGANISM: Artificial Sequence
<220> FEATURE:
<223> OTHER INFORMATION: Synthetic: Alt-R CRISPR-Cas9 crRNA 3

<400> SEQUENCE: 142
taccagtgcc agagcctcca                                              20

<210> SEQ ID NO 143
<211> LENGTH: 444
<212> TYPE: PRT

<213> ORGANISM: Artificial Sequence
<220> FEATURE:
<223> OTHER INFORMATION: Synthetic: H3.10C2.H1.hIgG1.N297G

<400> SEQUENCE: 143

```
Glu Val Gln Leu Val Glu Ser Gly Gly Gly Leu Val Gln Pro Gly Gly
1               5                   10                  15

Ser Leu Lys Leu Ser Cys Ala Thr Ser Gly Phe Pro Phe Ser Asn Val
            20                  25                  30

Trp Met His Trp Val Arg Gln Ala Ser Gly Lys Gly Leu Glu Trp Ile
        35                  40                  45

Ala His Ile Lys Ala Lys Ser Asp Asn Tyr Ala Thr Tyr Tyr Ala Glu
    50                  55                  60

Ser Val Lys Gly Arg Phe Thr Ile Ser Arg Asp Asp Ser Lys Thr Thr
65                  70                  75                  80

Ile Tyr Leu Gln Met Asn Ser Leu Lys Thr Glu Asp Thr Ala Val Tyr
                85                  90                  95

Tyr Cys Thr Gly Leu Asp Tyr Trp Gly Gln Gly Thr Thr Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
    210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Gly Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380
```

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
            405                 410                 415

Gly Asn Val Phe Ser Cys Ser Val Met His Glu Ala Leu His Asn His
        420                 425                 430

Tyr Thr Gln Lys Ser Leu Ser Leu Ser Pro Gly Lys
        435                 440

<210> SEQ ID NO 144
<211> LENGTH: 445
<212> TYPE: PRT
<213> ORGANISM: Artificial Sequence
<220> FEATURE:
<223> OTHER INFORMATION: Synthetic: hPara.09.H5.hIgG1.N297G

<400> SEQUENCE: 144

Glu Val Gln Leu Val Glu Ser Gly Gly Gly Leu Val Gln Pro Gly Gly
1               5                   10                  15

Ser Leu Lys Leu Ser Cys Ala Thr Ser Gly Phe Pro Phe Ser Asn Val
            20                  25                  30

Trp Leu His Trp Val Arg Gln Ala Ser Gly Lys Gly Pro Glu Trp Val
        35                  40                  45

Ala His Ile Lys Ala Lys Ser Asp Asn Tyr Ala Thr Tyr Tyr Ala Glu
    50                  55                  60

Ser Val Lys Gly Arg Phe Thr Ile Ser Arg Asp Asp Ser Lys Asn Thr
65                  70                  75                  80

Val Tyr Leu Gln Met Asn Ser Leu Lys Thr Glu Asp Thr Ala Val Tyr
                85                  90                  95

Tyr Cys Thr Asp Ile Leu Glu Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Gly Ser Thr Tyr Arg Val Val Ser Val Leu
    290                 295                 300

```
Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
            325                 330                 335

Ala Lys Gly Gln Pro Arg Glu Pro Gln Val Tyr Thr Leu Pro Pro Ser
        340                 345                 350

Arg Glu Glu Met Thr Lys Asn Gln Val Ser Leu Thr Cys Leu Val Lys
    355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 145
<211> LENGTH: 112
<212> TYPE: PRT
<213> ORGANISM: Artificial Sequence
<220> FEATURE:
<223> OTHER INFORMATION: Synthetic: h3.10C2.v1 Q100P Light Chain
      Variable Region

<400> SEQUENCE: 145

Asp Val Val Met Thr Gln Ser Pro Leu Ser Leu Pro Val Thr Pro Gly
1               5                   10                  15

Glu Pro Ala Ser Ile Ser Cys Arg Ser Arg Ser Leu Leu Thr Ser
            20                  25                  30

Lys Gly Ile Thr Ser Leu Tyr Trp Tyr Leu Gln Lys Pro Gly Gln Ser
        35                  40                  45

Pro Gln Leu Leu Ile Tyr Arg Met Ser Asn Leu Ala Ser Gly Ile Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Phe
                85                  90                  95

Leu Val Tyr Pro Tyr Thr Phe Gly Pro Gly Thr Lys Val Glu Ile Lys
            100                 105                 110

<210> SEQ ID NO 146
<211> LENGTH: 114
<212> TYPE: PRT
<213> ORGANISM: Artificial Sequence
<220> FEATURE:
<223> OTHER INFORMATION: Synthetic: h3.10C2.v1 Q100P Heavy Chain
      Variable Region

<400> SEQUENCE: 146

Glu Val Gln Leu Val Glu Ser Gly Gly Gly Leu Val Gln Pro Gly Gly
1               5                   10                  15

Ser Leu Lys Leu Ser Cys Ala Thr Ser Gly Phe Pro Phe Ser Asn Val
            20                  25                  30

Trp Met His Trp Val Arg Gln Ala Ser Gly Lys Gly Leu Glu Trp Ile
        35                  40                  45
```

```
Ala His Ile Lys Ala Lys Ser Asp Asn Tyr Ala Thr Tyr Tyr Ala Glu
        50                  55                  60

Ser Val Lys Gly Arg Phe Thr Ile Ser Arg Asp Asp Ser Lys Thr Thr
 65                  70                  75                  80

Ile Tyr Leu Gln Met Asn Ser Leu Lys Thr Glu Asp Thr Ala Val Tyr
                 85                  90                  95

Tyr Cys Thr Gly Leu Asp Tyr Trp Gly Gln Gly Thr Thr Val Thr Val
            100                 105                 110

Ser Ser

<210> SEQ ID NO 147
<211> LENGTH: 112
<212> TYPE: PRT
<213> ORGANISM: Artificial Sequence
<220> FEATURE:
<223> OTHER INFORMATION: Synthetic: h3.10C2.v1 I58V/Q100P Light Chain
      Variable Region

<400> SEQUENCE: 147

Asp Val Val Met Thr Gln Ser Pro Leu Ser Leu Pro Val Thr Pro Gly
 1               5                  10                  15

Glu Pro Ala Ser Ile Ser Cys Arg Ser Ser Arg Ser Leu Leu Thr Ser
             20                  25                  30

Lys Gly Ile Thr Ser Leu Tyr Trp Tyr Leu Gln Lys Pro Gly Gln Ser
         35                  40                  45

Pro Gln Leu Leu Ile Tyr Arg Met Ser Asn Leu Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ala Gln Phe
                 85                  90                  95

Leu Val Tyr Pro Tyr Thr Phe Gly Pro Gly Thr Lys Val Glu Ile Lys
            100                 105                 110

<210> SEQ ID NO 148
<211> LENGTH: 114
<212> TYPE: PRT
<213> ORGANISM: Artificial Sequence
<220> FEATURE:
<223> OTHER INFORMATION: Synthetic: h3.10C2.v1 I58V/Q100P Heavy Chain
      Variable Region

<400> SEQUENCE: 148

Glu Val Gln Leu Val Glu Ser Gly Gly Gly Leu Val Gln Pro Gly Gly
 1               5                  10                  15

Ser Leu Lys Leu Ser Cys Ala Thr Ser Gly Phe Pro Phe Ser Asn Val
             20                  25                  30

Trp Met His Trp Val Arg Gln Ala Ser Gly Lys Gly Leu Glu Trp Ile
         35                  40                  45

Ala His Ile Lys Ala Lys Ser Asp Asn Tyr Ala Thr Tyr Tyr Ala Glu
     50                  55                  60

Ser Val Lys Gly Arg Phe Thr Ile Ser Arg Asp Asp Ser Lys Thr Thr
 65                  70                  75                  80

Ile Tyr Leu Gln Met Asn Ser Leu Lys Thr Glu Asp Thr Ala Val Tyr
                 85                  90                  95
```

Tyr Cys Thr Gly Leu Asp Tyr Trp Gly Gln Gly Thr Thr Val Thr Val
                    100                 105                 110

Ser Ser

<210> SEQ ID NO 149
<211> LENGTH: 112
<212> TYPE: PRT
<213> ORGANISM: Artificial Sequence
<220> FEATURE:
<223> OTHER INFORMATION: Synthetic: h3.10C2.v1 Q100P/V104L Light Chain
      Variable Region

<400> SEQUENCE: 149

Asp Val Val Met Thr Gln Ser Pro Leu Ser Leu Pro Val Thr Pro Gly
1               5                   10                  15

Glu Pro Ala Ser Ile Ser Cys Arg Ser Ser Arg Ser Leu Leu Thr Ser
                20                  25                  30

Lys Gly Ile Thr Ser Leu Tyr Trp Tyr Leu Gln Lys Pro Gly Gln Ser
            35                  40                  45

Pro Gln Leu Leu Ile Tyr Arg Met Ser Asn Leu Ala Ser Gly Ile Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Phe
                85                  90                  95

Leu Val Tyr Pro Tyr Thr Phe Gly Pro Gly Thr Lys Leu Glu Ile Lys
                100                 105                 110

<210> SEQ ID NO 150
<211> LENGTH: 114
<212> TYPE: PRT
<213> ORGANISM: Artificial Sequence
<220> FEATURE:
<223> OTHER INFORMATION: Synthetic: h3.10C2.v1 Q100P/V104L Heavy Chain
      Variable Region

<400> SEQUENCE: 150

Glu Val Gln Leu Val Glu Ser Gly Gly Gly Leu Val Gln Pro Gly Gly
1               5                   10                  15

Ser Leu Lys Leu Ser Cys Ala Thr Ser Gly Phe Pro Phe Ser Asn Val
                20                  25                  30

Trp Met His Trp Val Arg Gln Ala Ser Gly Lys Gly Leu Glu Trp Ile
            35                  40                  45

Ala His Ile Lys Ala Lys Ser Asp Asn Tyr Ala Thr Tyr Tyr Ala Glu
    50                  55                  60

Ser Val Lys Gly Arg Phe Thr Ile Ser Arg Asp Asp Ser Lys Thr Thr
65                  70                  75                  80

Ile Tyr Leu Gln Met Asn Ser Leu Lys Thr Glu Asp Thr Ala Val Tyr
                85                  90                  95

Tyr Cys Thr Gly Leu Asp Tyr Trp Gly Gln Gly Thr Thr Val Thr Val
                100                 105                 110

Ser Ser

<210> SEQ ID NO 151
<211> LENGTH: 112
<212> TYPE: PRT
<213> ORGANISM: Artificial Sequence -continued

```
<220> FEATURE:
<223> OTHER INFORMATION: Synthetic: h3.10C2.H1-3.10C2.L10 Light Chain
      Variable Region

<400> SEQUENCE: 151

Asp Thr Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu Gly Val
            20                  25                  30

Arg Asp Ile Thr Ser Leu Tyr Trp Tyr Leu Gln Lys Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Phe
                85                  90                  95

Leu Arg Tyr Pro Tyr Thr Phe Gly Pro Gly Thr Lys Val Glu Ile Lys
            100                 105                 110

<210> SEQ ID NO 152
<211> LENGTH: 114
<212> TYPE: PRT
<213> ORGANISM: Artificial Sequence
<220> FEATURE:
<223> OTHER INFORMATION: Synthetic: h3.10C2.H1-3.10C2.L10 Heavy Chain
      Variable Region

<400> SEQUENCE: 152

Glu Val Gln Leu Val Glu Ser Gly Gly Gly Leu Val Gln Pro Gly Gly
1               5                   10                  15

Ser Leu Lys Leu Ser Cys Ala Thr Ser Gly Phe Pro Phe Ser Asn Val
            20                  25                  30

Trp Met His Trp Val Arg Gln Ala Ser Gly Lys Gly Leu Glu Trp Ile
        35                  40                  45

Ala His Ile Lys Ala Lys Ser Asp Asn Tyr Ala Thr Tyr Tyr Ala Glu
    50                  55                  60

Ser Val Lys Gly Arg Phe Thr Ile Ser Arg Asp Asp Ser Lys Thr Thr
65                  70                  75                  80

Ile Tyr Leu Gln Met Asn Ser Leu Lys Thr Glu Asp Thr Ala Val Tyr
                85                  90                  95

Tyr Cys Thr Gly Leu Asp Tyr Trp Gly Gln Gly Thr Thr Val Thr Val
            100                 105                 110

Ser Ser

<210> SEQ ID NO 153
<211> LENGTH: 16
<212> TYPE: PRT
<213> ORGANISM: Artificial Sequence
<220> FEATURE:
<223> OTHER INFORMATION: Synthetic: hPara.09.H5-3.10C2.L10 CDR L1

<400> SEQUENCE: 153

Arg Ser Ser Lys Ser Leu Leu Gly Val Arg Asp Ile Thr Ser Leu Tyr
1               5                   10                  15

<210> SEQ ID NO 154
<211> LENGTH: 7
<212> TYPE: PRT
<213> ORGANISM: Artificial Sequence
```

```
<220> FEATURE:
<223> OTHER INFORMATION: Synthetic: hPara.09. H5-3.10C2.L10 CDR L2

<400> SEQUENCE: 154

Arg Met Ser Asn Leu Ala Ser
1               5

<210> SEQ ID NO 155
<211> LENGTH: 9
<212> TYPE: PRT
<213> ORGANISM: Artificial Sequence
<220> FEATURE:
<223> OTHER INFORMATION: Synthetic: hPara.09. H5-3.10C2.L10 CDR L3

<400> SEQUENCE: 155

Ala Gln Phe Leu Arg Tyr Pro Tyr Thr
1               5

<210> SEQ ID NO 156
<211> LENGTH: 5
<212> TYPE: PRT
<213> ORGANISM: Artificial Sequence
<220> FEATURE:
<223> OTHER INFORMATION: Synthetic: hPara.09. H5-3.10C2.L10 CDR H1

<400> SEQUENCE: 156

Asn Val Trp Leu His
1               5

<210> SEQ ID NO 157
<211> LENGTH: 19
<212> TYPE: PRT
<213> ORGANISM: Artificial Sequence
<220> FEATURE:
<223> OTHER INFORMATION: Synthetic: hPara.09. H5-3.10C2.L10 CDR H2

<400> SEQUENCE: 157

His Ile Lys Ala Lys Ser Asp Asn Tyr Ala Thr Tyr Tyr Ala Glu Ser
1               5                   10                  15

Val Lys Gly

<210> SEQ ID NO 158
<211> LENGTH: 4
<212> TYPE: PRT
<213> ORGANISM: Artificial Sequence
<220> FEATURE:
<223> OTHER INFORMATION: Synthetic: hPara.09. H5-3.10C2.L10 CDR H3

<400> SEQUENCE: 158

Ile Leu Glu Tyr
1

<210> SEQ ID NO 159
<211> LENGTH: 16
<212> TYPE: PRT
<213> ORGANISM: Artificial Sequence
<220> FEATURE:
<223> OTHER INFORMATION: Synthetic: h3.10C2.H1-3.10C2.L10 light chain
      CDR1

<400> SEQUENCE: 159

Arg Ser Ser Lys Ser Leu Leu Gly Val Arg Asp Ile Thr Ser Leu Tyr
1               5                   10                  15

<210> SEQ ID NO 160
<211> LENGTH: 7
```

```
<212> TYPE: PRT
<213> ORGANISM: Artificial Sequence
<220> FEATURE:
<223> OTHER INFORMATION: Synthetic: h3.10C2.H1-3.10C2.L10 light chain
      CDR2

<400> SEQUENCE: 160

Arg Met Ser Asn Leu Ala Ser
1               5

<210> SEQ ID NO 161
<211> LENGTH: 9
<212> TYPE: PRT
<213> ORGANISM: Artificial Sequence
<220> FEATURE:
<223> OTHER INFORMATION: Synthetic: h3.10C2.H1-3.10C2.L10 light chain
      CDR3

<400> SEQUENCE: 161

Ala Gln Phe Leu Arg Tyr Pro Tyr Thr
1               5

<210> SEQ ID NO 162
<211> LENGTH: 5
<212> TYPE: PRT
<213> ORGANISM: Artificial Sequence
<220> FEATURE:
<223> OTHER INFORMATION: Synthetic: h3.10C2.H1-3.10C2.L10 heavy chain
      CDR1

<400> SEQUENCE: 162

Asn Val Trp Met His
1               5

<210> SEQ ID NO 163
<211> LENGTH: 19
<212> TYPE: PRT
<213> ORGANISM: Artificial Sequence
<220> FEATURE:
<223> OTHER INFORMATION: Synthetic: h3.10C2.H1-3.10C2.L10 heavy chain
      CDR2

<400> SEQUENCE: 163

His Ile Lys Ala Lys Ser Asp Asn Tyr Ala Thr Tyr Tyr Ala Glu Ser
1               5                   10                  15

Val Lys Gly

<210> SEQ ID NO 164
<211> LENGTH: 3
<212> TYPE: PRT
<213> ORGANISM: Artificial Sequence
<220> FEATURE:
<223> OTHER INFORMATION: Synthetic: h3.10C2.H1-3.10C2.L10 heavy chain
      CDR3

<400> SEQUENCE: 164

Leu Asp Tyr
1

<210> SEQ ID NO 165
<211> LENGTH: 232
<212> TYPE: PRT
<213> ORGANISM: Homo sapiens
<220> FEATURE:
<221> NAME/KEY: SITE
<222> LOCATION: (1)..(232)
<223> OTHER INFORMATION: Human IgG1 Fc LALAPG
```

<400> SEQUENCE: 165

Glu Pro Lys Ser Cys Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Gly Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 166
<211> LENGTH: 229
<212> TYPE: PRT
<213> ORGANISM: Homo sapiens
<220> FEATURE:
<221> NAME/KEY: SITE
<222> LOCATION: (1)..(229)
<223> OTHER INFORMATION: Human IgG4 Fc

<400> SEQUENCE: 166

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

```
Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
210                 215                 220

Leu Ser Leu Gly Lys
225
```

<210> SEQ ID NO 167
<211> LENGTH: 229
<212> TYPE: PRT
<213> ORGANISM: Homo sapiens
<220> FEATURE:
<221> NAME/KEY: SITE
<222> LOCATION: (1)..(229)
<223> OTHER INFORMATION: Human IgG4 Fc S228P

<400> SEQUENCE: 167

```
Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
210                 215                 220
```

-continued

```
Leu Ser Leu Gly Lys
225

<210> SEQ ID NO 168
<211> LENGTH: 214
<212> TYPE: PRT
<213> ORGANISM: Artificial Sequence
<220> FEATURE:
<223> OTHER INFORMATION: Synthetic: 3.17A9 light chain

<400> SEQUENCE: 168

Asp Ile Gln Met Thr Gln Ser Pro Ser Phe Leu Ser Ala Ser Val Gly
1               5                   10                  15

Asp Arg Val Thr Ile Asn Cys Lys Val Ser Gln Asn Val Asp Arg Asn
                20                  25                  30

Leu Asn Trp Tyr Gln Gln Asn Leu Gly Glu Pro Pro Lys Pro Leu Ile
            35                  40                  45

Asn Phe Ala Asn Ser Leu Gln Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Phe Cys Leu Gln His Asn Ser Trp Pro Leu
                85                  90                  95

Thr Phe Gly Ser Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 169
<211> LENGTH: 448
<212> TYPE: PRT
<213> ORGANISM: Artificial Sequence
<220> FEATURE:
<223> OTHER INFORMATION: Synthetic: 3.17A9 heavy chain

<400> SEQUENCE: 169

Glu Val Gln Leu Gln Gln Ser Gly Ala Glu Leu Gly Lys Pro Gly Thr
1               5                   10                  15

Ser Ile Lys Leu Ser Cys Lys Val Ser Gly Phe Asn Ile Arg Ser Thr
                20                  25                  30

Phe Met His Trp Val Asn Gln Arg Pro Gly Lys Gly Leu Glu Trp Ile
            35                  40                  45

Gly Arg Ile Asp Pro Ala Asn Gly Asn Thr Val Tyr Gly Glu Lys Phe
    50                  55                  60

Lys Asn Lys Ala Thr Leu Thr Ala Asp Thr Ser Ser Asn Thr Ala Tyr
65                  70                  75                  80
```

Met Gln Leu Ser Gln Leu Lys Ser Asp Asp Thr Ala Ile Tyr Phe Cys
            85                  90                  95

Ala Leu Glu Phe Gly Val Ser Trp Phe Glu Tyr Trp Gly Gln Gly Thr
            100                 105                 110

Leu Val Thr Val Ser Ser Ala Lys Thr Thr Ala Pro Ser Val Tyr Pro
            115                 120                 125

Leu Ala Pro Val Cys Gly Asp Thr Thr Gly Ser Ser Val Thr Leu Gly
130                 135                 140

Cys Leu Val Lys Gly Tyr Phe Pro Glu Pro Val Thr Leu Thr Trp Asn
145                 150                 155                 160

Ser Gly Ser Leu Ser Ser Gly Val His Thr Phe Pro Ala Val Leu Gln
            165                 170                 175

Ser Asp Leu Tyr Thr Leu Ser Ser Ser Val Thr Val Thr Ser Ser Thr
            180                 185                 190

Trp Pro Ser Gln Ser Ile Thr Cys Asn Val Ala His Pro Ala Ser Ser
            195                 200                 205

Thr Lys Val Asp Lys Lys Ile Glu Pro Arg Gly Pro Thr Ile Lys Pro
210                 215                 220

Cys Pro Pro Cys Lys Cys Pro Ala Pro Asn Leu Leu Gly Gly Pro Ser
225                 230                 235                 240

Val Phe Ile Phe Pro Pro Lys Ile Lys Asp Val Leu Met Ile Ser Leu
            245                 250                 255

Ser Pro Ile Val Thr Cys Val Val Asp Val Ser Glu Asp Asp Pro
            260                 265                 270

Asp Val Gln Ile Ser Trp Phe Val Asn Asn Val Glu Val His Thr Ala
            275                 280                 285

Gln Thr Gln Thr His Arg Glu Asp Tyr Asn Ser Thr Leu Arg Val Val
            290                 295                 300

Ser Ala Leu Pro Ile Gln His Gln Asp Trp Met Ser Gly Lys Glu Phe
305                 310                 315                 320

Lys Cys Lys Val Asn Asn Lys Asp Leu Pro Ala Pro Ile Glu Arg Thr
            325                 330                 335

Ile Ser Lys Pro Lys Gly Ser Val Arg Ala Pro Gln Val Tyr Val Leu
            340                 345                 350

Pro Pro Pro Glu Glu Glu Met Thr Lys Lys Gln Val Thr Leu Thr Cys
            355                 360                 365

Met Val Thr Asp Phe Met Pro Glu Asp Ile Tyr Val Glu Trp Thr Asn
            370                 375                 380

Asn Gly Lys Thr Glu Leu Asn Tyr Lys Asn Thr Glu Pro Val Leu Asp
385                 390                 395                 400

Ser Asp Gly Ser Tyr Phe Met Tyr Ser Lys Leu Arg Val Glu Lys Lys
            405                 410                 415

Asn Trp Val Glu Arg Asn Ser Tyr Ser Cys Ser Val Val His Glu Gly
            420                 425                 430

Leu His Asn His His Thr Thr Lys Ser Phe Ser Arg Thr Pro Gly Lys
            435                 440                 445

<210> SEQ ID NO 170
<211> LENGTH: 214
<212> TYPE: PRT
<213> ORGANISM: Artificial Sequence
<220> FEATURE:
<223> OTHER INFORMATION: Synthetic: 1.16B8 light chain

<400> SEQUENCE: 170

Asp Ile Gln Met Thr Gln Thr Pro Ser Ser Met Pro Ala Ser Leu Gly
1               5                   10                  15

Glu Arg Val Thr Ile Ser Cys Arg Ala Ser Gln Gly Ile Ser Asn Tyr
            20                  25                  30

Leu Asn Trp Tyr Gln Gln Lys Pro Asp Gly Thr Ile Lys Pro Leu Ile
        35                  40                  45

Tyr Tyr Thr Ser Asn Leu Gln Ser Gly Val Pro Ser Arg Phe Ser Gly
50                  55                  60

Ser Gly Ser Gly Thr Asp Tyr Ser Leu Thr Ile Ser Ser Leu Glu Pro
65                  70                  75                  80

Glu Asp Phe Ala Met Tyr Tyr Cys Gln Gln Tyr Asp Ser Ser Pro Trp
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Pro Ile Val Lys Ser
        195                 200                 205

Phe Asn Arg Asn Glu Cys
        210

<210> SEQ ID NO 171
<211> LENGTH: 447
<212> TYPE: PRT
<213> ORGANISM: Artificial Sequence
<220> FEATURE:
<223> OTHER INFORMATION: Synthetic: 1.16B8 heavy chain

<400> SEQUENCE: 171

Glu Val Gln Leu Val Glu Ser Gly Gly Leu Val Gln Pro Gly Arg
1               5                   10                  15

Ser Leu Lys Leu Ser Cys Ala Ala Ser Gly Phe Thr Phe Ser Asp Ser
            20                  25                  30

Ala Met Ala Trp Val Arg Gln Ala Pro Lys Lys Gly Leu Glu Trp Val
        35                  40                  45

Ala Thr Ile Ile Tyr Asp Thr Ser Ser Thr Tyr Tyr Arg Asp Ser Val
50                  55                  60

Lys Gly Arg Phe Thr Ile Ser Arg Asp Asn Ala Lys Ser Thr Leu Tyr
65                  70                  75                  80

Leu Gln Met Asp Ser Leu Arg Ser Glu Asp Thr Ala Thr Tyr Tyr Cys
                85                  90                  95

Ala Leu Phe Gly Val Asp Val Met Asp Ala Trp Gly Gln Gly Ala Ser
            100                 105                 110

Val Thr Val Ser Ser Ala Lys Thr Thr Ala Pro Ser Val Tyr Pro Leu
        115                 120                 125

```
Ala Pro Val Cys Gly Asp Thr Thr Gly Ser Ser Val Thr Leu Gly Cys
    130                 135                 140

Leu Val Lys Gly Tyr Phe Pro Glu Pro Val Thr Leu Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Thr Ser Ser Thr Trp
            180                 185                 190

Pro Ser Gln Ser Ile Thr Cys Asn Val Ala His Pro Ala Ser Ser Thr
        195                 200                 205

Lys Val Asp Lys Lys Ile Glu Pro Arg Gly Pro Thr Ile Lys Pro Cys
210                 215                 220

Pro Pro Cys Lys Cys Pro Ala Pro Asn Ala Ala Gly Gly Pro Ser Val
225                 230                 235                 240

Phe Ile Phe Pro Pro Lys Ile Lys Asp Val Leu Met Ile Ser Leu Ser
                245                 250                 255

Pro Ile Val Thr Cys Val Val Val Asp Val Ser Glu Asp Asp Pro Asp
            260                 265                 270

Val Gln Ile Ser Trp Phe Val Asn Asn Val Glu Val His Thr Ala Gln
        275                 280                 285

Thr Gln Thr His Arg Glu Asp Tyr Asn Ser Thr Leu Arg Val Val Ser
    290                 295                 300

Ala Leu Pro Ile Gln His Gln Asp Trp Met Ser Gly Lys Glu Phe Lys
305                 310                 315                 320

Cys Lys Val Asn Asn Lys Asp Leu Gly Ala Pro Ile Glu Arg Thr Ile
                325                 330                 335

Ser Lys Pro Lys Gly Ser Val Arg Ala Pro Gln Val Tyr Val Leu Pro
            340                 345                 350

Pro Pro Glu Glu Glu Met Thr Lys Lys Gln Val Thr Leu Thr Cys Met
        355                 360                 365

Val Thr Asp Phe Met Pro Glu Asp Ile Tyr Val Glu Trp Thr Asn Asn
    370                 375                 380

Gly Lys Thr Glu Leu Asn Tyr Lys Asn Thr Glu Pro Val Leu Asp Ser
385                 390                 395                 400

Asp Gly Ser Tyr Phe Met Tyr Ser Lys Leu Arg Val Glu Lys Lys Asn
                405                 410                 415

Trp Val Glu Arg Asn Ser Tyr Ser Cys Ser Val Val His Glu Gly Leu
            420                 425                 430

His Asn His His Thr Thr Lys Ser Phe Ser Arg Thr Pro Gly Lys
        435                 440                 445

<210> SEQ ID NO 172
<211> LENGTH: 107
<212> TYPE: PRT
<213> ORGANISM: Mus musculus
<220> FEATURE:
<221> NAME/KEY: SITE
<222> LOCATION: (1)..(107)
<223> OTHER INFORMATION: Murine Kappa (light chain) constant region

<400> SEQUENCE: 172

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30
```

```
Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
 50                  55                  60

Thr Tyr Ser Met Ser Ser Thr Leu Thr Leu Thr Lys Asp Glu Tyr Glu
 65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
                100                 105
```

<210> SEQ ID NO 173
<211> LENGTH: 20
<212> TYPE: DNA
<213> ORGANISM: Artificial Sequence
<220> FEATURE:
<223> OTHER INFORMATION: Synthetic: Sequence for Alt-R CRISPR-Cas9 crRNA

<400> SEQUENCE: 173
ttgtagattc cgcagcgtaa                                              20

<210> SEQ ID NO 174
<211> LENGTH: 20
<212> TYPE: DNA
<213> ORGANISM: Artificial Sequence
<220> FEATURE:
<223> OTHER INFORMATION: Synthetic: Sequence for Alt-R CRISPR-Cas9 crRNA

<400> SEQUENCE: 174
aatggtgaga gtgccaccca                                              20

<210> SEQ ID NO 175
<211> LENGTH: 20
<212> TYPE: DNA
<213> ORGANISM: Artificial Sequence
<220> FEATURE:
<223> OTHER INFORMATION: Synthetic: Sequence for Alt-R CRISPR-Cas9 crRNA

<400> SEQUENCE: 175
taccagtgcc agagcctcca                                              20

<210> SEQ ID NO 176
<211> LENGTH: 219
<212> TYPE: PRT
<213> ORGANISM: Artificial Sequence
<220> FEATURE:
<223> OTHER INFORMATION: Synthetic: hPara.09v2 light chain

<400> SEQUENCE: 176

```
Asp Val Val Met Thr Gln Ser Pro Leu Ser Leu Pro Val Thr Pro Gly
 1               5                  10                  15

Glu Pro Ala Ser Ile Ser Cys Arg Ser Ser Arg Ser Leu Leu Thr Ser
                20                  25                  30

Lys Gly Ile Thr Ser Leu Tyr Trp Tyr Leu Gln Lys Pro Gly Gln Ser
        35                  40                  45

Pro Gln Leu Leu Ile Tyr Arg Met Ser Asn Leu Ala Ser Gly Ile Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ala Gln Phe
                85                  90                  95
```

```
Leu Val Tyr Pro Tyr Thr Phe Gly Gln Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
            130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
     210                 215

<210> SEQ ID NO 177
<211> LENGTH: 46
<212> TYPE: PRT
<213> ORGANISM: Artificial Sequence
<220> FEATURE:
<223> OTHER INFORMATION: Synthetic: hTREM2 stalk domain comprising
      peptide residues 129-175 (Fig. 2A)

<400> SEQUENCE: 177

Leu Ala Asp Pro Leu Asp His Arg Asp Ala Gly Asp Leu Trp Phe Pro
1               5                   10                  15

Gly Glu Ser Glu Ser Phe Glu Asp Ala His Val Glu His Ser Ile Ser
            20                  25                  30

Arg Ser Leu Leu Glu Gly Glu Ile Pro Phe Pro Pro Thr Ser
            35                  40                  45
```

AGONISTS OF TREM2

CROSS-REFERENCE TO RELATED APPLICATIONS

This application claims priority to U.S. Provisional Application No. 63/188,800, filed May 14, 2021, the disclosure of which is hereby incorporated by reference in its entirety.

SEQUENCE LISTING

This application contains a Sequence Listing in computer readable form entitled "01164-0014-00US_ST25", created May 10, 2022, having a size of 115,000 Bytes, which is incorporated by reference herein.

FIELD

This application discloses, inter alia, certain antibodies that specifically bind to TREM2. In some embodiments, the antibodies act as TREM2 agonists.

BACKGROUND

TREM2 (triggering receptor expressed on myeloid cells 2) is an activating immune cell receptor expressed in the brain in microglia (Hickman et al., *Nat. Neurosci.* 16(12): 1896-1905 (2013); Zhang et al., *Neuron* 89: 37-53 (2016); Deczkowska et al., *Cell* 181:1207-1217 (2020); Hansen et al., *J. Cell Biology* 217(2): 459-472 (2018); Yeh et al., *Trends Mol. Med.* 23:512-533 (2017)). Certain TREM2 mutations have been identified as risk factors for Alzheimer's disease (AD) (Guerreiro et al., *N. Engl. J. Med.* 368: 117-27 (2013); Jonsson et al., *N. Engl. J. Med.* 368: 107-116 (2013)). Studies have also been performed in mouse models to understand how TREM2 influences the development of AD pathologies such as β-amyloid (Aβ) plaques and phosphorylated aggregates of the tau protein. An emerging consensus is that AP plaques have a less compacted morphology and are more damaging to surrounding neurites when TREM2 function is impaired (Meilandt et al., *J Neurosci.* 40:1872-19 (2020); Wang et al., *J. Exp. Medicine* 213:667-675 (2016); Yuan et al., *Neuron* 90:724-739 (2016)).

Aβ aggregates have been found to bind directly to recombinant TREM2 extracellular domain, although other studies suggest that certain phospholipids are the relevant ligand for TREM2. TREM2 also binds to APOE or APOJ when they are lipidated and facilitates uptake of APOE/APOJ-containing lipoparticles. (Yeh et al., *Neuron* 91: 328-340 (2016).) Furthermore, microglial uptake and degradation of Aβ are accelerated when Aβ oligomers are bound to APOE/APOJ lipoparticles, a process that is partially mediated by TREM2. After ligation, TREM2 elicits a DAP12/Fyn/Syk signaling cascade that influences a host of microglial processes, including phagocytosis, endocytosis, chemotaxis, CSF-1-mediated survival, aggregate degradation, and metabolic changes. Thus, TREM2 appears to be central to microglial activity in response to amyloid and lipids.

SUMMARY

The present disclosure relates to antibodies that specifically bind to TREM2 and act as TREM2 agonists, and that may have a particularly unique set of features, useful for the treatment of neurodegenerative diseases such as Alzheimer's Disease (AD) and multiple sclerosis (MS).

The TREM2 protein is a cellular transmembrane protein that is cleaved in an extracellular region referred to as the stalk region, leading to a soluble peptide, termed "soluble TREM2" or "sTREM2". TREM2 cleavage in vivo is thought to occur between residues H157 and S158, giving rise to sTREM2. This disclosure describes antibodies having the unique property of specifically binding to the stalk region in non-soluble, intact TREM2, without binding to the cleavage product, sTREM2. For example, certain antibodies herein not only act as TREM2 agonists, but also specifically bind to the stalk domain of TREM2 with dissociation constants ranging from 10 nM to as low as 100-500 pM, 10-50 pM, or 1-10 pM, and specifically bind to a TREM2 epitope spanning the H157-S158 cleavage site. These antibodies specifically bind to the TREM2 stalk region while not binding to soluble TREM2.

The specificity of these antibodies for uncleaved TREM2 may have several potential benefits in vivo, including avoiding unwanted binding of antibodies to soluble TREM2 in the periphery and brain after in vivo dosing and/or blocking the cleavage site and reducing the amount of sTREM2 that is shed from the cell surface. The lack of soluble TREM2 binding could be beneficial in vivo, e.g., by allowing more of the dosed anti-TREM2 antibody to reach the desired target of uncleaved TREM2 on the surface of cells. By way of example, and not limitation, this unique binding profile may prevent antibodies from unwanted binding to soluble TREM2 in vivo and ensure that antibodies more specifically target TREM2 on the surface of cells within the central nervous system rather than sTREM2 in the periphery.

Thus, the present disclosure encompasses certain antibodies that: (a) bind specifically to the TREM2 stalk domain and more specifically to a TREM2 epitope spanning the H157-S158 cleavage site, and (b) do not bind to soluble TREM2, and thus, may not present a risk of soluble TREM2 binding in vivo. In some embodiments, the antibodies of the present disclosure also (c) act as TREM2 agonists, for example, by inducing NFAT-controlled gene expression and/or Syk kinase phosphorylation in cultured cells, and (d) exhibit very high affinity for TREM2, e.g., specifically binding to TREM2 with dissociation constants of, for example, 100-500 pM, 10-50 pM, or 1-10 pM. In some embodiments, antibodies herein also inhibit shedding of soluble TREM2 in a human microglia cell model and in vivo in a mouse model, decrease levels of soluble TREM2 in plasma, CSF and/or the brain, enhance survival of human microglia cells, and increase Aβ plaque formation and compaction in a human microglia model (for example, as measured by increased Aβ plaque intensity and/or increased X04 plaque intensity in human microglia), and thus, may provide a number of neuroprotective activities.

The present disclosure encompasses, inter alia, an isolated antibody that specifically binds to triggering receptor expressed on myeloid cells-2 (TREM2), wherein the antibody comprises a heavy chain variable region (VH) comprising a CDR-H1 comprising the amino acid sequence of SEQ ID NO: 1, 9, 11, 19, or 62; a CDR-H2 comprising the amino acid sequence of SEQ ID NO: 2, 10, 12, 20, 55, 63, 65, or 73; and a CDR-H3 comprising the amino acid sequence as follows: $X_1$-$X_2$-$X_3$-Y, wherein $X_1$ and $X_2$ together are either I-L or L, and wherein $X_3$ is either D or E.

The disclosure also encompasses, for example, an isolated antibody that specifically binds to triggering receptor expressed on myeloid cells-2 (TREM2), wherein the antibody comprises a heavy chain variable region (VH) comprising a CDR-H1 comprising the amino acid sequence of SEQ ID NO: 1, 9, 11, 19, or 62; a CDR-H2 comprising the amino acid sequence of SEQ ID NO: 2, 10, 12, 20, 55, 63, 65, or 73; and a CDR-H3 comprising the amino acid sequence as follows: $X_1$-$X_2$-$X_3$-Y, wherein $X_1$ and $X_2$ together are either I-L or L, and wherein $X_3$ is either D or E; and a light chain variable region (VL) comprising a CDR-L1 comprising the amino acid sequence of SEQ ID NO: 4, 27, 37, 47, 57, or 67; a CDR-L2 comprising the amino acid sequence of SEQ ID NO: 5; and a CDR-L3 comprising the amino acid sequence of SEQ ID NO: 6, 29, 39, 49, 59, or 69. The disclosure further encompasses, for example, an isolated antibody that specifically binds to triggering receptor expressed on myeloid cells-2 (TREM2), wherein the antibody comprises a heavy chain variable region (VH) comprising a CDR-H1 comprising the amino acid sequence of SEQ ID NO: 1, 9, 11, or 19; a CDR-H2 comprising the amino acid sequence of SEQ ID NO: 2, 10, 12, or 20; and a CDR-H3 comprising the amino acid sequence as follows: $X_1$-$X_2$-$X_3$-Y, wherein $X_1$ and $X_2$ together are either I-L or L, and wherein $X_3$ is either D or E; and a light chain variable region (VL) comprising a CDR-L1 comprising the amino acid sequence of SEQ ID NO: 4, a CDR-L2 comprising the amino acid sequence of SEQ ID NO: 5, and a CDR-L3 comprising the amino acid sequence of SEQ ID NO: 6.

In some embodiments herein, the antibody has one or more, two or more, three or more, four or more, five or more, six or more, or all of the following properties:
  (a) specifically binds to the stalk domain of TREM2;
  (b) does not bind to soluble TREM2 (sTREM2);
  (c) specifically binds to a TREM2 polypeptide consisting of amino acids 146-161 (SEQ ID NO: 96) or 151-165 (SEQ ID NO: 97) with higher affinity than to a TREM2 polypeptide consisting of amino acids 139-158 (SEQ ID NO: 92) and/or 159-175 (SEQ ID NO: 94);
  (d) specifically binds to a TREM2 epitope spanning the H157-S158 cleavage site;
  (e) shows reduced binding affinity to a TREM2 stalk domain polypeptide comprising D152A, H157A, and I159A substitutions compared to a wild-type TREM2 stalk domain polypeptide (e.g., as measured by bilayer interferometry);
  (f) specifically binds to human and cynomolgus TREM2 with a KD of less than 1 nM, less than 0.7 nM, less than 0.6 nM, less than 0.5 nM, less than 0.4 nM, less than 0.3 nM at 37° C. by surface plasmon resonance (SPR); and
  (g) specifically binds to human and cynomolgus TREM2 with a $K_D$ of less than 100 pM, less than 50 pM, less than 10 pM, less than 7 pM, less than 5 pM, less than 4 pM, less than 3 pM, or less than 2 pM at 37° C. by surface plasmon resonance (SPR).

Furthermore, in some embodiments, the antibody has a VH sequence derived from rat IGHV6-8 germline segments and/or wherein the antibody has a VL sequence derived from rat IGKV2S11 germline segments. In some embodiments, the light chain variable region (VL) comprises a CDR-L1 comprising the amino acid sequence of SEQ ID NO: 4, 27, or 67; a CDR-L2 comprising the amino acid sequence of SEQ ID NO: 5; and a CDR-L3 comprising the amino acid sequence of SEQ ID NO: 6, 29, or 69. In some embodiments, the light chain variable region (VL) comprises a CDR-L1 comprising the amino acid sequence of SEQ ID NO: 4, a CDR-L2 comprising the amino acid sequence of SEQ ID NO: 5, and a CDR-L3 comprising the amino acid sequence of SEQ ID NO: 6. In some embodiments, the heavy chain variable region (VH) comprises a CDR-H1 comprising the amino acid sequence of SEQ ID NO: 1 or 9; a CDR-H2 comprising the amino acid sequence of SEQ ID NO: 2 or 10; and a CDR-H3 comprising the amino acid sequence of SEQ ID NO: 3; and wherein the light chain variable region (VL) comprises a CDR-L1 comprising the amino acid sequence of SEQ ID NO: 4, a CDR-L2 comprising the amino acid sequence of SEQ ID NO: 5, and a CDR-L3 comprising the amino acid sequence of SEQ ID NO: 6; or the heavy chain variable region (VH) comprises a CDR-H1 comprising the amino acid sequence of SEQ ID NO: 11 or 19; a CDR-H2 comprising the amino acid sequence of SEQ ID NO: 12 or 20; and a CDR-H3 comprising the amino acid sequence of SEQ ID NO: 13; and wherein the light chain variable region (VL) comprises a CDR-L1 comprising the amino acid sequence of SEQ ID NO: 4, a CDR-L2 comprising the amino acid sequence of SEQ ID NO: 5, and a CDR-L3 comprising the amino acid sequence of SEQ ID NO: 6. In some embodiments, the antibody comprises a VH that is at least 90%, at least 95%, at least 97%, or at least 99% identical to the amino acid sequence of SEQ ID NO: 7, 17, 30, 40, 50, 60, 70, 76, 77, 78, 81, 82, 83, 133, 135, 137, 139, 146, 148, 150, or 152. In some embodiments, the antibody comprises a VH that is at least 90%, at least 95%, at least 97%, or at least 99% identical to the amino acid sequence of SEQ ID NO: 7, 17, 133, 135, 137, 139, 146, 148, 150, or 152. In some embodiments, the antibody comprises a VL that is at least 90%, at least 95%, at least 97%, or at least 99% identical to the amino acid sequence of SEQ ID NO: 8, 18, 31, 41, 51, 61, 71, 79, 80, 84, 85, 132, 134, 136, 138, 145, 147, 149, or 151. In some embodiments, the antibody comprises a VL that is at least 90%, at least 95%, at least 97%, or at least 99% identical to the amino acid sequence of SEQ ID NO: 8, 18, 132, 134, 136, 138, 145, 147, 149, or 151. In some embodiments, the antibody comprises a VH comprising the amino acid sequence of SEQ ID NO: 7, 17, 133, 135, 137, 139, 146, 148, 150, or 152. In some embodiments, the antibody comprises a VL comprising the amino acid sequence of SEQ ID NO: 8, 18, 132, 134, 136, 138, 145, 147, 149, or 151.

The present disclosure also encompasses, inter alia, an isolated antibody that specifically binds to triggering receptor expressed on myeloid cells-2 (TREM2), wherein the antibody comprises:
  (a) a heavy chain variable region (VH) comprising a CDR-H1 comprising the amino acid sequence of SEQ ID NO: 1, a CDR-H2 comprising the amino acid sequence of SEQ ID NO: 2, and a CDR-H3 comprising the amino acid sequence of SEQ ID NO: 3; and a light chain variable region (VL) comprising a CDR-L1 comprising the amino acid sequence of SEQ ID NO: 4, a CDR-L2 comprising the amino acid sequence of SEQ ID NO: 5, and a CDR-L3 comprising the amino acid sequence of SEQ ID NO: 6;
  (b) a heavy chain variable region (VH) comprising a CDR-H1 comprising the amino acid sequence of SEQ ID NO: 9, a CDR-H2 comprising the amino acid sequence of SEQ ID NO: 10, and a CDR-H3 comprising the amino acid sequence of SEQ ID NO: 3; and a light chain variable region (VL) comprising a CDR-L1 comprising the amino acid sequence of SEQ ID NO: 4, a CDR-L2 comprising the amino acid sequence of SEQ ID NO: 5, and a CDR-L3 comprising the amino acid sequence of SEQ ID NO: 6;
  (c) a heavy chain variable region (VH) comprising a CDR-H1 comprising the amino acid sequence of SEQ ID NO: 11, a CDR-H2 comprising the amino acid sequence of SEQ ID NO: 12, and a CDR-H3 comprising the amino acid sequence of SEQ ID NO: 13; and a light chain variable region (VL) comprising a CDR-L1 comprising the amino acid sequence of SEQ ID NO:

14, a CDR-L2 comprising the amino acid sequence of SEQ ID NO: 15, and a CDR-L3 comprising the amino acid sequence of SEQ ID NO: 16;

(d) a heavy chain variable region (VH) comprising a CDR-H1 comprising the amino acid sequence of SEQ ID NO: 19, a CDR-H2 comprising the amino acid sequence of SEQ ID NO: 20, and a CDR-H3 comprising the amino acid sequence of SEQ ID NO: 13; and a light chain variable region (VL) comprising a CDR-L1 comprising the amino acid sequence of SEQ ID NO: 14, a CDR-L2 comprising the amino acid sequence of SEQ ID NO: 15, and a CDR-L3 comprising the amino acid sequence of SEQ ID NO: 16;

(e) a heavy chain variable region (VH) comprising a CDR-H1 comprising the amino acid sequence of SEQ ID NO: 24, a CDR-H2 comprising the amino acid sequence of SEQ ID NO: 25, and a CDR-H3 comprising the amino acid sequence of SEQ ID NO: 26; and a light chain variable region (VL) comprising a CDR-L1 comprising the amino acid sequence of SEQ ID NO: 27, a CDR-L2 comprising the amino acid sequence of SEQ ID NO: 28, and a CDR-L3 comprising the amino acid sequence of SEQ ID NO: 29;

(f) a heavy chain variable region (VH) comprising a CDR-H1 comprising the amino acid sequence of SEQ ID NO: 34, a CDR-H2 comprising the amino acid sequence of SEQ ID NO: 35, and a CDR-H3 comprising the amino acid sequence of SEQ ID NO: 36; and a light chain variable region (VL) comprising a CDR-L1 comprising the amino acid sequence of SEQ ID NO: 37, a CDR-L2 comprising the amino acid sequence of SEQ ID NO: 38, and a CDR-L3 comprising the amino acid sequence of SEQ ID NO: 39;

(g) a heavy chain variable region (VH) comprising a CDR-H1 comprising the amino acid sequence of SEQ ID NO: 44, a CDR-H2 comprising the amino acid sequence of SEQ ID NO: 45, and a CDR-H3 comprising the amino acid sequence of SEQ ID NO: 46; and a light chain variable region (VL) comprising a CDR-L1 comprising the amino acid sequence of SEQ ID NO: 47, a CDR-L2 comprising the amino acid sequence of SEQ ID NO: 48, and a CDR-L3 comprising the amino acid sequence of SEQ ID NO: 49;

(h) a heavy chain variable region (VH) comprising a CDR-H1 comprising the amino acid sequence of SEQ ID NO: 54, a CDR-H2 comprising the amino acid sequence of SEQ ID NO: 55, and a CDR-H3 comprising the amino acid sequence of SEQ ID NO: 56; and a light chain variable region (VL) comprising a CDR-L1 comprising the amino acid sequence of SEQ ID NO: 57, a CDR-L2 comprising the amino acid sequence of SEQ ID NO: 58, and a CDR-L3 comprising the amino acid sequence of SEQ ID NO: 59; or (i) a heavy chain variable region (VH) comprising a CDR-H1 comprising the amino acid sequence of SEQ ID NO: 64, a CDR-H2 comprising the amino acid sequence of SEQ ID NO: 65, and a CDR-H3 comprising the amino acid sequence of SEQ ID NO: 66; and a light chain variable region (VL) comprising a CDR-L1 comprising the amino acid sequence of SEQ ID NO: 67, a CDR-L2 comprising the amino acid sequence of SEQ ID NO: 68, and a CDR-L3 comprising the amino acid sequence of SEQ ID NO: 69.

In some embodiments, the antibody comprises the CDRs of part (a) above and further comprises a VH that is at least 90%, at least 95%, at least 97%, or at least 99% identical to the amino acid sequence of SEQ ID NO: 7;

comprises the CDRs of part (b) above and further comprises a VH that is at least 90%, at least 95%, at least 97%, or at least 99% identical to the amino acid sequence of SEQ ID NO: 7;

comprises the CDRs of part (c) above and further comprises a VH that is at least 90%, at least 95%, at least 97%, or at least 99% identical to the amino acid sequence of SEQ ID NO: 17;

comprises the CDRs of part (d) above and further comprises a VH that is at least 90%, at least 95%, at least 97%, or at least 99% identical to the amino acid sequence of SEQ ID NO: 17;

comprises the CDRs of part (e) above and further comprises a VH that is at least 90%, at least 95%, at least 97%, or at least 99% identical to the amino acid sequence of SEQ ID NO: 30;

comprises the CDRs of part (f) above and further comprises a VH that is at least 90%, at least 95%, at least 97%, or at least 99% identical to the amino acid sequence of SEQ ID NO: 40;

comprises the CDRs of part (g) above and further comprises a VH that is at least 90%, at least 95%, at least 97%, or at least 99% identical to the amino acid sequence of SEQ ID NO: 50;

comprises the CDRs of part (h) above and further comprises a VH that is at least 90%, at least 95%, at least 97%, or at least 99% identical to the amino acid sequence of SEQ ID NO: 60; or comprises the CDRs of part (i) above and further comprises a VH that is at least 90%, at least 95%, at least 97%, or at least 99% identical to the amino acid sequence of SEQ ID NO: 70.

In some embodiments, the antibody comprises the CDRs of part (a) above and further comprises a VL that is at least 90%, at least 95%, at least 97%, or at least 99% identical to the amino acid sequence of SEQ ID NO: 8;

comprises the CDRs of part (b) above and further comprises a VL that is at least 90%, at least 95%, at least 97%, or at least 99% identical to the amino acid sequence of SEQ ID NO: 8;

comprises the CDRs of part (c) above and further comprises a VL that is at least 90%, at least 95%, at least 97%, or at least 99% identical to the amino acid sequence of SEQ ID NO: 18;

comprises the CDRs of part (d) above and further comprises a VL that is at least 90%, at least 95%, at least 97%, or at least 99% identical to the amino acid sequence of SEQ ID NO: 18;

comprises the CDRs of part (e) above and further comprises a VL that is at least 90%, at least 95%, at least 97%, or at least 99% identical to the amino acid sequence of SEQ ID NO: 31;

comprises the CDRs of part (f) above and further comprises a VL that is at least 90%, at least 95%, at least 97%, or at least 99% identical to the amino acid sequence of SEQ ID NO: 41;

comprises the CDRs of part (g) above and further comprises a VL that is at least 90%, at least 95%, at least 97%, or at least 99% identical to the amino acid sequence of SEQ ID NO: 51;

comprises the CDRs of part (h) above and further comprises a VL that is at least 90%, at least 95%, at least 97%, or at least 99% identical to the amino acid sequence of SEQ ID NO: 61; or comprises the CDRs of part (i) above and further comprises a VL that is at least 90%, at least 95%, at least 97%, or at least 99% identical to the amino acid sequence of SEQ ID NO: 71.

In some cases, the antibody
comprises the CDRs of part (a) above and further comprises a VH comprising the amino acid sequence of SEQ ID NO: 7;
comprises the CDRs of part (b) above and further comprises a VH comprising the amino acid sequence of SEQ ID NO: 7;
comprises the CDRs of part (c) above and further comprises a VH comprising the amino acid sequence of SEQ ID NO: 17;
comprises the CDRs of part (d) above and further comprises a VH comprising the amino acid sequence of SEQ ID NO: 17;
comprises the CDRs of part (e) above and further comprises a VH comprising the amino acid sequence of SEQ ID NO: 30;
comprises the CDRs of part (f) above and further comprises a VH comprising the amino acid sequence of SEQ ID NO: 40;
comprises the CDRs of part (g) above and further comprises a VH comprising the amino acid sequence of SEQ ID NO: 50;
comprises the CDRs of part (h) above and further comprises a VH comprising the amino acid sequence of SEQ ID NO: 60; or
comprises the CDRs of part (i) above and further comprises a VH comprising the amino acid sequence of SEQ ID NO: 70.

In some cases, the antibody
comprises the CDRs of part (a) above and further comprises a VL comprising the amino acid sequence of SEQ ID NO: 8;
comprises the CDRs of part (b) above and further comprises a VL comprising the amino acid sequence of SEQ ID NO: 8;
comprises the CDRs of part (c) above and further comprises a VL comprising the amino acid sequence of SEQ ID NO: 18;
comprises the CDRs of part (d) above and further comprises a VL comprising the amino acid sequence of SEQ ID NO: 18;
comprises the CDRs of part (e) above and further comprises a VL comprising the amino acid sequence of SEQ ID NO: 31;
comprises the CDRs of part (f) above and further comprises a VL comprising the amino acid sequence of SEQ ID NO: 41;
comprises the CDRs of part (g) above and further comprises a VL comprising the amino acid sequence of SEQ ID NO: 51;
comprises the CDRs of part (h) above and further comprises a VL comprising the amino acid sequence of SEQ ID NO: 61; or
comprises the CDRs of part (i) above and further comprises a VL comprising the amino acid sequence of SEQ ID NO: 71.

In some cases, the antibody comprises a VH comprising the amino acid sequence of SEQ ID NO: 7 and a VL comprising the amino acid sequence of SEQ ID NO: 8. In some cases, the antibody comprises a VH comprising the amino acid sequence of SEQ ID NO: 17 and a VL comprising the amino acid sequence of SEQ ID NO: 18. In some cases, the antibody comprises a VL comprising from 1 to 5 amino acid substitutions in the framework region compared to human IGKV2-28*01 germline, optionally wherein the amino acid substitutions comprise Q100P and/or V104L. In some cases, the antibody:
comprises the CDRs of part (a) above and further comprises a VL comprising the amino acid sequence of SEQ ID NO: 145;
comprises the CDRs of part (b) above and further comprises a VL comprising the amino acid sequence of SEQ ID NO: 145;
comprises the CDRs of part (a) above and further comprises a VL comprising the amino acid sequence of SEQ ID NO: 147;
comprises the CDRs of part (b) above and further comprises a VL comprising the amino acid sequence of SEQ ID NO: 147;
comprises the CDRs of part (a) above and further comprises a VL comprising the amino acid sequence of SEQ ID NO: 149;
comprises the CDRs of part (b) above and further comprises a VL comprising the amino acid sequence of SEQ ID NO: 149;
comprises the CDRs of part (a) above and further comprises a VL comprising the amino acid sequence of SEQ ID NO: 151;
comprises the CDRs of part (b) above and further comprises a VL comprising the amino acid sequence of SEQ ID NO: 151;
comprises the CDRs of part (c) above and further comprises a VL comprising the amino acid sequence of SEQ ID NO: 132;
comprises the CDRs of part (d) above and further comprises a VL comprising the amino acid sequence of SEQ ID NO; 132;
comprises the CDRs of part (c) above and further comprises a VL comprising the amino acid sequence of SEQ ID NO: 134;
comprises the CDRs of part (d) above and further comprises a VL comprising the amino acid sequence of SEQ ID NO: 134;
comprises the CDRs of part (c) above and further comprises a VL comprising the amino acid sequence of SEQ ID NO: 136;
comprises the CDRs of part (d) above and further comprises a VL comprising the amino acid sequence of SEQ ID NO: 136;
comprises the CDRs of part (c) above and further comprises a VL comprising the amino acid sequence of SEQ ID NO: 138; or
comprises the CDRs of part (d) above and further comprises a VL comprising the amino acid sequence of SEQ ID NO: 138.

In some embodiments, an antibody herein has one or more, two or more, three or more, four or more, five or more, six or more, or all of the following properties:
(a) specifically binds to the stalk domain of TREM2;
(b) does not bind to soluble TREM2 (sTREM2);
(c) specifically binds to a TREM2 polypeptide consisting of amino acids 146-161 (SEQ ID NO: 96) or 151-165 (SEQ ID NO: 97) with higher affinity than to a TREM2 polypeptide consisting of amino acids 139-158 (SEQ ID NO: 92) and/or 159-175 (SEQ ID NO: 94);
(d) specifically binds to a TREM2 epitope spanning the H157-S158 cleavage site;
(e) shows reduced binding affinity to a TREM2 stalk domain polypeptide comprising D152A, H157A, and I159A substitutions compared to a wild-type TREM2 stalk domain polypeptide (e.g., as measured by bilayer interferometry);

(f) specifically binds to human and cynomolgus TREM2 with a $K_D$ of less than 1 nM, less than 0.7 nM, less than 0.6 nM, less than 0.5 nM, less than 0.4 nM, or less than 0.3 nM, or 100-500 pM or 100-200 pM at 37° C. by surface plasmon resonance (SPR); and (g) specifically binds to human and cynomolgus TREM2 with a $K_D$ of less than 100 pM, less than 50 pM, less than 10 pM, less than 7 pM, less than 5 pM, less than 4 pM, less than 3 pM, or less than 2 pM, or 10-50 pM or 10-25 pM at 37° C. by surface plasmon resonance (SPR).

The application also encompasses, for instance, an isolated antibody that specifically binds triggering receptor expressed on myeloid cells-2 (TREM2), wherein the antibody comprises:

a VH comprising the amino acid sequence of SEQ ID NO: 146 and a VL comprising the amino acid sequence of SEQ ID NO: 145;

a VH comprising the amino acid sequence of SEQ ID NO: 148 and a VL comprising the amino acid sequence of SEQ ID NO: 147;

a VH comprising the amino acid sequence of SEQ ID NO: 150 and a VL comprising the amino acid sequence of SEQ ID NO: 149; or a VH comprising the amino acid sequence of SEQ ID NO: 152 and a VL comprising the amino acid sequence of SEQ ID NO: 151. In some embodiments, the antibody has one or more, two or more, three or more, four or more, five or more, or all of the following properties:

(a) specifically binds to the stalk domain of TREM2;
(b) does not bind to soluble TREM2 (sTREM2);
(c) specifically binds to a TREM2 polypeptide consisting of amino acids 146-161 (SEQ ID NO: 96) or 151-165 (SEQ ID NO: 97) with higher affinity than to a TREM2 polypeptide consisting of amino acids 139-158 (SEQ ID NO: 92) and/or 159-175 (SEQ ID NO: 94);
(d) specifically binds to a TREM2 epitope spanning the H157-S158 cleavage site;
(e) shows reduced binding affinity to a TREM2 stalk domain polypeptide comprising D152A, H157A, and I159A substitutions compared to a wild-type TREM2 stalk domain polypeptide (e.g., as measured by bilayer interferometry); and
(f) specifically binds to human and cynomolgus TREM2 with a $K_D$ of less than 1 nM, less than 0.7 nM, less than 0.6 nM, less than 0.5 nM, less than 0.4 nM, or less than 0.3 nM, or 100-500 pM or 100-200 pM at 37° C. by surface plasmon resonance (SPR).

The application further encompasses, for example, an isolated antibody that specifically binds triggering receptor expressed on myeloid cells-2 (TREM2), wherein the antibody comprises:

a VH comprising the amino acid sequence of SEQ ID NO: 133 and a VL comprising the amino acid sequence of SEQ ID NO: 132;

a VH comprising the amino acid sequence of SEQ ID NO: 135 and a VL comprising the amino acid sequence of SEQ ID NO: 134;

a VH comprising the amino acid sequence of SEQ ID NO: 137 and a VL comprising the amino acid sequence of SEQ ID NO: 136; or a VH comprising the amino acid sequence of SEQ ID NO: 139 and a VL comprising the amino acid sequence of SEQ ID NO: 138. In some embodiments, the antibody has one or more, two or more, three or more, four or more, five or more, or all of the following properties:

(a) specifically binds to the stalk domain of TREM2;
(b) does not bind to soluble TREM2 (sTREM2);
(c) specifically binds to a TREM2 polypeptide consisting of amino acids 146-161 (SEQ ID NO: 96) or 151-165 (SEQ ID NO: 97) with higher affinity than to a TREM2 polypeptide consisting of amino acids 139-158 (SEQ ID NO: 92) and/or 159-175 (SEQ ID NO: 94);
(d) specifically binds to a TREM2 epitope spanning the H157-S158 cleavage site;
(e) shows reduced binding affinity to a TREM2 stalk domain polypeptide comprising D152A, H157A, and I159A substitutions compared to a wild-type TREM2 stalk domain polypeptide (e.g., as measured by bilayer interferometry); and
(f) specifically binds to human and cynomolgus TREM2 with a $K_D$ of less than 100 pM, less than 50 pM, less than 10 pM, less than 7 pM, less than 5 pM, less than 4 pM, less than 3 pM, or less than 2 pM, or 10-50 pM or 10-25 pM at 37° C. by surface plasmon resonance (SPR).

In some cases, an antibody herein has one or more, two or more, three or more, four or more, five or more, six or more, seven or more, eight or more, or all of the following characteristics:

(a) induces luciferase reporter activity in Jurkat-NFAT luciferase reporter cells expressing human TREM2;
(b) decreases levels of sTREM2 in vivo in plasma;
(c) inhibits shedding of sTREM2 in Jurkat-NFAT luciferase reporter cells expressing human TREM2;
(d) induces tyrosine phosphorylation in human MDM cells;
(e) SYK phosphorylation in human MDM cells;
(f) enhances survival of human iPSC-derived microglia in absence of IL-34 and CSF-1;
(g) inhibits shedding of sTREM2 in human iPSC-derived microglia;
(h) induces SYK phosphorylation in human iPSC-derived microglia; and
(i) increases total Aβ plaque intensity and/or average X04 plaque intensity in presence of Aβ oligomers in human iPSC-derived microglia (e.g., as described in the assay of Example 17 herein). In some embodiments, the antibody herein also has a low off-target binding score (e.g. a score of <1) in an off-target binding assay (e.g., as described in Example 10 herein).

In some embodiments, the antibody is an antibody fragment, such as an Fv, single-chain Fv (scFv), Fab, Fab', or (Fab')$_2$. In some embodiments, the antibody is an IgG antibody, such as an IgG1, IgG2, IgG3, or IgG4 antibody. In some such cases, the antibody comprises a wild-type, human IgG1 or IgG4 Fc region. In some such cases, the antibody comprises a human IgG1 Fc region comprising (a) an N297G substitution, (b) L234A, L235A, and P329G substitutions (LALAPG substitutions), or (c) N297G, M428L, and N434S substitutions. In some embodiments herein, the antibody has reduced effector function, or is effectorless, or does not bind to FcγR. In some embodiments, the antibody comprises a human IgG1 Fc region comprising an N297G substitution. In some embodiments herein, the antibody comprises a heavy chain comprising the amino acid sequence of SEQ ID NO: 144 and/or a light chain comprising the amino acid sequence of SEQ ID NO: 176. In some embodiments, the antibody comprises a heavy chain comprising or consisting of the amino acid sequence of SEQ ID NO: 144 but lacking the C-terminal lysine of SEQ ID NO:

144 or lacking the C-terminal glycine and lysine of SEQ ID NO: 144 and/or a light chain comprising or consisting of the amino acid sequence of SEQ ID NO: 176. In some embodiments, the antibody comprises a heavy chain consisting of the amino acid sequence of SEQ ID NO: 144 and/or a light chain consisting of the amino acid sequence of SEQ ID NO: 176. In some embodiments herein, the antibody comprises a human IgG4 Fc region comprising an S228P substitution or comprising S228P, M252Y, S254T, and T256E substitutions. In some embodiments herein, the antibody is a full length antibody. In some embodiments herein, the antibody is an IgG antibody lacking a C-terminal lysine in the heavy chain constant region.

The disclosure herein also encompasses, for instance, an isolated antibody that specifically binds to triggering receptor expressed on myeloid cells-2 (TREM2), wherein the antibody comprises a heavy chain comprising or consisting of the amino acid sequence of SEQ ID NO: 17 and/or a light chain comprising or consisting of the amino acid sequence of SEQ ID NO: 18. The disclosure herein further encompasses an isolated antibody that specifically binds to triggering receptor expressed on myeloid cells-2 (TREM2), wherein the antibody comprises a heavy chain comprising or consisting of the amino acid sequence of SEQ ID NO: 144 and/or a light chain comprising or consisting of the amino acid sequence of SEQ ID NO: 176. The disclosure herein also encompasses an isolated antibody that specifically binds to triggering receptor expressed on myeloid cells-2 (TREM2), wherein the antibody comprises a heavy chain comprising or consisting of the amino acid sequence of SEQ ID NO: 144 but lacking the C-terminal lysine of SEQ ID NO: 144 or lacking the C-terminal glycine and lysine of SEQ ID NO: 144 and/or a light chain comprising or consisting of the amino acid sequence of SEQ ID NO: 176. The disclosure also encompasses an isolated antibody that specifically binds to triggering receptor expressed on myeloid cells-2 (TREM2), wherein the antibody comprises a heavy chain consisting of the amino acid sequence of SEQ ID NO: 144 and/or a light chain consisting of the amino acid sequence of SEQ ID NO: 176. In some embodiments, the antibody specifically binds to the TREM2 stalk domain and does not bind to soluble TREM2 (sTREM2), and wherein the antibody specifically binds to a TREM2 epitope spanning the H157-S158 cleavage site and/or specifically binds to a TREM2 polypeptide consisting of amino acids 146-161 (SEQ ID NO: 96) or 151-165 (SEQ ID NO: 97) with higher affinity than to a TREM2 polypeptide consisting of amino acids 139-158 (SEQ ID NO: 92) and/or 159-175 (SEQ ID NO: 94). In some embodiments, the antibody specifically binds to the TREM2 stalk domain and does not bind to soluble TREM2 (sTREM2), and wherein the antibody is a TREM2 agonist. In some embodiments herein, the antibody has one or more, two or more, three or more, four or more, five or more, six or more, or all of the following properties:
(a) specifically binds to the stalk domain of TREM2;
(b) does not bind to soluble TREM2 (sTREM2);
(c) specifically binds to a TREM2 polypeptide consisting of amino acids 146-161 (SEQ ID NO: 96) or 151-165 (SEQ ID NO: 97) with higher affinity than to a TREM2 polypeptide consisting of amino acids 139-158 (SEQ ID NO: 92) and/or 159-175 (SEQ ID NO: 94);
(d) specifically binds to a TREM2 epitope spanning the H157-S158 cleavage site;
(e) shows reduced binding affinity to a TREM2 stalk domain polypeptide comprising D152A, H157A, and I159A substitutions compared to a wild-type TREM2 stalk domain polypeptide (e.g., as measured by bilayer interferometry);
(f) specifically binds to human and cynomolgus TREM2 with a $K_D$ of less than 1 nM, less than 0.7 nM, less than 0.6 nM, less than 0.5 nM, less than 0.4 nM, less than 0.3 nM at 37° C. by surface plasmon resonance (SPR); and
(g) specifically binds to human and cynomolgus TREM2 with a $K_D$ of less than 100 pM, less than 50 pM, less than 10 pM, less than 7 pM, less than 5 pM, less than 4 pM, less than 3 pM, or less than 2 pM at 37° C. by surface plasmon resonance (SPR). In some embodiments, for example, the antibody shows reduced binding affinity to a TREM2 stalk domain polypeptide comprising D152A, H157A, and I159A substitutions compared to a wild-type TREM2 stalk domain polypeptide (e.g., as measured by bilayer interferometry) and/or specifically binds to human and cynomolgus TREM2 with a $K_D$ of less than 100 pM, less than 50 pM, less than 10 pM, less than 7 pM, less than 5 pM, less than 4 pM, less than 3 pM, or less than 2 pM, or 10-50 pM or 10-25 pM at 37° C. by surface plasmon resonance (SPR). And in some embodiments, the antibody has one or more, two or more, three or more, four or more, five or more, six or more, seven or more, eight or more, or all of the following characteristics:
(a) induces luciferase reporter activity in Jurkat-NFAT luciferase reporter cells expressing human TREM2;
(b) decreases levels of sTREM2 in vivo in plasma;
(c) inhibits shedding of sTREM2 in Jurkat-NFAT luciferase reporter cells expressing human TREM2;
(d) induces tyrosine phosphorylation in human MDM cells;
(e) SYK phosphorylation in human MDM cells;
(f) enhances survival of human iPSC-derived microglia in absence of IL-34 and CSF-1;
(g) inhibits shedding of sTREM2 in human iPSC-derived microglia;
(h) induces SYK phosphorylation in human iPSC-derived microglia; and
(i) increases total Aβ plaque intensity and/or average X04 plaque intensity in presence of Aβ oligomers in human iPSC-derived microglia (e.g., as described in the assay of Example 17 herein). In some embodiments, the antibody also has a low off-target binding score (e.g. a score of <1) in an off-target binding assay (e.g., as described in Example 10 herein).

The disclosure herein also encompasses an isolated antibody that specifically binds to triggering receptor expressed on myeloid cells-2 (TREM2), wherein the antibody comprises a heavy chain variable region (VH) and a light chain variable region (VL), wherein the VH comprises a CDR-H1 comprising the amino acid sequence of SEQ ID NO: 11 or 19; a CDR-H2 comprising the amino acid sequence of SEQ ID NO: 12 or 20; and a CDR-H3 comprising the amino acid sequence of SEQ ID NO: 13, and further wherein the antibody specifically binds to the TREM2 stalk domain and does not bind to soluble TREM2 (sTREM2), wherein the antibody is a TREM2 agonist, and wherein the antibody specifically binds to a TREM2 epitope spanning the H157-S158 cleavage site and/or specifically binds to a TREM2 polypeptide consisting of amino acids 146-161 (SEQ ID NO: 96) or 151-165 (SEQ ID NO: 97) with higher affinity than to a TREM2 polypeptide consisting of amino acids 139-158 (SEQ ID NO: 92) and/or 159-175 (SEQ ID NO: 94). In some embodiments, for example, the antibody shows reduced binding affinity to a TREM2 stalk domain polypeptide comprising D152A, H157A, and I159A substitutions compared to a wild-type TREM2 stalk domain polypeptide (e.g., as measured by bilayer interferometry) and/or specifically binds to human and cynomolgus TREM2 with a $K_D$ of less than 100 pM, less than 50 pM, less than 10 pM, less than 7 pM, less than 5 pM, less than 4 pM, less than 3 pM, or less than 2 pM, or 10-50 pM or 10-25 pM at 37° C. by surface plasmon resonance (SPR). And in some embodiments, the antibody has one or more, two or more, three or more, four or more, five or more, six or more, seven or more, eight or more, or all of the following characteristics:
  (a) induces luciferase reporter activity in Jurkat-NFAT luciferase reporter cells expressing human TREM2;
  (b) decreases levels of sTREM2 in vivo in plasma;
  (c) inhibits shedding of sTREM2 in Jurkat-NFAT luciferase reporter cells expressing human TREM2;
  (d) induces tyrosine phosphorylation in human MDM cells;
  (e) SYK phosphorylation in human MDM cells;
  (f) enhances survival of human iPSC-derived microglia in absence of IL-34 and CSF-1;
  (g) inhibits shedding of sTREM2 in human iPSC-derived microglia;
  (h) induces SYK phosphorylation in human iPSC-derived microglia; and
  (i) increases total Aβ plaque intensity and/or average X04 plaque intensity in presence of Aβ oligomers in human iPSC-derived microglia (e.g., as described in the assay of Example 17 herein). In some embodiments, the antibody also has a low off-target binding score (e.g. a score of <1) in an off-target binding assay (e.g., as described in Example 10 herein). Further, in some embodiments, the VH comprises the amino acid sequence of SEQ ID NO: 17, 133, 135, 137, or 139, or wherein the antibody comprises a heavy chain comprising or consisting of the amino acid sequence of SEQ ID NO: 144. In some cases, the antibody comprises a human IgG1 Fc region comprising (a) an N297G substitution, (b) L234A, L235A, and P329G substitutions (LALAPG substitutions), or (c) N297G, M428L, and N434S substitutions. In some cases, the antibody has reduced effector function, or is effectorless, or does not bind to FcγR.

In some embodiments herein, an antibody is a bispecific or multispecific antibody, or is conjugated covalently or noncovalently to at least one other molecule. In some cases, the antibody is conjugated covalently or noncovalently to at least one other molecule, wherein the at least one other molecule comprises a detection label and/or a drug.

The present disclosure also includes a pharmaceutical composition comprising an antibody as described herein and a pharmaceutically acceptable carrier. The disclosure also encompasses an isolated nucleic acid or set of two or more nucleic acids encoding the antibody disclosed herein. The disclosure also includes an isolated vector comprising one or more nucleic acids encoding the heavy chain and the light chain of the antibody herein. The disclosure further encompasses an isolated host cell comprising the nucleic acid or vector. The disclosure also encompasses a method of producing an antibody that specifically binds to TREM2 comprising culturing the host cell under conditions suitable for the expression of the antibody. In some cases, the method includes recovering the antibody from the host cell. The disclosure also encompasses an antibody produced by the method.

The present disclosure further includes a method of treating a condition associated with TREM2 loss of function in a subject in need thereof, comprising administering an antibody herein or a pharmaceutical composition herein to the subject. In some embodiments, the disclosure includes a method of reducing levels of sTREM2 in a subject in need thereof, comprising administering an antibody herein or a pharmaceutical composition herein to the subject. In some cases, the condition is, or the subject suffers from, a neuroinflammatory or neurodegenerative disease. In some cases, the neuroinflammatory or neurodegenerative disease is Alzheimer's disease, Parkinson's disease, frontotemporal dementia, dementia, multiple sclerosis (MS), amyotrophic lateral sclerosis (ALS), Nasu-Hakola disease, Guillain-Barré Syndrome (GBS), lysosomal storage disease, sphingomyelinlipidosis (Neimann-Pick C), mucopolysaccharidosis II/IIIB, metachromatic leukodystrophy, multifocal motor neuropathy, neuro-Behcet's disease, neuromyelitis optica (NMO), optic neuritis, polymyositis, dermatomyositis, stroke, transverse myelitis, traumatic brain injury, or spinal cord injury. In some cases, the disease is Alzheimer's disease. In some cases, the disease is MS.

The present disclosure also encompasses an antibody or a pharmaceutical composition herein for use in treating a condition associated with TREM2 loss of function in a subject in need thereof. In some embodiments, the disclosure herein encompasses an antibody or a pharmaceutical composition herein for use in reducing levels of sTREM2 in a subject in need thereof. In some cases, the condition is, or the subject suffers from, a neuroinflammatory or neurodegenerative disease. In some cases, the neuroinflammatory or neurodegenerative disease is Alzheimer's disease, Parkinson's disease, frontotemporal dementia, dementia, multiple sclerosis (MS), amyotrophic lateral sclerosis (ALS), Nasu-Hakola disease, Guillain-Barré Syndrome (GBS), lysosomal storage disease, sphingomyelinlipidosis (Neimann-Pick C), mucopolysaccharidosis II/IIIB, metachromatic leukodystrophy, multifocal motor neuropathy, neuro-Behcet's disease, neuromyelitis optica (NMO), optic neuritis, polymyositis, dermatomyositis, stroke, transverse myelitis, traumatic brain injury, or spinal cord injury. In some cases, the disease is Alzheimer's disease. In some cases, the disease is MS.

The present disclosure further includes use of an antibody herein or a pharmaceutical composition herein in the preparation of a medicament for treating a condition associated with TREM2 loss of function in a subject in need thereof. The disclosure herein also includes use of an antibody or a pharmaceutical composition herein in the preparation of a medicament for reducing levels of sTREM2 in a subject in need thereof. In some cases, the condition is, or the subject suffers from, a neuroinflammatory or neurodegenerative disease. In some cases, the neuroinflammatory or neurodegenerative disease is Alzheimer's disease, Parkinson's disease, frontotemporal dementia, dementia, multiple sclerosis (MS), amyotrophic lateral sclerosis (ALS), Nasu-Hakola disease, Guillain-Barré Syndrome (GBS), lysosomal storage disease, sphingomyelinlipidosis (Neimann-Pick C), mucopolysaccharidosis II/IIIB, metachromatic leukodystrophy, multifocal motor neuropathy, neuro-Behcet's disease, neuromyelitis optica (NMO), optic neuritis, polymyositis, dermatomyositis, stroke, transverse myelitis, traumatic brain injury, or spinal cord injury. In some cases, the disease is Alzheimer's disease. In some cases, the disease is MS.

Additional objects and advantages will be set forth in part in the description which follows, and in part will be understood from the description, or may be learned by practice. The objects and advantages will be realized and attained by means of the elements and combinations particularly pointed out in the appended claims. It is to be understood that both the foregoing general description and the following detailed description are exemplary and explanatory only and are not restrictive of the claims. For example, in addition to the various embodiments depicted and claimed herein, the disclosed subject matter is also directed to other embodiments having other combinations of the features disclosed and claimed herein. As such, the particular features presented herein, especially presented as aspects or embodiments, can be combined with each other in other manners within the scope of the disclosed subject matter such that the disclosed subject matter includes any suitable combination of the features disclosed herein. The description of specific embodiments of the disclosed subject matter herein is presented for purposes of illustration and description. It is not intended to be exhaustive or to limit the disclosed subject matter to those embodiments disclosed.

BRIEF DESCRIPTION OF THE DRAWINGS

FIG. 1 shows a summary of anti-TREM2 clones obtained by hybridoma with different immunization strategies.

FIGS. 2A-B provide various TREM2 stalk peptide sequences and strength of binding to each peptide by three different antibodies. FIG. 2A shows the sequence of peptide fragments within the TREM2 stalk region. The TREM2 residues flanking the TREM2 cleavage site between residues 157 and 158 are shown in boldface. FIG. 2B shows binding data (in nM) for three antibodies to the peptides of FIG. 2A. Binding is shown in shades of gray (with darker shades indicating stronger binding) along with A620 absorbance values.

FIGS. 3A-B show light and heavy chain variable region amino acid sequences of anti-TREM2 antibodies. Amino acid differences relative to the 3.10C2 variable region sequences are indicated in black. CDR regions according to Chothia or Kabat are indicated above the sequences, with the Kabat CDR definitions also underlined. FIG. 3A shows light chain variable region sequences for 5 clones. FIG. 3B shows heavy chain variable region sequences for 6 clones.

FIG. 5 shows a summary of alanine/glycine mutations impacting binding of anti-TREM2 antibodies. Grey boxes indicate mutations impacting either the off-rate binding or the total binding of different antibodies. The amino acid residue and position in TREM2 are shown in top rows of the table. The two residues in TREM2 that flank the cleavage site in the protein are highlighted in grey in the same row. Antibody AL2p-31 is a humanized, high-affinity variant of mouse antibody 9F5. Antibody Para.09 has the antibody 3.2H7 light chain.

FIGS. 6A-B show humanized 3.10C2 CDR graft variant sequences. Variable region sequences are aligned to human framework sequences used for humanization. Differences with framework sequences (top sequences) are highlighted in black. CDR regions in the Kabat definition are underlined. "3.10C2" in each figure refers to the rat 3.10C2 variable region sequence. FIG. 6A shows light chain variable region sequences for 3 variants. FIG. 6B shows heavy chain variable region sequences for 4 variants.

FIGS. 7A-B show expression yields of 3.10C2 CDR graft clones. FIG. 7A shows expression yields as measured by titer (mg/L) of humanized IgG variants with different heavy and light chain humanized variants. Clones L9 and L10 are identical to clones L1 and L5 respectively (see FIG. 6A) but with a Q100P mutation in framework 4. FIG. 7B shows expression yields of Fab fragments (mg) with the humanized 3.10C2-H1 heavy chain variants combined to the humanized 3.10C2-L1 variant or rat 3.10C2 light chain.

FIGS. 8A-B show humanized 3.27H7 light chain and Para.09 heavy chain CDR graft variant sequences. Variable region sequences are aligned to human framework sequences used for humanization. Differences with framework sequences (top sequences) are highlighted in black. CDR regions in the Kabat definition are underlined. "3.27H7" and "Para.09" are the rat variable region sequences. FIG. 8A shows light chain variable region sequences of three variants. FIG. 8B shows heavy chain variable region sequences of four variants.

FIGS. 9A-B show sequences of the variable region and CDRs of antibody h3.10C2.v1. Kabat CDR regions are underlined. FIG. 9A shows light chain variable region sequence. FIG. 9B shows heavy chain variable region sequence.

FIG. 10 shows scanning mutagenesis of antibody 3.10C2. FIG. 10 shows a distribution of dissociation rates of antibody 3.10C2 heavy chain CDR single point mutants at 37° C. The dissociation rate of antibody 3.10C2 determined in the same set of experiments is shown with the dotted line. Two 3.10C2 point mutants with lower dissociation rates relative to wild-type 3.10C2 are indicated, with the fold-improvement for each one shown in parentheses. Data for 440 mutants shown.

FIG. 11 shows expression yields (mg/L) after protein A chromatography of rat and humanized variants of Para.09 produced in CHO cells. The isotype of each antibody is indicated.

FIGS. 12A-B show amino acid sequences of the variable regions of antibody hPara.09.v2. Kabat CDR regions are underlined. FIG. 12A shows light chain variable region sequence. FIG. 12B shows heavy chain variable region sequence.

FIGS. 13A and B show sequence and CDR regions of the light chains (FIG. 13A) and heavy chains (FIG. 13B) of hPara.09.v2 and hPara.09.v2 mutants. The Q100P, I58V, and V104L mutations and other mutations in the light chain relative to hPara.09.v2 are highlighted. Kabat CDR regions are underlined.

FIGS. 14A-B show sequence and CDR regions of the variable regions of the light chains (FIG. 14A) and the heavy chains (FIG. 14B) antibody h3.10C2.v1 and h3.10C2.v1 mutants. The Q100P, I58V, and L104V mutations in the light chain are highlighted. Kabat CDR regions are underlined.

FIG. 15 shows normalized baculovirus (BV) ELISA reactivity of four anti-TREM2 antibodies (parental and humanized): chimeric clones with rat variable regions and human IgG1 constant regions and humanized variants h3.10C2.v1 and hPara.09.v2 with human IgG1 constant regions with a N297G mutation to eliminate Fc receptor binding.

FIG. 16 shows antibodies that bind and do not bind to soluble TREM2 (sTREM2) in vitro. FIG. 16 shows normalized values for sTREM2 binding for tested antibodies: Control antibody 1.16B8 (CTL), rat Para.09— LC 3.27H7 mIgG2a LALAPG (Para09), rat 3.10C2 mIgG2a LALAPG (3.10C2), rat 3.18E5 mIgG2a LALAPG (3.18E5), rat 3.50G1 mIgG2a LALAPG (3.50G1), rat 3.27H7 mIgG2a LALAPG (3.27H7), rat 3.36F5 mIgG2a LALAPG (3.36F5), A.9F5 (also called 9F5 herein), AL2p-12, AL2p-31, AL2p-58, BM.3D3, BM.42E8, BM.RS9, BM.14D3, and BM.14D8.

FIG. 17 shows 8 antibodies that induced modest to strong luciferase expression in the cells: 3.10C2, 3.18E5, 3.27H7, 3.50G1, 3.17G12, 3.27H5, 3.41B10, and 3.47B1.

FIG. 20A shows the effect of increasing concentrations of rat 1.20A2 mIgG2a LALAPG, rat Para.09 mIgG2a LALAPG, and rat 3.10C2 mIgG2a LALAPG antibodies on sTREM2 levels. FIG. 20B shows the effect of humanized h3.10C2.v1 and hPara.09.v2 antibodies in human IgG1 N297G format.

In FIG. 22B, phosphorylation was also compared to hMDM cells modified to reduce TREM2 expression (gTREM2). FIG. 22C shows the effect of SYK phosphorylation with increasing doses of humanized antibodies hPara.09.v2 N297G or hPara.09.v2 Q100P/V104L N297G, or a control antibody. pSYK levels were measured and normalized to total SYK amounts. n=6 from 3 independent biological specimens.

FIG. 23A shows survival of Wild-type (WT, thin line) or TREM2 KO (KO, dotted line) iPSC microglia induced by treatment with increasing doses of hPara.09 v2, h3.10C2.v1, measured as fold of response induced by control antibody (gD hIgG1 N297G) treatment. Error bar+/−SEM. FIG. 23B shows survival of iPSC-MG cells in response to treatment with antibodies at increasing doses (0, 1, 10, 100 ng). Antibodies are grouped according to TREM2 binding (residue spans shown at top of figure). Error bar+/−SEM. FIG. 23C shows pSYK induction by humanized antibodies (hPara09.v2 N297G, hPara09.v2.Q100P/V104L N297G) in the iPSC-MG at 1, 4, and 24 hour time points. Error bar+/−SEM. * $P<0.05$,  $P<0.01$, ** $<0.0001$. FIG. 23D shows the effect of increasing concentrations of humanized Para.09.v2 antibody or an anti-gD control antibody on microglia survival in the presence and absence of a SYK inhibitor (SYKi). Error bar+/−SEM. FIG. 23E shows microglia survival and $EC_{50}$ (in nM, shown in table below graph) of the listed anti-TREM2 antibodies as compared to a control anti-gD antibody. Error bar+/−SEM.

FIG. 24A shows immunofluorescence images of Aβ plaque-like structure and Aβ aggregate formation around iPSC microglia treated with hPara.09.Q100P hIgG1 N297G or control gD.hIgG1.N297G. From left to right, panels show: staining for AP, amyloid plaque (Methoxy X04 staining), microglia staining (IBA1 staining), and merged images from all three stains, showing colocation of staining for IBA1 positive microglia, AP, and amyloid plaque. FIG. 24B shows total Aβ plaque intensity in the presence of increasing concentrations of several humanized anti-TREM2 antibodies or a control anti-gD antibody, all in human IgG1 N297G format. $EC_{50}$ values are provided in nM for each antibody in the table below the graph. Error bar+/−SEM. FIG. 24C shows average X04 iPSC-MG plaque intensity at increasing antibody concentrations of several humanized anti-TREM2 antibodies or a control anti-gD antibody, all in human IgG1 N297G format. $EC_{50}$ values are provided in nM for each antibody in the table below the curve.

FIGS. 25A-B show percent sTREM2 relative to control antibody (gp120) in plasma (FIG. 25A) and brain homogenates (FIG. 25B) samples from mice treated with 3.10C2 and Para.09 antibodies in murine IgG2 LALAPG format. FIG. 25C shows sTREM2 levels (pg/ml) in plasma from mice treated with increasing doses of Para.09 and AL2p58 antibodies in murine IgG2a LALAPG format, as compared to an isotype control.

FIGS. 26A-C show sTREM2 levels measured over 2 days in CSF (FIG. 26A), plasma (FIG. 26B), and brain (FIG. 26C). FIGS. 26D-F show sTREM2 levels measured over 28 days in CSF (FIG. 26D), plasma (FIG. 26E), and brain (FIG. 26F).

DESCRIPTION OF EXEMPLARY EMBODIMENTS

Definitions

Figure 4:
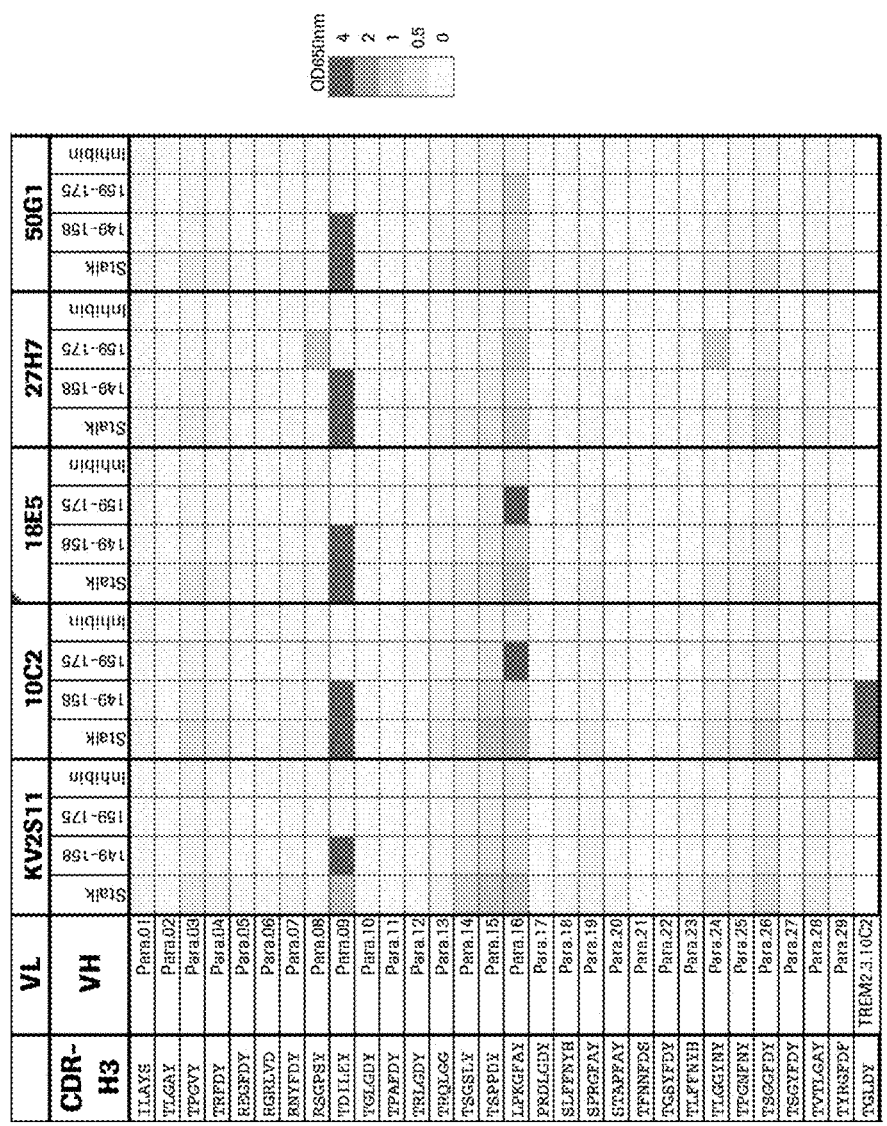
FIG. 4 shows an ELISA screen of antibodies with IGHV6-8 clones from a rat repertoire deep sequencing dataset combined with different light chains. Stalk, 149-158, 159-175 and Inhibin in the table refer to the stalk region of TREM2, fragments 149-158 and 159-175 of the stalk and a 30-mer inhibin control peptide, respectively. ELISA signal is shown in shades of gray. CDR H3 sequences of clones in the IMGT definition (length 5) are shown in the column to the left. Clone 3.10C2 was paired only to its own cognate light chain. KV2S11 refers to a light chain with the IGK2S11 germline segment in the germline sequence configuration and a similar VJ junctional sequence as the 3.10C2 antibody group.

As used herein, the term about refers to a numeric value, including, for example, whole numbers, fractions, and percentages, whether or not explicitly indicated. The term about generally refers to a range of numerical values (e.g., +/−5-10% of the recited range) that one of ordinary skill in the art would consider equivalent to the recited value (e.g., having the same function or result). When terms such as at least and about precede a list of numerical values or ranges, the terms modify all of the values or ranges provided in the list. In some instances, the term about may include numerical values that are rounded to the nearest significant figure.

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular.

In this application, the use of "or" means "and/or" unless stated otherwise. In the context of a multiple dependent claim, the use of "or" refers back to more than one preceding independent or dependent claim in the alternative only. Also, terms such as "element" or "component" encompass both elements and components comprising one unit and elements and components that comprise more than one subunit unless specifically stated otherwise.

Exemplary techniques used in connection with recombinant DNA, oligonucleotide synthesis, tissue culture and transformation (e.g., electroporation, lipofection), enzymatic reactions, and purification techniques are described, e.g., in Sambrook et al. Molecular Cloning: A Laboratory Manual ($2^{nd}$ ed., Cold Spring Harbor Laboratory Press, Cold Spring Harbor, N.Y. (1989)), among other places.

As utilized in accordance with the present disclosure, the following terms, unless otherwise indicated, shall be understood to have the following meanings:

"TREM2" or "Triggering receptor expressed on myeloid cells-2," as used herein, refers to a human TREM2 protein ("hTREM2"), unless expressly noted otherwise (i.e., murine TREM2, or cynomolgus TREM2, or the like). An exemplary hTREM2 amino acid sequence, including the signal sequence of amino acids 1-18, is shown in SEQ ID NO: 21, while an exemplary sequence without the signal sequence is shown in SEQ ID NO: 22. TREM2 including the signal sequence may also be referred to as the "precursor" or "preprotein" form of the protein, while TREM2 without the signal sequence may be referred to as the "mature" form of the protein. The membrane-bound form of the protein includes a V-type immunoglobulin (Ig) domain (at amino acids 19-128) followed by a TREM2 "stalk" domain (at amino acids 129-174; SEQ ID NO: 90), which collectively form the "extracellular domain" of the protein, followed by a transmembrane domain (residues 175-197), and a cytosolic domain (residues 198-230). A soluble form of the protein, "soluble TREM2" or "sTREM2" herein, may be generated in the body either by cleavage in the stalk domain or by alternative splicing. For example, proteases may cleave the protein between H157 and S158, cleaving of soluble TREM2, comprising the N-terminal portion of the protein up to the H157, e.g., residues 19-157. An exemplary sTREM2 amino acid sequence is shown in SEQ ID NO: 23. The portion of the protein that may get cleaved off to form sTREM2 is also known as the "ectodomain," and comprises residues 19-157. In general herein, the term "TREM2" as used herein refers to the membrane-bound form of the protein unless the context explicitly clarifies that both forms of the protein are being referenced. In addition, hTREM2 comprises several isoforms or alleles whose native sequences or splicing may differ from that shown in SEQ ID Nos: 21 and 22 and as described in the Examples section herein. The term TREM2 comprises all of these native forms of TREM2 unless a particular isoform or sequence is referred to.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured by common methods known in the art, including those described herein. Specific illustrative and exemplary methods for measuring binding affinity are described in the following.

The term "antibody" herein refers to a molecule comprising at least complementarity-determining region (CDR) 1, CDR2, and CDR3 of a heavy chain and at least CDR1, CDR2, and CDR3 of a light chain, wherein the molecule is capable of binding to antigen. The term is used in the broadest sense and encompasses various antibody structures, including but not limited to monoclonal antibodies, polyclonal antibodies, multispecific antibodies (e.g., bispecific antibodies, diabodies, etc.), full length antibodies, single-chain antibodies, antibody conjugates, and antibody fragments, so long as they exhibit the desired TREM2-specific binding activity.

An "isolated" antibody is one that has been separated from a component of its natural environment. In some aspects, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC) methods. For a review of methods for assessment of antibody purity, see, e.g., Flatman et al., *J. Chromatogr. B* 848:79-87 (2007).

An "antigen" refers to the target of an antibody, i.e., the molecule to which the antibody specifically binds. The term "epitope" denotes the site on an antigen, either proteinaceous or non-proteinaceous, to which an antibody binds. Epitopes on a protein can be formed both from contiguous amino acid stretches (linear epitope) or comprise non-contiguous amino acids (conformational epitope), e.g., coming in spatial proximity due to the folding of the antigen, i.e. by the tertiary folding of a proteinaceous antigen. Linear epitopes are typically still bound by an antibody after exposure of the proteinaceous antigen to denaturing agents, whereas conformational epitopes are typically destroyed upon treatment with denaturing agents. In some cases, a TREM2 "epitope" herein may "span" a site, such as a natural proteinase cleavage site or break point, in the molecule, meaning that there are close contacts between one or more antibody residues and the antigen on either side of the cleavage site, or that the antibody binds to TREM2 peptides that span the site. In such cases, the TREM2 epitope includes residues on each side of the cleavage site or break point.

In this disclosure, "specifically binds" or "specific binding" and similar terms means that the binding affinity is sufficiently strong that the interaction between the members of the binding pair cannot be due to random molecular associations (i.e. "nonspecific binding"). Specific binding typically requires a dissociation constant ($K_D$) of 1 μM or less. Specific binding may often, for example, involve a $K_D$ for TREM2 of 10 nM or less.

An "anti-TREM2 antibody" or a "TREM2-antibody" or an "antibody that specifically binds TREM2" or an "antibody that binds to TREM2" and similar phrases refer to an antibody that specifically binds to TREM2 as defined herein.

Certain antibodies herein "do not bind to soluble TREM2." As used herein, this means that the antibodies, when assayed in an ELISA assay, may not show any more than 10% binding to sTREM2, and in some cases do not show any more than 5% binding to sTREM2, wherein % binding is normalized against that of positive control antibody 1.16B8, whose binding to sTREM2 is set to 100%. The control antibody 1.16B8 light chain sequence is shown in SEQ ID NO: 170, and its heavy chain sequence is shown in SEQ ID NO: 171. In some embodiments, the ELISA assay may be performed as shown in Example 11 below and FIG. 16. In some embodiments, antibody 3.17A9 is used as a detection agent in the assay. The detection antibody 3.17A9 light chain sequence is shown in SEQ ID NO: 168, and its heavy chain sequence shown in SEQ ID No: 169. Certain antibodies herein "do not bind to FcγR," or have a heavy chain constant region or Fc region that "does not bind to FcγR," which means that binding is not detected above trace levels in a suitable in vitro binding assay.

The term "heavy chain" refers to a polypeptide comprising at least a heavy chain variable region, with or without a leader sequence. In some embodiments, a heavy chain comprises at least a portion of a heavy chain constant region. The term "full-length heavy chain" refers to a polypeptide comprising a heavy chain variable region and a heavy chain constant region, with or without a leader sequence.

The term "light chain" refers to a polypeptide comprising at least a light chain variable region, with or without a leader sequence. In some embodiments, a light chain comprises at least a portion of a light chain constant region. The term "full-length light chain" refers to a polypeptide comprising a light chain variable region and a light chain constant region, with or without a leader sequence.

The term "hypervariable region" or "HVR" as used herein refers to each of the regions of an antibody variable region which are hypervariable in sequence and which determine antigen binding specificity, for example "complementarity determining regions" ("CDRs"). Generally, antibodies comprise six CDRs: three in the VH (CDR-H1 or heavy chain CDR1, CDR-H2, CDR-H3), and three in the VL (CDR-L1, CDR-L2, CDR-L3). Unless otherwise indicated, the CDRs are determined according to the sequence table herein, and the amino acid positions of regions and domains of the heavy and light chain are numbered according to the Kabat numbering system described in Kabat, et al., *Sequences of Proteins of Immunological Interest*, 5th ed., Public Health Service, *National Institutes of Health*, Bethesda, MD (1991). In some cases, both Kabat and Chothia heavy chain CDR1 and CDR2 are provided in the sequence table. In the case of SEQ ID Nos: 1-6 and 9-10, and 11-16 and 19-20, the Kabat and Chothia CDRs differ in the CDR-H1 and CDR-H2 but are the same in the remaining four CDRs. One of skill in the art will understand that the CDR designations can also be determined according to McCallum, or any other scientifically accepted nomenclature system. See, e.g., Chothia and Lesk, J. Mol. Biol. 196:901-917 (1987); Kabat et al., *Sequences of Proteins of Immunological Interest, 5th* Ed. Public Health Service, National Institutes of Health, Bethesda, MD (1991); MacCallum et al. *J. Mol. Biol.* 262: 732-745 (1996)). Antigen contacts occurring at amino acid residues 27c-36 (L1), 46-55 (L2), 89-96 (L3), 30-35b (H1), 47-58 (H2), and 93-101 (H3) constitute MacCallum CDRs.

"Framework" or "FR" refers to the residues of the variable region residues that are not part of the complementary determining regions (CDRs). The FR of a variable region generally consists of four FRs: FR1, FR2, FR3, and FR4. Accordingly, the CDR and FR sequences generally appear in the following sequence in VH (or VL): FR1-CDR-H1(CDR-L1)-FR2-CDR-H2(CDR-L2)-FR3-CDR-H3(CDR-L3)-FR4.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three complementary determining regions (CDRs). See, e.g., Kindt et al. *Kuby Immunology*, 6$^{th}$ ed., W.H. Freeman and Co., page 91 (2007). A variable domain may comprise heavy chain (HC) CDR1-FR2-CDR2-FR3-CDR3 with or without all or a portion of FR1 and/or FR4; and light chain (LC) CDR1-FR2-CDR2-FR3-CDR3 with or without all or a portion of FR1 and/or FR4. That is, a variable domain may lack a portion of FR1 and/or FR4 so long as it retains antigen-binding activity. A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The light chain and heavy chain "constant regions" of an antibody refer to additional sequence portions outside of the FRs and CDRs and variable regions. Certain antibody fragments may lack all or some of the constant regions. From N- to C-terminus, each heavy chain has a variable domain (VH), also called a variable heavy domain or a heavy chain variable region, followed by three constant heavy domains (CH1, CH2, and CH3). Similarly, from N- to C-terminus, each light chain has a variable domain (VL), also called a variable light domain or a light chain variable region, followed by a constant light (CL) domain.

The term "Fc region" herein is used to define a C-terminal region of an immunoglobulin heavy chain that contains at least a portion of the constant region. The term includes native sequence Fc regions and variant Fc regions. In one aspect, a human IgG heavy chain Fc region extends from Cys226, or from Pro230, to the carboxyl-terminus of the heavy chain. However, antibodies produced by host cells may undergo post-translational cleavage of one or more, particularly one or two, amino acids from the C-terminus of the heavy chain. Therefore, an antibody produced by a host cell by expression of a specific nucleic acid molecule encoding a full-length heavy chain may include the full-length heavy chain, or it may include a cleaved variant of the full-length heavy chain. This may be the case where the final two C-terminal amino acids of the heavy chain are glycine (G446) and lysine (K447, numbering according to EU index). Therefore, the C-terminal lysine (Lys447), or the C-terminal glycine (Gly446) and lysine (Lys447), of the Fc region may or may not be present. Thus, a "full-length IgG1" for example, includes an IgG1 with Gly446 and Lys447, or without Lys447, or without both Gly446 and Lys447. Amino acid sequences of heavy chains including an Fc region are denoted herein without C-terminal glycine-lysine dipeptide if not indicated otherwise. In one aspect, a heavy chain including an Fc region as specified herein, comprised in an antibody according to the invention, may comprise Gly446 and Lys447 (numbering according to EU index). In one aspect, a heavy chain including an Fc region as specified herein, comprised in an antibody according to the invention, may comprise Gly446 (numbering according to EU index). Unless otherwise specified herein, numbering of amino acid residues in the Fc region or constant region is according to the EU numbering system, also called the EU index, as described in Kabat et al., *Sequences of Proteins of Immunological Interest*, 5$^{th}$ Ed. Public Health Service, National Institutes of Health, Bethesda, MD, 1991.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g., B cell receptor); and B cell activation. Antibodies with "intact effector function," for example, comprise a heavy chain constant region or Fc region that possesses the native, intact effector functions of its particular isotype, such as a wild-type heavy chain constant region or Fc region, or one that possesses modification that have not been shown to impact effector functions. In contrast, antibody heavy chain constant regions or Fc regions may be modified in various ways, such as by amino acid substitution, insertion, or deletion, or by glycosylation modifications, to either reduce or enhance effector function, depending upon the use of an antibody. Herein, some antibodies may have "intact effector function," while others may be "effectorless," meaning that they do not show detectable CDC or ADCC activity or that they comprise a heavy chain constant region or Fc region that has previously been shown to have no detectable CDC or ADCC activity. In other cases, antibodies may have a mutant Fc region or heavy chain constant region with "reduced effector function" compared to the corresponding wild-type Fc or heavy chain constant region (e.g., that has previously been shown to have reduced effector function, or that has reduced effector function in the context of the antibodies here). Such antibodies with reduced effector function may, for example, show a lower degree of CDC and/or ADCC activity and/or FcγR binding activity compared to the corresponding wild-type Fc region, and/or may retain some effector functions such as binding to particular Fc receptors such as FcRn, but combined with low or no detectable CDC or ADCC or FcγR binding activity, for example.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. In certain aspects, the antibody is of the IgG$_1$ isotype. In certain aspects, the antibody is of the IgG$_1$ isotype with the P329G, L234A and L235A mutation to reduce Fc-region effector function. In other aspects, the antibody is of the IgG$_2$ isotype. In certain aspects, the antibody is of the IgG$_4$ isotype with the S228P mutation in the hinge region to improve stability of IgG$_4$ antibody. In some aspects, the antibody may have a non-human IgG constant region, and may be, for example, a murine IgG$_2$a antibody such as a murine IgG$_2$a LALAPG antibody. The heavy chain constant domains that correspond to the different classes of immunoglobulins are called α, δ, ε, γ, and μ, respectively. The light chain of an antibody may be assigned to one of two types, called kappa (κ) and lambda (λ), based on the amino acid sequence of its constant domain.

An "antibody fragment" refers to a molecule other than an intact antibody that comprises a portion of an intact antibody that binds the antigen (i.e. TREM2) to which the intact antibody binds. Examples of antibody fragments include but are not limited to Fv, Fab, Fab', Fab'-SH, F(ab')$_2$; diabodies; linear antibodies; single-chain antibody molecules (e.g., scFv, and scFab); single domain antibodies (dAbs); and multispecific antibodies formed from antibody fragments. For a review of certain antibody fragments, see Holliger and Hudson, Nature Biotechnology 23:1126-1136 (2005).

The terms "full length antibody", "intact antibody", and "whole antibody" are used herein interchangeably to refer to an antibody having a structure substantially similar to a native antibody structure or, in the case of an IgG antibody, having heavy chains that contain an Fc region as defined herein.

The term "chimeric" antibody refers to an antibody in which a portion of the heavy and/or light chain is derived from a particular source or species, while the remainder of the heavy and/or light chain is derived from a different source or species.

A "humanized" antibody refers to a chimeric antibody comprising amino acid residues from non-human CDRs and amino acid residues from human FRs. In certain aspects, a humanized antibody will comprise substantially all of at least one, and typically two, variable domains, in which all or substantially all of the CDRs correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "multispecific" antibody is one that binds specifically to more than one target antigen, while a "bispecific" antibody is one that binds specifically to two antigens. An "antibody conjugate" is an antibody conjugated to one or more heterologous molecule(s), including but not limited to a therapeutic agent or a label.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity for the purposes of the alignment. Alignment for purposes of determining percent amino acid sequence identity can be achieved in various ways that are within the skill in the art, for instance, using publicly available computer software such as BLAST, BLAST-2, Clustal W, Megalign (DNASTAR) software or the FASTA program package. Those skilled in the art can determine appropriate parameters for aligning sequences, including any algorithms needed to achieve maximal alignment over the full length of the sequences being compared. Alternatively, the percent identity values can be generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087 and is described in WO 2001/007611.

Unless otherwise indicated, for purposes herein, percent amino acid sequence identity values are generated using the ggsearch program of the FASTA package version 36.3.8c or later with a BLOSUM50 comparison matrix. The FASTA program package was authored by W. R. Pearson and D. J. Lipman (1988), "Improved Tools for Biological Sequence Analysis", PNAS 85:2444-2448; W. R. Pearson (1996) "Effective protein sequence comparison" Meth. Enzymol. 266:227-258; and Pearson et. Al. (1997) Genomics 46:24-36 and is publicly available from fasta.bioch.virginia.edu/fasta_www2/fasta_down.shtml or Ebi.ac.uk/Tools/sss/fasta. Alternatively, a public server accessible at fasta.bioch.virginia.edu/fasta_www2/index.cgi can be used to compare the sequences, using the ggsearch (global protein: protein) program and default options (BLOSUM50; open: −10; ext: −2; Ktup=2) to ensure a global, rather than local, alignment is performed. Percent amino acid identity is given in the output alignment header.

The term "nucleic acid molecule" or "polynucleotide" includes any compound and/or substance that comprises a polymer of nucleotides. Each nucleotide is composed of a base, specifically a purine- or pyrimidine base (i.e. cytosine (C), guanine (G), adenine (A), thymine (T) or uracil (U)), a sugar (i.e. deoxyribose or ribose), and a phosphate group. Often, the nucleic acid molecule is described by the sequence of bases, whereby said bases represent the primary structure (linear structure) of a nucleic acid molecule. The sequence of bases is typically represented from 5' to 3'. Herein, the term nucleic acid molecule encompasses deoxyribonucleic acid (DNA) including e.g., complementary DNA (cDNA) and genomic DNA, ribonucleic acid (RNA), in particular messenger RNA (mRNA), synthetic forms of DNA or RNA, and mixed polymers comprising two or more of these molecules. The nucleic acid molecule may be linear or circular. In addition, the term nucleic acid molecule includes both sense and antisense strands, as well as single stranded and double stranded forms. Moreover, the herein described nucleic acid molecule can contain naturally occurring or non-naturally occurring nucleotides. Examples of non-naturally occurring nucleotides include modified nucleotide bases with derivatized sugars or phosphate backbone linkages or chemically modified residues. Nucleic acid molecules also encompass DNA and RNA molecules which are suitable as a vector for direct expression of an antibody of the invention in vitro and/or in vivo, e.g., in a host or patient. Such DNA (e.g., cDNA) or RNA (e.g., mRNA) vectors, can be unmodified or modified. For example, mRNA can be chemically modified to enhance the stability of the RNA vector and/or expression of the encoded molecule so that mRNA can be injected into a subject to generate the antibody in vivo (see e.g., Stadler et al, Nature Medicine 2017, published online 12 Jun. 2017, doi:10.1038/nm.4356 or EP 2 101 823 B1).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-TREM2 antibody" refers to one or more nucleic acid molecules encoding anti-TREM2 antibody heavy and light chains (or fragments thereof), including such nucleic acid molecule(s) in a single vector or separate vectors, and such nucleic acid molecule(s) present at one or more locations in a host cell.

The term "vector", as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

The terms "host cell", "host cell line", and "host cell culture" are used interchangeably and refer to cells into which exogenous nucleic acid has been introduced, including the progeny of such cells.

The term "signal sequence" or "leader sequence" refers to a sequence of amino acid residues located at the N terminus of a polypeptide that facilitates secretion of a polypeptide from a mammalian cell. A leader sequence may be cleaved upon export of the polypeptide from the mammalian cell, forming a mature protein. Leader sequences may be natural or synthetic, and they may be heterologous or homologous to the protein to which they are attached. Nonlimiting exemplary leader sequences also include leader sequences from heterologous proteins. In some embodiments, an antibody lacks a leader sequence. In some embodiments, an antibody comprises at least one leader sequence, which may be selected from native antibody leader sequences and heterologous leader sequences.

The term "shedding" as used herein refers to the process of creating a soluble TREM2 from a membrane-bound TREM2 by proteolytic cleavage of the stalk region of the protein. In vivo, "shedding" may occur at the cell surface, for example, due to cleavage of TREM2 on the cell membrane by a metalloproteinase or other enzyme. In some cases, cleavage occurs between H157 and S158 of the protein, forming sTREM2 from the ectodomain residues 19-157.

The term "agonist" as used herein refers to a substance, such as an antibody, that causes an increase in at least one activity or function of a molecule to which it binds, or otherwise activates or helps to activate the molecule. The term "antagonist" as used herein refers to a substance, such as an antibody, that causes a decrease in at least one activity or function of a molecule to which it binds, or that otherwise blocks or inhibits at least one activity or function of the molecule.

An "agonist anti-TREM2 antibody" or similar phrases herein, for example, refers to an antibody that induces luciferase reporter activity in Jurkat-NFAT reporter cells expressing human TREM2 and/or that induces SYK phosphorylation (p-SYK) in Jurkat-NFAT reporter cells expressing human TREM2, in human monocyte-derived macrophage (MDM) cells and/or in human induced pluripotent stem cell (iPSC)-derived microglia cells. Agonist anti-TREM2 antibodies may also have further activities, as described herein, such as enhancing survival of human iPSC-derived microglia in the absence of IL-34 and CSF-1, and activating TREM2 signaling in human macrophages and microglia, among other activities, for example.

The terms "subject" and "patient" are used interchangeably herein to refer to a human. In some embodiments, methods of treating other mammals, including, but not limited to, rodents, simians, felines, canines, equines, bovines, porcines, ovines, caprines, mammalian laboratory animals, mammalian farm animals, mammalian sport animals, and mammalian pets, are also provided.

"Treatment," as used herein, covers any administration or application of a therapeutic for disease in a human, or other mammal, and includes inhibiting the disease or progression of the disease, inhibiting or slowing the disease or its progression, arresting or slowing its development, inhibiting, reducing, or slowing development of at least one symptom of the disease, slowing the time to onset of the disease, preventing onset of at least one disease symptom, slowing the time to onset of at least one disease symptom, partially or fully relieving the disease, or curing the disease, for example, by causing regression, or restoring or repairing a lost, missing, or defective function; or stimulating an inefficient process. The terms "inhibition" or "inhibit" refer to a decrease or cessation of any symptom or phenotypic characteristic or to the decrease or cessation in the incidence, degree, or likelihood of that symptom or characteristic.

A "pharmaceutically acceptable carrier" refers to a nontoxic solid, semisolid, or liquid filler, diluent, encapsulating material, formulation auxiliary, or carrier conventional in the art for use with a therapeutic agent that together comprise a "pharmaceutical composition" for administration to a subject. A pharmaceutically acceptable carrier is non-toxic to recipients at the dosages and concentrations employed and is compatible with other ingredients of the formulation. The pharmaceutically acceptable carrier is appropriate for the formulation employed. For example, if the therapeutic agent is to be administered orally, the carrier may be a gel capsule. If the therapeutic agent is to be administered subcutaneously, the carrier ideally is not irritable to the skin and does not cause injection site reaction.

The term "effective amount" herein refers to an amount that is sufficient to result in a desired outcome, such as treatment, inhibition, or reduction as described above.

Development of Unique Anti-TREM2 Antibodies

The disclosure herein encompasses anti-TREM2 antibodies. In some embodiments herein, the antibodies have a unique set of properties. For example, certain antibodies herein (a) bind specifically to the TREM2 stalk domain at an epitope spanning the cleavage site between residues 157 and 158, and also bind specifically to a polypeptide consisting of residues 151-165 of TREM2, (b) do not bind to soluble TREM2, and thus, may not present a significant risk of soluble TREM2 binding in vivo, (c) act as TREM2 agonists, and (d) specifically bind to TREM2 with dissociation constants of, for example, 100-500 pM, 10-50 pM, or 1-10 pM.

Figure 3A:
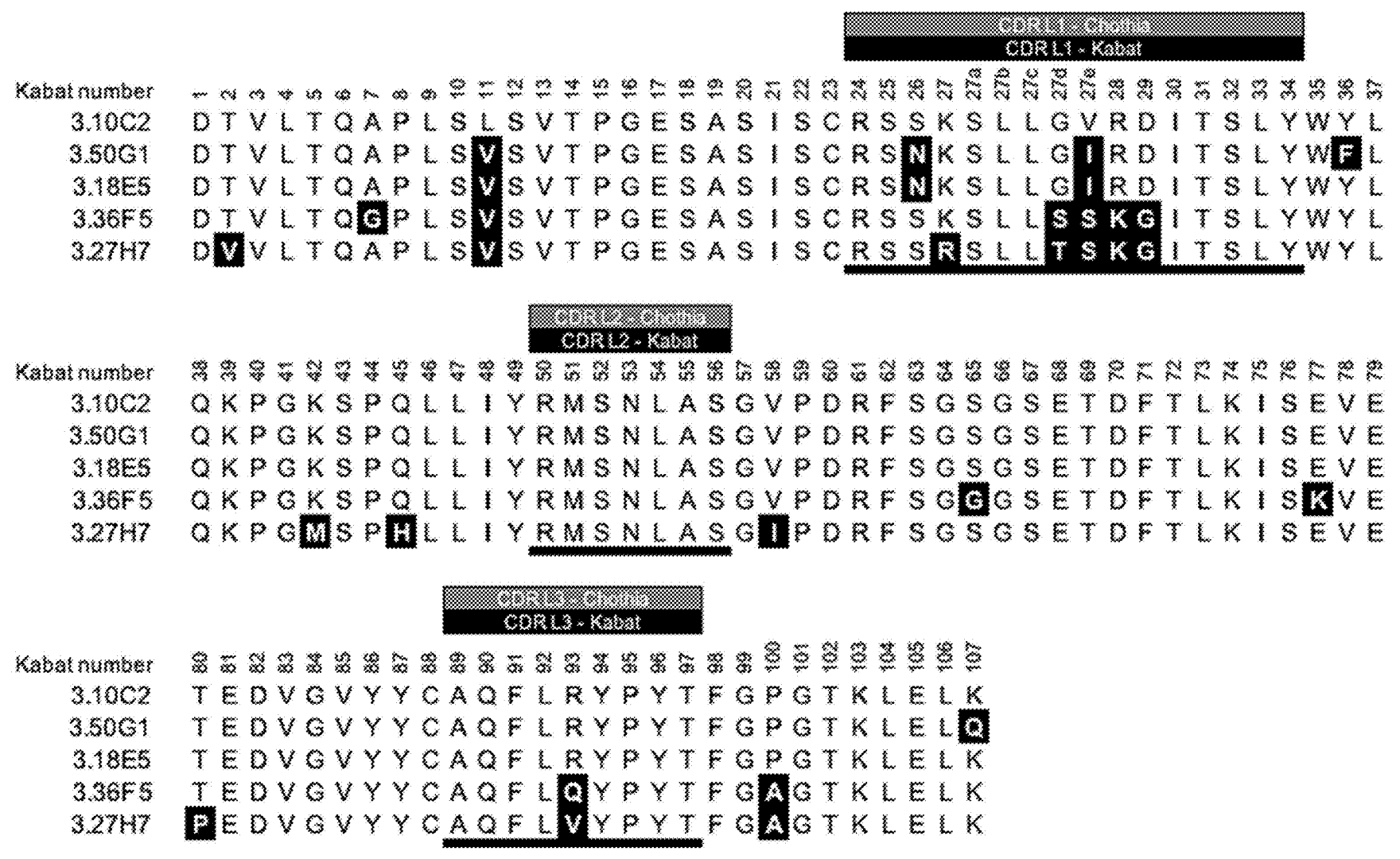

As described in the Examples section below, particular exemplary antibodies herein were obtained in part following an initial screen of rat anti-human TREM2 antibodies. A particular set of rat anti-human TREM2 antibodies that specifically bind to a binding epitope in the region of amino acids 151-165 of TREM2 were found to have both relatively high affinity and a lack of binding to soluble TREM2, unlike other antibodies found in the screen and unlike other previously described anti-TREM2 antibodies. This set of antibodies includes rat anti-human antibodies 3.10C2, 3.50G1, 3.18E5, 3.27H7 (also called the "3.10C2 group antibodies") and 3.36F5. (See FIGS. 3A-3B, and also FIGS. 2A-2B and 16.)

Further TREM2-immunized rat immune repertoire deep sequencing experiments were conducted on the heavy chain variable region to obtain antibodies with yet higher affinity for TREM2. This experiment led to the identification of the Para.09 heavy chain variable region, which is clonally unrelated to the 3.10C2 group antibodies and differs in the heavy chain CDR3 compared to the previously identified antibodies of the 3.10C2 group. (See FIGS. 4 and 8B.) The Para.09 heavy chain variable region was combined with light chain variable regions from the previously identified 3.10C2 group antibodies. The affinity of the resulting Fab fragments for human and cynomolgus TREM2 was on the order of 1-5 pM (i.e. $1-5 \times 10^{-12}$M). (See Table 1 and Example 5.)

The rat anti-human antibodies were then humanized. Antibodies h3.10C2.v1 and hPara.09.v2 are examples of humanized antibodies herein. (See FIGS. 9A-B and 12A-B.) Further modifications of the light chain framework regions of the humanized antibodies were then conducted, for example, to improve properties such as expression yield. Particular modifications at positions 58, 100, and/or 104, for example, of the light chain framework regions (e.g., I58V, Q100P, and/or V104L, (as used herein, the nomenclature convention is "amino acid-position-new amino acid," i.e., I58V denotes amino acid I at position 58 is changed to amino acid V)) resulted in humanized antibodies that not only retain the features of the starting rat anti-human antibodies, such as high affinity for the TREM2 stalk domain, but that also express in relatively high yield. Such exemplary antibodies are shown in FIGS. 13A-B and 14A-B. As further described in Examples 11 and 13-17 below, for instance, antibodies herein are TREM2 agonists and also display a number of other beneficial biological properties in vitro and in vivo.

Exemplary Anti-TREM2 Antibody Sequences

In some embodiments, the disclosure encompasses an isolated antibody that specifically binds to TREM2, wherein the antibody comprises a heavy chain variable region (VH) and a light chain variable region (VL), wherein the VH comprises a CDR-H1 comprising the amino acid sequence of SEQ ID NO: 1, 9, 11, 19, or 62 and a CDR-H2 comprising the amino acid sequence of SEQ ID NO: 2, 10, 12, 20, 55, 63, 65, or 73. In some embodiments, the VL comprises a CDR-L1 comprising the amino acid sequence of SEQ ID NO: 4, 27, 37, 47, 57, or 67; a CDR-L2 comprising the amino acid sequence of SEQ ID NO: 5; and a CDR-L3 comprising the amino acid sequence of SEQ ID NO: 6, 29, 39, 49, 59, or 69. In some embodiments, the VH comprises a CDR-H3 comprising the amino acid sequence as follows: $X_1$-$X_2$-$X_3$-Y, wherein $X_1$ and $X_2$ together are either I-L or L, and wherein $X_3$ is either D or E. In some embodiments, the antibody comprises a VH derived from rat IGHV6-8 germline segments. In some embodiments, the antibody comprises a VL derived from rat IGKV2S11 germline segments. In some embodiments, the antibody comprises a VH derived from rat IGHV6-8 and a VL derived from rat IGKV2S11.

Figure 3B:
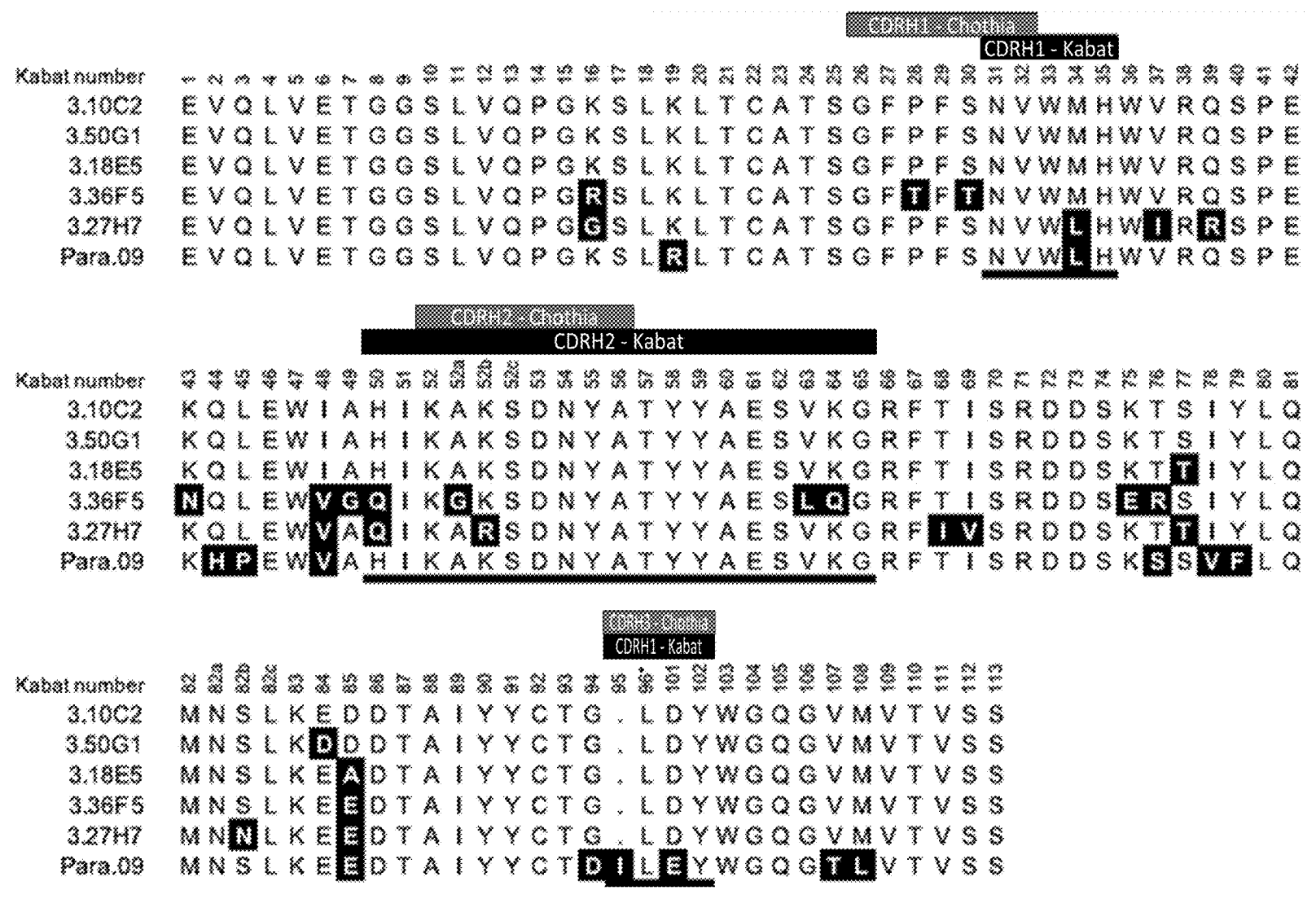

In some embodiments, the disclosure encompasses an isolated antibody that specifically binds to TREM2, wherein the antibody comprises a heavy chain variable region (VH) comprising a CDR-H1 comprising the amino acid sequence of SEQ ID NO: 1, 9, 11, 19, or 62; a CDR-H2 comprising the amino acid sequence of SEQ ID NO: 2, 10, 12, 20, 55, 63, 65, or 73; and a CDR-H3 comprising the amino acid sequence as follows: $X_1$-$X_2$-$X_3$-Y, wherein $X_1$ and $X_2$ together are either I-L or L, and wherein $X_3$ is either D or E; and a light chain variable region (VL) comprising a CDR-L1 comprising the amino acid sequence of SEQ ID NO: 4, 27, 37, 47, 57, or 67; a CDR-L2 comprising the amino acid sequence of SEQ ID NO: 5; and a CDR-L3 comprising the amino acid sequence of SEQ ID NO: 6, 29, 39, 49, 59, or 69. For example, such antibodies are shown in FIG. 3A-3B. Examples include antibodies comprising the heavy chain Kabat CDRs of 3.10C2, 3.50G1, 3.18E5, 3.36F5, and 3.27H7, as well as Para.09. In some cases, the antibody comprises a heavy chain variable region (VH) comprising a CDR-H1 comprising the amino acid sequence of SEQ ID NO: 1, 9, 11, or 19; a CDR-H2 comprising the amino acid sequence of SEQ ID NO: 2, 10, 12, or 20; and a CDR-H3 comprising the amino acid sequence as follows: $X_1$-$X_2$-$X_3$-Y, wherein $X_1$ and $X_2$ together are either I-L or L, and wherein $X_3$ is either D or E; and a light chain variable region (VL) comprising a CDR-L1 comprising the amino acid sequence of SEQ ID NO: 4, a CDR-L2 comprising the amino acid sequence of SEQ ID NO: 5, and a CDR-L3 comprising the amino acid sequence of SEQ ID NO: 6.

In some cases, the light chain variable region (VL) comprises the light chain CDRs of either 3.10C2 or 3.27H7. For example, the antibody light chain variable region may comprise a CDR-L1 comprising the amino acid sequence of SEQ ID NO: 4, 27, or 67; a CDR-L2 comprising the amino acid sequence of SEQ ID NO: 5; and a CDR-L3 comprising the amino acid sequence of SEQ ID NO: 6, 29, or 69. In some cases, the antibody comprises the light chain CDRs of 3.27H7, i.e., a CDR-L1 comprising the amino acid sequence of SEQ ID NO: 4, a CDR-L2 comprising the amino acid sequence of SEQ ID NO: 5, and a CDR-L3 comprising the amino acid sequence of SEQ ID NO: 6.

In some cases, the heavy chain variable region (VH) comprises a CDR-H1 comprising the amino acid sequence of SEQ ID NO: 1 or 9; a CDR-H2 comprising the amino acid sequence of SEQ ID NO: 2 or 10; and a CDR-H3 comprising the amino acid sequence of SEQ ID NO: 3; and wherein the light chain variable region (VL) comprises a CDR-L1 comprising the amino acid sequence of SEQ ID NO: 4, a CDR-L2 comprising the amino acid sequence of SEQ ID NO: 5, and a CDR-L3 comprising the amino acid sequence of SEQ ID NO: 6. In other cases, the heavy chain variable region (VH) comprises a CDR-H1 comprising the amino acid sequence of SEQ ID NO: 11 or 19; a CDR-H2 comprising the amino acid sequence of SEQ ID NO: 12 or 20; and a CDR-H3 comprising the amino acid sequence of SEQ ID NO: 13; and wherein the light chain variable region (VL) comprises a CDR-L1 comprising the amino acid sequence of SEQ ID NO: 4, a CDR-L2 comprising the amino acid sequence of SEQ ID NO: 5, and a CDR-L3 comprising the amino acid sequence of SEQ ID NO: 6.

In some embodiments, an antibody herein may comprise a heavy chain variable region amino acid sequence that is at least 90%, 95%, 97%, or 99% identical to that of a sequence shown in FIG. 3B. In some embodiments, an antibody herein may comprise a heavy chain variable region amino acid sequence that is at least 90%, 95%, 97%, or 99% identical to that of a sequence shown in FIG. 6B. In some embodiments, an antibody herein may comprise a heavy chain variable region amino acid sequence that is at least 90%, 95%, 97%, or 99% identical to that of a sequence shown in FIG. 8B. In some embodiments, an antibody herein may comprise a heavy chain variable region amino acid sequence that is at least 90%, 95%, 97%, or 99% identical to that of a sequence shown in FIG. 9B. In some embodiments, an antibody herein may comprise a heavy chain variable region amino acid sequence that is at least 90%, 95%, 97%, or 99% identical to that of a sequence shown in FIG. 12B. In some embodiments, an antibody herein may comprise a heavy chain variable region amino acid sequence that is at least 90%, 95%, 97%, or 99% identical to that of a sequence shown in FIG. 13B. In some embodiments, an antibody herein may comprise a heavy chain variable region amino acid sequence that is at least 90%, 95%, 97%, or 99% identical to that of a sequence shown in FIG. 14B. In some embodiments, the antibody framework regions may be chimeric or humanized.

In some cases, the antibody comprises a VH that is at least 90%, at least 95%, at least 97%, or at least 99% identical to the amino acid sequence of SEQ ID NO: 7 or 17. In some embodiments, the antibody comprises a VH that is at least 90%, at least 95%, at least 97%, or at least 99% identical to the amino acid sequence of SEQ ID NO: 7, 17, 30, 40, 50, 60, 70, 76, 77, 78, 81, 82, 83, 133, 135, 137, 139, 146, 148, 150, or 152. In some embodiments, the antibody comprises a VH that is at least 90%, at least 95%, at least 97%, or at least 99% identical to the amino acid sequence of SEQ ID NO: 7, 17, 133, 135, 137, 139, 146, 148, 150, or 152. In other cases, the antibody comprises a VH comprising the amino acid sequence of SEQ ID NO: 7, 17, 30, 40, 50, 60, 70, 76, 77, 78, 81, 82, 83, 133, 135, 137, 139, 146, 148, 150, or 152. In some embodiments, the antibody comprises a VH comprising the amino acid sequence of SEQ ID NO: 7, 17, 133, 135, 137, 139, 146, 148, 150, or 152.

In some embodiments, the antibody light chain variable region comprises an amino acid sequence at least 90%, 95%, 97%, or 99% identical to that of a sequence shown in FIG. 3A. In some embodiments, the antibody light chain variable region comprises an amino acid sequence at least 90%, 95%, 97%, or 99% identical to that of a sequence shown in FIG. 6A. In some embodiments, the antibody light chain variable region comprises an amino acid sequence at least 90%, 95%, 97%, or 99% identical to that of a sequence shown in FIG. 8A. In some embodiments, the antibody light chain variable region comprises an amino acid sequence at least 90%, 95%, 97%, or 99% identical to that of a sequence shown in FIG. 9A. In some embodiments, the antibody light chain variable region comprises an amino acid sequence at least 90%, 95%, 97%, or 99% identical to that of a sequence shown in FIG. 12A. In some embodiments, the antibody light chain variable region comprises an amino acid sequence at least 90%, 95%, 97%, or 99% identical to that of a sequence shown in FIG. 13A. In some embodiments, the antibody light chain variable region comprises an amino acid sequence at least 90%, 95%, 97%, or 99% identical to that of a sequence shown in FIG. 14A. In some embodiments, the light chain variable region frameworks are humanized or chimeric.

In some embodiments, the antibody comprises a VL that is at least 90%, at least 95%, at least 97%, or at least 99% identical to the amino acid sequence of SEQ ID NO: 8 or 18. In some embodiments, the antibody comprises a VL that is at least 90%, at least 95%, at least 97%, or at least 99% identical to the amino acid sequence of SEQ ID NO: 8, 18, 31, 41, 51, 61, 71, 79, 80, 84, 85, 132, 134, 136, 138, 145, 147, 149, or 151. In some embodiments, the antibody comprises a VL that is at least 90%, at least 95%, at least 97%, or at least 99% identical to the amino acid sequence of SEQ ID NO: 8, 18, 132, 134, 136, 138, 145, 147, 149, or 151. In some embodiments, the antibody comprises a VL comprising amino acid sequence of SEQ ID NO: 8 or 18. In some embodiments, the antibody comprises a VL comprising the amino acid sequence of SEQ ID NO: 8, 18, 31, 41, 51, 61, 71, 79, 80, 84, 85, 132, 134, 136, 138, 145, 147, 149, or 151. In some embodiments, the antibody comprises a VL comprising the amino acid sequence of SEQ ID NO: 8, 18, 132, 134, 136, 138, 145, 147, 149, or 151.

In some embodiments, the antibody comprises the heavy chain CDRs of antibody 3.10C2, 3.50G1, 3.18E5, 3.36F5, 3.27H7 or Para.09 and the light chain CDRs of antibody 3.27H7. In some embodiments, the antibody comprises the heavy chain CDRs of antibody 3.10C2 or Para.09 and the light chain CDRs of antibody 3.27H7. (See FIGS. 3A-B.) In some embodiments, the antibody is humanized or chimeric.

In some embodiments, the antibody comprises one of the following sets of CDRs:
(a) a heavy chain variable region (VH) comprising a CDR-H1 comprising the amino acid sequence of SEQ ID NO: 1, a CDR-H2 comprising the amino acid sequence of SEQ ID NO: 2, and a CDR-H3 comprising the amino acid sequence of SEQ ID NO: 3; and a light chain variable region (VL) comprising a CDR-L1 comprising the amino acid sequence of SEQ ID NO: 4, a CDR-L2 comprising the amino acid sequence of SEQ ID NO: 5, and a CDR-L3 comprising the amino acid sequence of SEQ ID NO: 6;
(b) a heavy chain variable region (VH) comprising a CDR-H1 comprising the amino acid sequence of SEQ ID NO: 9, a CDR-H2 comprising the amino acid sequence of SEQ ID NO: 10, and a CDR-H3 comprising the amino acid sequence of SEQ ID NO: 3; and a light chain variable region (VL) comprising a CDR-L1 comprising the amino acid sequence of SEQ ID NO: 4, a CDR-L2 comprising the amino acid sequence of SEQ ID NO: 5, and a CDR-L3 comprising the amino acid sequence of SEQ ID NO: 6;
(c) a heavy chain variable region (VH) comprising a CDR-H1 comprising the amino acid sequence of SEQ ID NO: 11, a CDR-H2 comprising the amino acid sequence of SEQ ID NO: 12, and a CDR-H3 comprising the amino acid sequence of SEQ ID NO: 13; and a light chain variable region (VL) comprising a CDR-L1 comprising the amino acid sequence of SEQ ID NO: 14, a CDR-L2 comprising the amino acid sequence of SEQ ID NO: 15, and a CDR-L3 comprising the amino acid sequence of SEQ ID NO: 16;
(d) a heavy chain variable region (VH) comprising a CDR-H1 comprising the amino acid sequence of SEQ ID NO: 19, a CDR-H2 comprising the amino acid sequence of SEQ ID NO: 20, and a CDR-H3 comprising the amino acid sequence of SEQ ID NO: 13; and a light chain variable region (VL) comprising a CDR-L1 comprising the amino acid sequence of SEQ ID NO: 14, a CDR-L2 comprising the amino acid sequence of SEQ ID NO: 15, and a CDR-L3 comprising the amino acid sequence of SEQ ID NO: 16;
(e) a heavy chain variable region (VH) comprising a CDR-H1 comprising the amino acid sequence of SEQ ID NO: 24, a CDR-H2 comprising the amino acid sequence of SEQ ID NO: 25, and a CDR-H3 comprising the amino acid sequence of SEQ ID NO: 26; and a light chain variable region (VL) comprising a CDR-L1 comprising the amino acid sequence of SEQ ID NO: 27, a CDR-L2 comprising the amino acid sequence of SEQ ID NO: 28, and a CDR-L3 comprising the amino acid sequence of SEQ ID NO: 29;
(f) a heavy chain variable region (VH) comprising a CDR-H1 comprising the amino acid sequence of SEQ ID NO: 34, a CDR-H2 comprising the amino acid sequence of SEQ ID NO: 35, and a CDR-H3 comprising the amino acid sequence of SEQ ID NO: 36; and a light chain variable region (VL) comprising a CDR-L1 comprising the amino acid sequence of SEQ ID NO: 37, a CDR-L2 comprising the amino acid sequence of SEQ ID NO: 38, and a CDR-L3 comprising the amino acid sequence of SEQ ID NO: 39;
(g) a heavy chain variable region (VH) comprising a CDR-H1 comprising the amino acid sequence of SEQ ID NO: 44, a CDR-H2 comprising the amino acid sequence of SEQ ID NO: 45, and a CDR-H3 comprising the amino acid sequence of SEQ ID NO: 46; and a light chain variable region (VL) comprising a CDR-L1 comprising the amino acid sequence of SEQ ID NO: 47, a CDR-L2 comprising the amino acid sequence of SEQ ID NO: 48, and a CDR-L3 comprising the amino acid sequence of SEQ ID NO: 49;
(h) a heavy chain variable region (VH) comprising a CDR-H1 comprising the amino acid sequence of SEQ ID NO: 54, a CDR-H2 comprising the amino acid sequence of SEQ ID NO: 55, and a CDR-H3 comprising the amino acid sequence of SEQ ID NO: 56; and a light chain variable region (VL) comprising a CDR-L1 comprising the amino acid sequence of SEQ ID NO: 57, a CDR-L2 comprising the amino acid sequence of SEQ ID NO: 58, and a CDR-L3 comprising the amino acid sequence of SEQ ID NO: 59; or
(i) a heavy chain variable region (VH) comprising a CDR-H1 comprising the amino acid sequence of SEQ ID NO: 64, a CDR-H2 comprising the amino acid sequence of SEQ ID NO: 65, and a CDR-H3 comprising the amino acid sequence of SEQ ID NO: 66; and a light chain variable region (VL) comprising a CDR-L1 comprising the amino acid sequence of SEQ ID NO: 67, a CDR-L2 comprising the amino acid sequence of SEQ ID NO: 68, and a CDR-L3 comprising the amino acid sequence of SEQ ID NO: 69. CDRs (a) through (i) are also referred to in the subsequent four paragraphs.

In some embodiments, the antibody:
(a) comprises the CDRs of (a) or (b) from the paragraph above and further comprises a VH that is at least 90%, at least 95%, at least 97%, or at least 99% identical to the amino acid sequence of SEQ ID NO: 7;
(c) comprises the CDRs of (c) or (d) from the paragraph above and further comprises a VH that is at least 90%, at least 95%, at least 97%, or at least 99% identical to the amino acid sequence of SEQ ID NO: 17;
(e) comprises the CDRs of (e) from the paragraph above and further comprises a VH that is at least 90%, at least 95%, at least 97%, or at least 99% identical to the amino acid sequence of SEQ ID NO: 30;
(f) comprises the CDRs of (f) from the paragraph above and further comprises a VH that is at least 90%, at least 95%, at least 97%, or at least 99% identical to the amino acid sequence of SEQ ID NO: 40;
(g) comprises the CDRs of (g) from the paragraph above and further comprises a VH that is at least 90%, at least 95%, at least 97%, or at least 99% identical to the amino acid sequence of SEQ ID NO: 50;
(h) comprises the CDRs of (h) from the paragraph above and further comprises a VH that is at least 90%, at least 95%, at least 97%, or at least 99% identical to the amino acid sequence of SEQ ID NO: 60; or
(i) comprises the CDRs of (i) from the paragraph above and further comprises a VH that is at least 90%, at least 95%, at least 97%, or at least 99% identical to the amino acid sequence of SEQ ID NO: 70

In some embodiments, the antibody:
(a) comprises the CDRs of (a) or (b) above and further comprises a VL that is at least 90%, at least 95%, at least 97%, or at least 99% identical to the amino acid sequence of SEQ ID NO: 8;
(c) comprises the CDRs of (c) or (d) above and further comprises a VL that is at least 90%, at least 95%, at least 97%, or at least 99% identical to the amino acid sequence of SEQ ID NO: 18;
(e) comprises the CDRs of (e) above and further comprises a VL that is at least 90%, at least 95%, at least 97%, or at least 99% identical to the amino acid sequence of SEQ ID NO: 31;
(f) comprises the CDRs of (f) above and further comprises a VL that is at least 90%, at least 95%, at least 97%, or at least 99% identical to the amino acid sequence of SEQ ID NO: 41;
(g) comprises the CDRs of (g) above and further comprises a VL that is at least 90%, at least 95%, at least 97%, or at least 99% identical to the amino acid sequence of SEQ ID NO: 51;
(h) comprises the CDRs of (h) above and further comprises a VL that is at least 90%, at least 95%, at least 97%, or at least 99% identical to the amino acid sequence of SEQ ID NO: 61; or
(i) comprises the CDRs of (i) above and further comprises a VL that is at least 90%, at least 95%, at least 97%, or at least 99% identical to the amino acid sequence of SEQ ID NO: 71.

In some cases, the antibody:
(a) comprises the CDRs of (a) and further comprises a VH comprising the amino acid sequence of SEQ ID NO: 7;
(b) comprises the CDRs of (b) and further comprises a VH comprising the amino acid sequence of SEQ ID NO: 7;
(c) comprises the CDRs of (c) and further comprises a VH comprising the amino acid sequence of SEQ ID NO: 17;
(d) comprises the CDRs of (d) and further comprises a VH comprising the amino acid sequence of SEQ ID NO: 17;
(e) comprises the CDRs of (e) and further comprises a VH comprising the amino acid sequence of SEQ ID NO: 30;
(f) comprises the CDRs of (f) and further comprises a VH comprising the amino acid sequence of SEQ ID NO: 40;
(g) comprises the CDRs of (g) and further comprises a VH comprising the amino acid sequence of SEQ ID NO: 50;
(h) comprises the CDRs of (h) and further comprises a VH comprising the amino acid sequence of SEQ ID NO: 60; or
(i) comprises the CDRs of (i) and further comprises a VH comprising the amino acid sequence of SEQ ID NO: 70

In some cases, the antibody:
(a) comprises the CDRs of (a) and further comprises a VL comprising the amino acid sequence of SEQ ID NO: 8;
(b) comprises the CDRs of (b) and further comprises a VL comprising the amino acid sequence of SEQ ID NO: 8;
(c) comprises the CDRs of (c) and further comprises a VL comprising the amino acid sequence of SEQ ID NO: 18;
(d) comprises the CDRs of (d) and further comprises a VL comprising the amI acid sequence of SEQ ID NO: 18;
(e) comprises the CDRs of (e) and further comprises a VL comprising the amino acid sequence of SEQ ID NO: 31;
(f) comprises the CDRs of (f) and further comprises a VL comprising the amino acid sequence of SEQ ID NO: 41;
(g) comprises the CDRs of (g) and further comprises a VL comprising the amino acid sequence of SEQ ID NO: 51;
(h) comprises the CDRs of (h) and further comprises a VL comprising the amino acid sequence of SEQ ID NO: 61; or
(i) comprises the CDRs of (i) and further comprises a VL comprising the amino acid sequence of SEQ ID NO: 71.

Figure 6B:
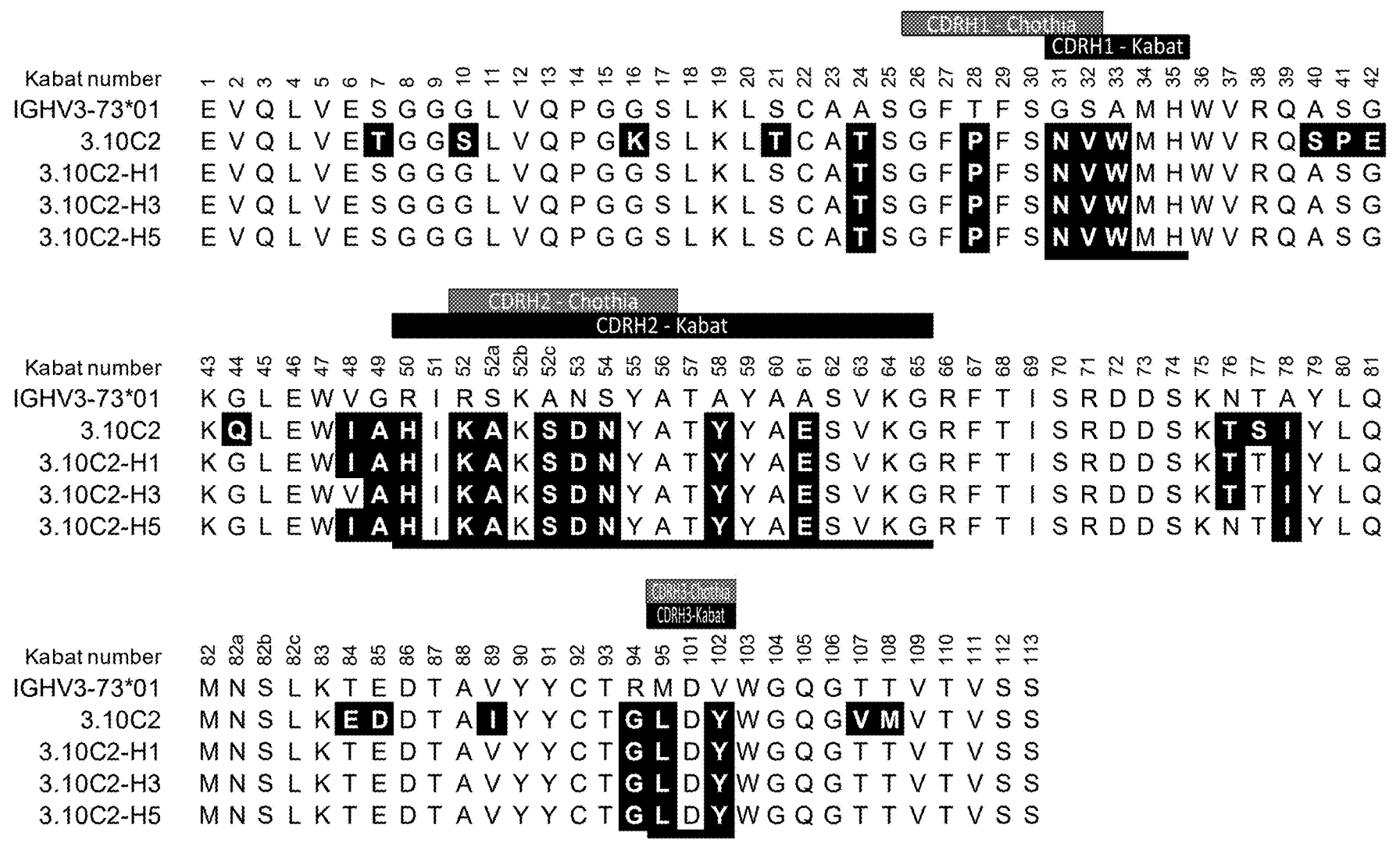
Figure 8A:
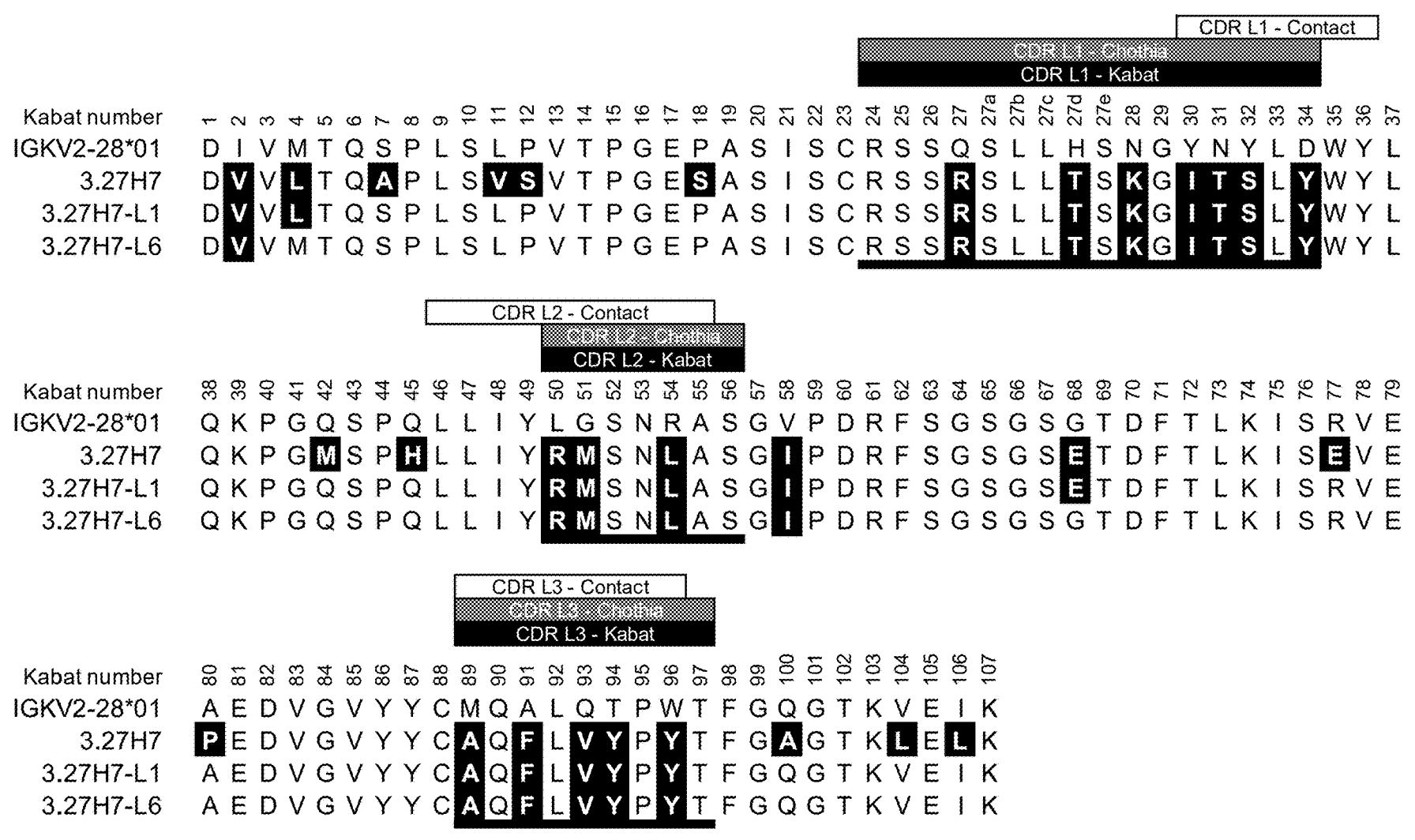

As noted above, in some embodiments, the VH and/or VL are humanized. In some embodiments, the antibody comprises a light chain and heavy chain as shown in FIG. 6A-B, for example, e.g. combining 3.10C2L1 with 3.10C2H1, H3 or H5, or combining 3.10C2L5 with 3.10C2H1, H3, or H5. In some embodiments, the antibody comprises a light chain and heavy chain as shown in FIGS. 8A-B, for example, e.g. combining 3.27H7L1 with Para.09H1, H5, or H7, or combining 3.27H7L6 with Para.09H1, H5, or H7. In some embodiments, the antibody comprises a VH comprising a CDR-H1 comprising the amino acid sequence of SEQ ID NO: 1 or 11; a CDR-H2 comprising the amino acid sequence of SEQ ID NO: 2 or 12; and a CDR-H3 comprising the amino acid sequence as follows: $X_1$-$X_2$-$X_3$-Y, wherein $X_1$ and $X_2$ together are either I-L or L, and wherein $X_3$ is either D or E; and further comprises VH framework regions that are at least 90%, at least 95%, at least 97%, or at least 99% identical to those of human IGHV-73*01 (SEQ ID NO: 74). (See FIGS. 6B and 8B.) In some embodiments, the antibody comprises a VL comprising a CDR-L1 comprising the amino acid sequence of SEQ ID NO: 4, 14 or 27; a CDR-L2 comprising the amino acid sequence of SEQ ID NO: 5, 15, or 28; and a CDR-L3 comprising the amino acid sequence of SEQ ID NO: 6, 16, or 29; and further comprising VL framework regions that are at least 90%, at least 95%, at least 97%, or at least 99% identical to those of human IGKV-28*01 (SEQ ID NO: 75). (See FIGS. 6A and 8A.) In some embodiments, the antibody comprises a VH comprising the amino acid sequence of SEQ ID NO: 76, 77, or 78. In some embodiments, the antibody comprises a VL comprising the amino acid sequence of SEQ ID NO: 79 or 80. In some embodiments, the antibody comprises a VH comprising the amino acid sequence of SEQ ID NO: 76, 77, or 78 and further comprises a VL comprising the amino acid sequence of SEQ ID NO: 79 or 80. (See FIGS. 6A-B.) In some embodiments, the antibody comprises a VH comprising the amino acid sequence of SEQ ID NO: 81, 82, or 83. In some embodiments, the antibody comprises a VL comprising the amino acid sequence of SEQ ID NO: 84 or 85. In some embodiments, the antibody comprises a VH comprising the amino acid sequence of SEQ ID NO: 81, 82, or 83 and comprises a VL comprising the amino acid sequence of SEQ ID NO: 84 or 85. (See FIGS. 8A-B.)

In some embodiments as described above, the antibody comprises a VH comprising the amino acid sequence of SEQ ID NO: 7 and a VL comprising the amino acid sequence of SEQ ID NO: 8. (See FIGS. 9A-B; i.e., h3.10C2.v1.) In some embodiments as described above, the antibody comprises a VH comprising the amino acid sequence of SEQ ID NO: 17 and a VL comprising the amino acid sequence of SEQ ID NO: 18. (See FIGS. 10A-B; i.e., hPara.09.v2.) In any of the embodiments above, the antibody may be humanized or chimeric (i.e., having humanized or chimeric framework regions).

In some embodiments, the framework regions of the antibodies are further modified after humanization, for example, to improve properties such as expression yield. In some embodiments, the antibody comprises a light chain according to SEQ ID NO: 18, but with a substitution at one to five residues in the framework regions. In some embodiments, the antibody comprises a light chain according to SEQ ID NO: 18, but with a substitution at one or more of I58, Q100, and V104, such as I58V, Q100P, and/or V104L in the framework regions. In some embodiments, the antibody comprises a light chain according to SEQ ID NO: 18, but with a Q100P substitution, both an I58V and Q100P substitution, or both a Q100P and V104L substitution. (See, e.g., FIGS. 13A and 14A.) In some such embodiments, the antibody comprises one of the following sets of VH and VL: (a) SEQ ID Nos: 133 and 132 (antibody hPara.09.v2 Q100P); (b) SEQ ID Nos: 135 and 134 (antibody hPara.09.v2 I58V/Q100P); (c) SEQ ID Nos: 137 and 136 (antibody hPara.09.v2 Q100P/V104L); (d) SEQ ID Nos: 146 and 145 (antibody h3.10C2.v1 Q100P); (e) SEQ ID Nos: 148 and 147 (antibody h3.10C2.v1 I58V/Q100P); or (f) SEQ ID Nos: 150 and 149 (antibody h3.10C2.v1 Q100P/V104L). In other embodiments, the antibody comprises the VH and VL of SEQ ID Nos: 139 and 138 (h3.10C2.H1-3.10C2.L10). In yet other embodiments, the antibody comprises the VH and VL of SEQ ID NO: 152 and 151 (hPara.09.H5-3.10C2.L10).

In some embodiments, the antibody comprises a VL comprising from 1 to 10 amino acid substitutions in the framework region compared to human IGKV2-28*01 germline (see FIG. 8A, showing the Kabat/Chothia framework and CDR regions of IGKV2-28*01). In some cases, the antibody comprises a VL comprising from 1 to 5 amino acid substitutions in the framework region compared to human IGKV2-28*01. In some embodiments, these amino acid substitutions comprise Q100P or V104L or both Q100P and V104L. In some such cases, the VL comprises a Val at position 58, while in other cases, the VL comprises an Ile at position 58 (e.g., Q100P and 58V or Q100P and V58I in comparison to IGKV2-28*01).

In any of the embodiments herein, the antibody may be an antibody fragment, such as an Fv, single-chain Fv (scFv), Fab, Fab', or (Fab')$_2$. In other embodiments, the antibody may be a whole antibody (i.e., comprising heavy and light chain constant regions.) In other embodiments, the antibody may be an IgG, IgA, or IgM antibody. In some embodiments, the antibody may have a wild-type human IgG1 Fc region or a wild-type human IgG4 Fc region, a human IgG4 S228P Fc region, a human IgG4 S228P/M252Y/S254T/T256E Fc region, a human IgG1 N297G Fc region, a human IgG1 LALAPG (L234A/L235A/P329G) Fc region, or a human IgG1 N297G/M428L/N434S Fc region. If a murine IgG antibody, the antibody may be an mIgG1 or mIgG2 or mIgG2 LALAPG antibody. An antibody may, in some cases, comprise a full-length heavy chain and/or a full-length light chain. In some cases, the antibody may lack the C-terminal Lys or the C-terminal Lys and Gly residues of the heavy chain constant region. In other cases, the antibody contains one or both of those C-terminal residues.

In some embodiments, the antibody comprises a heavy chain comprising or consisting of the amino acid sequence of SEQ ID NO: 144. In some embodiments, the antibody comprises a light chain comprising or consisting of the amino acid sequence of SEQ ID NO: 176. In some embodiments, the antibody comprises a heavy chain comprising or consisting of the amino acid sequence of SEQ ID NO: 144 and a light chain comprising or consisting of the amino acid sequence of SEQ ID NO: 176. In some embodiments, the antibody comprises a heavy chain comprising or consisting of the amino acid sequence of SEQ ID NO: 144 but lacking the C-terminal lysine of SEQ ID NO: 144 or lacking the C-terminal glycine and lysine of SEQ ID NO: 144 and a light chain comprising or consisting of the amino acid sequence of SEQ ID NO: 176. In some embodiments, the antibody comprises a heavy chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 144. In some embodiments, the antibody comprises a light chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 176. In some embodiments, the antibody comprises a heavy chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 144 and a light chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 176. In some embodiments, the antibody comprises a heavy chain comprising or consisting of the amino acid sequence of SEQ ID NO: 144, optionally without the C-terminal lysine or glycine-lysine, and a light chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 176. In some embodiments, the antibody comprises a heavy chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 144 and a light chain comprising or consisting of the amino acid sequence of SEQ ID NO: 176. In some embodiments, the antibody comprises a heavy chain comprising an amino acid sequence with 1, 2, 3, 4, or 5 amino acid substitutions, insertions, or deletions in comparison to the amino acid sequence of SEQ ID NO: 144. In some embodiments, the antibody comprises a light chain comprising an amino acid sequence with 1, 2, 3, 4, or 5 amino acid substitutions, insertions, or deletions in comparison to the amino acid sequence of SEQ ID NO: 176. In some embodiments, the antibody comprises a heavy chain comprising an amino acid sequence with 1, 2, 3, 4, or 5 amino acid substitutions, insertions, or deletions in comparison to the amino acid sequence of SEQ ID NO: 144 and a light chain comprising an amino acid sequence with 1, 2, 3, 4, or 5 amino acid substitutions, insertions, or deletions in comparison to the amino acid sequence of SEQ ID NO: 176. In some embodiments, the antibody comprises a heavy chain comprising or consisting of the amino acid sequence of SEQ ID NO: 144, optionally without the C-terminal lysine or glycine-lysine, and a light chain comprising an amino acid sequence with 1, 2, 3, 4, or 5 amino acid substitutions, insertions, or deletions in comparison to the amino acid sequence of SEQ ID NO: 176. In some embodiments, the antibody comprises a heavy chain comprising an amino acid sequence with 1, 2, 3, 4, or 5 amino acid substitutions, insertions, or deletions in comparison to the amino acid sequence of SEQ ID NO: 144 and a light chain comprising or consisting of the amino acid sequence of SEQ ID NO: 176. In any of the above cases allowing for sequence variation in SEQ ID NO: 144 and/or SEQ ID NO: 176, in some embodiments such sequence variation is limited to the antibody framework and/or constant regions, such that the antibody also comprises heavy chain CDRs of SEQ ID NOS: 11, 12, and 13 or alternatively 19, 20, and 13, and/or light chain CDRs of SEQ ID NOS: 14, 15, and 16. In other embodiments, such sequence variation in SEQ ID NO: 144 and/or SEQ ID NO: 176 is limited to the antibody constant regions, such that the antibody also comprises SEQ ID NO: 17 and/or 18.

In some cases, the antibody may be bispecific or multispecific. In some cases, the antibody may be conjugated to another molecule, such as a label or drug either directly or through a linker.

In some cases, the antibody has intact effector function. In some cases, the antibody has an Fc region with reduced effector function. In other cases, the antibody has an Fc region that is effectorless. For example, the Fc region of antibody therapeutics can bind to complement component C1q and Fc-gamma receptors (FcγR) to elicit cellular effector responses such as phagocytosis, cytokine release, and production of reactive oxygen species. (See, e.g., X. Wang, et al., Protein & Cell 9:63-73 (2018); S. B. Mkaddem et al., *Frontiers in Immunology* doi.org/10.3389/fimmu.2019.00811 (2019).) Hyperactivation of these pathways may be detrimental in the CNS, particularly in the context of pathology. (D. J. DiSabato et al., *J. Neurochemistry* 139 (S2): 136-153 (2016).) Clinically, antibody therapeutics directed against amyloid beta that have intact effector function and bind to amyloid beta aggregates greatly increase incidence of a potentially harmful side-effect, ARIA (amyloid-related imaging abnormalities), whereas ARIA has not been observed from antibodies that bind only to monomeric forms of amyloid beta or antibodies that have reduced effector function. (M. Filippi et al., *JAMA Neurol.* 79 (3): 291-304 (2022).) In some embodiments, for instance as described in the Examples and figures herein, antibodies herein with reduced effector function (such comprising a human IgG1 heavy chain constant region with either a LALAPG or an N297G mutation, as described above) were sufficient to elicit microglial responses in the CNS via TREM2 stimulation.

Exemplary Antibody Variants, Fragments, and Constant Regions

In a further aspect, an antibody specifically binding to TREM2 herein may incorporate any of the features, singly or in combination, as described in the sections below.

Antibody Fragments

In certain embodiments, an antibody provided herein is an antibody fragment. Antibody fragments include, but are not limited to, Fab, Fab', Fab'-SH, F(ab')2, Fv, and scFv fragments, and other fragments described below. For a review of certain antibody fragments, see Hudson et al. *Nat. Med.* 9:129-134 (2003). For a review of scFv fragments, see, e.g., Pluckthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,'87,458. For discussion of Fab and F(ab')2 fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., Nat. Med. 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, MA; see, e.g., U.S. Pat. No. 6,248,516).

Antibody fragments can be made by various techniques, including but not limited to proteolytic digestion of an intact antibody as well as production by recombinant host cells (e.g. *E. coli* or phage), as described herein.

Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA*, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing specificity determining region (SDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to framework regions selected using the "best-fit" method (see, e.g., S ims et al. *J. Immunol.* 151:2296 (1993)); framework regions derived from the consensus sequence of human antibodies of a particular subgroup of light or heavy chain variable regions (see, e.g., Carte r et al. *Proc. Natl. Acad. Sci. USA*, 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

In some embodiments, the humanized antibodies may comprise a human IgG1, IgG2, IgG3, or IgG4 heavy chain constant region.

Bispecific or Multispecific Antibodies

In certain embodiments, an antibody provided herein is a multispecific antibody, for example, a bispecific antibody. Multispecific antibodies are monoclonal antibodies that have binding specificities for at least two different sites. In certain embodiments, one of the binding specificities is TREM2 and the other is for any other antigen. In certain embodiments, bispecific antibodies may bind to two different epitopes of TREM2. Bispecific antibodies may also be used to localize drugs such as cytotoxic agents or to localize detection labels to cells that express TREM2. some embodiments, the multispecific antibody (e.g., bispecific antibody) comprises a first variable domain comprising the CDRs or variable regions as described herein. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science,* 229: 81 (1985)); using leucine zippers to produce bi-specific antibodies (see, e.g., Kostelny et al., *J. Imm"nol.,* 1"8(5):1547-1553 (1992)); using "diabody" technology for making bispecific antibody fragments (see, e.g., Hollinger et al., *Proc. Natl. Acad. Sci. USA,* 90:6444-6448 (1993)); and using single-chain Fv (sFv) dimers (see, e.g. Gruber et al., *J. Immunol.,* 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g. US 2006/0025576.

Further Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding. Specific examples of humanized variants that were generated are described, for example, in FIGS. 6A-B, 8A-B, 9A-B and 12A-B herein.

Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table A under the heading of "preferred substitutions." More substantial changes are provided in Table A under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or increased or reduced ADCC or CDC activity.

TABLE A

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; AspIys; Arg | Gln |
| Asp (D) | Glu; Asn | Glu |
| CysI) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or residues that contact antigen, with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, NJ, (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

Glycosylation Variants

Alterations in glycosylation of an Fc region, as well as certain Fc region mutations, can impact the effector function of an antibody, by enhancing or reducing effector function, or in some cases may render an antibody effectorless.

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one aspect, antibodies may be modified to reduce or eliminate glycosylation at Asn297, such as by mutating that residue to a glycine or another amino acid (N297G). In other cases, other residues in an Fc region may be modified to reduce ADCC activity and/or CDC activity or to reduce or modify Fc-gamma receptor binding.

In another embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300 (EU numbering), due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. Biotech. Bioeng. 87: 614 (2004); Kanda, Y. et al., *Biotechnol. Bioeng.,* 94(4):680-688 (2006); and WO2003/085107). In some embodiments, antibodies may have a human IgG1, IgG2, IgG3, or IgG4 heavy chain constant region, for example, comprising a mutation at Asn297 (EU numbering) to decrease fucosylation or alternatively, to eliminate glycosylation. In some embodiments, antibodies may have an Asn297Ala or Asn297Gly mutation.

Antibody variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).
Fc Region Variants In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g., a substitution) at one or more amino acid positions.

In certain embodiments, the invention contemplates an antibody variant that possesses some but not all effector functions (i.e. to produce an antibody with reduced effector function or to produce an effectorless antibody), which may make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express Fc(RI, FcγRII and FcγRIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest are described in U.S. Pat. No. 5,500,362 (see, e.g. Hellstrom, I. et al. *Proc. Nat? Acad. Sci. USA* 83:7059-7063 (1986)) and Hellstrom, I et al., *Proc. Nat'l Acad. Sci. USA* 82:1499-1502 (1985); 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, CA; and CytoTox 96® non-radioactive cytotoxicity assay (Promega, Madison, WI). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103: 2738-2743 (2004)). FcRn binding and in vivo clearance/half-life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056; EU numbering of residues). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581; EU numbering). In some embodiments, the antibody comprises an engineered alanine at amino acid position 265 according to EU numbering convention. In some embodiments, the antibody comprises an engineered alanine at amino acid position 297 according to EU numbering convention.

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half-lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434 (EU numbering), e.g., substitution of Fc region residue 434 (U.S. Pat. No. 7,371, 826). See also Duncan & Winter, *Nature* 322:738-40 (1988); U.S. Pat. Nos. 5,648,260; 5,624,821; and WO 94/29351 concerning other examples of Fc region variants.

In some embodiments, the antibody may have a wild-type human IgG1 Fc region or a wild-type human IgG4 Fc region, a human IgG4 S228P Fc region, a human IgG4 S228P/M252Y/S254T/T256E Fc region, a human IgG1 N297G Fc region, a human IgG1 LALAPG (L234A/L235A/P329G) Fc region, or a human IgG1 N297G/M428L/N434S Fc region. (All positions are in EU numbering.)

Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

Antibody Derivatives and Conjugates

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

In some embodiments, an anti-TREM2 antibody is conjugated to a detection label and/or a drug. As used herein, a detection label is a moiety that facilitates detection of the antibody and/or facilitates detection of a molecule to which the antibody binds. Nonlimiting exemplary detection labels include, but are not limited to, radioisotopes, fluorescent groups, enzymatic groups, chemiluminescent groups, biotin, epitope tags, metal-binding tags, etc.

Exemplary Properties of Particular Anti-TREM2 Antibodies

As described in the Examples herein, a set of rat anti-human anti-TREM2 antibodies were identified from screens herein followed by deep sequencing analysis that have a unique set of properties, including, for example, (a) binding specifically to the TREM2 stalk domain at an epitope spanning the cleavage site between residues 157 and 158, and also specifically binding to a polypeptide consisting of residues 151-165, and more specifically binding within residues 151-161 of hTREM2, (b) not binding to soluble TREM2, (c) acting as TREM2 agonists, and (d) specifically binding to TREM2 with high affinity. These rat anti-human antibodies, 3.10C2, 3.27H7, 3.50G1, 3.18E5 (the "3.10C2 group"), 3.36F5, and Para.09, and their humanized variants, may have these and additional properties, which are described in more detail below.

Binding Affinity

In some embodiments, antibodies herein specifically bind to both human and cynomolgus TREM2 with high affinity. For example, in some embodiments, an anti-TREM2 antibody herein may bind to human TREM2 with a $K_D$ of less than 1 nM, less than 0.5 nM, less than 100 pM, less than 50 pM, less than 25 pM, less than 10 pM, less than 7 pM, less than 5 pM, less than 4 pM, less than 3 pM, or less than 2 pM, for example, at 37° C. by surface plasmon resonance (SPR). In some embodiments, an anti-TREM2 antibody herein may bind to cynomolgus TREM2 with a $K_D$ of less than 1 nM, less than 0.5 nM, less than 100 pM, less than 50 pM, less than 10 pM, less than 7 pM, less than 5 pM, less than 4 pM, less than 3 pM, or less than 2 pM, for example, at 37° C. by SPR.

In some embodiments, an anti-TREM2 antibody herein binds to hTREM2 with a $K_D$ of less than 500 pM (i.e., less than 0.5 nM). In some embodiments, an anti-TREM2 antibody herein binds to hTREM2 with a $K_D$ of less than 200 pM (i.e., less than 0.2 nM). In some embodiments, an anti-TREM2 antibody herein binds to hTREM2 with a $K_D$ of less than 100 pM (i.e., less than 0.1 nM). In some embodiments, an anti-TREM2 antibody herein binds to hTREM2 with a $K_D$ of less than 50 pM (i.e., less than 5E-11M or less than 0.05 nM). In some embodiments, an anti-TREM2 antibody herein binds to hTREM2 with a $K_D$ of 10-100 pM, 10-50 pM, 10-25 pM, or 1-10 pM. In some embodiments, an anti-TREM2 antibody herein binds to cynomolgus TREM2 with a $K_D$ of less than 500 pM (i.e. less than 5E-10M or less than 0.5 nM). In some embodiments, an anti-TREM2 antibody herein binds to cyno TREM2 with a $K_D$ of less than 200 pM (i.e. less than 2E-10M or less than 0.2 nM). In some embodiments, an anti-TREM2 antibody herein binds to cyno TREM2 with a $K_D$ of less than 100 pM (i.e., less than 1E-10M or less than 0.1 nM). In some embodiments, an anti-TREM2 antibody herein binds to cyno TREM2 with a $K_D$ of less than 50 pM (i.e. less than 5E-11M or less than 0.05 nM). In some embodiments, an anti-TREM2 antibody herein binds to cyno TREM2 with a $K_D$ of 10-100 pM, 10-50 pM, or 10-25 pM. In some embodiments, an anti-TREM2 antibody herein binds to both human and cyno TREM2 with a $K_D$ of 100-500 pM, 10-100 pM, 10-50 pM, 10-25 pM, or 1-10 pM.

For example, both Fab and IgG versions of the original rat anti-human 3.10C2 antibody bound to hTREM2 with $K_D$ of about 200 pM. For example, h3.10C2.v1 bound to both human and cyno TREM2 with $K_D$ of between 100 and 500 pM. For example, rat anti-human antibodies with the Para.09 heavy chain with different light chains based on the 3.10C2 antibody group bound to human and cyno TREM2 with a $K_D$ of between 1 and 5 pM. Humanized hPara.09.v2 bound to human and cyno TREM2 with a $K_D$ of 10-25 pM. Further humanized versions of 3.10C2 bound to human and cyno TREM2 with a $K_D$ of 100-200 pM and further humanized versions of Para.09 bound to human and cyno TREM2 with a $K_D$ of 10-50 pM.

A $K_D$ herein may be measured by SPR, for example, using a BIACORE® SPR assay. For example, an assay using a BIACORE®-2000 or a BIACORE®-3000 or a BIACORE®-T200 (BIAcore, Inc., Piscataway, NJ) can be performed with immobilized antibody chips. Association rates ($k_{on}$) and dissociation rates ($k_{off}$) can be calculated using a simple one-to-one Langmuir binding model (e.g., by BIACORE® Evaluation Software version 3.2) by simultaneously fitting the association and dissociation sensorgrams. The equilibrium dissociation constant ($K_D$) is calculated as the ratio $k_{off}/k_{on}$. See, e.g., Chen et al., J. Mol. Biol. 293:865-881 (1999).

In the Examples below, affinity was measured by SPR in one of two formats. In one format TREM2-Fc was immobilized on protein A chips and soluble anti-TREM2 Fab fragments used as ligands. In the second format, anti-TREM2 IgG was immobilized on anti-CH1 Biacore™ chips and used soluble monomeric TREM2 as ligand. For example, $K_D$ measurements shown in Tables 1, 4, and 6 were determined by SPR at 37° C.

Epitope and Lack of Soluble TREM2 Binding, and Inhibition of TREM2 Shedding

As shown in the Examples section, the present disclosure provides antibodies that specifically bind within the stalk domain of TREM2 which spans residues 129-174 of hTREM2 (See SEQ ID NO: 90) but do not bind to soluble TREM2 (sTREM2; residues 19-157 of hTREM2), in contrast to other anti-TREM2 antibodies previously described in the literature as stalk binders. sTREM2 is formed through cleavage of TREM2 between residues H157 and S158, and generally comprises residues 19-157 of TREM2. In some embodiments, binding to the stalk domain of TREM2 may be shown by conducting a binding assay to a polypeptide comprising residues 129-174 (SEQ ID NO: 90) or residues 129-175 of TREM2 (SEQ ID NO: 177; FIG. 2A), which comprises the stalk domain and the first transmembrane domain residue. The results provided herein show that the 3.10C2, Para.09, 3.50G1, 3.18E5, 3.36F5, or 3.27H7 antibodies of the present disclosure, as well as the humanized versions of those antibodies described herein such as Para.09.v2, 3.10C2.v1, likely bind to an epitope that spans the H157-S158 cleavage site, that is disrupted upon cleavage of TREM2 at the H157-S158 cleavage site, and that is not present in sTREM2. (See, for example, FIGS. 2A-B and 5.) In contrast, a number of anti-TREM2 antibodies described in the literature show binding to soluble TREM2 and likely recognize a different epitope that is not disrupted by cleavage of intact TREM2, even though, in some cases, they may contact residues around the cleavage site (see, e.g., FIG. 5). Therefore, the present disclosure provides antibodies with a property not found in other anti-TREM2 antibodies—the ability to bind to intact TREM2 but not sTREM2, despite seeming to interact with a similar region of the protein as prior antibodies that bind sTREM2.

As noted previously, certain antibodies herein do not bind to soluble TREM2. As used herein, this means that the antibodies, when assayed in an ELISA assay, may not show any more than 10% binding to sTREM2, and in some cases do not show any more than 5% binding to sTREM2, wherein % binding is normalized against that of positive control antibody 1.16B8, whose binding to sTREM2 is set to 100%. The control antibody 1.16B8 light chain sequence is shown in SEQ ID NO: 170, and its heavy chain sequence is shown in SEQ ID NO: 171. In some embodiments, antibody 3.17A9 is used as a detection agent in the ELISA assay. The detection antibody 3.17A9 light chain sequence is shown in SEQ ID NO: 168, and heavy chain sequence shown in SEQ ID No: 169. In some embodiments, a polypeptide comprising residues 19-157 of hTREM2 may be used to assay the binding (e.g., residues 19-157 of SEQ ID NO: 21). In some embodiments, antibodies do not bind to soluble TREM2 in an ELISA assay in which binding is normalized against that of control antibody 1.16B8, in which detection antibody 3.17A9 is used as a detection reagent, and in which sTREM2 is a polypeptide comprising residues 19-157 of SEQ ID NO: 21. In some embodiments, the ELISA assay may be performed as shown in Example 11 below and in FIG. 16.

Figure 16:
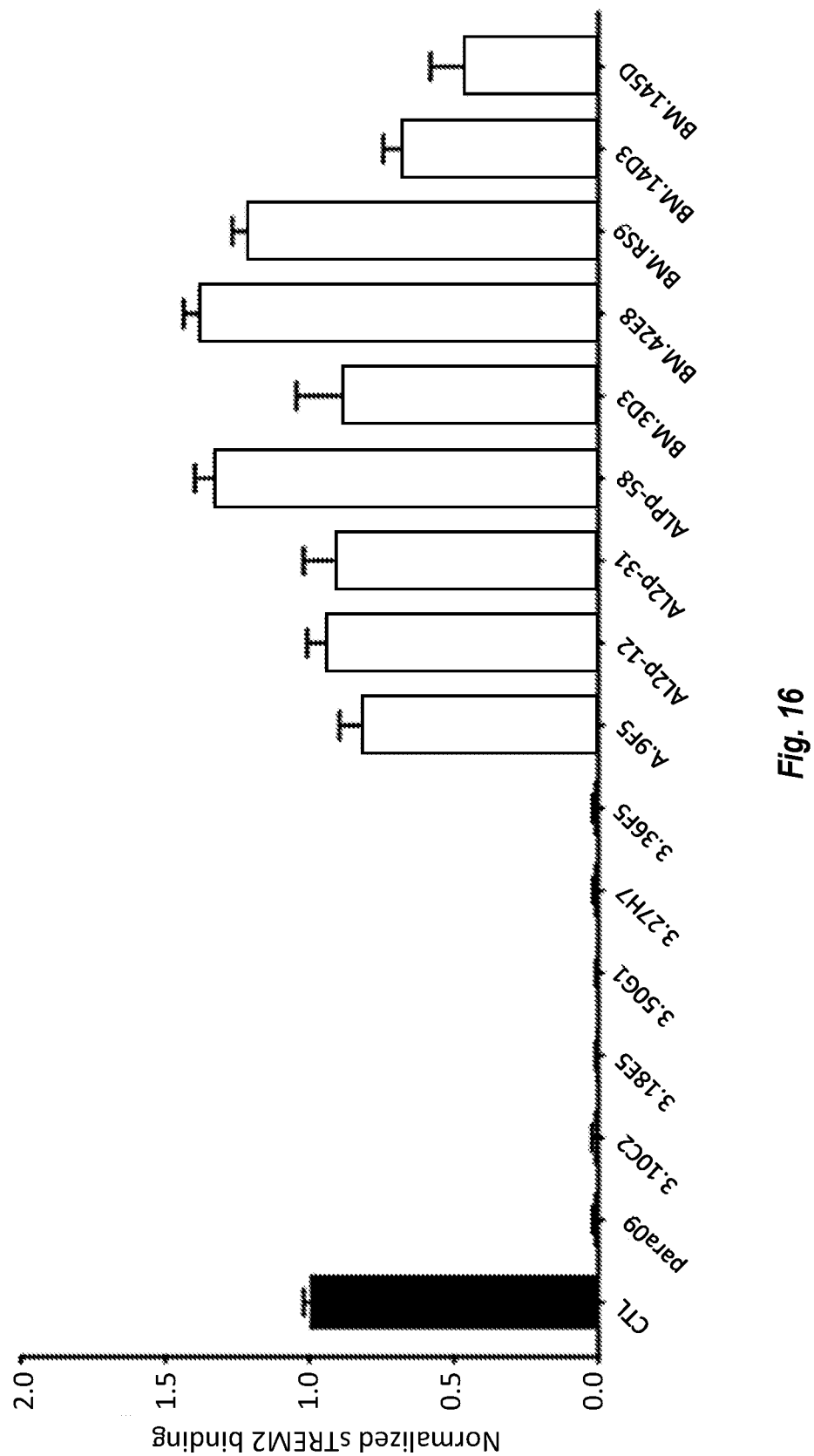

For example, as shown in an Example 11 herein, the human TREM2 ELISA assay measured binding of antibodies to sTREM2 by coating onto plate wells the antibody to be tested as capture reagents and with biotinylated IgV-reactive monoclonal antibody 3.17A9 used as the detection reagent. Control antibody 1.16B8 was used as a positive control antibody to establish the standard for sTREM2 binding. For example, in this assay, rat Para.09— LC 3.27H7 mIgG2a LALAPG (Para09), rat 3.10C2 mIgG2a LALAPG (3.10C2), rat 3.18E5 mIgG2a LALAPG (3.18E5), rat 3.50G1 mIgG2a LALAPG (3.50G1), rat 3.27H7 mIgG2a LALAPG (3.27H7), rat 3.36F5 mIgG2a LALAPG (3.36F5) all did not show any binding to sTREM2 (see FIG. 16, showing normalized sTREM2 binding of near zero for those antibodies in contrast to the 1.116B8 control). The humanized antibody Para.09.v2 antibody with a hIgG1 N297G constant region was also tested for sTREM2 binding and, like rat Para.09 with mIgG2 LALAPG, did not show any binding to sTREM2. Accordingly, in some embodiments, antibodies herein, such as those shown in FIG. 16 and humanized variants of such antibodies such as such as Para.09.v2, 3.10C2.v1, do not bind to soluble TREM2. In some embodiments, those antibodies bind to the TREM2 stalk domain but do not bind to soluble TREM2.

Lack of binding to sTREM2 may be advantageous in vivo as it might significantly reduce or eliminate the possibility of unwanted binding between antibody and sTREM2 in vivo. For example, without being limited by mechanism, sTREM2 could act as a "decoy" to an anti-TREM2 antibody otherwise, so that antibody molecules in vivo are less available to bind to TREM2 on the cell surface.

As shown in the Examples and accompanying Figures herein, antibodies herein may also bind to residues within the stalk region of TREM2 at a region spanning the H157-S158 cleavage site, specifically within residues ranging from 149-168, 146-169, 146-161, and 151-165 of TREM2. This unique cleavage-site spanning epitope may explain why antibodies herein may both bind to the TREM2 stalk and also not bind to soluble TREM2. (See, e.g., FIG. 5.) In some embodiments, an antibody herein binds specifically to a TREM2 polypeptide consisting of amino acids 146-161 (SEQ ID NO: 96) and/or 151-165 (SEQ ID NO: 97) with higher affinity than to a TREM2 polypeptide consisting of amino acids 139-158 (SEQ ID NO: 92) and/or 159-175 (SEQ ID NO: 94). In some cases, an antibody herein binds specifically to a TREM2 polypeptide consisting of amino acids 149-168 (SEQ ID NO: 93), 146-169 (SEQ ID NO: 95), 146-161 (SEQ ID NO: 96), and/or 151-165 (SEQ ID NO: 97) with higher affinity than to a TREM2 polypeptide consisting of amino acids 139-158 (SEQ ID NO: 92) and/or 159-175 (SEQ ID NO: 94). In some embodiments, an antibody herein binds specifically to a TREM2 polypeptide consisting of amino acids 146-161 (SEQ ID NO: 96) and/or 151-165 (SEQ ID NO: 97) with higher affinity than to a TREM2 polypeptide consisting of amino acids 139-158 (SEQ ID NO: 92) and to one consisting of 159-175 (SEQ ID NO: 94). In some cases, an antibody herein binds specifically to a TREM2 polypeptide consisting of amino acids 149-168 (SEQ ID NO: 93), 146-169 (SEQ ID NO: 95), 146-161 (SEQ ID NO: 96), and/or 151-165 (SEQ ID NO: 97) with higher affinity than to a TREM2 polypeptide consisting of amino acids 139-158 (SEQ ID NO: 92) and to one consisting of 159-175 (SEQ ID NO: 94).

As shown in the Examples provided herein, the data suggest that the antibodies of the present disclosure specifically bind to an epitope within residues 151-161 of TREM2. (See FIGS. 2A and 2B.) In some embodiments, antibodies herein bind to an epitope including one or more of Asp-152, His-154, Val-155, Glu-156, His-157, Ser-158, Ile-159 and Ser-160, spanning the TREM2 cleavage site at H157-5158. (See FIG. 5.) In some embodiments, antibodies herein bind to an epitope comprising residues 152, 154, 157, 158 and 159. In some embodiments, antibodies herein specifically bind to an epitope including Asp-152, His-157, and Ile-159. In certain embodiments, antibodies herein bind to an epitope including one or more of residues Asp-152, His-154, Val-155, Glu-156, His-157 and Ile-159. In some embodiments, antibodies herein bind to an epitope including Glu-156 and Ser-160. Alanine scanning analysis shows that TREM2 binding of antibody Para.09, comprising the Para.09 heavy chain variable region paired with the light chain variable region of antibody 3.27H7, is impacted by alanine mutations at Asp-152, His-157, and Ile-159, for example. (FIG. 5.)

Para.09 and 3.10C2 have a similar pattern in the alanine scanning assay, except that binding of 3.10C2 is additionally impacted by alanine mutations at H154 and S158. (FIG. 5.)

In some embodiments, an antibody herein, such as Para.09 or 3.10C2 including humanized variants of such antibodies such as Para.09.v2 and 3.10C2.v1, also decreases levels of sTREM2 in vivo, such as in murine plasma, CSF, or brain tissue, compared to a control antibody that does not specifically bind to TREM2 (e.g., an isotype control), as measured by an ELISA assay. For example, in some embodiments, an ELISA assay may be performed by determining a change in the level of soluble TREM2 from a plasma, CSF, or brain tissue sample incubated in the presence of anti-TREM2 antibodies compared to an isotype control antibody. Reduced levels of sTREM2 in the presence of anti-TREM2 antibodies are indicative of inhibition of sTREM2 shedding.

Figure 25A:
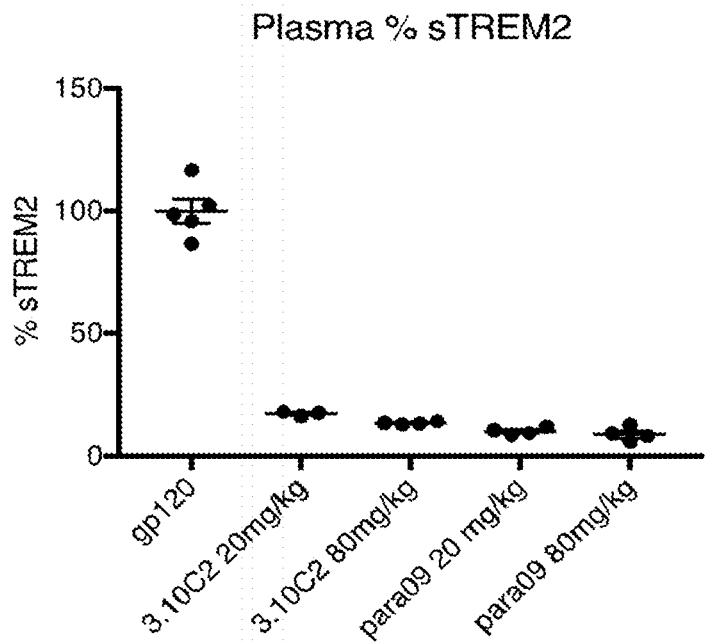
FIGS. 25A-25C show sTREM2 levels in mice treated with anti-TREM2 or control antibodies.
Figure 25B:
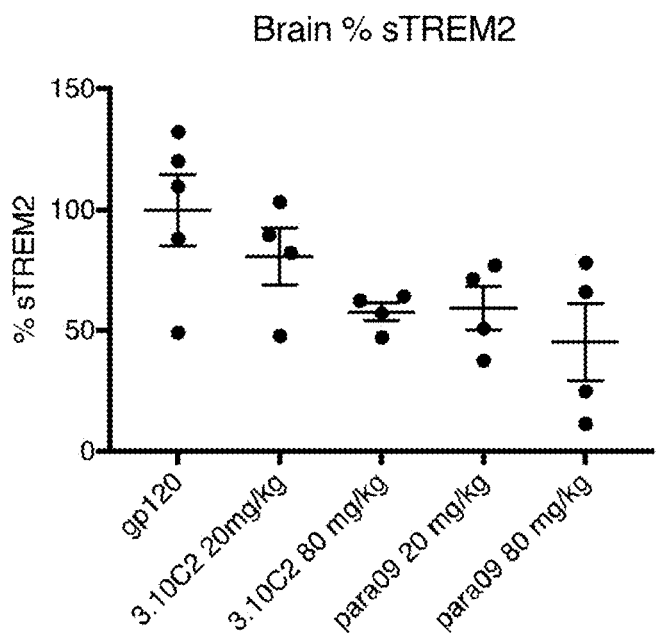
Figure 25C:
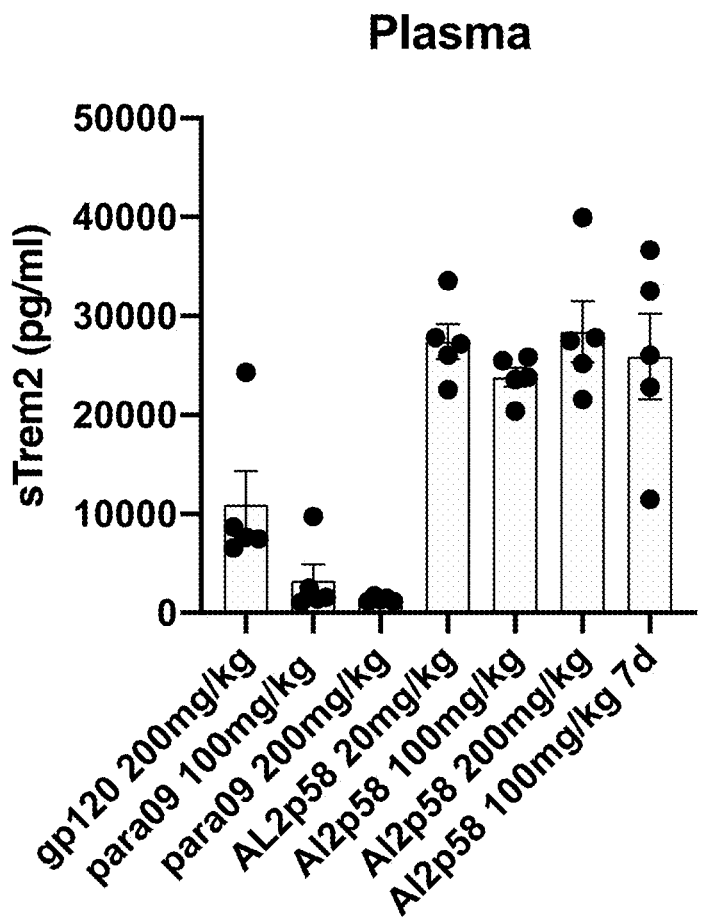

As shown in Example 18A-B below, the lack of binding to sTREM2 is also correlated with this depletion of sTREM2 in vivo (in murine plasma, CSF, and brain tissue). In contrast to a comparator antibody, treatment with exemplary antibody Para.09 led to substantially lower levels of plasma sTREM2 below baseline control levels, whereas treatment with the comparator anti-TREM2 antibody increased levels of sTREM2 in plasma by several fold. (Example 18B and FIG. 25C.) For example, Para.09 antibodies in a mIgG2 LALAPG background in mice caused a 70-85% decrease in soluble TREM2 levels in plasma for at least 7 days after administration, while the comparator antibody increased sTREM2 levels over the same period by more than 2-fold. (FIG. 25C.) Thus, in some embodiments, antibodies herein such as Para.09 and 3.10C2 and their humanized variants such as Para.09.v2 and 3.10C2.v1, cause a decrease in soluble TREM2 levels in murine plasma for at least 7 days after administration to mice. Antibodies of the present disclosure with increased specificity for intact TREM2 and lack of binding to sTREM2 in vivo, therefore, may have particular utility in situations where elevated sTREM2 levels are undesirable.

Accordingly, antibodies herein such as Para.09 and 3.10C2 and their humanized variants may possess any one or more of the following properties: (a) specific binding to the stalk domain of TREM2; (b) not binding to soluble TREM2 (sTREM2); (c) specific binding to a TREM2 polypeptide consisting of amino acids 146-161 (SEQ ID NO: 96) or 151-165 (SEQ ID NO: 97) with higher affinity than to a TREM2 polypeptide consisting of amino acids 139-158 (SEQ ID NO: 92) and/or 159-175 (SEQ ID NO: 94); (d) specific binding to a TREM2 epitope spanning the H157-S158 cleavage site; (e) reduced binding affinity to a TREM2 stalk domain polypeptide comprising D152A, H157A, and I159A substitutions compared to a wild-type TREM2 stalk domain polypeptide (e.g., as measured by bilayer interferometry); and (f) specific binding to human and cynomolgus TREM2 with a $K_D$ of less than 100 pM, less than 50 pM, less than 10 pM, less than 7 pM, less than 5 pM, less than 4 pM, less than 3 pM, or less than 2 pM, or 10-50 pM or 10-25 pM at 37° C. by surface plasmon resonance (SPR). In some cases, and antibody may possess two or more of the above properties, three or more of the above properties, four or more of the above properties, five or more of the above properties, or all of the above properties. For example, in some cases, an antibody herein does not bind to soluble TREM2 and also shows specific binding to a TREM2 epitope spanning the H157-S158 cleavage site and/or shows specific binding to a TREM2 polypeptide consisting of amino acids 146-161 (SEQ ID NO: 96) or 151-165 (SEQ ID NO: 97) with higher affinity than to a TREM2 polypeptide consisting of amino acids 139-158 (SEQ ID NO: 92) and/or 159-175 (SEQ ID NO: 94). In some such cases, the antibody also specifically binds to human and cynomolgus TREM2 with a $K_D$ of less than 100 pM, less than 50 pM, less than 10 pM, less than 7 pM, less than 5 pM, less than 4 pM, less than 3 pM, or less than 2 pM, or 10-50 pM or 10-25 pM at 37° C. by surface plasmon resonance (SPR). For example, in some cases, an antibody herein does not bind to soluble TREM2 and specifically binds to the stalk domain of TREM2. In some cases, an antibody herein does not bind to soluble TREM2 and has reduced binding affinity to a TREM2 stalk domain polypeptide comprising D152A, H157A, and I159A substitutions compared to a wild-type TREM2 stalk domain polypeptide (e.g., as measured by bilayer interferometry). In some such cases, the antibody also specifically binds to human and cynomolgus TREM2 with a $K_D$ of less than 100 pM, less than 50 pM, less than 10 pM, less than 7 pM, less than 5 pM, less than 4 pM, less than 3 pM, or less than 2 pM, or 10-50 pM or 10-25 pM at 37° C. by surface plasmon resonance (SPR). Furthermore, in some cases, the antibody also has intact effector function. In some cases, the antibody also has an Fc region with reduced effector function. In other cases, the antibody also has an Fc region that is effectorless. For example, in some cases the antibody comprises a hIgG1 Fc region with an N297G substitution.

In certain exemplary embodiments, the antibody comprises a heavy chain variable region (VH) and a light chain variable region (VL), wherein the VH comprises a CDR-H1 comprising the amino acid sequence of SEQ ID NO: 11 or 19; a CDR-H2 comprising the amino acid sequence of SEQ ID NO: 12 or 20; and a CDR-H3 comprising the amino acid sequence of SEQ ID NO: 13, and further wherein the antibody does not bind to soluble TREM2 (sTREM2), wherein the antibody is a TREM2 agonist as described further in the following section. In some embodiments, the VH comprises the amino acid sequence of SEQ ID NO: 17, 133, 135, 137, or 139 or an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 17, 133, 135, 137, or 139; or the antibody comprises a heavy chain comprising or consisting of the amino acid sequence of SEQ ID NO: 144 with or without the C-terminal lysine or C-terminal glycine-lysine, or comprises an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 144. In some cases, antibody also specifically binds to a TREM2 epitope spanning the H157-S158 cleavage site and/or specifically binds to a TREM2 polypeptide consisting of amino acids 146-161 (SEQ ID NO: 96) or 151-165 (SEQ ID NO: 97) with higher affinity than to a TREM2 polypeptide consisting of amino acids 139-158 (SEQ ID NO: 92) and/or 159-175 (SEQ ID NO: 94). In some cases, the antibody does not bind to soluble TREM2 and has reduced binding affinity to a TREM2 stalk domain polypeptide comprising D152A, H157A, and I159A substitutions compared to a wild-type TREM2 stalk domain polypeptide (e.g., as measured by bilayer interferometry). In some cases, the antibody also specifically binds to human and cynomolgus TREM2 with a $K_D$ of less than 100 pM, less than 50 pM, less than 10 pM, less than 7 pM, less than 5 pM, less than 4 pM, less than 3 pM, or less than 2 pM, or 10-50 pM or 10-25 pM at 37° C. by surface plasmon resonance (SPR). Furthermore, in some cases, the antibody also has intact effector function. In some cases, the antibody also has an Fc region with reduced effector function. In other cases, the antibody also has an Fc region that is effectorless. For example, in some cases the antibody comprises a hIgG1 Fc region with an N297G substitution. In any of these cases, in some embodiments, the antibody may possess the light chain CDRs 1-3 of 3.10C2, 3.50G1, 3.18E5, 3.36F5, or 3.27H7.

Antibodies described herein may also have one or more of the additional biological activities described in the next section along with any combination of the above properties described in this section.

Additional Biological Activities

In some embodiments, antibodies herein, such as Para.09 and 3.10C2 and their humanized variants, may have one or more, two or more, three or more, four or more, five or more, or six or more, seven or more, eight or more, or all of the following further characteristics: (a) inducing luciferase reporter activity in Jurkat-NFAT luciferase reporter cells expressing human TREM2; (b) decreasing levels of sTREM2 in vivo in plasma; (c) inhibiting shedding of sTREM2 in Jurkat-NFAT luciferase reporter cells expressing human TREM2; (d) inducing tyrosine phosphorylation in human MDM cells; (e) inducing SYK phosphorylation in human MDM cells; (f) enhancing survival of human iPSC-derived microglia in absence of IL-34 and CSF-1; (g) inhibiting shedding of sTREM2 in human iPSC-derived microglia; (h) inducing SYK phosphorylation in human iPSC-derived microglia; and (i) increasing total Aβ plaque intensity and/or average X04 plaque intensity in presence of Aβ oligomers in human iPSC-derived microglia (e.g., as described in the assay of Example 17 herein).

Accordingly, in some embodiments, an antibody herein, such as Para.09 and 3.10C2 and their humanized variants, also reduces sTREM2 levels (i.e., inhibits sTREM2 shedding) in cultured cells, including in Jurkat cells that have been engineered to express human TREM2, or alternatively, in human monocyte-derived macrophages (MDMs) or in human induced pluripotent stem cell (iPSC)-derived microglia. In some cases, sTREM2 levels in cell culture assays may be measured by ELISA assays.

Figure 18A:
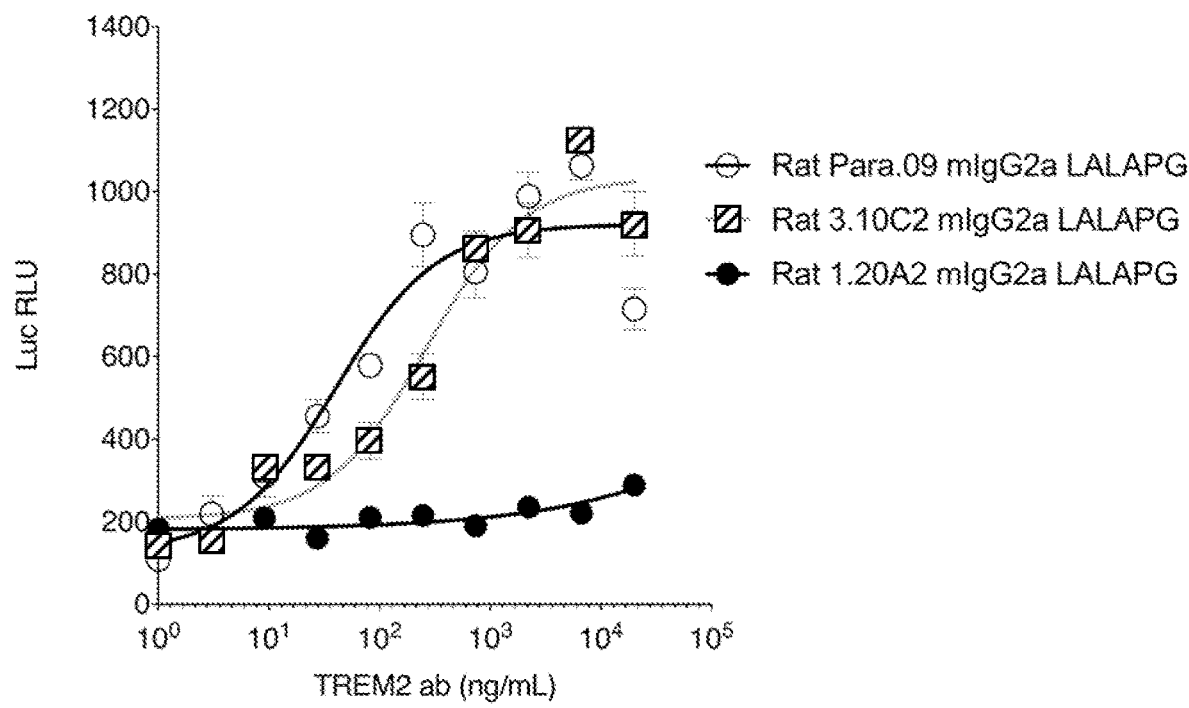
FIGS. 18A-B show the effect of increasing concentrations of rat anti-human and humanized anti-TREM2 antibodies expression of luciferase in the Jurkat-NFAT luciferase reporter cells expressing human TREM2. Luciferase signal in the presence of various concentrations of rat anti-human antibodies in mIgG2 LALAPG format (FIG. 18A) and humanized hPara.09.v2 and h3.10C2.v1 antibodies (FIG. 18B) is shown after 24 hours.
Figure 18B:
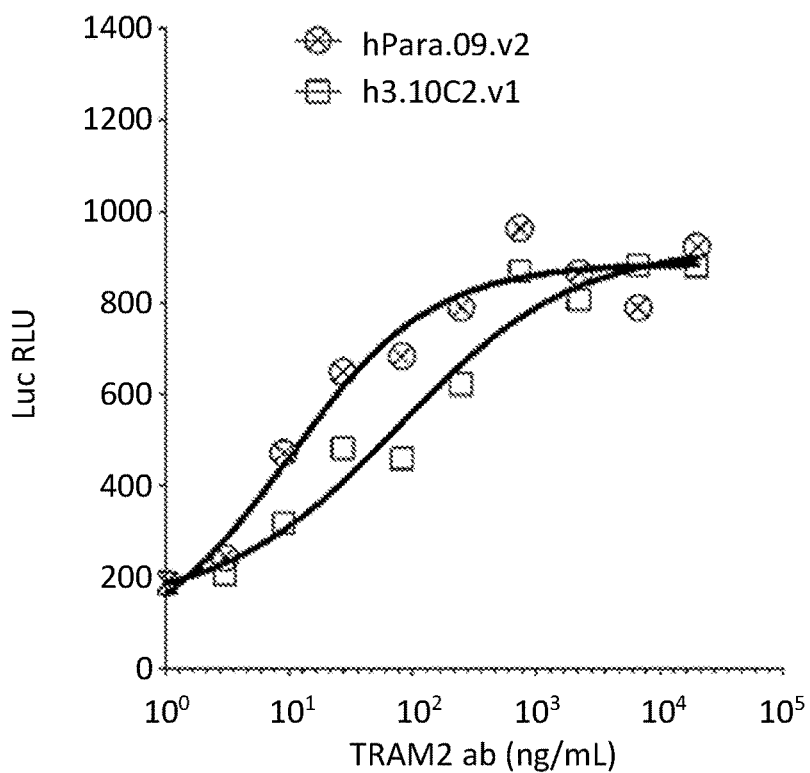
Figure 19A:
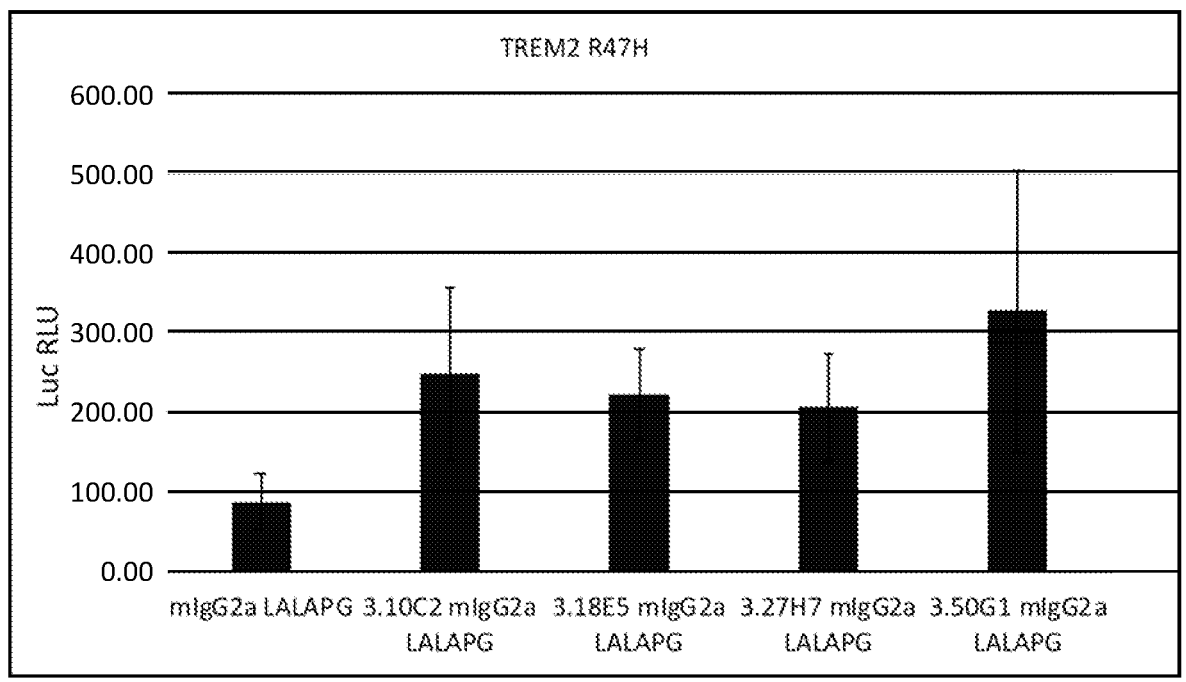
FIGS. 19A-C show induction of luciferase expression by rat anti-human 3.10C2, 3.18E5, 3.27H7 and 3.50G1 mIgG2a LALAPG antibodies in a Jurkat-NFAT luciferase reporter cell line expressing hTREM2 mutant R47H (FIG. 19A), R62H (FIG. 19B), or H157Y (FIG. 19C).
Figure 19B:
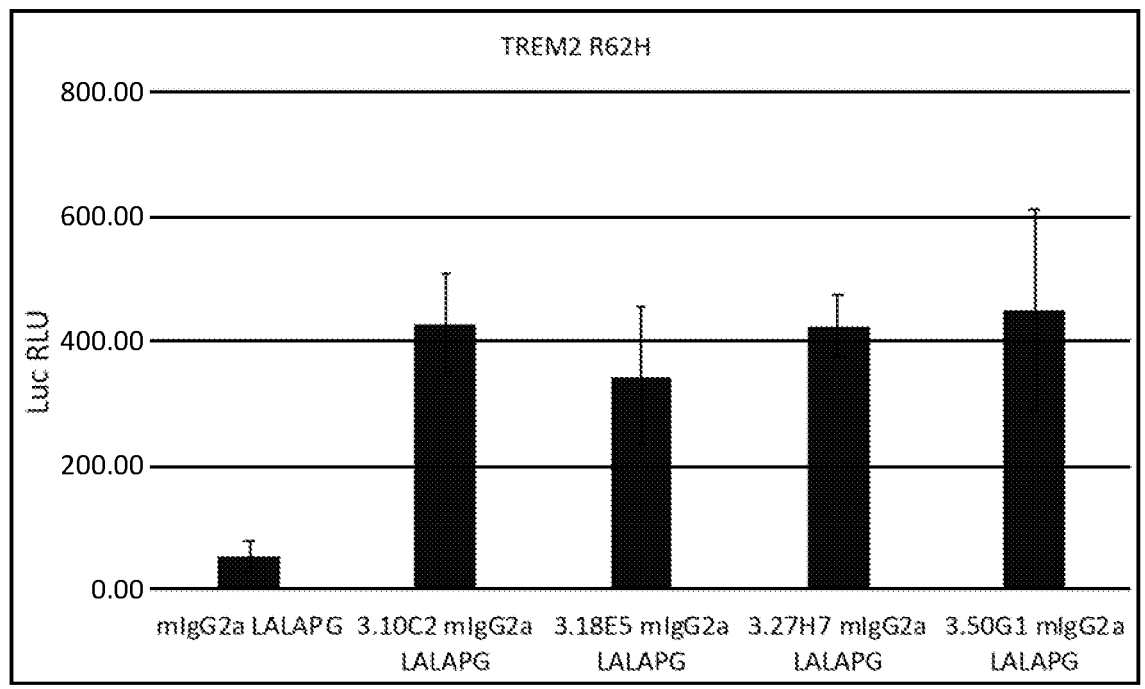
Figure 19C:
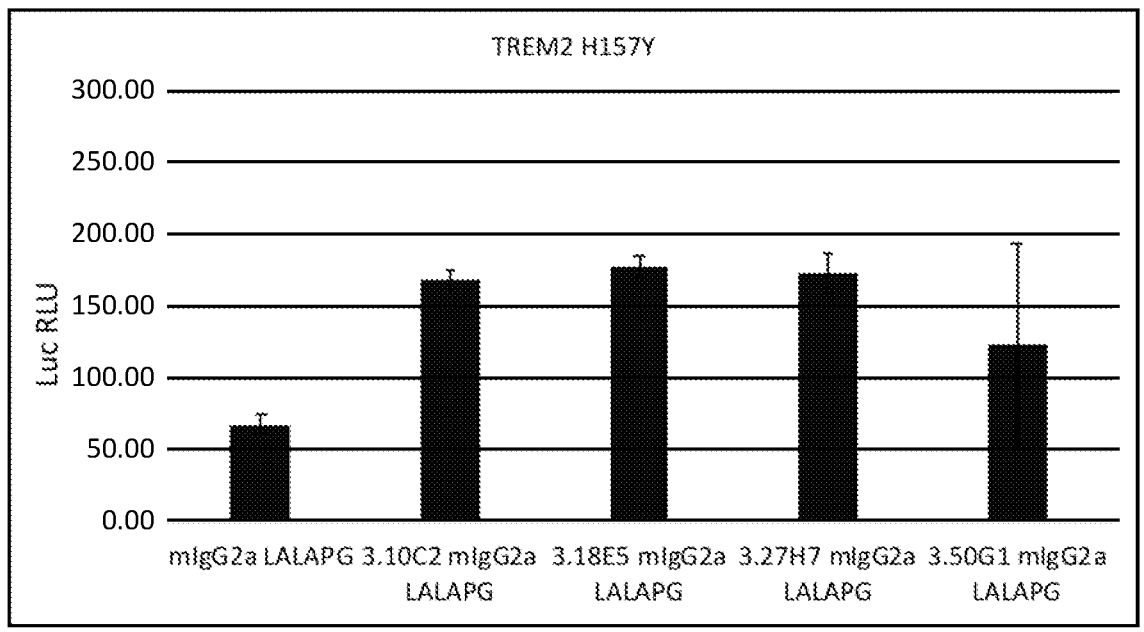

In some embodiments, an antibody herein is a TREM2 agonist. For example, in some embodiments, an antibody herein induces reporter gene expression in Jurkat-NFAT reporter cells expressing human TREM2. For example, TREM2 activity may result in cell signaling events that lead to enhanced gene expression under the control of NFAT (nuclear factor of activated T cells). NFAT activity can be assessed, for instance, using Jurkat cells engineered to express a reporter gene such as firefly luciferase in response to activation of gene expression by an NFAT transcription factor. To test the effect of anti-TREM2 antibodies on NFAT-controlled gene expression, Jurkat-NFAT reporter cells can be constructed that express human TREM2. In some embodiments, an antibody herein enhances reporter gene expression in a Jurkat-NFAT reporter cell expressing human TREM2. (See FIGS. 18A-B.) In some embodiments, an antibody herein also enhances reporter gene expression in a Jurkat-NFAT reporter cell expressing a human TREM2 mutant, such as hTREM2 R47H, hTREM2 R62H, and/or H157Y. (See FIGS. 19A-C.)

TREM2 activity, and accordingly, agonism by anti-TREM2 antibodies, may also be assessed by levels of phosphorylation of tyrosine residues generally or by levels of phosphorylation of Syk kinase, which is a kinase that becomes phosphorylated upon activation of TREM2-related cell signaling. Thus, in some embodiments, an antibody herein increases TREM2 activity as measured by an increase in one or both of pan phospho-tyrosine (pY) levels and phosphorylated Syk kinase (p-SYK) levels in one or more of Jurkat-NFAT reporter cells expressing human TREM2, human iPSC-derived microglia, or human MDM cells. In some embodiments, an antibody herein increases SYK phosphorylation in human iPSC-derived microglia, and human MDM cells.

In some embodiments, antibodies herein also enhance survival of human iPSC-derived microglia when those cells are cultured in the absence of IL-34 and CSF-1, which are ordinarily required to promote survival and growth of the cells. For example, humanized antibodies hPara.09.v2, h3.10C2.v1, hPara.09 Q100P V104L, and hPara.09 Q100P each enhanced iPSC-derived microglia survival with $EC_{50}$'s ranging from 65 pM to 610 pM (respectively 65 pM, 350 pM, 190 pM, and 610 pM). (See Example 17 and FIG. 23E.) Accordingly, in some embodiments, an antibody herein may enhance iPSC-derived microglia survival in the absence of IL-34 and CSF-1 with an $EC_{50}$ ranging from 60 pM to 700 pM, such as from 60 pM to 400 pM, or from 60 pM to 200 pM. Furthermore, in some embodiments, an antibody may enhance microglia survival in the absence of IL-34 and CSF-1 by at least 3-fold, or by 3-8 fold over that of an isotype control antibody, such as by 3-6 fold, 3-5 fold, 5-8 fold, or 3-4 fold. (See FIGS. 23D-E.)

In some embodiments, antibodies herein increase Aβ plaque intensity and/or increase X04 plaque intensity in the presence of Aβ oligomers in human iPSC-derived microglia. (See Example 17 and FIGS. 24A-C.) Plaque formation and compaction, for example, may be measured as an increased intensity when staining iPSC-derived microglia with particular marker dyes, such as those recognizing Aβ (i.e., measuring "Aβ intensity" or "Aβ plaque intensity") or Aβ plaques (X04 marker, measuring "X04 intensity" or "X04 plaque intensity"). In some cases, a "total" Aβ plaque intensity may be determined. And in some cases, an "average" X04 plaque intensity may be measured. An example of an assay for measuring plaque formation and compaction, total Aβ plaque intensity and average X04 plaque intensity is shown in Example 17 and FIG. 24A-C.

In some embodiments, antibodies herein increase Aβ plaque formation and compaction in iPSC-derived microglia, as shown by increases in one or both of total Aβ plaque intensity and average X04 intensity compared to an isotype control antibody. For example, in some embodiments, presence of an antibody increases total Aβ plaque intensity by 4-6 fold compared to an isotype control antibody. In some embodiments, an antibody herein has an $EC_{50}$ for increase in total Aβ plaque intensity of between 100 and 800 nM. For example, as shown in FIG. 24B, antibodies hPara.09.v2, h3.10C2.v1, hPara.09 Q100P V104L, and hPara.09 Q100P increased total Aβ plaque intensity in a human iPSC-derived microglia model plaque assay with $EC_{50}$'s of 330 nM, 130 nM, 770 nM, and 120 nM, respectively. Furthermore, in some embodiments, presence of an antibody increases average X04 plaque intensity in the assay by 2-3 fold compared to an isotype control antibody. In some embodiments, an antibody herein has an $EC_{50}$ for increase in average X04 plaque intensity of between 10 and 500 nM. For example, as shown in FIG. 24C, antibodies hPara.09.v2, h3.10C2.v1, hPara.09 Q100P V104L, and hPara.09 Q100P increased average X04 plaque intensity in a human iPSC-derived microglia model plaque assay with $EC_{50}$'s of 320 nM, 11 nM, 40 nM, and 500 nM, respectively.

Data from Jurkat-NFAT reporter cells expressing human TREM2, and from the MDM and iPSC-derived microglia models indicate that antibodies herein may have neuroprotective activities, for example. For instance, antibodies herein may have a combination of biological activities of enhancing survival of human iPSC-derived microglia, increasing p-SYK phosphorylation and/or NFAT-controlled gene expression, and promoting Aβ plaque formation and compaction in presence of Aβ oligomers in human iPSC-derived microglia. In some embodiments, an antibody herein also shows little to no significant off-target binding in a BV ELISA assay. (Hotzel et al., *Landes Bioscience* dx.doi.org/10.4161/mabs.22189 (2012).) An exemplary BV ELISA assay is as described in Example 10 below. In such an assay, for example, antibodies may have high (score>5), medium (score of 1-5) and low (non-detectable, score<1) off-target binding. In some embodiments, when antibodies herein were tested in parallel with antibodies previously determined to have high medium, and low off-target binding scores, antibodies herein were found to have low off-target binding scores, i.e. below 1. (See FIG. 15.) In particular, 3.10C2.v1 and Para.09.v2 prepared in a human IgG1 N297G constant region background, showed low off-target binding in this assay (i.e., a score less than 1) despite also having affinity for TREM2 in the 100-500 pM and 10-50 pM range, respectively. A low score in this assay, for example, may indicate that the antibody is less likely to bind to incorrect targets in vivo, which correlates with favorable pharmacokinetic properties in human and cynomolgus monkeys and may be beneficial for reducing toxicity and side effects due to off-target binding in vivo.

Sequences and Properties of Certain Exemplary Humanized Antibodies

Antibody h3.10C2.v1

In some aspects, the disclosure relates to an antibody comprising a heavy chain variable region and a light chain variable region, wherein the heavy chain variable region comprises an amino acid sequence comprising the heavy chain CDRs of the 3.10C2 antibody, comprising SEQ ID NOS: 1, 2, and 3 (Kabat), or comprising SEQ ID Nos: 9, 10, and 3 (Chothia). (See FIG. 9B.) In some embodiments, the antibody comprises a heavy chain variable region and a light chain variable region, wherein the light chain variable region comprises an amino acid sequence comprising the light chain CDRs of the 3.10C2.v1 antibody, based on those of the 3.27H7 Fab, comprising SEQ ID NOS: 4, 5, and 6. (See FIG. 9A.) In some embodiments, the antibody comprises the heavy chain and the light chain CDRs of 3.10C2.v1, comprising SEQ ID NOS: 1-6. In some embodiments, the antibody comprises the heavy chain and the light chain CDRs of 3.10C2.v1, comprising SEQ ID NOS: 9, 10, 3, 4, 5, and 6.

In some embodiments, the antibody comprises heavy chain CDRs of SEQ ID NOS: 1, 2, and 3 or alternatively 9, 10, and 3, and/or the light chain CDRs of SEQ ID NOS: 4, 5, and 6, and further comprises a heavy chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 7. In some embodiments, the antibody comprises heavy chain CDRs of SEQ ID NOS: 1, 2, and 3 or alternatively 9, 10, and 3, and/or light chain CDRs of SEQ ID NOS: 4, 5, and 6, and further comprises a light chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 8. In some embodiments, the antibody comprises heavy chain CDRs of SEQ ID NOS: 1, 2, and 3 or alternatively 9, 10, and 3, and/or light chain CDRs of SEQ ID NOS: 4, 5, and 6, and further comprises a heavy chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 7, and a light chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 8. In some embodiments, the antibody comprises heavy chain CDRs of SEQ ID NOS: 1, 2, and 3 or alternatively 9, 10, and 3, and/or light chain CDRs of SEQ ID NOS: 4, 5, and 6, and further comprises a heavy chain variable region comprising the amino acid sequence of SEQ ID NO: 7. In some embodiments, the antibody comprises heavy chain CDRs of SEQ ID NOS: 1, 2, and 3 or alternatively 9, 10, and 3, and/or light chain CDRs of SEQ ID NOS: 4, 5, and 6, and further comprises a light chain variable region comprising the amino acid sequence of SEQ ID NO: 8. In some embodiments, the antibody comprises heavy chain CDRs of SEQ ID NOS: 1, 2, and 3 or alternatively 9, 10, and 3, and/or light chain CDRs of SEQ ID NOS: 4, 5, and 6, and further comprises a heavy chain variable region comprising the amino acid sequence of SEQ ID NO: 7, but with up to 5, such as 1, 2, 3, 4, or 5 amino acid substitutions, insertions, or deletions, in the heavy chain framework regions of SEQ ID NO: 7. In some embodiments, the antibody comprises heavy chain CDRs of SEQ ID NOS: 1, 2, and 3 or alternatively 9, 10, and 3, and/or light chain CDRs of SEQ ID NOS: 4, 5, and 6, and further comprises a light chain variable region comprising the amino acid sequence of SEQ ID NO: 8, but with up to 5, such as 1, 2, 3, 4, or 5 amino acid substitutions, insertions, or deletions, in the light chain framework regions of SEQ ID NO: 8. In some embodiments, the antibody comprises a heavy chain variable region comprising the amino acid sequence of SEQ ID NO: 7 and a light chain variable region comprising the amino acid sequence of SEQ ID NO: 8, but with up to 5 amino acid substitutions, insertions, or deletions, such as 1, 2, 3, 4, or 5 amino acid substitutions, insertions, or deletions, in the framework regions of SEQ ID NO: 7 and/or SEQ ID NO: 8.

In some embodiments, the antibody comprises a heavy chain variable region comprising the amino acid sequence of SEQ ID NO: 7 and a light chain variable region comprising the amino acid sequence of SEQ ID NO: 8. In some embodiments, the antibody further comprises a heavy chain and/or a light chain constant region.

In any of the embodiments herein, the antibody may be an antibody fragment, such as an Fv, single-chain Fv (scFv), Fab, Fab', or (Fab')$_2$. In other embodiments, the antibody may be a whole antibody (i.e., comprising heavy and light chain constant regions.) In other embodiments, the antibody may be an IgG, IgA, or IgM antibody. In some embodiments, the antibody may have a wild-type human IgG1 Fc region or a wild-type human IgG4 Fc region, a human IgG4 S228P Fc region, a human IgG4 S228P/M252Y/S254T/T256E Fc region, a human IgG1 N297G Fc region, a human IgG1 LALAPG (L234A/L235A/P329G) Fc region, or a human IgG1 N297G/M428L/N434S Fc region. If a murine IgG antibody, the antibody may be an mIgG1 or mIgG2 or mIgG2 LALAPG antibody. An antibody may, in some cases, comprise a full length heavy chain and/or a full length light chain. In some cases, the antibody may lack the C-terminal Lys or the C-terminal Lys and Gly residues of the heavy chain constant region. In other cases, the antibody contains one or both of those C-terminal residues. In some cases, the antibody may be bispecific or multispecific. In some cases, the antibody may be conjugated to another molecule, such as a label or drug either directly or through a linker. In some cases, the antibody has intact effector function. In some cases, the antibody has an Fc region with reduced effector function. In other cases, the antibody has an Fc region that is effectorless. For example, in some cases the antibody comprises a hIgG1 Fc region with an N297G substitution.

In some embodiments, the antibody may have certain properties described in more detail below. For example, in some aspects, the antibody has one or more, two or more, three or more, four or more, five or more, or all of the following characteristics: (a) specifically binds to the stalk domain of TREM2 and specifically binds to a polypeptide consisting of residues 151-165 of hTREM2 (SEQ ID NO: 97); (b) does not bind to soluble TREM2 (sTREM2); and (c) specifically binds to human and cynomolgus TREM2 with a $K_D$ of less than 1 nM, less than 0.7 nM, less than 0.6 nM, less than 0.5 nM, less than 0.4 nM, or less than 0.3 nM, or from 100-500 pM or 100-200 pM at 37° C. by surface plasmon resonance (SPR). In further aspects, the antibody may also (d) specifically bind to an epitope spanning the H157-S158 cleavage site of TREM2; (e) specifically bind to a TREM2 polypeptide consisting of amino acids 146-161 (SEQ ID NO: 96) or 151-165 (SEQ ID NO: 97) with higher affinity than to a TREM2 polypeptide consisting of amino acids 139-158 (SEQ ID NO: 92) and/or 159-175 (SEQ ID NO: 94); and (f) show reduced binding affinity to a TREM2 stalk domain polypeptides individually comprising D152A, H157A, and I159A substitutions compared to a wild-type TREM2 stalk domain polypeptide (e.g., as measured by bilayer interferometry). Accordingly, in some cases, the antibody (a) does not bind to soluble TREM2 and (b) specifically binds to the stalk domain of TREM2. In some cases, the antibody (a) does not bind to soluble TREM2 and (b) specifically binds to a TREM2 epitope spanning the H157-S158 cleavage site of TREM2 and/or (c) specifically bind to a TREM2 polypeptide consisting of amino acids 146-161 (SEQ ID NO: 96) or 151-165 (SEQ ID NO: 97) with higher affinity than to a TREM2 polypeptide consisting of amino acids 139-158 (SEQ ID NO: 92) and/or 159-175 (SEQ ID NO: 94). In some cases, the antibody (a) does not bind to soluble TREM2 and (b) shows reduced binding affinity to a TREM2 stalk domain polypeptides individually comprising D152A, H157A, and I159A substitutions compared to a wild-type TREM2 stalk domain polypeptide (e.g., as measured by bilayer interferometry). In further cases, the antibody (c) specifically binds to human and cynomolgus TREM2 with a $K_D$ of less than 1 nM, less than 0.7 nM, less than 0.6 nM, less than 0.5 nM, less than 0.4 nM, or less than 0.3 nM, or from 100-500 pM or 100-200 pM at 37° C. by surface plasmon resonance (SPR) at 37° C. by surface plasmon resonance (SPR).

In some aspects, the antibody is a TREM2 agonist that specifically binds to an epitope spanning the H157-S158 cleavage site of TREM2 and does not bind to soluble TREM2. In some aspects, the antibody is a TREM2 agonist that specifically binds to an epitope spanning the H157-S158 cleavage site of TREM2; does not bind to soluble TREM2; and specifically binds to human and cynomolgus TREM2 with a $K_D$ of less than 1 nM, less than 0.7 nM, less than 0.6 nM, less than 0.5 nM, less than 0.4 nM, or less than 0.3 nM, or from 100-500 pM or 100-200 pM at 37° C. by surface plasmon resonance (SPR), at 37° C. by surface plasmon resonance (SPR). In some cases, the antibody is a TREM2 agonist that specifically binds to an epitope spanning the H157-S158 cleavage site of TREM2; and does not bind to soluble TREM2. In any of these cases, the antibody may further have one or more of the further properties (a) to (i) listed below.

In some cases, the antibody also has a low off-target binding score (e.g. a score of <1) in an off-target binding assay, such as a BV ELISA assay, (an example is an assay performed as described in Example 10 herein). In some cases, such antibodies may act as TREM2 agonists, and may also have one or more of properties (a) to (i) listed below as well.

Specifically, in some aspects, the antibody may also have one or more, two or more, three or more, four or more, five or more, six or more, seven or more, eight or more, or all of the following characteristics: (a) induces luciferase reporter activity in Jurkat-NFAT reporter cells expressing human TREM2; (b) decreases levels of sTREM2 in vivo in plasma; (c) inhibits shedding of sTREM2 and/or induces internalization of human TREM2 in Jurkat-NFAT luciferase reporter cells; (d) induces tyrosine phosphorylation in human MDM cells expressing human TREM2; (e) induces SYK phosphorylation (p-SYK) in human MDM cells expressing human TREM2; (f) enhances survival of human iPSC-derived microglia; (g) inhibits shedding of sTREM2 in human iPSC-derived microglia; (h) activates TREM2 signaling in human iPSC-derived microglia; and (i) increases total Aβ plaque intensity and/or average X04 plaque intensity in presence of Aβ oligomers in human iPSC-derived microglia.

h3.10C2.v1 Variant Antibodies

In some embodiments, an antibody herein may comprise the heavy and light chain CDRs of h3.10C2.v1 as well as the heavy chain framework regions of the h3.10C2.v1 antibody, as described above and shown in FIGS. 9A-B, but have additional modifications in the antibody light chain, e.g., as shown in FIG. 14A. For example, in some embodiments, certain light chain modifications may be made in the framework regions to improve expression yield, and the like, as described in the Examples below.

In some embodiments, the antibody comprises one of the following sets of VH and VL: (a) SEQ ID Nos: 146 and 145 (antibody h3.10C2.v1 Q100P); (b) SEQ ID Nos: 148 and 147 (antibody h3.10C2.v1 I58V/Q100P); or (c) SEQ ID Nos: 150 and 149 (antibody h3.10C2.v1 Q100P/V104L). In some embodiments, the antibody further comprises a heavy chain and/or a light chain constant region.

In any of the embodiments herein, the antibody may be an antibody fragment, such as an Fv, single-chain Fv (scFv), Fab, Fab', or (Fab')₂. In other embodiments, the antibody may be a whole antibody (i.e., comprising heavy and light chain constant regions.) In other embodiments, the antibody may be an IgG, IgA, or IgM antibody. In some embodiments, the antibody may have a wild-type human IgG1 Fc region or a wild-type human IgG4 Fc region, a human IgG4 S228P Fc region, a human IgG4 S228P/M252Y/S254T/T256E Fc region, a human IgG1 N297G Fc region, a human IgG1 LALAPG (L234A/L235A/P329G) Fc region, or a human IgG1 N297G/M428L/N434S Fc region. If a murine IgG antibody, the antibody may be an mIgG1 or mIgG2 or mIgG2 LALAPG antibody. An antibody may, in some cases, comprise a full length heavy chain and/or a full length light chain. In some cases, the antibody may lack the C-terminal Lys or the C-terminal Lys and Gly residues of the heavy chain constant region. In other cases, the antibody contains one or both of those C-terminal residues. In some cases, the antibody may be bispecific or multispecific. In some cases, the antibody may be conjugated to another molecule, such as a label or drug either directly or through a linker. In some cases, the antibody has intact effector function. In some cases, the antibody has an Fc region with reduced effector function. In other cases, the antibody has an Fc region that is effectorless. For example, in some cases the antibody comprises a hIgG1 Fc region with an N297G substitution.

In some embodiments, the antibody may have certain properties described in more detail below. For example, in some aspects, the antibody has one or more, two or more, three or more, four or more, five or more, or all of the following characteristics: (a) specifically binds to the stalk domain of TREM2; (b) does not bind to soluble TREM2 (sTREM2); and (c) specifically binds to human and cynomolgus TREM2 with a $K_D$ of less than 1 nM, less than 0.7 nM, less than 0.6 nM, less than 0.5 nM, less than 0.4 nM, or less than 0.3 nM, or 100-500 pM or 100-200 pM at 37° C. by surface plasmon resonance (SPR). In further aspects, the antibody may also (d) specifically bind to an epitope spanning the H157-5158 cleavage site of TREM2; (e) specifically bind to a TREM2 polypeptide consisting of amino acids 146-161 (SEQ ID NO: 96) or 151-165 (SEQ ID NO: 97) with higher affinity than to a TREM2 polypeptide consisting of amino acids 139-158 (SEQ ID NO: 92) and/or 159-175 (SEQ ID NO: 94); and (f) show reduced binding affinity to a TREM2 stalk domain polypeptides individually comprising D152A, H157A, and I159A substitutions compared to a wild-type TREM2 stalk domain polypeptide (e.g., as measured by bilayer interferometry). Accordingly, in some cases, the antibody (a) does not bind to soluble TREM2 and (b) specifically binds to the stalk domain of TREM2. In some cases, the antibody (a) does not bind to soluble TREM2 and (b) specifically binds to a TREM2 epitope spanning the H157-S158 cleavage site of TREM2 and/or (c) specifically bind to a TREM2 polypeptide consisting of amino acids 146-161 (SEQ ID NO: 96) or 151-165 (SEQ ID NO: 97) with higher affinity than to a TREM2 polypeptide consisting of amino acids 139-158 (SEQ ID NO: 92) and/or 159-175 (SEQ ID NO: 94). In some cases, the antibody (a) does not bind to soluble TREM2 and (b) shows reduced binding affinity to a TREM2 stalk domain polypeptides individually comprising D152A, H157A, and I159A substitutions compared to a wild-type TREM2 stalk domain polypeptide (e.g., as measured by bilayer interferometry). In some of these cases, the antibody also (c) specifically binds to human and cynomolgus TREM2 with a $K_D$ of less than 1 nM, less than 0.7 nM, less than 0.6 nM, less than 0.5 nM, less than 0.4 nM, or less than 0.3 nM, or 100-500 pM or 100-200 pM at 37° C. by surface plasmon resonance (SPR).

In some aspects, the antibody is a TREM2 agonist that specifically binds to an epitope spanning the H157-S158 cleavage site of TREM2 and does not bind to soluble TREM2. In some aspects, the antibody is a TREM2 agonist that specifically binds to an epitope spanning the H157-S158 cleavage site of TREM2; does not bind to soluble TREM2; and specifically binds to human and cynomolgus TREM2 with a $K_D$ of less than 1 nM, less than 0.7 nM, less than 0.6 nM, less than 0.5 nM, less than 0.4 nM, or less than 0.3 nM, or 100-500 pM or 100-200 pM, at 37° C. by surface plasmon resonance (SPR). In some aspects, the antibody is a TREM2 agonist that specifically binds to an epitope spanning the H157-S158 cleavage site of TREM2; and does not bind to soluble TREM2.

In some cases, the antibody also has a low off-target binding score (e.g. a score of <1) in an off-target binding assay (performed as described in Example 10 herein). In some cases, such antibodies may act as TREM2 agonists, and may also have one or more of properties (a) to (i) listed below as well.

Specifically, in some aspects, the antibody may also have one or more, two or more, three or more, four or more, five or more, six or more, seven or more, eight or more, or all of the following further characteristics: (a) Induces luciferase reporter activity in Jurkat-NFAT reporter cells expressing human TREM2; (b) Decreases levels of sTREM2 in vivo in plasma; (c) Inhibits shedding of sTREM2 in Jurkat-NFAT luciferase reporter cells; (d) Induces tyrosine phosphorylation in human MDM cells; (e) Induces SYK phosphorylation in human MDM cells; (f) Enhances survival of human iPSC-derived microglia in the absence of IL34 and CSF1; (g) Inhibits shedding of sTREM2 in human iPSC-derived microglia; (h) Induces SYK phosphorylation in human iPSC-derived microglia; and (i) Increases total Aβ plaque intensity and/or average X04 plaque intensity in presence of Aβ oligomers in human iPSC-derived microglia.

In some embodiments, antibodies comprise one of the following sets of VH and VL: (a) SEQ ID Nos: 146 and 145 (antibody h3.10C2.v1 Q100P); (b) SEQ ID Nos: 148 and 147 (antibody h3.10C2.v1 I58V/Q100P); and (c) SEQ ID Nos: 150 and 149 (antibody h3.10C2.v1 Q100P/V104L).

Antibody hPara.09.v2

In some embodiments, the antibody comprises the heavy and light chain CDRs of antibody Para.09.v2, in which the heavy chain CDRs are based on the Para.09 heavy chain and the light chain CDRs are based on the 3.27H7 Fab. In some embodiments, an antibody herein comprises heavy chain CDRs of SEQ ID NOS: 11, 12, and 13 (Kabat) or alternatively 19, 20, and 13 (Chothia), and/or the light chain CDRs of SEQ ID NOS: 14, 15, and 16. In some embodiments, the antibody comprises heavy chain CDRs of SEQ ID NOS: 11, 12, and 13 (Kabat) or alternatively 19, 20, and 13 (Chothia), and/or the light chain CDRs of SEQ ID NOS: 14, 15, and 16, and further comprises a heavy chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 17. In some embodiments, the antibody comprises heavy chain CDRs of SEQ ID NOS: 11, 12, and 13 or alternatively 19, 20, and 13, and/or light chain CDRs of SEQ ID NOS: 14, 15, and 16, and further comprises a light chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 18. In some embodiments, the antibody comprises heavy chain CDRs of SEQ ID NOS: 11, 12, and 13 or alternatively 19, 20, and 13, and/or light chain CDRs of SEQ ID NOS: 14, 15, and 16, and further comprises a heavy chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 17, and a light chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 18. In some embodiments, the antibody comprises heavy chain CDRs of SEQ ID NOS: 11, 12, and 13 or alternatively 19, 20, and 13, and/or light chain CDRs of SEQ ID NOS: 14, 15, and 16, and further comprises a heavy chain variable region comprising the amino acid sequence of SEQ ID NO: 17. In some embodiments, the antibody comprises heavy chain CDRs of SEQ ID NOS: 11, 12, and 13 or alternatively 19, 20, and 13, and/or light chain CDRs of SEQ ID NOS: 14, 15, and 16, and further comprises a light chain variable region comprising the amino acid sequence of SEQ ID NO: 18. In some embodiments, the antibody comprises heavy chain CDRs of SEQ ID NOS: 11, 12, and 13 or alternatively 19, 20, and 13, and/or light chain CDRs of SEQ ID NOS: 14, 15, and 16, and further comprises a heavy chain variable region comprising the amino acid sequence of SEQ ID NO: 17, but with up to 5, such as 1, 2, 3, 4, or 5 amino acid substitutions, insertions, or deletions, in the heavy chain framework regions of SEQ ID NO: 17. In some embodiments, the antibody comprises heavy chain CDRs of SEQ ID NOS: 11, 12, and 13 or alternatively 19, 20, and 13, and/or light chain CDRs of SEQ ID NOS: 14, 15, and 16, and further comprises a light chain variable region comprising the amino acid sequence of SEQ ID NO: 18, but with up to 5, such as 1, 2, 3, 4, or 5 amino acid substitutions, insertions, or deletions, in the light chain framework regions of SEQ ID NO: 18. In some embodiments, the antibody comprises a heavy chain variable region comprising the amino acid sequence of SEQ ID NO: 17 and a light chain variable region comprising the amino acid sequence of SEQ ID NO: 18, but with up to 5 amino acid substitutions, insertions, or deletions, such as 1, 2, 3, 4, or 5 amino acid substitutions, insertions, or deletions, in the framework regions of SEQ ID NO: 17 and/or SEQ ID NO: 18.

In some embodiments, the antibody comprises a heavy chain variable region comprising the amino acid sequence of SEQ ID NO: 17 and a light chain variable region comprising the amino acid sequence of SEQ ID NO: 18. In some embodiments, the antibody further comprises a heavy chain and/or a light chain constant region.

In any of the embodiments herein, the antibody may be an antibody fragment, such as an Fv, single-chain Fv (scFv), Fab, Fab', or (Fab')$_2$. In other embodiments, the antibody may be a whole antibody (i.e., comprising heavy and light chain constant regions.) In other embodiments, the antibody may be an IgG, IgA, or IgM antibody. In some embodiments, the antibody may have a wild-type human IgG1 Fc region or a wild-type human IgG4 Fc region, a human IgG4 S228P Fc region, a human IgG4 S228P/M252Y/S254T/T256E Fc region, a human IgG1 N297G Fc region, a human IgG1 LALAPG (L234A/L235A/P329G) Fc region, or a human IgG1 N297G/M428L/N434S Fc region. If a murine IgG antibody, the antibody may be an mIgG1 or mIgG2 or mIgG2 LALAPG antibody. An antibody may, in some cases, comprise a full length heavy chain and/or a full length light chain. In some cases, the antibody may lack the C-terminal Lys or the C-terminal Lys and Gly residues of the heavy chain constant region. In other cases, the antibody contains one or both of those C-terminal residues. In some cases, the antibody may be bispecific or multispecific. In some cases, the antibody may be conjugated to another molecule, such as a label or drug either directly or through a linker. In some cases, the antibody has intact effector function. In some cases, the antibody has an Fc region with reduced effector function. In other cases, the antibody has an Fc region that is effectorless. For example, in some cases the antibody comprises a hIgG1 Fc region with an N297G substitution.

In some embodiments, the antibody comprises a heavy chain comprising or consisting of the amino acid sequence of SEQ ID NO: 144. In some embodiments, the antibody comprises a light chain comprising or consisting of the amino acid sequence of SEQ ID NO: 176. In some embodiments, the antibody comprises a heavy chain comprising or consisting of the amino acid sequence of SEQ ID NO: 144 and a light chain comprising or consisting of the amino acid sequence of SEQ ID NO: 176. In some embodiments, the antibody comprises a heavy chain comprising or consisting of the amino acid sequence of SEQ ID NO: 144 but lacking the C-terminal lysine of SEQ ID NO: 144 or lacking the C-terminal glycine and lysine of SEQ ID NO: 144 and a light chain comprising or consisting of the amino acid sequence of SEQ ID NO: 176. In some embodiments, the antibody comprises a heavy chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 144. In some embodiments, the antibody comprises a light chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 176. In some embodiments, the antibody comprises a heavy chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 144 and a light chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 176. In some embodiments, the antibody comprises a heavy chain comprising or consisting of the amino acid sequence of SEQ ID NO: 144, optionally without the C-terminal lysine or glycine-lysine, and a light chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 176. In some embodiments, the antibody comprises a heavy chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 144 and a light chain comprising or consisting of the amino acid sequence of SEQ ID NO: 176. In some embodiments, the antibody comprises a heavy chain comprising an amino acid sequence with 1, 2, 3, 4, or 5 amino acid substitutions, insertions, or deletions in comparison to the amino acid sequence of SEQ ID NO: 144. In some embodiments, the antibody comprises a light chain comprising an amino acid sequence with 1, 2, 3, 4, or 5 amino acid substitutions, insertions, or deletions in comparison to the amino acid sequence of SEQ ID NO: 176. In some embodiments, the antibody comprises a heavy chain comprising an amino acid sequence with 1, 2, 3, 4, or 5 amino acid substitutions, insertions, or deletions in comparison to the amino acid sequence of SEQ ID NO: 144 and a light chain comprising an amino acid sequence with 1, 2, 3, 4, or 5 amino acid substitutions, insertions, or deletions in comparison to the amino acid sequence of SEQ ID NO: 176. In some embodiments, the antibody comprises a heavy chain comprising or consisting of the amino acid sequence of SEQ ID NO: 144, optionally without the C-terminal lysine or glycine-lysine, and a light chain comprising an amino acid sequence with 1, 2, 3, 4, or 5 amino acid substitutions, insertions, or deletions in comparison to the amino acid sequence of SEQ ID NO: 176. In some embodiments, the antibody comprises a heavy chain comprising an amino acid sequence with 1, 2, 3, 4, or 5 amino acid substitutions, insertions, or deletions in comparison to the amino acid sequence of SEQ ID NO: 144 and a light chain comprising or consisting of the amino acid sequence of SEQ ID NO: 176. In any of the above cases allowing for sequence variation in SEQ ID NO: 144 and/or SEQ ID NO: 176, in some embodiments such sequence variation is limited to the antibody framework and/or constant regions, such that the antibody also comprises heavy chain CDRs of SEQ ID NOS: 11, 12, and 13 or alternatively 19, 20, and 13, and/or light chain CDRs of SEQ ID NOS: 14, 15, and 16. In other embodiments, such sequence variation in SEQ ID NO: 144 and/or SEQ ID NO: 176 is limited to the antibody constant regions, such that the antibody also comprises SEQ ID NO: 17 and/or 18.

In some embodiments, the antibody may have certain properties described in more detail below.

For example, in some aspects, the antibody has one or more, two or more, three or more, four or more, five or more, or all of the following characteristics: (a) specifically binds to the stalk domain of TREM2; (b) does not bind to soluble TREM2 (sTREM2); and (c) specifically binds to human and cynomolgus TREM2 with a $K_D$ of less than 100 pM, less than 50 pM, less than 10 pM, less than 7 pM, less than 5 pM, less than 4 pM, less than 3 pM, or less than 2 pM, such as 10-50 pM or 10-25 pM at 37° C. by surface plasmon resonance (SPR). In further aspects, the antibody may also (d) specifically bind to an epitope spanning the H157-S158 cleavage site of TREM2; (e) specifically bind to a TREM2 polypeptide consisting of amino acids 146-161 (SEQ ID NO: 96) or 151-165 (SEQ ID NO: 97) with higher affinity than to a TREM2 polypeptide consisting of amino acids 139-158 (SEQ ID NO: 92) and/or 159-175 (SEQ ID NO: 94); and (f) show reduced binding affinity to a TREM2 stalk domain polypeptides individually comprising D152A, H157A, and I159A substitutions compared to a wild-type TREM2 stalk domain polypeptide (e.g., as measured by bilayer interferometry). Accordingly, by way of examples, in some aspects, the antibody specifically binds to an epitope spanning the H157-S158 cleavage site of TREM2 and does not bind to soluble TREM2. In some such cases, the antibody also specifically binds to human and cynomolgus TREM2 with a $K_D$ of less than 100 pM, less than 50 pM, less than 10 pM, less than 7 pM, less than 5 pM, less than 4 pM, less than 3 pM, or less than 2 pM, such as 10-50 pM or 10-25 pM. In some aspects, the antibody specifically binds to an epitope spanning the H157-S158 cleavage site of TREM2 and/or specifically binds to a TREM2 polypeptide consisting of amino acids 146-161 (SEQ ID NO: 96) or 151-165 (SEQ ID NO: 97) with higher affinity than to a TREM2 polypeptide consisting of amino acids 139-158 (SEQ ID NO: 92) and/or 159-175 (SEQ ID NO: 94); and also does not bind to soluble TREM2. In some such cases, the antibody also specifically binds to human and cynomolgus TREM2 with a $K_D$ of less than 100 pM, less than 50 pM, less than 10 pM, less than 7 pM, less than 5 pM, less than 4 pM, less than 3 pM, or less than 2 pM, such as 10-50 pM or 10-25 pM., at 37° C. by surface plasmon resonance (SPR). In some aspects, the antibody specifically binds to the stalk domain of TREM2; and does not bind to soluble TREM2. In some such cases, the antibody also specifically binds to human and cynomolgus TREM2 with a $K_D$ of less than 100 pM, less than 50 pM, less than 10 pM, less than 7 pM, less than 5 pM, less than 4 pM, less than 3 pM, or less than 2 pM, such as 10-50 pM or 10-25 pM. In some aspects, the antibody does not bind to soluble TREM2; and specifically binds to human and cynomolgus TREM2 with a $K_D$ of less than 100 pM, less than 50 pM, less than 10 pM, less than 7 pM, less than 5 pM, less than 4 pM, less than 3 pM, or less than 2 pM, such as 10-50 pM or 10-25 pM, at 37° C. by surface plasmon resonance (SPR). In some cases, the antibody does not bind to soluble TREM2 and shows reduced binding affinity to a TREM2 stalk domain polypeptides individually comprising D152A, H157A, and I159A substitutions compared to a wild-type TREM2 stalk domain polypeptide (e.g., as measured by bilayer interferometry). In some such cases, the antibody also specifically binds to human and cynomolgus TREM2 with a $K_D$ of less than 100 pM, less than 50 pM, less than 10 pM, less than 7 pM, less than 5 pM, less than 4 pM, less than 3 pM, or less than 2 pM, such as 10-50 pM or 10-25 pM. In some cases, the antibody has intact effector function. In some cases, the antibody has an Fc region with reduced effector function. In other cases, the antibody has an Fc region that is effectorless. For example, in some cases the antibody comprises a hIgG1 Fc region with an N297G substitution.

In some cases, the antibody also has a low off-target binding score (e.g. a score of <1) in an off-target binding assay (performed as described in Example 10 herein). In some cases, the antibody may have a lower $K_D$ for human TREM2 than an antibody comprising the heavy and light chain CDRs of 3.10C2.

In some aspects, the antibody is a TREM2 agonist that specifically binds to an epitope spanning the H157-S158 cleavage site of TREM2 and does not bind to soluble TREM2. In some aspects, the antibody is a TREM2 agonist that specifically binds to an epitope spanning the H157-S158 cleavage site of TREM2; does not bind to soluble TREM2. In some aspects, the antibody is a TREM2 agonist that specifically binds to an epitope spanning the H157-S158 cleavage site of TREM2; and does not bind to soluble TREM2; and also specifically binds to human and cynomolgus TREM2 with a $K_D$ of less than 100 pM, less than 50 pM, less than 10 pM, less than 7 pM, less than 5 pM, less than 4 pM, less than 3 pM, or less than 2 pM, such as 10-50 pM or 10-25 pM, at 37° C. by surface plasmon resonance (SPR). In some cases, the antibody has intact effector function. In some cases, the antibody has an Fc region with reduced effector function. In other cases, the antibody has an Fc region that is effectorless. For example, in some cases the antibody comprises a hIgG1 Fc region with an N297G substitution.

In any of these cases, the antibody may further have one or more of the further properties (a) to (i) listed below.

Specifically, in some aspects, the antibody may also have one or more, two or more, three or more, four or more, five or more, six or more, seven or more, eight or more, or all of the following characteristics: (a) Induces luciferase reporter activity in Jurkat-NFAT reporter cells expressing human TREM2; (b) Decreases levels of sTREM2 in vivo in plasma; (c) Inhibits shedding of sTREM2 in Jurkat-NFAT luciferase reporter cells expressing human TREM2; (d) Induces tyrosine phosphorylation in human MDM cells; (e) Induces SYK phosphorylation in human MDM cells; (f) Enhances survival of human iPSC-derived microglia in the absence of IL-34 and CSF-1; (g) Inhibits shedding of sTREM2 in human iPSC-derived microglia; (h) Induces SYK phosphorylation in human iPSC-derived microglia; and (i) Increases total Aβ plaque intensity and/or average $X_{04}$ plaque intensity in presence of Aβ oligomers in human iPSC-derived microglia. In some embodiments, the antibody may have higher luciferase reporter activity (e.g., a lower EC50 in a Jurkat-NFAT reporter assay as described in the Examples herein) than an antibody comprising the heavy and light chain CDRs of 3.10C2. In some embodiments, the antibody may show greater inhibition of sTREM2 shedding in Jurkat-NFAT reporter cells (e.g., in an assay as described in the Examples) compared to an antibody comprising the heavy and light chain CDRs of 3.10C2.

hPara.09.v2 Variant Antibodies

Figure 13A:
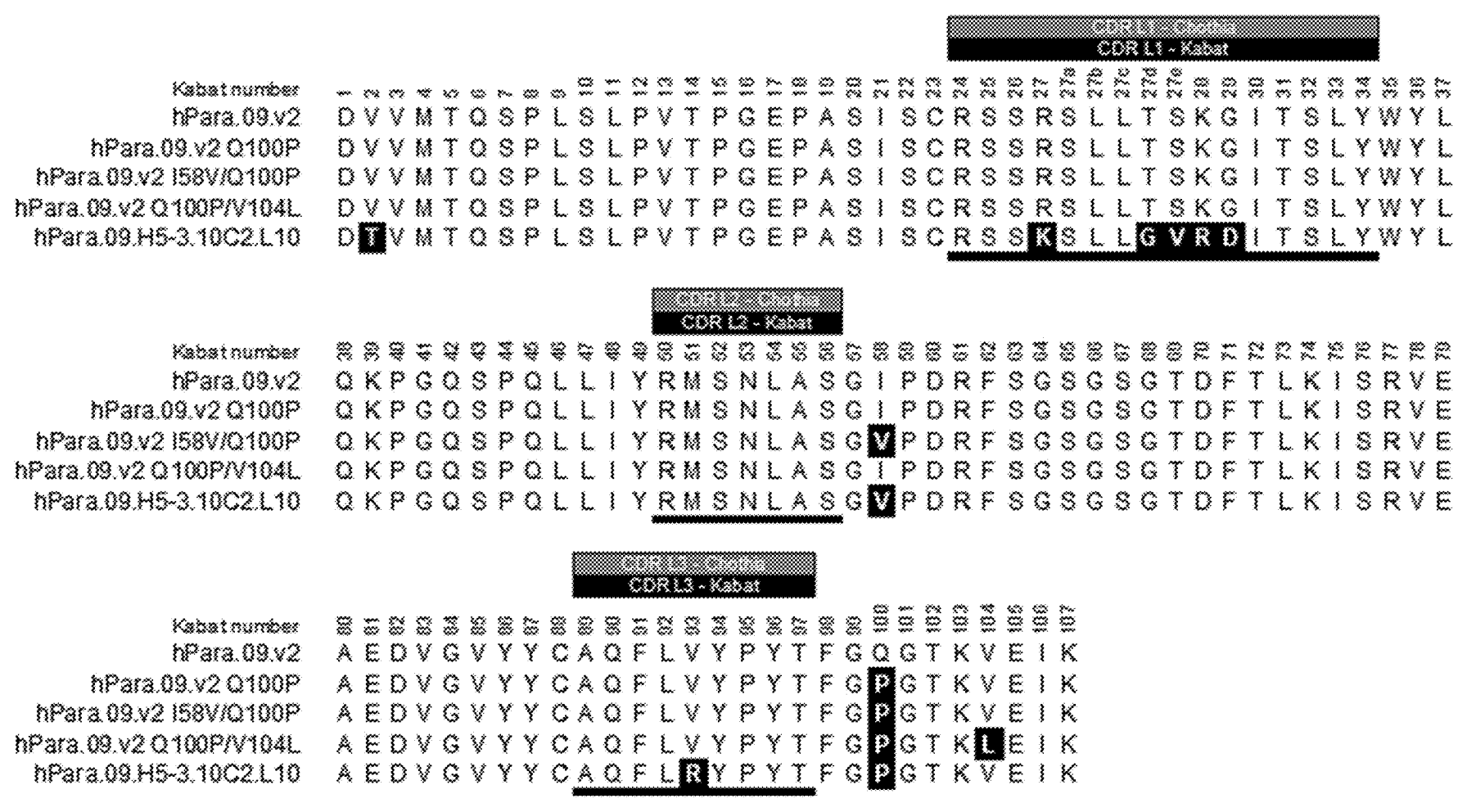

In some embodiments, an antibody herein may comprise the heavy and light chain CDRs of hPara.09.v2 as well as the heavy chain framework regions of the hPara.09.v2 antibody, as described above and shown in FIGS. 12A-B, but have additional modifications in the antibody light chain, e.g., as shown in FIG. 13A. For example, in some embodiments, certain light chain modifications may be made in the framework regions to improve expression yield as described in the Examples below.

In some such embodiments, the antibody comprises one of the following sets of VH and VL: (a) SEQ ID Nos: 133 and 132 (antibody hPara.09.v2 Q100P); (b) SEQ ID Nos: 135 and 134 (antibody hPara.09.v2 I58V/Q100P); (c) SEQ ID Nos: 137 and 136 (antibody hPara.09.v2 Q100P/V104L). In some embodiments, the antibody further comprises a heavy chain and/or a light chain constant region. In some embodiments, the antibody light chain comprises or consists of the amino acid sequence of SEQ ID NO: 176.

In any of the embodiments herein, the antibody may be an antibody fragment, such as an Fv, single-chain Fv (scFv), Fab, Fab', or (Fab')$_2$. In other embodiments, the antibody may be a whole antibody (i.e., comprising heavy and light chain constant regions.) In other embodiments, the antibody may be an IgG, IgA, or IgM antibody. In some embodiments, the antibody may have a wild-type human IgG1 Fc region or a wild-type human IgG4 Fc region, a human IgG4 S228P Fc region, a human IgG4 S228P/M252Y/S254T/T256E Fc region, a human IgG1 N297G Fc region, a human IgG1 LALAPG (L234A/L235A/P329G) Fc region, or a human IgG1 N297G/M428L/N434S Fc region. If a murine IgG antibody, the antibody may be an mIgG1 or mIgG2 or mIgG2 LALAPG antibody. An antibody may, in some cases, comprise a full length heavy chain and/or a full length light chain. In some cases, the antibody may lack the C-terminal Lys or the C-terminal Lys and Gly residues of the heavy chain constant region. In other cases, the antibody contains one or both of those C-terminal residues. In some cases, the antibody may be bispecific or multispecific. In some cases, the antibody may be conjugated to another molecule, such as a label or drug either directly or through a linker. In some cases, the antibody has intact effector function. In some cases, the antibody has an Fc region with reduced effector function. In other cases, the antibody has an Fc region that is effectorless. For example, in some cases the antibody comprises a hIgG1 Fc region with an N297G substitution.

In some embodiments, the antibody may have certain properties described in more detail below. For example, in some aspects, the antibody has one or more, two or more, three or more, four or more, five or more, or all of the following characteristics: (a) specifically binds to the stalk domain of TREM2; (b) does not bind to soluble TREM2 (sTREM2); and (c) specifically binds to human and cynomolgus TREM2 with a $K_D$ of less than 100 pM, less than 50 pM, less than 10 pM, less than 7 pM, less than 5 pM, less than 4 pM, less than 3 pM, or less than 2 pM, or 10-50 pM or 10-25 pM at 37° C. by surface plasmon resonance (SPR). In further aspects, the antibody may also (d) specifically bind to an epitope spanning the H157-S158 cleavage site of TREM2; (e) specifically bind to a TREM2 polypeptide consisting of amino acids 146-161 (SEQ ID NO: 96) or 151-165 (SEQ ID NO: 97) with higher affinity than to a TREM2 polypeptide consisting of amino acids 139-158 (SEQ ID NO: 92) and/or 159-175 (SEQ ID NO: 94); and (f) show reduced binding affinity to a TREM2 stalk domain polypeptides individually comprising D152A, H157A, and I159A substitutions compared to a wild-type TREM2 stalk domain polypeptide (e.g., as measured by bilayer interferometry). Accordingly, by way of examples, in some aspects, the antibody specifically binds to an epitope spanning the H157-S158 cleavage site of TREM2 and does not bind to soluble TREM2. In some such cases, the antibody also specifically binds to human and cynomolgus TREM2 with a $K_D$ of less than 100 pM, less than 50 pM, less than 10 pM, less than 7 pM, less than 5 pM, less than 4 pM, less than 3 pM, or less than 2 pM, such as 10-50 pM or 10-25 pM. In some aspects, the antibody specifically binds to an epitope spanning the H157-S158 cleavage site of TREM2 and/or specifically binds to a TREM2 polypeptide consisting of amino acids 146-161 (SEQ ID NO: 96) or 151-165 (SEQ ID NO: 97) with higher affinity than to a TREM2 polypeptide consisting of amino acids 139-158 (SEQ ID NO: 92) and/or 159-175 (SEQ ID NO: 94); and also does not bind to soluble TREM2. In some such cases, the antibody also specifically binds to human and cynomolgus TREM2 with a $K_D$ of less than 100 pM, less than 50 pM, less than 10 pM, less than 7 pM, less than 5 pM, less than 4 pM, less than 3 pM, or less than 2 pM, such as 10-50 pM or 10-25 pM., at 37° C. by surface plasmon resonance (SPR). In some aspects, the antibody specifically binds to the stalk domain of TREM2; and does not bind to soluble TREM2. In some such cases, the antibody also specifically binds to human and cynomolgus TREM2 with a $K_D$ of less than 100 pM, less than 50 pM, less than 10 pM, less than 7 pM, less than 5 pM, less than 4 pM, less than 3 pM, or less than 2 pM, such as 10-50 pM or 10-25 pM. In some aspects, the antibody does not bind to soluble TREM2; and specifically binds to human and cynomolgus TREM2 with a $K_D$ of less than 100 pM, less than 50 pM, less than 10 pM, less than 7 pM, less than 5 pM, less than 4 pM, less than 3 pM, or less than 2 pM, such as 10-50 pM or 10-25 pM, at 37° C. by surface plasmon resonance (SPR). In some cases, the antibody does not bind to soluble TREM2 and shows reduced binding affinity to a TREM2 stalk domain polypeptides individually comprising D152A, H157A, and I159A substitutions compared to a wild-type TREM2 stalk domain polypeptide (e.g., as measured by bilayer interferometry). In some such cases, the antibody also specifically binds to human and cynomolgus TREM2 with a $K_D$ of less than 100 pM, less than 50 pM, less than 10 pM, less than 7 pM, less than 5 pM, less than 4 pM, less than 3 pM, or less than 2 pM, such as 10-50 pM or 10-25 pM. In some cases, the antibody has intact effector function. In some cases, the antibody has an Fc region with reduced effector function. In other cases, the antibody has an Fc region that is effectorless. For example, in some cases the antibody comprises a hIgG1 Fc region with an N297G substitution.

In some cases, the antibody also has a low off-target binding score (e.g. a score of <1) in an off-target binding assay (performed as described in Example 10 herein). In some cases, the antibody may have a lower $K_D$ for human TREM2 than an antibody comprising the heavy and light chain CDRs of 3.10C2. In some aspects, the antibody is a TREM2 agonist that specifically binds to an epitope spanning the H157-S158 cleavage site of TREM2 and does not bind to soluble TREM2. In some aspects, the antibody is a TREM2 agonist that specifically binds to an epitope spanning the H157-S158 cleavage site of TREM2; does not bind to soluble TREM2. In some aspects, the antibody is a TREM2 agonist that specifically binds to an epitope spanning the H157-S158 cleavage site of TREM2; and does not bind to soluble TREM2; and also specifically binds to human and cynomolgus TREM2 with a $K_D$ of less than 100 pM, less than 50 pM, less than 10 pM, less than 7 pM, less than 5 pM, less than 4 pM, less than 3 pM, or less than 2 pM, such as 10-50 pM or 10-25 pM, at 37° C. by surface plasmon resonance (SPR). In some cases, the antibody has intact effector function. In some cases, the antibody has an Fc region with reduced effector function. In other cases, the antibody has an Fc region that is effectorless. For example, in some cases the antibody comprises a hIgG1 Fc region with an N297G substitution.

In any of these cases, the antibody may further have one or more of the further properties (a) to (i) listed below.

In some aspects, the antibody may also have one or more, two or more, three or more, four or more, five or more, six or more, seven or more, eight or more, or all of the following characteristics: (a) Induces luciferase reporter activity in Jurkat-NFAT reporter cells expressing human TREM2; (b) Decreases levels of sTREM2 in vivo in plasma; (c) Inhibits shedding of sTREM2 human TREM2 in Jurkat-NFAT luciferase reporter cells expressing human TREM2; (d) Induces tyrosine phosphorylation in human MDM cells; (e) Induces SYK phosphorylation in human MDM cells; (f) Enhances survival of human iPSC-derived microglia in the absence of IL-34 and CSF-1; (g) Inhibits shedding of sTREM2 in human iPSC-derived microglia; (h) Induces SYK phosphorylation in human iPSC-derived microglia; and (i) Increases total Aβ plaque intensity and/or average X04 plaque intensity in presence of Aβ oligomers in human iPSC-derived microglia. In some embodiments, the antibody may have higher luciferase reporter activity (e.g., a lower EC50 in a Jurkat-NFAT reporter assay as described in the Examples herein) than an antibody comprising the heavy and light chain CDRs of 3.10C2. In some embodiments, the antibody may show greater inhibition of sTREM2 shedding in Jurkat-NFAT reporter cells (e.g., in an assay as described in the Examples) compared to an antibody comprising the heavy and light chain CDRs of 3.10C2.

In some embodiments, antibodies comprise one of the following sets of VH and VL: (a) SEQ ID Nos: 133 and 132 (antibody hPara.09.v2 Q100P); (b) SEQ ID Nos: 135 and 134 (antibody hPara.09.v2 I58V/Q100P); (c) SEQ ID Nos: 137 and 136 (antibody hPara.09.v2 Q100P/V104L).

Nucleic Acids Encoding Antibodies

Nucleic acid molecules comprising polynucleotides that encode one or more chains of anti-TREM2 antibodies are also provided. In some embodiments, a nucleic acid molecule comprises a polynucleotide that encodes a heavy chain or a light chain of an anti-TREM2 antibody. In some embodiments, a nucleic acid molecule comprises both a polynucleotide that encodes a heavy chain and a polynucleotide that encodes a light chain, of an anti-TREM2 antibody. In some embodiments, a first nucleic acid molecule comprises a first polynucleotide that encodes a heavy chain and a second nucleic acid molecule comprises a second polynucleotide that encodes a light chain.

In some such embodiments, the heavy chain and the light chain are expressed from one nucleic acid molecule, or from two separate nucleic acid molecules, as two separate polypeptides. In some embodiments, such as when an antibody is an scFv, a single polynucleotide encodes a single polypeptide comprising both a heavy chain and a light chain linked together.

In some embodiments, a polynucleotide encoding a heavy chain or light chain of an anti-TREM2 antibody comprises a nucleotide sequence that encodes a leader sequence, which, when translated, is located at the N terminus of the heavy chain or light chain. As discussed above, the leader sequence may be the native heavy or light chain leader sequence, or may be another heterologous leader sequence.

Nucleic acid molecules may be constructed using recombinant DNA techniques conventional in the art. In some embodiments, a nucleic acid molecule is an expression vector that is suitable for expression in a selected host cell.

Vectors and Host Cells and Methods of Production

Vectors comprising polynucleotides that encode anti-TREM2 heavy chains and/or anti-TREM2 light chains are provided. Vectors comprising polynucleotides that encode anti-TREM2 heavy chains and/or anti-TREM2 light chains are also provided. Such vectors include, but are not limited to, DNA vectors, phage vectors, viral vectors, retroviral vectors, etc. In some embodiments, a vector comprises a first polynucleotide sequence encoding a heavy chain and a second polynucleotide sequence encoding a light chain. In some embodiments, the heavy chain and light chain are expressed from the vector as two separate polypeptides. In some embodiments, the heavy chain and light chain are expressed as part of a single polypeptide, such as, for example, when the antibody is an scFv.

In some embodiments, a first vector comprises a polynucleotide that encodes a heavy chain and a second vector comprises a polynucleotide that encodes a light chain. In some embodiments, the first vector and second vector are transfected into host cells in similar amounts (such as similar molar amounts or similar mass amounts). In some embodiments, a mole- or mass-ratio of between 5:1 and 1:5 of the first vector and the second vector is transfected into host cells. In some embodiments, a mass ratio of between 1:1 and 1:5 for the vector encoding the heavy chain and the vector encoding the light chain is used. In some embodiments, a mass ratio of 1:2 for the vector encoding the heavy chain and the vector encoding the light chain is used.

In some embodiments, a vector is selected that is optimized for expression of polypeptides in CHO or CHO-derived cells, or in NS0 cells. Exemplary such vectors are described, e.g., in Running Deer et al., *Biotechnol. Prog.* 20:880-889 (2004).

In some embodiments, a vector is chosen for in vivo expression of anti-TREM2 heavy chains and/or anti-TREM2 light chains in animals, including humans. In some such embodiments, expression of the polypeptide is under the control of a promoter that functions in a tissue-specific manner. For example, liver-specific promoters are described, e.g., in PCT Publication No. WO 2006/076288

For recombinant production of an anti-TREM2 antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology*, Vol. 248 (B. K. C. Lo, ed., Humana Press, Totowa, NJ, 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BEM); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR⁻ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, NJ), pp. 255-268 (2003).

Anti-TREM2 antibodies may be purified by any suitable method. Such methods include, but are not limited to, the use of affinity matrices or hydrophobic interaction chromatography. Suitable affinity ligands include the TREM2 ECD and ligands that bind antibody constant regions. For example, a Protein A, Protein G, Protein A/G, or an antibody affinity column may be used to bind the constant region and to purify an anti-TREM2 antibody. Hydrophobic interactive chromatography, for example, a butyl or phenyl column, may also suitable for purifying some polypeptides. Many methods of purifying polypeptides are known in the art. In some embodiments, an anti-TREM2 antibody is produced in a cell-free system. Nonlimiting exemplary cell-free systems are described, e.g., in Sitaraman et al., *Methods Mol. Biol.* 498: 229-44 (2009); Spirin, *Trends Biotechnol.* 22: 538-45 (2004); Endo et al., *Biotechnol. Adv.* 21: 695-713 (2003).

Methods of Pharmaceutical Use

The present disclosure also encompasses methods of using anti-TREM2 antibodies herein, for example, in pharmaceutical treatments. For example, the disclosure encompasses methods of treating a condition associated with TREM2 loss of function in a subject. The disclosure also encompasses methods of reducing levels of sTREM2 in a subject.

In some cases, the condition is a neuroinflammatory or neurodegenerative disease. Examples include, for instance, Alzheimer's disease, Parkinson's disease, frontotemporal dementia, dementia, multiple sclerosis (MS), amyotrophic lateral sclerosis (ALS), Nasu-Hakola disease, Guillain-Barré Syndrome (GBS), lysosomal storage disease, sphingomyelinlipidosis (Neimann-Pick C), mucopolysaccharidosis metachromatic leukodystrophy, multifocal motor neuropathy, neuro-Behcet's disease, neuromyelitis optica (NMO), optic neuritis, polymyositis, dermatomyositis, stroke, transverse myelitis, traumatic brain injury, or spinal cord injury. In some cases, the condition is Alzheimer's disease. In some cases, the condition is MS.

For example, pathological hallmarks of Alzheimer's Disease (AD) include extracellular deposits of beta-amyloid peptides that form amyloid plaques and intracellular deposits of aggregated hyperphosphorylated tau called neurofibrillary tangles. These pathologies are followed by an increase in brain inflammation, including activated astrocytes and microglia, and neurodegeneration. Familial forms of AD may be caused by mutations in presenilin 1/2 and amyloid precursor protein genes. Transgenic mice expressing these human mutations as well as a mutation in the Tau protein show similar age-dependent increases in Abeta pathology, hyperphosphorylated Tau and neurodegeneration. Mutations causing a loss of TREM2 function result in irregular microglial compaction of plaque, elevated neuritic dystrophy surrounding the plaque, elevated abeta-induced tau pathology and neurodegeneration. Without wishing to be bound by theory, enhancing TREM2 activity may enhance microglia activity and facilitate the removal of toxic amyloid-beta peptides, by engulfment or compaction into less toxic amyloid plaques, thus treating AD.

Multiple sclerosis (MS) is a disease characterized by an autoimmune related demyelination in the CNS. In patients, the disease presents in episodes of symptoms such as ataxia, limb weakness, and optic neuritis among other neurological effects. Current treatments involve immune suppressing agents, and may have limited effectiveness, while no therapy effectively prevents or reverses the disease. Remyelinating therapies have been proposed as an approach for treating and possibly reversing MS. Compounds and therapies which promote oligodendrocyte differentiation from progenitors (OPCs) to mature, myelinating oligodendrocytes have been considered a possible route to a remyelinating therapy, as well as treatments which modify glial cells. Specifically, microglia are thought to have a role in clearing myelin debris, promoting new myelin to form. TREM2 loss of function leads to hypomyelinating leukodystrophy, and TREM2 knock-out mice have a profound impairment in remyelination and recovery in animal models of MS. Without wishing to be bound by theory, activation of the TREM2 pathway may accelerate remyelination, thus treating MS.

In various embodiments, anti-TREM2 antibodies may be administered in vivo by various routes, including, but not limited to, oral, intravenous, subcutaneous, parenteral, intranasal, intramuscular, intradermal, topical, transdermal, and intrathecal, or otherwise by implantation or inhalation. The subject compositions may be formulated into preparations in solid, semi-solid, liquid, or gaseous forms; including, but not limited to, tablets, capsules, powders, granules, ointments, solutions, suppositories, enemas, injections, inhalants, and aerosols. A nucleic acid molecule encoding an anti-TREM2 antibody may be administered, either directly or in a vector such as a viral vector. The appropriate formulation and route of administration may be selected according to the intended application.

In various embodiments, compositions comprising anti-TREM2 antibodies are provided in formulations with a wide variety of pharmaceutically acceptable carriers (see, e.g., Gennaro, *Remington: The Science and Practice of Phar-* macy with Facts and Comparisons: Drugfacts Plus, 20th ed. (2003); Ansel et al., Pharmaceutical Dosage Forms and Drug Delivery Systems, 7th ed., Lippencott Williams and Wilkins (2004); Kibbe et al., Handbook of Pharmaceutical Excipients, 3rd ed., Pharmaceutical Press (2000)). Various pharmaceutically acceptable carriers, which include vehicles, adjuvants, and diluents, are available. Moreover, various pharmaceutically acceptable auxiliary substances, such as pH adjusting and buffering agents, tonicity adjusting agents, stabilizers, wetting agents and the like, are also available. Non-limiting exemplary carriers include saline, buffered saline, dextrose, water, glycerol, ethanol, and combinations thereof.

In various embodiments, compositions comprising anti-TREM2 antibodies may be formulated for injection or infusion, by dissolving, suspending, or emulsifying them in an aqueous or nonaqueous solvent, such as vegetable or other oils, synthetic aliphatic acid glycerides, esters of higher aliphatic acids, or propylene glycol; and if desired, with conventional additives such as solubilizers, isotonic agents, suspending agents, emulsifying agents, stabilizers and preservatives. In various embodiments, the compositions may be formulated for inhalation, for example, using pressurized acceptable propellants such as dichlorodifluoromethane, propane, nitrogen, and the like. The compositions may also be formulated, in various embodiments, into sustained release microcapsules, such as with biodegradable or non-biodegradable polymers. A non-limiting exemplary biodegradable formulation includes poly lactic acid-glycolic acid polymer. A non-limiting exemplary non-biodegradable formulation includes a polyglycerin fatty acid ester. Certain methods of making such formulations are described, for example, in EP 1 125 584 A1.

Pharmaceutical packs and kits comprising one or more containers, each containing one or more doses of an anti-TREM2 antibody are also provided. In some embodiments, a unit dosage is provided wherein the unit dosage contains a predetermined amount of a composition comprising an anti-TREM2 antibody, with or without one or more additional agents. In some embodiments, such a unit dosage is supplied in single-use prefilled syringe for injection. In various embodiments, the composition contained in the unit dosage may comprise saline, sucrose, or the like; a buffer, such as phosphate, or the like; and/or be formulated within a stable and effective pH range. Alternatively, in some embodiments, the composition may be provided as a lyophilized powder that may be reconstituted upon addition of an appropriate liquid, for example, sterile water. In some embodiments, the composition comprises one or more substances that inhibit protein aggregation, including, but not limited to, sucrose and arginine. In some embodiments, a composition of the invention comprises heparin and/or a proteoglycan.

EXAMPLES

Example 1: Preparation of Rat Anti-TREM2 Antibodies

A. Materials and Methods

To generate anti-human TREM2 antibodies, Sprague Dawley rats (Charles River, Hollister, CA) or TREM2 knockout mice (Genentech, South San Francisco) were immunized with various antigen formats: human TREM2 extracellular domain (ECD) protein emulsified with Complete Freund's Adjuvant or Ribi; extracellular vesicles (EV) expressing human full length TREM2; or pDNA encoding full length human TREM2 delivered via gene gun or hydrodynamic tail vein (HTV) injection (FIG. 1).

Lymph nodes and spleens from immunized animals were harvested and B cells were isolated as follows. For rats, class switched B cells were enriched using a cocktail of biotinylated antibodies (CD4, CD8a, CD11b/c, CD161, HIS48, IgM) from BD Biosciences followed by magnetic separation (Miltenyi Biotec, San Diego, CA) using streptavidin beads. For mice, a pan B cell Isolation kit (Miltenyi Biotec, San Diego, CA) was used to enrich for B cells, followed by magnetic depletion of IgM-positive B cells (biotinylated anti-IgM 11/41, BD Biosciences). IgM-depleted B cells were fused with Sp2ab myeloma cells (Abeome, Athens, GA) via electrofusion (Harvard Apparatus, Holliston, MA). After overnight recovery in Clonacell-HY Medium C (StemCell Technologies, Canada), cells were selected in HAT (hypoxanthine-aminopterin-thymidine) (Sigma-Aldrich). Fused hybridomas were then harvested and stained with anti-rat IgG-Alexa 488 (Jackson ImmunoResearch) for rat hybridomas, or anti-mouse IgG FITC (Bethyl Labs) for mouse hybridomas, and fluorescent conjugated human TREM2-Alexa Fluor 643 (Novus Biological). Single IgG+/human TREM2+hybridoma cells were sorted into 96-well plates using a FACSAriaIII sorter (BD, Franklin Lakes, NJ) and cultured for 7 days. Supernatants were screened by ELISA against human TREM2 antigen, and ELISA-positive clones were scaled-up. Purified IgG (Gamma Bind Plus, GE Healthcare, Pittsburgh, PA) from hybridoma supernatants was screened by FACS for cell surface binding using DOX-inducible human TREM2 expressing 293 cells and functional activity.

B. Results

A total of 1,650 hybridoma clones specifically bound immobilized human TREM2 in an ELISA format (FIG. 1). Of these, 947 bound in FACS to 293 cells expressing human TREM2 (FIG. 1). The variable regions of immunoglobulin genes of FACS-positive hybridoma clones were then sequenced.

A total of 229 unique clones were identified, with a majority coming from SD rats immunized with human TREM2 ECD (FIG. 1). The variable region sequences of unique FACS-positive anti-TREM2 clones were used for cloning as mouse IgG2a, effectorless mouse IgG2a with LALAPG (L234A/L235A/P329G, Eu numbering system), chimeric human IgG1, chimeric effectorless human IgG1 LALAPG (L234A/L235A/P329G) and chimeric effectorless human IgG1 N297G by gene synthesis (GeneWiz). Recombinant IgG were transiently expressed in CHO cells and purified by protein A and size exclusion chromatography. Selected clones were also cloned as chimeric human Fab fragments in CHO cells and purified by anti-CH1 affinity chromatography followed by size exclusion chromatography.

Example 2: Epitope Specificity of Anti-TREM2 Clones

A. Materials and Methods

Antibodies were screened for binding to peptides from the human TREM2 stalk (TREM2 residues 129-174). Peptides with overlapping sequences, ranging from TREM2 residues 129-175, were used to provide coverage for the entire stalk (FIG. 2A). The antibody epitopes were mapped to the stalk region of human TREM2 using enzyme-linked immunosorbent assay (ELISA). Overlapping biotinylated peptides were captured in ELISA plates coated with streptavidin. The binding of antibodies to peptides was detected with an anti-mouse IgG conjugated to horseradish peroxidase.

B. Results

Several antibody groups that bind to stalk peptide fragments of human TREM2 were found, with three rat anti-human antibodies generally binding to residues 151 to 161 of TREM2: antibodies 3.10C2, 3.18E5, and 3.50G1 in FIG. 2B (binding affinities in nM). In particular, these three antibodies bound to peptides of residues 146-169, 146-161, 149-168 or 151-165 of the hTREM2 stalk at least as well, if not better, than to a peptide consisting of residues 129-175. These four peptides each encompass the region from residue 151 to residue 161 of the hTREM2 stalk and include the His157-Ser158 cleavage location on the hTREM2 stalk, which is also depicted in FIG. 2A. Affinity of those antibodies for all of the other tested peptides was significantly reduced in comparison to affinity for the 129-175 peptide.

Example 3: Affinities of Rat Anti-TREM2 Antibodies

A. Materials and Methods

Forty-six rat anti-human antibodies were tested for binding affinity to the hTREM2 and cynomolgus TREM2 stalk. Antibody binding affinities for hTREM2 stalk and cynomolgus TREM2 stalk were measured by surface plasmon resonance (SPR) using a Biacore™ T200 apparatus. TREM2 stalk antigens (human or cynomolgus) were immobilized on anti-human IgG1 Fc Biacore™ chips and anti-TREM2 antibody clones were bound to immobilized TREM2 at 37° C. Binding affinities, $K_D$ (nM) were measured and recorded.

B. Results

The binding affinities of the forty-six tested antibodies against hTREM2 stalk were measured—the measured $K_D$ values ranged from 1.13 µM to 0.01 nM. Several antibodies were selected for binding measurements against cynomolgus TREM2 stalk. From the initial group of antibodies tested, five antibodies (3.10C2, 3.50G1, 3.18E5, 3.36F5, and 3.27H7) had particularly low $K_D$ values for both human and cynomolgus TREM2 stalk regions. The binding affinities of antibodies 3.10C2, 3.50G1, 3.18E5, 3.36F5, and 3.27H7 for hTREM2 stalk were 0.24 nM, 0.61 nM, 0.26 nM, 10 nM, and 0.22 nM, respectively. The binding affinities of antibodies 3.10C2, 3.50G1, 3.18E5, 3.36F5, and 3.27H7 for cynomolgus TREM2 stalk were 0.25 nM, 0.57 nM, 0.30 nM, 12 nM, and 0.26 nM, respectively. These clones are independent clones in the same B cell clonal lineage and their sequences of the CDR and variable regions of 3.10C2, 3.50G1, 3.18E5, 3.36F5, and 3.27H7 are shown in FIGS. 3A-B. Of those initial five antibodies, four had $K_D$ values below 1 nM, specifically the 3.10C2, 3.50G1, 3.18E5, and 3.27H7. These four antibodies are referred to collectively below as the "3.10C2 group" of antibodies.

Example 4: Deep Sequencing of Rat Antibody Clones and Identification of Clone Para.09

Further studies were performed with a goal of identifying clones from an immunized rat antibody repertoire deep sequencing dataset that would have similar binding and activity properties as the 3.10C2, 3.50G1, 3.18E5, and 3.27H7 group of antibodies (collectively the "3.10C2 group") and the 3.36E5 antibody clone, but with even higher affinity for TREM2.

A. Rationale and Introduction

It has been previously shown that, in rodent antibody repertoires, antibodies specific for an antigen that share the same VH and VL germline segments tend to share epitope specificity with a high frequency despite CDR H3 diversity (Hsiao et al., mAbs 12:1, 1722541, doi:10.1080/19420862.2020.1722541 (2020)). Therefore, it was possible that additional antibodies from immunized rats with IGHV6-8 and IGKV2S11 germline segments but different CDR H3 sequences might recognize the same epitope as the 3.10C2 group of antibodies if these were TREM2-specific. Mining for clonally independent antibodies that bind antigen in a similar mode has been described for anti-HIV-1 gp120 antibodies from infected donors (Zhu et al., Proc. Natl. Acad. Sci. USA 110:E4088-E4097, doi:10.1073/pnas.1306262110 (2013).). However, similar phylogenetic techniques as used for the HIV-1 antibodies were not available in the case of the 3.10C2 group of antibodies. There were at least three reasons for this: (1) the mutational load of the 3.10C2 group of antibodies was relatively low; (2) the important features of the 3.10C2 group of antibodies for antigen binding were not known; and (3) clonally independent antibodies in the same class as the 3.10C2 group were not known. The mining of cross-lineage, cross-donor antibodies by deep sequencing has been described only in the context of highly similar, long CDR H3 sequences that provide substantial sequence information for mining of specific clonal types from the repertoire (Zhu et al., Proc. Natl. Acad. Sci. USA 110:E4088-E4097, doi:10.1073/pnas.1306262110 (2013)). In contrast, relatively limited information was available to mine the repertoire for clonally independent antibodies of the 3.10C2 group in this case, including a very short CDR H3 sequence that provides little specific sequence information for mining. Thus, only $V_H$ and $V_L$ germline segment pairing information was available in the 3.10C2 group for mining, but this information lacked specificity for mining as many clones of different specificities in the repertoire, including specific for antigens other than TREM2, share the same germline segment pairings.

In addition, clone 3.36F5 has a very similar VH as the 3.10C2 group of clones, with rat IGHV6-8 germline segment and Kabat CDR H3 sequence LDY (or TGLDY in the IMGT system) but has a different light chain, with germline segment IGKV2U18 (germline segment described in Goldstein et al., Commun. Biol. 2:304, doi:10.1038/s42003-019-0551-y (2019)). (See FIG. 3B.) Therefore, light chains with similar IGKV segments may also substitute for the 3.10C2 group of clones to mine deep sequencing datasets. Lastly, because these clones do not descend from the same B cell, clonally independent VH sequences that share the same specificity as the 3.10C2 group of clones could be derived from any TREM2-immunized rat that expresses the heavy chain IGHV6-8 germline segment and the light chain IGKV2S11, IGKV2U18 or similar germline segments.

A mining strategy for clones outside clonal lineages in deep sequencing datasets has been recently described (Richardson et al., mAbs doi:10.1080/19420862.2020.1869409 (2021)). However, that method, unlike the one described here, relies on amino acid identities including CDR H3 and is limited to sequences with the same CDR H3 length (Richardson et al., 2021). The search strategy used here ignores the CDR H3 sequence entirely, even allowing different CDR H3 lengths, in contradiction to the currently held view that CDR H3 is a major specificity determinant, implicit in the search strategy of Richardson et al., which includes CDR H3 sequence in the identity calculation for clone selection. In addition, the method we describe here, unlike that Richardson et al., does not explicitly require a given level of amino acid identity over any set of residues between clones, only $V_H$ germline segment used, and in fact, seeks to identify clones with widely divergent CDR H3 sequences. Thus, mining by $V_H$ germline segment, ignoring CDR H3 sequence properties, allows, in principle, a wider search for independent clones with the same epitope specificity than the method of Richardson et al. while obviating the need for information-rich sequence properties as implemented by Zhu et al.

B. Materials and Methods

The VH repertoire of 3 immunized rats was sequenced by paired-end Illumina sequencing using rat-specific primers for cDNA synthesis and PCR amplification. Briefly, bone marrow and spleen tissues from the same set of pooled 3 rats from which the 3.10C2 group clones were derived by hybridoma using lymph node tissues were used to extract total RNA and used in an RT-PCR step to amplify whole repertoire VH segments with the rat VH germline segment primers specific for the sequences encoding the first residues of the framework 1 region and constant region primers specific for rat IgG and IgA isotypes. Amplicons were submitted to paired-end sequencing in an Illumina HiSeg™ instrument. Sequence reads were assembled into full-length VH sequences and parsed for germline segment and CDR boundaries using Absolve™ as previously described (Goldstein et al., Commun. Biol. 2:304, doi:10.1038/s42003-019-0551-y (2019)).

29 clones from independent clonotypes with the IGHV6-8 germline segment and diverse CDR H3 sequences were selected and paired to different light chains of the 3.10C2 clonal group for expression of IgG fragments. DNA clones encoding full-length heavy and light chains of the selected variants were transfected into Expi293 cells in 1-ml scale and IgG was purified by protein A chromatography as previously described (Bos et al., *Biotechnol. Bioeng.* 112: 1832-4, doi:10.1002/bit.25601 (2015); Luan et al., *Mabs* 10:624-35, doi:10.1080/19420862.2018.1445450 (2018)).

Clones were tested for binding to TREM2 stalk peptides in an ELISA format. The heavy chain CDR3 of each clone is shown in FIG. 4 (left column).

C. Results

Of the 29 selected clones, one clone, called Para.09, bound robustly to the human TREM2 stalk peptide (TREM2 residues 129-175) and to a TREM2 peptide fragment from residue 149 to 158 in ELISA when paired to light chains of the 3.10C2 group, similar to a 3.10C2 control (FIG. 4). The CDR H3 sequence of clone Para.09 is 1 residue longer than the CDR H3 of the 3.10C2 group and has a different IGHJ germline segment (IGHJ3 instead of IGHJ2), showing that Para.09 is not a clonal variant of the 3.10C2 group but rather an independently generated clonal lineage in the rat repertoire. In addition, Para.09 has 2 amino acid differences in CDR H3 relative to the 3.10C2 group when ignoring the insertion (TG-LDY versus TDILEY for 3.10C2 and Para.09, respectively, insertion underlined and differences highlighted in boldface and italicized) (FIG. 3B). That is, only half (3 out of 6 in the IMGT system, 2 out of 4 in the Kabat system) of the residues of CDR H3 of Para.09 are the same in similar positions in clone 3.10C2. Highlighting the independent clonal origin of Para.09 relative to the 3.10C2 class of clones, Para.09 has a rat IGHJ3 germline segment in the heavy chain framework 4 region, whereas the 3.10C2 group of clones have a rat IGHJ2 germline segment.

In addition, CDR H3 sequence alone does not predict TREM2 binders. This is exemplified by clone Para.10, which does not bind TREM2 stalk or peptide fragment 149-158, the epitope bound by antibodies in the 3.10C2 group, when paired to any of the 3.10C2 group or germline light chains (FIGS. 3A-B). This clone has a CDR H3 that is 1 residue longer than that in the 3.10C2 group (and the same length as Para.09 CDR H3) while differing from these in no other positions (TGL-DY versus TGLGDY for 3.10C2 and Para.10, respectively, insertion underlined). That is, there are no obvious sequence properties in the Para.09 CDR H3 region that makes this clone an obvious anti-TREM2 candidate. Finally, the frequency of 3.10C2 group and Para.09 lineage sequences in the deep sequencing datasets explains the reason for the unlikely finding of Para.09 clones by hybridoma: whereas there were 8,283 read counts for the 147 unique 3.10C2 group VH sequences in the deep sequencing dataset, there were only 47 sequence reads for the 4 unique Para.09-related VH clones. Given that with count frequencies of the 3.10C2 group VH sequences only 4 of 174 hybridomas were in this group, the likelihood of identifying the low frequency Para.09 clones by hybridoma or similar techniques is presumed to be very low.

Example 5: Binding Affinity of Para.09 Fab Fragments

A. Materials and Methods

Antibody fragments comprising the heavy chain of clone Para.09 paired with light chains antibodies 3.10C2, 3.18E5, 3.27H7, and 3.50G1 (the "3.10C2 group") were tested for affinity for human and cynomolgus TREM2 by SPR in a Biacore™ T200 apparatus. Briefly, clone variants were expressed as Fab fragments and purified by anti-CH1 affinity chromatography followed by size exclusion chromatography. TREM2-Fc antigens were immobilized on anti-human IgG1 Fc Biacore™ chips and soluble Para.09 variant and 3.10C2 clone Fab fragments were bound to immobilized TREM2 at 37° C.

B. Results

All Para.09 clone variants showed significantly higher affinity than a Fab comprising the heavy and light chain variable regions of antibody 3.10C2, irrespective of light chain used and despite the high similarity of CDR H1 and H2 in Para.09 relative to 3.10C2 (Table 1). This indicates that CDR H3 is critical for the higher binding affinity. The higher affinities were reflected by both higher association ($k_a$) and lower dissociation ($k_d$) rates in binding kinetics. Results are shown in Table 1 below.

TABLE 1

Affinities of Fab fragments of Para.09 clones with different light chains for human and cynomolgus TREM2 at 37° C.

| Fab fragment | Human TREM2 | | | Cynomolgus TREM2 | | |
|---|---|---|---|---|---|---|
| (Light chain) | $K_D$ (M) | $k_a$ (1/Ms) | $k_d$ (1/s) | $K_D$ (M) | $k_a$ (1/Ms) | $k_d$ (1/s) |
| 3.10C2 (3.10C2) | 2.0E−10 | 8.5E+05 | 1.7E−04 | 2.2E−10 | 6.8E+05 | 1.5E−04 |
| Para.09 (3.10C2) | 3.8E−12 | 7.1E+06 | 2.7E−05 | 1.6E−12 | 4.8E+06 | 7.8E−06 |
| Para.09 (3.18E5) | 5.0E−12 | 5.6E+06 | 2.8E−05 | 2.4E−12 | 3.8E+06 | 8.9E−06 |

TABLE 1-continued

Affinities of Fab fragments of Para.09 clones with different light chains for human and cynomolgus TREM2 at 37° C.

| Fab fragment | Human TREM2 | | | Cynomolgus TREM2 | | |
|---|---|---|---|---|---|---|
| (Light chain) | $K_D$ (M) | $k_a$ (1/Ms) | $k_d$ (1/s) | $K_D$ (M) | $k_a$ (1/Ms) | $k_d$ (1/s) |
| Para.09 (3.27H7) | 4.2E−12 | 6.3E+06 | 2.7E−05 | 2.5E−12 | 4.8E+06 | 1.2E−05 |
| Para.09 (3.50G1) | 1.1E−12 | 5.1E+06 | 5.8E−06 | 2.0E−12 | 3.9E+06 | 7.9E−06 |

Example 6: Mapping of Residues in the TREM2 Stalk that Interact with the Antibodies A. Materials and Methods While the epitope of Para.09 was expected to reside in the same region as antibodies in the 3.10C2 group, based on how the antibody was generated, more detailed studies were conducted to assess the importance of individual residues on binding. Epitope mapping of clone Para.09, antibody 3.10C2, and other antibodies of the 3.10C2 group such as 3.50G1, was carried out by testing the binding to synthetic TREM2 peptides with single alanine point mutations of residues 149 to 161 or an alanine to glycine mutation at position 153 (FIG. 5). Binding to the synthetic peptides was tested by biolayer interferometry (BLI) in an Octet Red instrument, immobilizing synthetic peptides in streptavidin-coated sensor tips and binding the peptides to free soluble Fab fragments, to avoid avidity effects that obscure effects on binding. This was necessary because the effect of single mutations on antibody binding is not apparent due to their high affinity, especially Para.09, which allows robust binding to mutant peptides even with a lowered affinity to the mutants. Thus, reduced binding or faster dissociation of Fab fragments was used as a readout for the impact of the mutations on antibody binding.

B. Results

The overlapping peptide mapping provided an approximate span for the epitope of 3.10C2, 3.18E5 and 3.50G1 from ranging from residue Glu-151 to the interval between residues Ile-159 to Arg-161, included (FIGS. 2A-B). The further mapping of 3.10C2, 3.50G1 and Para.09 by mutational scanning as described in this Example showed that the residues with side-chains important for binding are located within a range from Asp-152 to Ile-159, included, consistent with the binding to overlapping peptides. As shown in FIG. 5, antibodies 3.10C2 and 3.50G1, both in the 3.10C2 group, had similar binding profiles, with the synthetic peptides comprising alanine mutations at positions 152, 154, 157, 158 and 159, spanning the TREM2 cleavage site, each impacting binding of the Fab fragment to the peptide. Specifically, important TREM2 residue side-chains for binding include at least Asp-152, His-157 and Ile-159 for each of 3.10C2, 3.50G1 and Para.09 antibodies. Examination of crystal structures of huPara.09.v2 Q100P and hu3.10C2.v1 Q100P in complex with a peptide with residues 148 to 165 of TREM2 (resolution=2A) additionally showed that the main contacts of TREM2 with the two antibodies are mediated by residues Asp-152, His-154, Val-155, Glu-156, His-157 and Ile-159 (residues identified by scanning mutagenesis are underlined). Antibody 3.50G1 was also impacted by the E156A and S160A mutations whereas 3.10C2 was not. Another antibody clone according to the present disclosure, 3.47B1, had a more restricted set of mutations impacting binding to TREM2, with only H157A and I159A having detectable effects on binding (FIG. 5). Antibody Para.09, comprising the Para.09 heavy chain variable region paired with the light chain variable region of antibody 3.27H7 (thus, also called Para.09-L27H7 herein), had a similar pattern as 3.10C2 except that no impact on binding was observed for mutations H154A and S158A (FIG. 5). Further examination of crystal structures showed that 3.10C2 and Para.09 are highly similar in the complex structures, with differences in the angles and number of contacts and the depth of hydrophobic pockets likely brought about by the different CDR H3 lengths of both antibodies that may account for observed differences.

Several previously described anti-TREM2 antibodies were also assessed for binding to the stalk region of TREM2 using mutational scanning. For antibodies 14D3 and 14D8 (described, e.g., in WO2018015573), the A153G mutation impacted binding while the D152A and S158A mutations did not (FIG. 5), indicating differences in epitope specificity between the 3.10C2 group and Para.09 relative to the 14D3/14D8 antibodies. The previously described 9F5 and AL2p-31 antibodies (described in WO2017062672 and/or WO201928292), the latter being a humanized and affinity-matured version of 9F5, had a distinct pattern of sensitivity to mutations compared to the 3.10C2, 3.50G1, and Para.09-L27H7 antibodies, extending from residue 150 to residue 156 or 157 just before the cleavage site (FIG. 5). In contrast to 3.10C2, 3.50G1, and Para.09-L27H7, alanine mutations from residues 158 to 161 did not impact the binding of 9F5 and AL2p-31 Fabs. Thus, these previously described antibodies appear distinct in that they do not interact with residues on either side of the cleavage site but rather only with residues found in sTREM2 upon cleavage.

Example 7: Humanization of Antibody 3.10C2

A. Materials and Methods

Antibody 3.10C2 was humanized in VK2 and VH3 frameworks by CDR grafting. Briefly, CDR regions of the rat antibodies were grafted into light chain IGKV2-28*01 and heavy chain IGKV3-73*01 frameworks, the closest human germlines of these antibodies (FIGS. 6A-B). CDR regions included, for the light chain, Kabat positions 24-34 (CDR L1), 50-56 (CDR L2) and 89-97 (CDR L3), and, for the heavy chain, Kabat positions 26-35 (CDR H1), 50-65 (CDR H2) and 93-102 (CDR H3). Rat framework residues known as "Vernier" positions and in the domain interface that differed between the rat antibodies and human germlines were added to the CDR grafts to rescue binding to antigen, as it is normally done in CDR graft humanizations (see for example U.S. Pat. No. 8,426,147). These included in this case light chain residues 2, 4 and 68 and heavy chain framework residues 24, 48, 49, 76 and 78 (FIGS. 6A-B). Variants with different sets of human and mouse framework residues were expressed as human IgG1 in Expi293 cells and purified by Protein A chromatography.

The humanized heavy chain variants were tested for affinity by combining the heavy chain variants with the 3.10C2-L1 light chain. These variants were expressed as Fab fragments, purified by protein A chromatography, and tested for affinity for TREM2-Fc coated on a protein A chip with a Biacore™ T200 apparatus.

B. Results

Figure 7A:
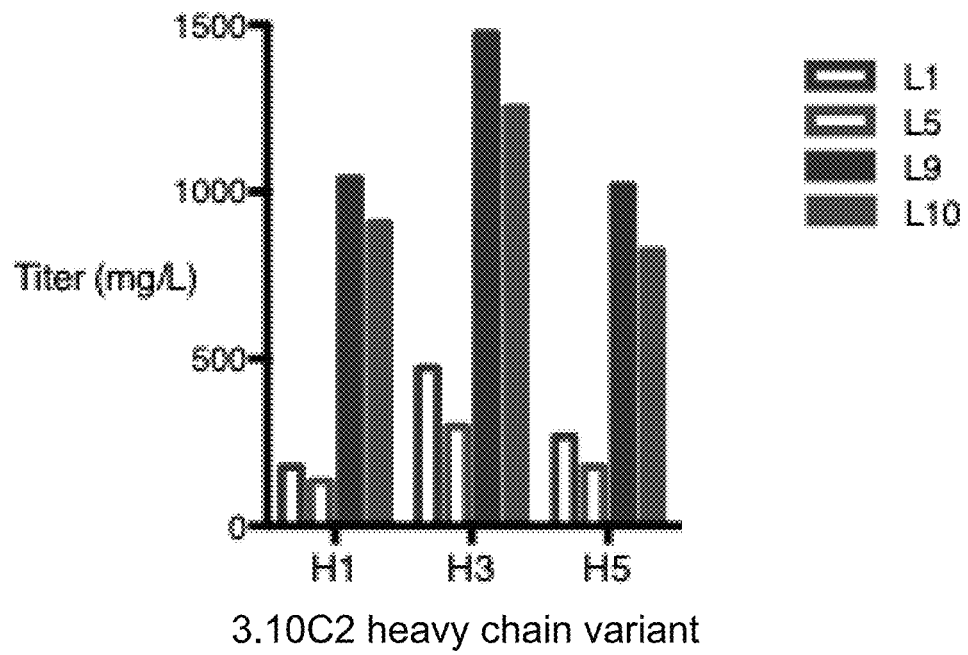

Purification yields of the humanized variants with the 3.10C2-L1 light chain variant with all rat framework Vernier residues were consistently low (FIG. 7A). Another light chain variant, 3.10C2-L5, with rat framework residue Thr-2 and human residues Met-4 and Gly-68 also had consistently low yields in Expi293 cells (FIG. 7A).

Two humanized variants, 3.10C2-H3/3.10C2-L1 and 3.10C2-H5/3.10C2-L1 Fab fragments had dissociation rates comparable to the rat 3.10C2 Fab fragment but with significantly reduced association rates (Table 2). The other variants had significantly lower dissociation rates (Table 2).

TABLE 2

Screening of humanized 3.10C2 heavy chain variants at 37° C.

| Rat framework residues | Fab variant | $k_a$ (M$^{-1}$s$^{-1}$) | $k_d$ (s$^{-1}$) |
| --- | --- | --- | --- |
| N/A | Rat 3.10C2 | 7.2E+05 | 1.9E−04 |
| T24, A49, T76, I78 | H3 | 3.7E+04 | 5.6E−04 |
| T24, I48, A49, I78 | H5 | 1.7E+05 | 8.0E−04 |
| T24, A49 | H7 | 1.2E+06 | 1.8E−02 |
| T24, I78 | H2 | 5.2E+05 | 5.9E−03 |
| I48, I78 | H4 | 1.2E+06 | 2.4E−02 |
| T24, A49, I78 | H6 | 2.1E+05 | 1.3E−03 |

The low expression of humanized variants combined with the unexpected low association rate of Fab variants tested in solution suggested a defect in expression and product quality. Replacing Pro-100 (rat residue) with Gln-100 (human residue) in the light chain, a Framework 4 position not typically included in humanization, in light chains L9 and L10 (corresponding to light chains 1 and 5 with Pro-100, respectively) restored expression of IgG in the context of several humanized heavy chain variants (FIG. 7A)-yet retained an elution peak corresponding to heavy chain (HH) dimers.

Figure 7B:
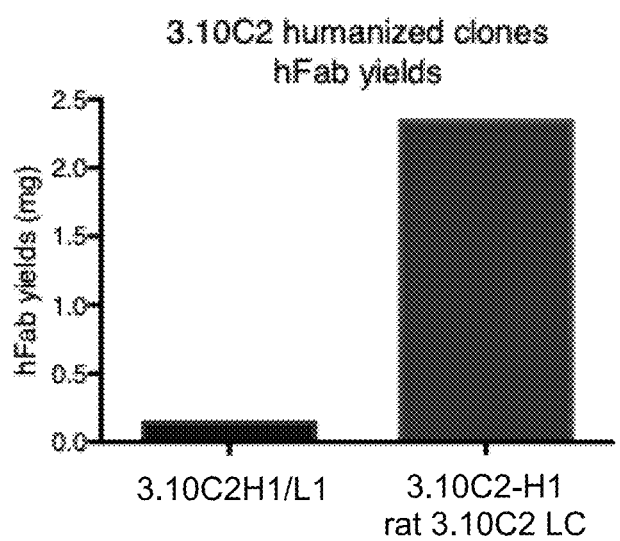

The results with the light chain Pro-100 mutants suggested that the poor expression was due to a defect in the light chain. We confirmed this by expressing hybrid Fab fragments comprised of the 3.10C2-H1 heavy chain (humanized variant with framework positions 24, 48, 49, 76 and 78 as the 3.10C2 rat residues) combined either with the humanized 3.10C2-L1 or rat 3.10C2 light chains. The 3.10C2-H1/3.10C2-L1 humanized variant expressed poorly whereas the hybrid Fab fragment with the 3.10C2-H1 heavy chain and the rat 3.10C2 light chain expressed robustly (FIG. 7B), confirming that the light chain of the humanized 3.10C2 has a defect in expression. We investigated if other light chains of the 3.10C2 antibody group would be better suited for humanization and expression.

We tested whether a humanized light chain variant of anti-TREM2 antibody 3.27H7, a clonal variant of 3.10C2, paired with the humanized 3.10C2 heavy chains would lead to better expression and product quality of humanized variants. The 3.27H7 light chain was humanized in the same framework as the 3.10C2 light chain, including light chain framework residues 2, 4, 58 and 68 in the grafts (FIGS. 8A-B). Humanized 3.10C2 heavy chain variants were combined with humanized 3.27H7 light chain variants to produce human IgG1 with the N297G mutation.

Four humanized 3.10C2/3.27H7 hybrid variants were expressed and purified. The 3.10C2-H1/3.27H7-L1 clone expressed well, at 246 mg/L in transiently transfected CHO cells, after purification by protein A chromatography and showed a monodisperse peak with 99.5% of the material.

The variants 3.10C2-H3/3.27H7-L1 IgG and 3.10C2-H3/3.27H7-L6 IgG also expressed well in CHO cells, at 364 and 408 mg/L. However, some heavy chain—heavy chain (HH) dimer was detectable by mass spectrometry in the purified samples.

Variant 3.10C2-H1/3.27H7-L6 IgG expressed well in CHO cells, at 356 mg/L, showed a monodisperse peak by size exclusion chromatography and no detectable HH dimer by mass spectrometry under non-reducing conditions. This variant was re-named as h3.10C2.v1 and its sequences are shown in FIGS. 9A-B.

Affinity of h3.10C2.v1 (FIGS. 9A-B) for human and cynomolgus TREM2 was determined by SPR in a Biacore™ T200 apparatus in two formats, both at 37° C. In one format TREM2-Fc was immobilized on protein A chips and soluble anti-TREM2 Fab fragments used as ligands. In the second format, anti-TREM2 IgG was immobilized on anti-CH1 Biacore™ chips and used soluble monomeric TREM2 as ligand. The affinity of humanized antibody h3.10C2.v1 for hTREM2 ranged from 390 to 420 pM whereas the affinity for cynomolgus monkey TREM2 was a similar 430 pM (Table 3). Thus, the humanized anti-TREM2 h3.10C2.v1 was found to express well and retain high affinity for both human and cynomolgus TREM2.

Example 8: Affinity Maturation of Antibody 3.10C2 Heavy Chain by Saturation Mutagenesis A. Materials and Methods A library of mutants based on the 3.10C2 antibody heavy chain was constructed by overlap recombinant PCR with the goal of further improving antibody affinity. The DNA fragments encoding heavy and light chains were mixed, one mix for each mutant, and used to transfect Expi293 cells in 1 ml scale and purified by protein A chromatography as previously described (Bos et al., *Biotechnol. Bioeng.* (2015); Luan et al., *Mabs* (2018)).

The resulting library consists of individual IgG clones, each with one mutation per molecule in the heavy chain variable regions. Clones were screened for off-rate (dissociation rate) by SPR in a Biacore™ 8K instrument using anti-human Fab chips to capture mutant IgGs and soluble monomeric TREM2 as ligand.

B. Results

Figure 10:
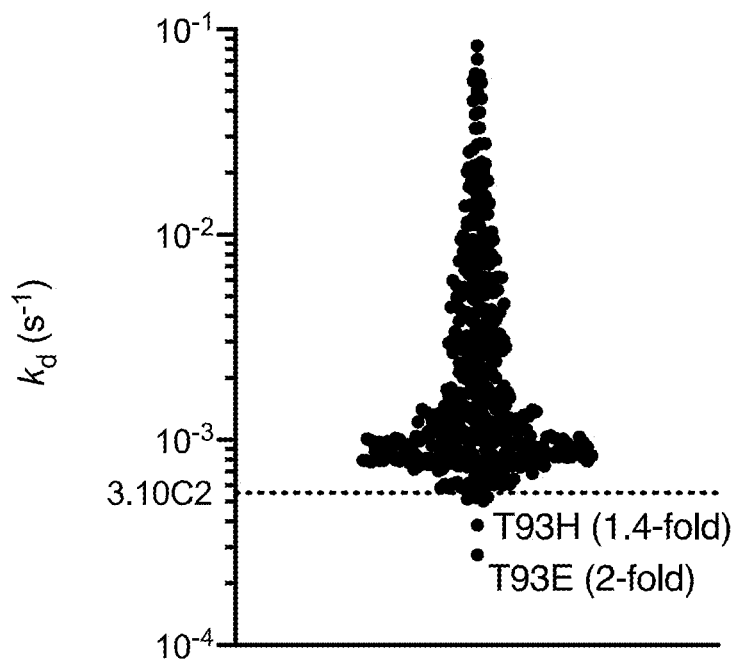

Only 2 of several hundred mutant clones generated, comprising mutations T93E and T93H, had a significant but relatively small (1.4 to 2-fold) reduction in off-rate relative to the parental 3.10C2 clone (FIG. 10). Interestingly, mutations G94D and D101E, the respective CDR H3 residues of Para.09 relative to the same positions in antibody 3.10C2, either diminished the affinity (G94D) or abolished (D101E) binding of 3.10C2 for TREM2 (FIG. 10), indicating that the CDR H3 of Para.09 is not structurally equivalent to the CDR H3 of 3.10C2. In addition, the scanning mutagenesis (FIG. 10) indicated that clone 3.10C2 affinity was nearly at a maximum and cannot be easily improved by mutagenesis of heavy chain CDRs. Thus, the substantially higher affinity achieved with clone Para.09 against the same epitope as the 3.10C2 group required substantial changes in CDR H3, including an insertion, that were not easily accessible by traditional affinity optimization methods which explore variations of the same structural CDR H3 sequence and but not structurally distinct solutions in CDR H3.

Example 9: Humanization of Antibody Para.09

A. Materials and Methods

Antibody Para.09, comprising the Para.09 heavy chain variable region and the 3.27H7 light chain variable region (also called Para.09-27H7) was humanized in VK2 and VH3 frameworks by CDR grafting using the same frameworks as for antibody 3.10C2. Briefly, CDR regions of the rat Para.09 VH sequence were grafted into the heavy chain IGKV3-73*01 framework, the closest human germlines of this antibody (FIG. 9B). The light chain for Para.09 humanization used the same humanized light chain variants of antibody 3.27H7 described above (FIG. 9A). Rat framework residues known as "Vernier" positions and in the domain interface that differed between the rat antibodies and human germlines were added to the CDR grafts to rescue binding to antigen, as described in Example 7 for the 3.10C2 antibody humanization. A variant called Para.09-H1/3.27H7-L1, with all the framework Vernier positions was expressed as a human IgG1 with the N297G mutation in CHO cells.

B. Results

Figure 11:
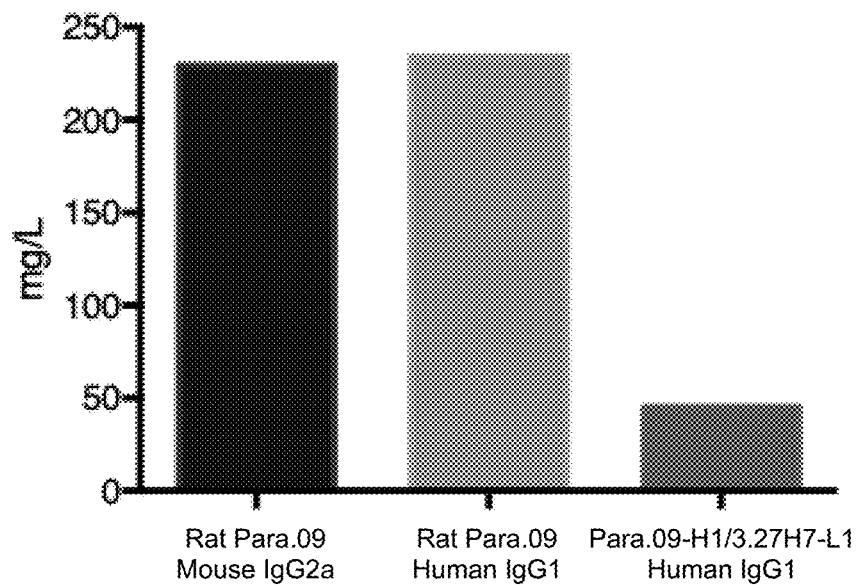

Purification yield of the humanized Para.09-H1/3.27H7-L1 was low compared to the chimeric antibodies with either mouse IgG2a or human IgG1 constant regions (FIG. 11). However, expression of humanized Para.09-H1 heavy chain paired to 3.27H7-L6, the same light chain as in h3.10C2.v1, in CHO cells yielded high levels of IgG (314 mg/L of culture), no HH dimers and relatively few other side-products of IgG assembly. Further analysis of heavy chain variants with fewer rat framework residues led to the identification of Para.09-H5 as the variant with the fewest rat residues that, when combined to light chain 3.27H7-L6, yielded high levels of IgG expression in CHO cells (544 mg/L of culture) without detectable HH dimers. This variant was called hPara.09.v2, and its sequences are shown in FIGS. 12A-B. The monovalent affinities of this variant, re-named hPara.09.v2 (FIGS. 12A-B), for TREM2, determined as described above for the h3.10C2.v1 IgG and Fab fragments, ranged from 11 to 21 pM for hTREM2 and 18 to 22 pM for cynomolgus monkey TREM2 (Table 3).

ized Para.09.v2 (i.e., hPara.09.v2; sequences are shown in FIGS. 12A-B), (3) rat 3.10C2 (sequences are shown in FIGS. 6A-B), (4) humanized 3.10C2.v1 (i.e., h.310.C2.v1; sequences are shown in FIGS. 9A-B).

Example 10: Determination of Off-Target Binding

A. Materials and Methods

The potential for the rat and humanized antibodies to bind to "off-targets" (i.e., targets other than the intended TREM2) was tested with an ELISA assay using baculovirus particles as antigen (BV ELISA; Hotzel et al., *Landes Bioscience* dx.doi.org/10.4161/mabs.22189 (2012)). Normalization was performed by dividing the ELISA absorbance reading of antibody samples by the absorbance reading of a blank well without test antibody as previously described. (Id.) Control antibodies previously shown to have high (score>5), medium (score around 5) and low (non-detectable, score below 1) off-target binding in this assay were tested in parallel. Four antibodies were tested, chimeric clones with rat variable regions and human IgG1 constant regions and humanized variants h3.10C2.v1 and hPara.09.v2 with human IgG1 constant regions with a N297G mutation.

B. Results

Figure 15:
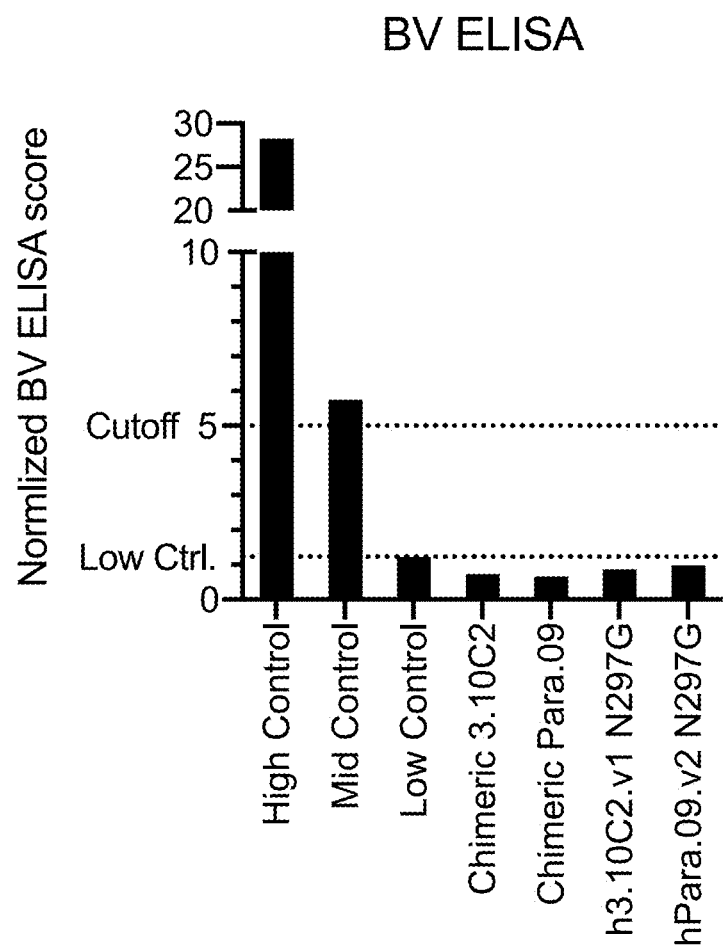

Chimeric rat antibodies with human IgG1 constant regions had very low reactivity in the assay, with scores below 1 (FIG. 15). Similarly, normalized BV ELISA scores of humanized anti-TREM2 antibodies h3.10C2.v1 and hPara.09.v2, both as human IgG1 N297G, were below 1 (FIG. 15), indicating no detectable propensity for off-target binding. Thus, the humanized h3.10C2.v1 and hPara.09.v2 antibodies have high affinity of binding for TREM2, in the mid to low-picomolar range, while retaining favorable, low or non-detectable off-target binding potential.

Example 11: Determination of Binding to Soluble TREM2

A. Materials and Methods

A human TREM2 ELISA assay was used to measure binding of more than forty antibodies to soluble TREM2 (sTREM2) as follows: test anti-hTREM2 antibodies were coated onto plate wells as capture reagents and a bioti-

TABLE 3

Binding affinities of hPara.09.v2 and h3.10C2.v1 for human TREM2 and cynomolgus TREM2

| | Ab type | Ab Format | Human TREM2 | | | Cynomolgus TREM2 | | |
|---|---|---|---|---|---|---|---|---|
| | | | $K_D$ (pM) | $k_a$ (1/Ms) | $k_d$ (1/s) | $K_D$ (pM) | $k_a$ (1/Ms) | $k_d$ (1/s) |
| hPara.09.v2 | Humanized | Fab | 21 | $3.0 \times 10^6$ | $6.1 \times 10^{-5}$ | 22 | $2.9 \times 10^6$ | $6.3 \times 10^{-5}$ |
| h3.10C2.v1 | | | 390 | $1.5 \times 10^6$ | $5.7 \times 10^{-4}$ | 430 | $1.4 \times 10^6$ | $6.2 \times 10^{-4}$ |
| hPara.09.v2 | | IgG | 16 | $2.3 \times 10^6$ | $3.5 \times 10^{-5}$ | | | |
| h3.10C2.v1 | | | 420 | $8.4 \times 10^5$ | $3.5 \times 10^{-4}$ | | | |
| Para.09 | Rat | Fab | 15 | $2.3 \times 10^6$ | $3.5 \times 10^{-5}$ | 18 | $2.3 \times 10^6$ | $4.1 \times 10^{-5}$ |
| 3.10C2 | | | 190 | $9.1 \times 10^5$ | $1.8 \times 10^{-4}$ | 220 | $9.1 \times 10^5$ | $2.0 \times 10^{-4}$ |
| Para.09 | | IgG | 11 | $2.0 \times 10^6$ | $2.1 \times 10^{-5}$ | | | |
| 3.10C2 | | | 120 | $7.8 \times 10^5$ | $9.6 \times 10^{-5}$ | | | |

In summary, TREM2 binding epitopes of a series of rat anti-TREM2 antibodies were determined and binding affinities were measured. See Examples 1-6. Candidate antibodies were engineered for improved TREM2 affinity and expression yield, and humanized. See Examples 7-9. Antibodies identified included: (1) rat Para.09 (which comprises a 3.27H7 light chain and a Para.09 heavy chain; i.e., Para.09-L27H7; sequences are shown in FIGS. 3A-B), (2) humannylated IgV-reactive monoclonal antibody, 3.17A9, was used as the detection reagent. Antibody 1.16B8 was used as a control antibody to establish the standard for sTREM2 binding. Plates coated with test or control antibody were incubated with diluted culture supernatant from bone marrow-derived macrophage (BMDM) cultures from transgenic mice expressing hTREM2. sTREM2 is constitutively produced by the BMDM cultures expressing hTREM2 and shed into the culture supernatant. Measurements were recorded at 450 nm for detection and 570 nm for background. The 3.17A9/1.16B8 antibody pair was selected over reagents provided in the R&D Systems kit as the commercial reagents were not compatible with sTREM2 detection of some of the antibodies tested. Control antibody 1.16B8 light chain sequence is shown in SEQ ID NO: 170, and its heavy chain sequence is shown in SEQ ID NO: 171. Detection antibody 3.17A9 light chain sequence is shown in SEQ ID NO: 168, and heavy chain sequence shown in SEQ ID No: 169.

B. Results

FIG. 16 shows values for sTREM2 binding for antibodies. Binding was normalized to the control (CTL) antibody 1.16B8, which was set to 1. Normalized sTREM2 binding is shown for: rat Para.09— LC 3.27H7 mIgG2a LALAPG (Para09), rat 3.10C2 mIgG2a LALAPG (3.10C2), rat 3.18E5 mIgG2a LALAPG (3.18E5), rat 3.50G1 mIgG2a LALAPG (3.50G1), rat 3.27H7 mIgG2a LALAPG (3.27H7), rat 3.36F5 mIgG2a LALAPG (3.36F5), A.9F5, AL2p-12, AL2p-31, AL2p-58, BM.3D3, BM.42E8, BM.RS9, BM.14D3, and BM.14D8. The tested antibodies rat Para.09— LC 3.27H7 mIgG2a LALAPG (Para09), rat 3.10C2 mIgG2a LALAPG (3.10C2), rat 3.18E5 mIgG2a LALAPG (3.18E5), rat 3.50G1 mIgG2a LALAPG (3.50G1), rat 3.27H7 mIgG2a LALAPG (3.27H7), rat 3.36F5 mIgG2a LALAPG (3.36F5) comprise a mIgG2a LALAPG heavy chain constant region. Of the antibodies tested, only 3.10C2, Para.09 and clonally related antibodies 3.18E5, 3.50G1, 3.27H7, and 3.36F5 did not show any binding to sTREM2 (see FIG. 16, showing normalized sTREM2 binding of near zero for those antibodies in contrast to the 1.116B8 control). The humanized antibody Para.09.v2 antibody with a hIgG1 N297G constant region was also tested for sTREM2 binding and, like rat Para.09 with mIgG2 LALAPG, did not show any binding to sTREM2.

Additionally, nine antibodies previously described in literature as binding to stalk hTREM2 were tested in this experiment, including A.9F5 (also called 9F5), AL2p-12, AL2p-31, AL2p-58, BM.3D3, BM.42E8, BM.RS9, BM.14D3, and BM.14D8, described, for example, in WO2018015573, WO201955841, WO2017062672 and/or WO201928292. Unlike the 3.10C2, Para.09, 3.18E5, 3.50G1, 3.27H7, and 3.36F5 antibodies, the nine previously described antibodies tested here bound to sTREM2 in the assay (see FIG. 16, showing normalized sTREM2 binding of 0.5 to 1.5 for those antibodies). This result is surprising when considered together with the binding profiles of the antibodies tested, as the tested antibodies have epitopes in the TREM2 stalk region, and the result may reflect the unique epitopes of the 3.10C2, Para.09, 3.18E5, 3.50G1, 3.27H7, and 3.36F5 antibodies in comparison to the previously described antibodies. (See, e.g., FIG. 5.)

The peptide mapping and mutational scanning results described in earlier Examples may offer a basis for the differences in binding to soluble TREM2 observed between 3.10C2/Para.09/3.50G1 and antibody 9F5 and its derivatives. The epitope for Para.09, 3.10C2 and 3.50G1 straddles the ADAM10 cleavage site between His-157 and Ser-158, with important contact sites on both sides of the cleavage site as determined by mutational scanning and structural analysis. (See FIG. 5.) In contrast, as noted in Example 6 above, the epitope for A.9F5 (9F9 in FIG. 5) and its derivative AL2p-31 is located entirely on the N-terminal side of the TREM2 cleavage site. (See FIG. 5.) This difference in TREM2 contact points may account for the observed difference in binding to sTREM2 resulting in these previously described antibodies binding to soluble TREM2.

Surprisingly, however, antibodies 14D3 and 14D8 have a pattern of binding to alanine mutant peptides that appears similar to antibodies 3.10C2, 3.50G1 and Para.09 (FIG. 5) but still show robust binding to sTREM2, in a monovalent and physiologically relevant manner (FIG. 16). This was very surprising as the 3.10C2 and Para.09, with their very high affinities, might be expected to retain binding for the partial epitope in soluble TREM2 while the lower affinity (3 to 5 nM) 14D3 and 14D8 antibodies might more easily lose binding to these partial epitopes. This shows that the binding profile described in earlier Examples may not account for all interactions between anti-TREM2 antibodies and TREM2 necessary for anti-TREM2 antibodies to discriminate between full-length, membrane-bound TREM2 and soluble TREM2 forms, further establishing the uniqueness of the antibodies of the present disclosure.

Thus, as these results show, antibodies having the binding profile of 3.10C2, Para.09, 3.18E5, and 3.50G1 antibodies are unique. These antibodies effectively bind to TREM2 stalk region while not binding to soluble TREM2. The specificity of these antibodies may have several potential benefits, including allowing soluble TREM2 in the periphery and brain after in vivo dosing to remain free of the dosed antibodies. The high affinity of these antibodies for their epitope spanning the cleavage site of intact TREM2 and their lack of binding to cleaved, soluble TREM2 could be beneficial in vivo in any of several ways—ranging from allowing more of the dosed anti-TREM2 antibody to reach the desired target of TREM2 on the surface of cells, to reducing the amount of sTREM2 that is shed from the cell surface.

Example 12: Anti-TREM2 Antibodies Induce TREM2-dependent and NFAT-driven Luciferase Activities A. Materials and Methods Jurkat-based luciferase reporter cell lines were used to test the ability of full length anti-hTREM2 antibodies to induce human TREM2-related signaling. TREM2 activation and its interaction at the cellular membrane with DAP12 (DNAX-activating protein of 12 kiloDaltons) may induce phosphorylation of Syk kinase (spleen tyrosine kinase, whose phosphorylated form is designated pSYK or phospho-SYK) and other cell signaling events in the cytoplasm, ultimately resulting in activation of nuclear factor of activated T cells (NEAT)-controlled gene expression. Thus, both phosphorylation of Syk kinase and NEAT-controlled gene expression may be used to determine the effect of antibodies on TREM2 activity and whether the antibodies agonize TREM2. In this assay, Jurkat cells were engineered to express a luciferase reporter under the control of an NFAT response element, and also to co-express human TREM2 and DAP12, in order to test whether addition of antibodies would induce expression of the reporter gene due to activation of NEAT.

A parental Jurkat luciferase reporter cell line (human T lymphocyte; Signosis) was engineered to stably express firefly luciferase reporter gene under the control of NFAT response element. The parental Jurkat luciferase reporter cell line was then transduced using a MSCV-based retroviral vector to co-express TREM2 (wildtype or mutants) and DAP12, to generate Jurkat-NEAT luciferase TREM2 reporter cell lines.

Jurkat reporter assays were used to test for agonistic effects of anti-human TREM2 antibodies compared to an isotype control antibody. Each antibody and isotype control were added in soluble form at 10 µg/mL to the Jurkat-NEAT luciferase reporter cells and incubated at 37° C. for 24 hours. Luciferase activity was measured by adding Bright-Glo™ substrate (Promega Catalog No. E2610). After a 3-minute incubation at room temperature, luminescence measurements were recorded using the M1000 program on Tecan plate reader.

To determine time-dependent reporter activities of anti-human TREM2 antibodies, Jurkat-NEAT luciferase reporter cells were cultured in the presence of anti-TREM2 antibodies each at 10 µg/mL for 3, 6 or 24 hours prior to the addition of Bright-Glo™ substrate for measurement of luciferase activities.

B. Results

Figure 17:
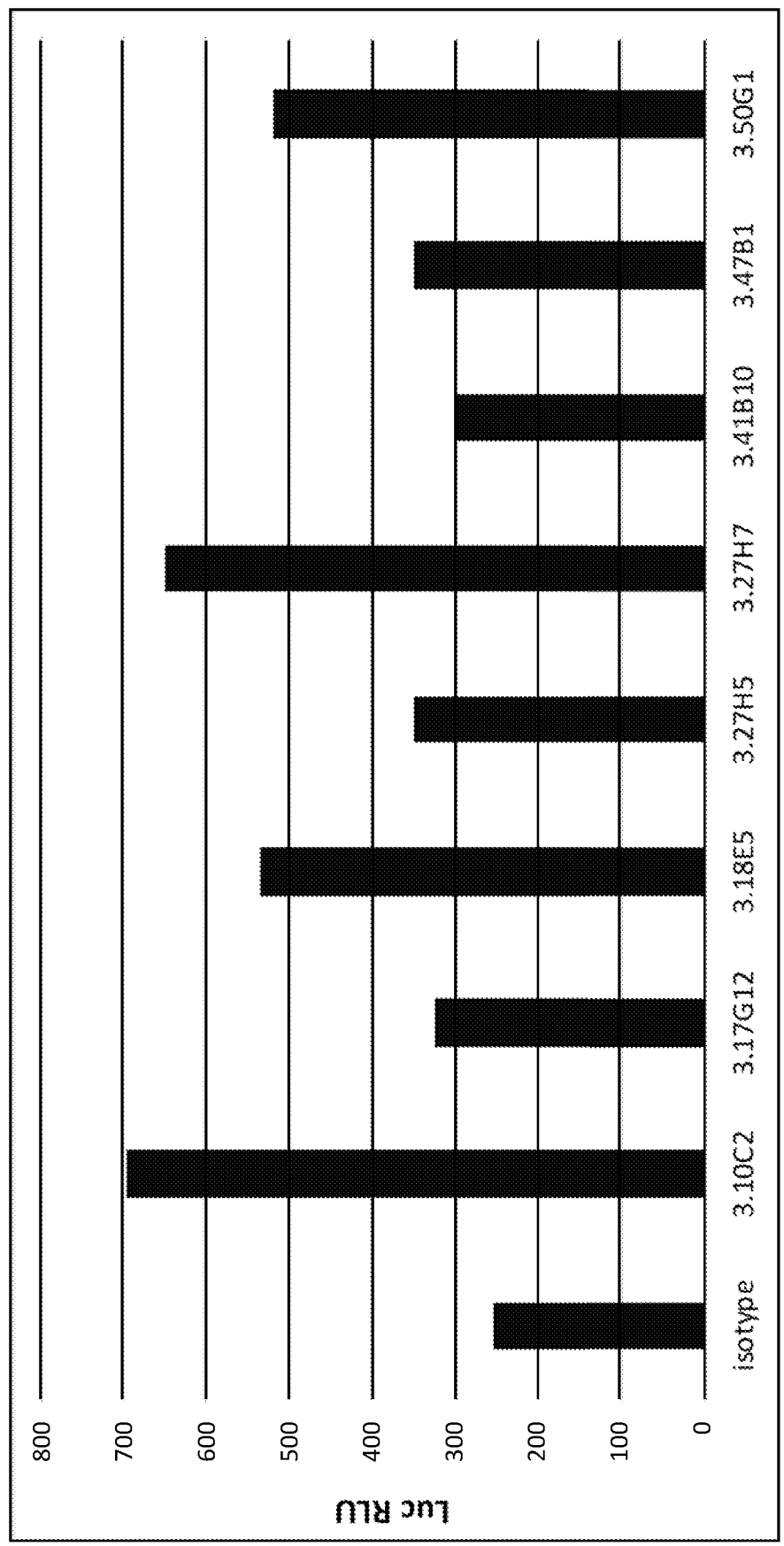
FIG. 17 shows Jurkat reporter activities of recombinant antibodies in mIgG2a format. Jurkat cells were engineered to express luciferase under the control of NFAT (nuclear factor of activated T cells) and to express human TREM2.

Fifty-six rat anti-human TREM2 antibodies (in the form of recombinant mIgG2a), identified in the screens of Example 1, were screened in a Jurkat reporter assay. Out of these 56, only 8 antibodies, including the four "3.10C2 group" antibodies: 3.10C2, 3.18E5, 3.27H7 and 3.50G1, induced luciferase reporter activities in Luc RLU (Luciferase relative light units) compared with isotype control, suggesting that these anti-TREM2 antibodies can mimic natural ligand activities in the Jurkat-NFAT luciferase reporter cells (FIG. 17). Of those 8 antibodies, the four "3.10C2 group" antibodies: 3.10C2, 3.18E5, 3.27H7 and 3.50G1, demonstrated comparably strong agonism while four other tested antibodies showed only modest agonistic activities (FIG. 17). The remaining 48 tested antibodies had Luc RLU values that were less than the isotype control These data indicate that the 3.10C2 group antibodies, which bind specifically to a particular epitope at positions 151-165 of the TREM2 stalk have relatively strong agonist activity, in comparison to antibodies binding outside of that region of the stalk.

The same 56 antibodies were also tested in a time course assay using Jurkat-NFAT reporter cells. Of the tested antibodies, the "3.10C2 group" antibodies 3.10C2, 3.18E5, 3.27H7, and 3.50G1 also demonstrated strong time-dependent agonist activity (Luc RLU fold change) compared with isotype.

Example 13: Anti-TREM2 Antibodies in mIgG2a LALAPG or hIgG1 N297G Format Induce Luciferase Activity in Jurkat Reporter Cells A. Materials and Methods The rat anti-human antibodies Para.09 and 3.10C2 were engineered to comprise a murine IgG2a LALAPG Fc region (to reduce effector function of the Fc) and further tested for agonist activity in Jurkat-NFAT luciferase reporter cells. The humanized antibodies Para.09.v2 and 3.10C2 were similarly engineered in human IgG1 N297G format to reduce effector function and were also tested. Jurkat-based luciferase reporter assays were performed as described above in Example 12. To test dose-dependent activities of anti-human TREM2 antibodies, Jurkat-NFAT luciferase reporter cells were cultured in the presence of serially diluted anti-human TREM2 antibodies for 24 hours.

Anti-hTREM2 antibody activity against common hTREM2 mutations was also assessed: Jurkat-NFAT luciferase reporter cell lines were constructed that express three hTREM2 mutants: R47H, R62H, and H157Y, respectively. Presence of these mutants may correlate with increased risk of Alzheimer's disease.

Supernatant samples were collected for TREM2 shedding analysis prior to the addition of Bright-Glo™ substrate (Promega Catalog No. E2610) for the measurement of luciferase-driven luminescence.

B. Results

Both rat and humanized antibodies demonstrated agonist activities at 24 hours as shown by induction of luciferase reporter activity. See FIG. 18A (rat antibodies) and FIG. 18B (humanized antibodies). These data further demonstrate that both rat and humanized Para.09 and 3.10C2 antibodies have agonist activities, and that such activities are not related to antibody effector functions.

The four "3.10C2 group" antibodies (in mIgG2a LALAPG format) 3.10C2, 3.18E5, 3.27H7 and 3.50G1 also induced luciferase activity in the Jurkat-NFAT reporter cells engineered to express three hTREM2 mutants, R47H (FIG. 19A), R62H (FIG. 19B), and H157Y (FIG. 19C), respectively. These results demonstrate that the anti-hTREM2 antibodies have agonist activity against both wild-type hTREM2 and against these hTREM2 mutations, and therefore, that they may be useful in patients with these mutant TREM2 proteins.

Example 14: Anti-TREM2 Antibodies in mIgG2a LALAPG or hIgG1 N297G Format Block TREM2 Shedding in Jurkat Reporter Cells A. Materials and Methods TREM2 shedding, releasing soluble TREM2, may occur in Alzheimer's disease patients decades before disease onset. Soluble TREM2 binding to amyloid plaques may in turn interrupt neuron-protective plaque compaction by microglia. Thus, both rat and humanized Para.09 and 3.10C2 antibodies herein were tested in the Jurkat-NFAT luciferase reporter cells described in Example 12 and 13 to determine if they can also inhibit TREM2 shedding. To determine TREM2 shedding inhibition activities of soluble anti-human TREM2 antibodies in Jurkat-NFAT luciferase reporter cells, supernatants were harvested from the reporter assay plates at 24 hours and sTREM2 was measured using ELISA assay as described above in Example 11.

The activities of humanized Para.09 variants, hPara.09 v2, hPara.09 v2.Q100P/V104L and hPara.09.v2 Q100P, in the Jurkat-NFAT reporter and TREM2 shedding inhibition assays were next compared to the activities of the humanized 3.10C2.v1 antibody. Jurkat-NFAT luciferase reporter cells were cultured in the presence of serially diluted humanized antibodies for 24 hours, and tested as described above.

B. Results

Figure 20A:
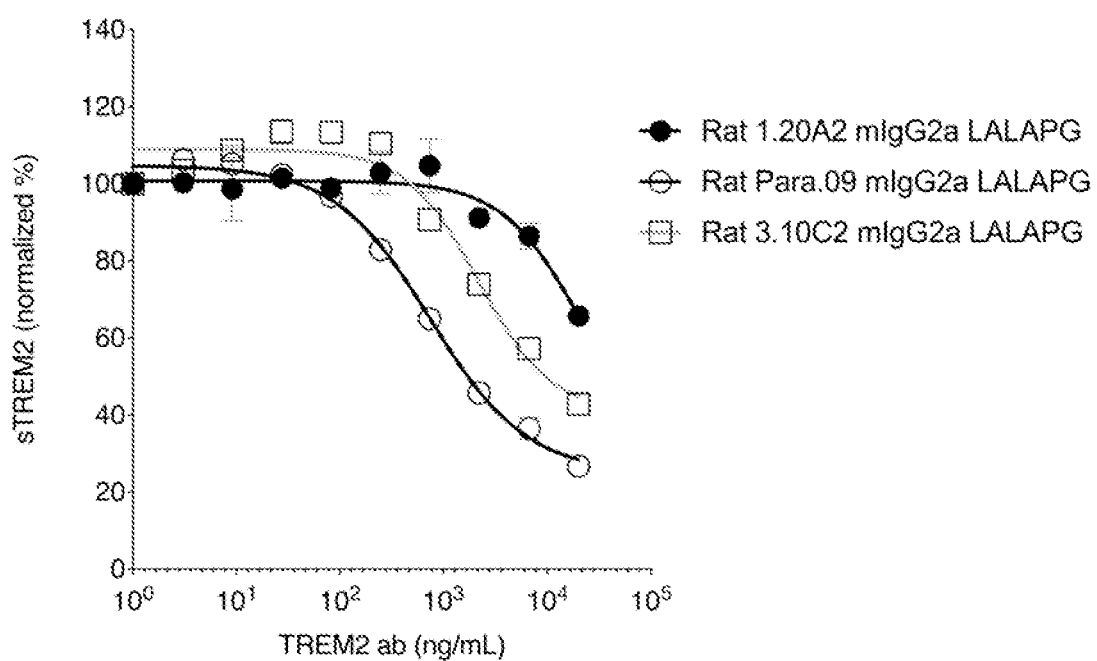
FIGS. 20A-B and D show the effect of rat anti-human and humanized antibodies on sTREM2 shedding in the Jurkat-NFAT luciferase reporter cell line expressing hTREM2 after 24 hours, as measured by ELISA.
Figure 20B:
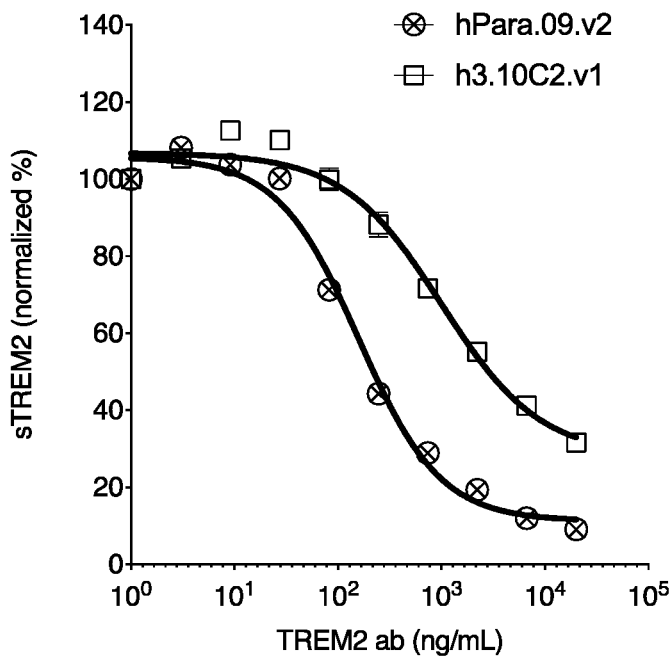

In the ELISA assay, Para.09 in mIgG2a LALAPG form demonstrated strongest TREM2 shedding inhibition activity compared to other tested antibodies in the same format. The humanized antibody hPara.09.v2 in hIgG1 N297G format demonstrated stronger TREM2 shedding inhibition than the humanized antibody h3.10C2 v1 in hIgG1 N297G format (See FIG. 20B). Inhibition of sTREM2 shedding by the rat antibodies is shown in contrast to another antibody (1.20A2 mIgG2a LALAPG), which shows little shedding inhibition in the assay. (See FIG. 20A).

Figure 20C:
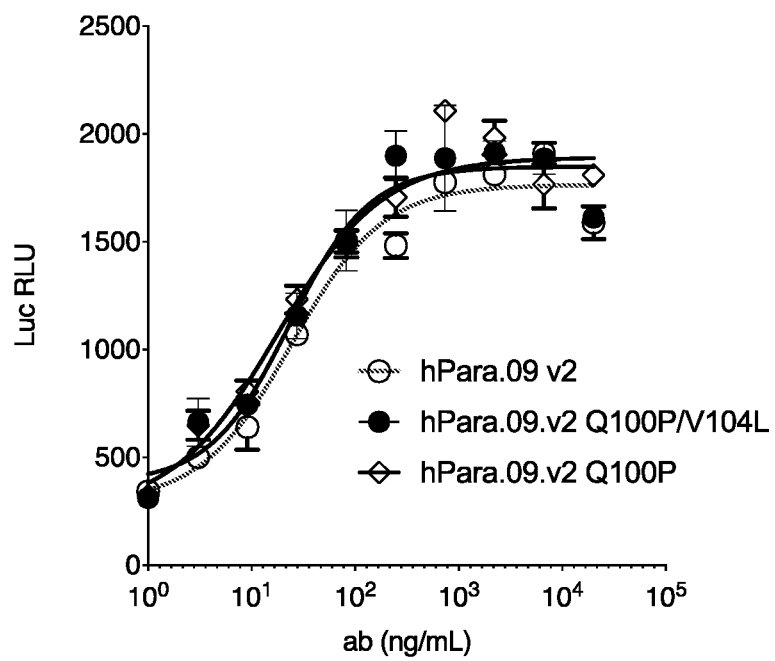
FIG. 20C shows luciferase expression induced by the hPara.09 v2, hPara.09.v2 Q100P/V104L, and hPara.09.v2 Q100P antibodies.
Figure 20D:
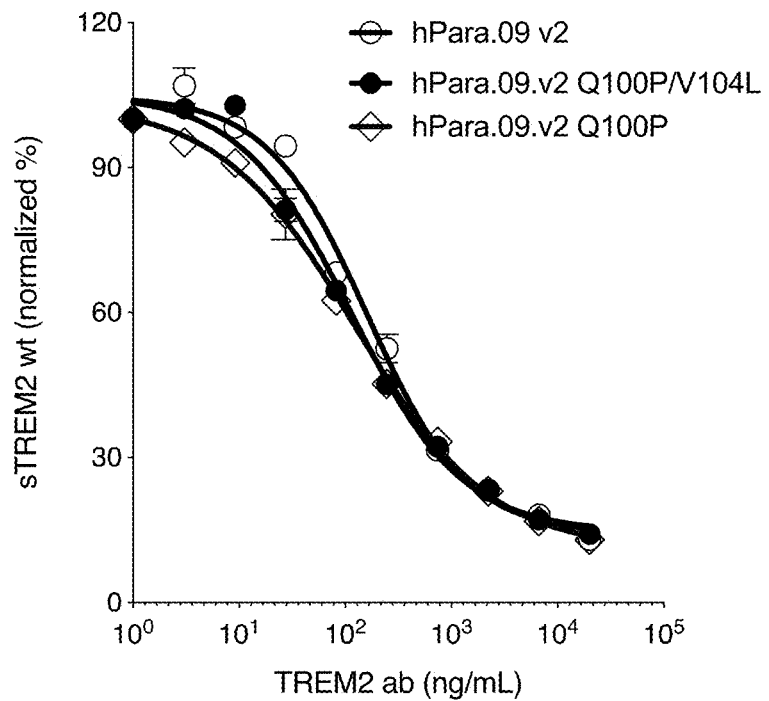
FIG. 20D shows the effect of humanized antibodies hPara.09 v2, hPara.09.v2 Q100P/V104L, and hPara.09.v2 Q100P.

Variants hPara.09 v2.Q100PN104L and hPara.09.v2 Q100P, are identical to hPara.09v2 except for the Q100P/V104L and Q100P mutations, respectively (FIGS. 13A-B). As shown in FIGS. 20C-D, hPara.09 v2, hPara.09 v2.Q100P/V104L and hPara.09.v2 Q100P in hIgG1 N297G format demonstrated comparable activities. In addition, consistent with results shown in Example 13, the activities of those three Para.09 humanized antibodies were higher than that of the humanized 3.10C2.v1 antibody.

The measured potency of TREM2 antibodies in the Jurkat NFAT luciferase reporter cells (EC$_{50}$) and TREM2 shedding inhibition (IC$_{50}$) are summarized below in Table 4.

TABLE 4

Potency of TREM2 antibodies (EC$_{50}$) and TREM2 shedding inhibition (IC$_{50}$)

| Anti-human TREM2 Abs | EC50, ng/mL | IC50, ng/mL |
| --- | --- | --- |
| hPara.09.v2 | 24.52 | 161.50 |
| hPara.09.v2 Q100P/V104L | 23.23 | 113.90 |
| hPara.09.v2 Q100P | 17.80 | 123.40 |
| 3.10C2.v1 hIgG1 N297G | 76.00 | 975.00 |
| Rat para.09 mIgG2a LALAPG | 40.00 | NA |
| Rat 3.10C2 mIgG1a LALAPG | 279.60 | NA |
| Rat 1.20A2 mIgG2a LALAPG | NA | 7915.00 |

(NA = not available)

Example 15: Soluble Anti-TREM2 Antibodies Block TREM2 Shedding in Human iPSC-Derived Microglia A. Materials and Methods Since TREM2 is expressed in vivo in microglia cells, inhibition of TREM2 shedding was next tested in human iPSC-derived microglia cells. To determine TREM2 shedding inhibition by anti-human TREM2 antibodies in human iPSC-derived microglia (Cellular Dynamics), the iPSC-microglia were cultured with maintenance media (Cellular Dynamics) in the presence of soluble anti-TREM2 mIgG2a LALAPG antibodies at 10 ug/mL. ADAM10 protease inhibitor GI254023X (Sigma-Aldrich) was used as a positive control for blocking sTREM2 cleavage and shedding. The culture supernatant samples were harvested at day 3 for ELISA assay using the R&D assay kit.

B. Results

Figure 21:
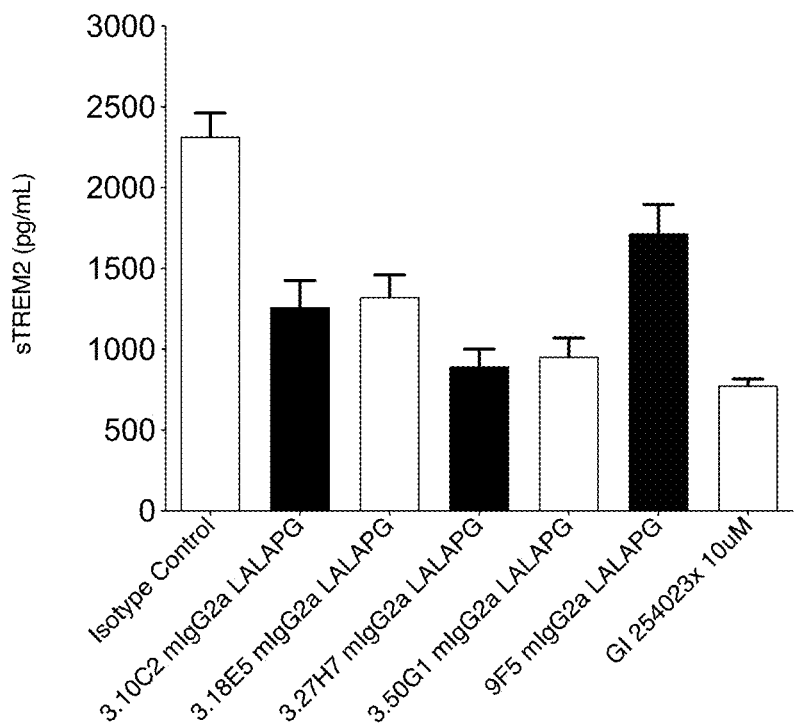
FIG. 21 shows the effect of antibodies 3.10C2, 3.18E5, 3.27H7, 3.50G1, and 9F5 with murine IgG2 LALAPG on TREM2 shedding in human induced pluripotent stem cell (iPSC)-derived microglia.

Rat anti-human TREM2 antibodies 3.10C2, 3.18E5, 3.27H7 and 3.50G1 reduced sTREM2 at comparable levels to GI254023X, a potent and selective metalloproteinase inhibitor for the α-secretase ADAM10, while previously described antibody 9F5 inhibited TREM2 shedding to lesser extent (FIG. 21). These data suggest that TREM2 shedding is blocked by the 3.10C2, 3.18E5, 3.27H7 and 3.50G1 agonistic anti-TREM2 antibodies and cell membrane-bound TREM2 may also be stabilized by these same antibodies. These data also confirm the data from the Jurkat-NFAT cells in a cell type that expresses TREM2 in vivo.

Example 16: Phospho-Tyrosine and pSYK Activation Following TREM2 Stimulation in Primary Human Monocyte-Derived Macrophages (MDMs)

As noted above, binding of TREM2 to DAP12 at the cell membrane leads to activation of TREM2-related cell signaling in part through the phosphorylation of Syk kinase (SYK), to form pSYK. Thus, the effects of anti-TREM2 antibodies on SYK phosphorylation, as well as on pan tyrosine phosphorylation, were determined in a human macrophage model system, in order to further assess agonist activity of the antibodies. To ensure that changes in phosphorylation are due to TREM2 activity, tests were also run in the context of TREM2 deletion. Antibodies were tested in human IgG1 N297G format to reduce antibody effector activity.

A. Materials and Methods

1. Isolation and Culture of Human Monocyte Derived Macrophages

Human peripheral blood mononuclear cells (PBMCs) were isolated from consenting healthy donor buffy coats using Ficoll® Paque Plus (Sigma Aldrich). Next, CD14$^+$ C16$^-$ monocytes were isolated from PBMCs using the classical monocyte isolation kit (Miltenyi Biotec) per kit instructions. Flow through was collected and spun down at 300×g for 10 min, then resuspended in growth medium. Cells were diluted to a final concentration of 10% DMSO, frozen, and stored in liquid nitrogen for future use. For each experiment, aliquots from multiple donors were thawed and monocyte derived macrophages (hMDMs) were differentiated in culture for 5 to 7 days in high glucose DMEM containing 10% heat-inactivated serum and 50 ng/mL recombinant human M-CSF (Peprotech) with partial media changes every other day.

To form guide RNA duplexes targeting TREM2, Alt-R CRISPR-Cas9 crRNA (Integrated DNA Technologies) based on sequences TTGTAGATTCCGCAGCGTAA or AATGGTGAGAGTGCCACCCA or TACCAGTGCCAGAGCCTCCA (SEQ ID Nos: 173, 174, and 175, respectively) were dissolved to 100 uM in Duplex buffer (Integrated DNA Technologies) and mixed at a 1 to 1 molar ratio with Alt-R tracrRNA dissolved at 100 uM in Duplex buffer. The crRNA and tracrRNA mixtures were hybridized by incubation at 95° C. for 5 min, followed by 15 min incubation at room temperature and storage at −20° C. Ribonucleoprotein complexes were formed by mixing crRNA/tracrRNA duplexes with 5 μg Alt-RS.p. HiFi Cas9 Nuclease V3 (Integrated DNA Technologies) at a 3 to 1 molar ratio and incubating at room temperature for at least 15 min. The two ribonucleoprotein complexes for the two separate guide RNA sequences were combined at a 1 to 1 ratio, and both guide RNAs were transfected into hMDMs.

To generate TREM2-deficient cell pools, hMDMs were collected 16-24 hours after thawing, centrifuged 500×g for 5 min, and resuspended in P3 primary nucleofection solution (Lonza) to a concentration of 2-4×10$^6$ cells per 20 μL reaction. Each 20 μL reaction was mixed with a total of 10 μg of Cas9 complexed with the three TREM2-targeting guide RNAs and immediately transferred to supplied nucleofector cassette strips (Lonza). The strip was loaded into the Lonza 4D-nucleofector (4D-Nucleofector Core Unit: Lonza, AAF-1002B; 4D Nucleofector X Unit: AAF-1002X) and electroporated using the CM-137 pulse program. Cells were recovered, diluted into growth medium to 10$^6$ cells per mL and plated for 5-7 days. Efficient knockout (>90%) was confirmed by TIDE analysis and FACS.

2. Measurement of Pan Tyrosine and SYK Phosphorylation

For all experiments, hMDMs were switched into low glucose media and deprived of M-CSF and serum for 24 hours prior to addition of anti-TREM2 antibodies. hMDMs were incubated for 10 or 20 minutes at 37° C. with antibodies. Following antibody stimulation, culture media was removed and cells were lysed in RIPA buffer containing cOmplete mini protease inhibitor (Roche) and phosSTOP (Roche) phosphatase inhibitors. After protein lysates were collected, samples were used to measure both pan phospho-Tyrosine (pY) and phospho-SYK activity. For pY expression, samples were run on a Western blot and membranes were incubated overnight at 4° C. with P-Y-1000 (1:1000, Cell Signaling Technology) and anti-beta actin (1:1000, Sigma Aldrich). Secondary fluorescent antibodies were added the next day for 1 hour in the dark at room temp and imaged using the Odyssey infrared imaging platform (1:10, 000, LI-COR). Band intensities were calculated in ImageStudio Lite (LI-COR) and all samples were normalized to loading controls before normalization to isotype control.

Total SYK and phospho-SYK were measured using the respective AlphaLISA® SureFire® Ultra™ assays (PerkinElmer) per kit instructions. Briefly, protein lysates were incubated with Acceptor beads for 1 hour followed by a subsequent 1-hour incubation with Streptavidin-coated donor beads in the dark. After which, plates were imaged using the compatible Synergy™ Neo2 plate reader (BioTek). For phospho-SYK quantifications, samples first were normalized to total SYK then to isotype control antibody.

B. Results

Figure 22A:
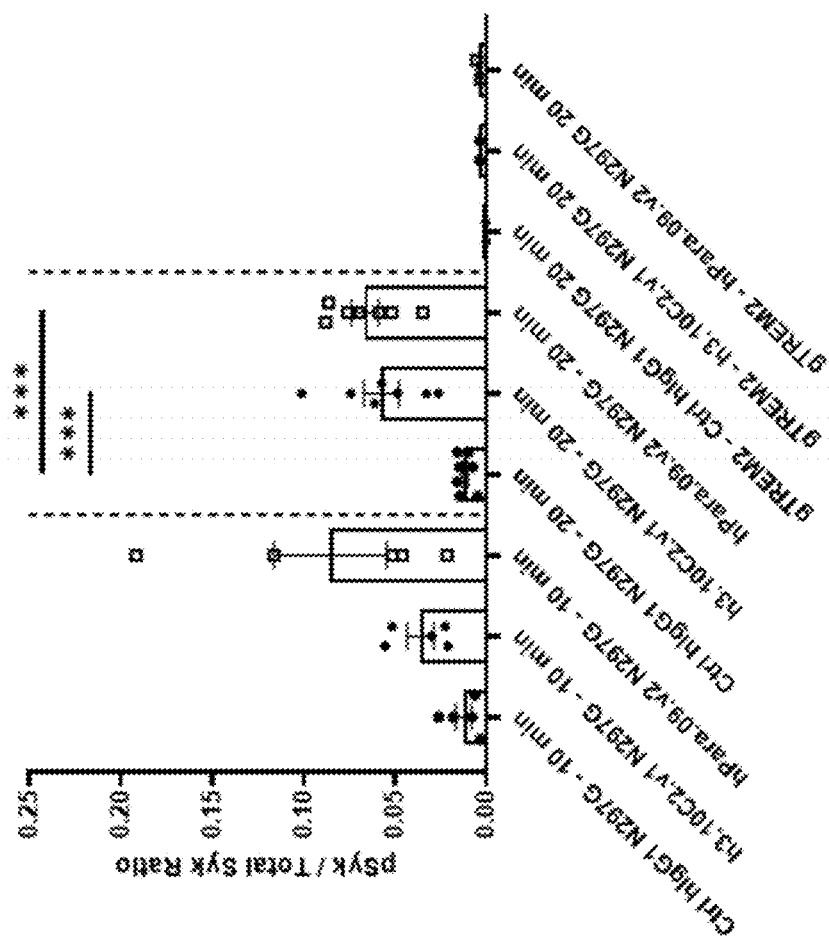
FIGS. 22A-C show pan phospho-tyrosine (pY) levels (FIG. 22A) and phospho-SYK (pSYK) levels (FIG. 22B-C) in primary human monocyte derived macrophage (hMDM) cells after incubation with humanized anti-TREM2 antibodies for the stated 10-20 minute time periods (FIG. 22A-B) or dose ranges (FIG. 22C).
Figure 22B:
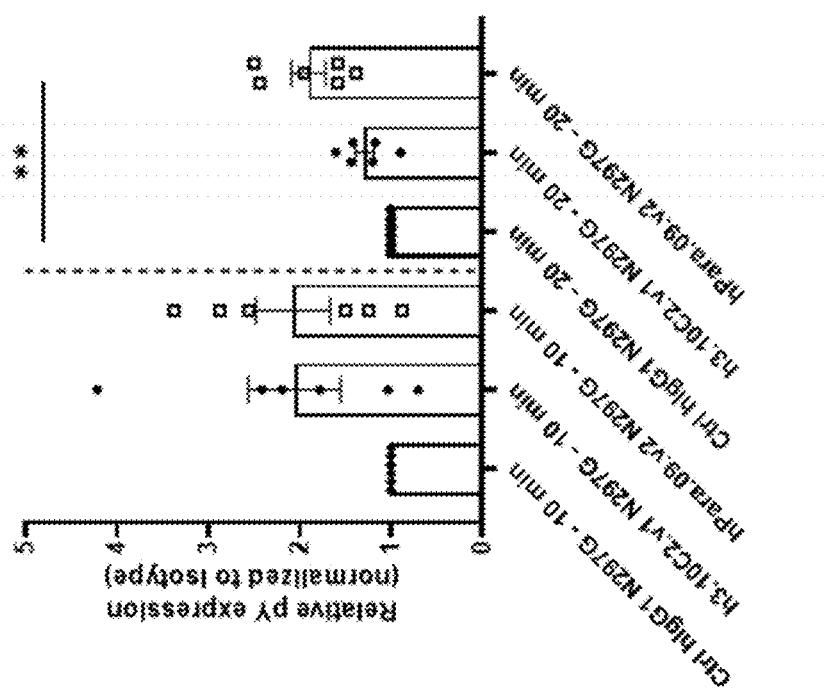
Figure 22C:
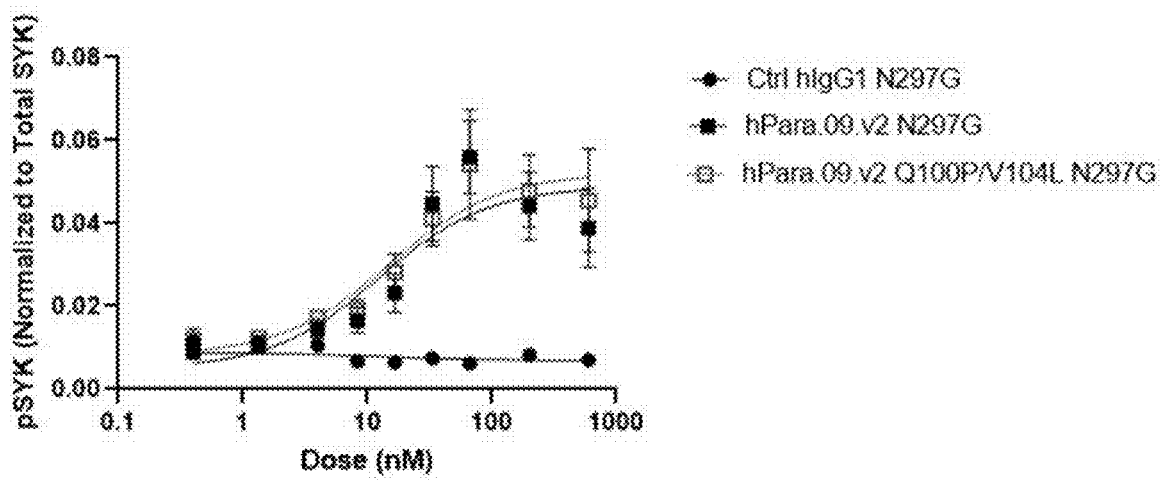

In FIG. 22A, pan phospho-tyrosine activity was assessed on Western blots. Relative to isotype control, hPara.09.v2 N297G treatment demonstrated a significant increase in pY at 20 minutes after stimulation. In FIG. 22B, phospho-SYK levels were measured with the alphaLISA® assay kit, and all samples were normalized to total SYK levels. Significant increases in pSYK were observed from both hPara09.v2 and h3.10C2.v1 antibodies at 20 minutes. No increase in pSYK was observed in TREM2-deficient cells (cells transfected with a Cas9 ribonucleoprotein complex including guide RNA targeting TREM2, or gTREM2) 20 min after antibody treatment. Mean±SEM, n=6 from 5 separate biological specimens, or n=2 from 2 separate biological specimens for gTREM2 $p<0.01$ *$p<0.001$ (one-way ANOVA with Dunnett's test comparing to isotype control condition). As shown in FIG. 22C, stimulation with humanized antibodies hPara.09.v2 N297G and hPara.09.v2 Q100P/V104L N297G increased phospho-SYK levels in primary hMDM.

Example 17: Anti-TREM2 Antibody Para.09 Promotes Human iPSC Microglia Survival

As TREM2 is expressed in the brain in microglia cells, further experiments were performed in a human iPSC-derived microglia cell model system to determine effects of antibodies on microglia survival, sTREM2 shedding, SYK phosphorylation, and formation and compaction of Aβ plaques.

A. Materials and Methods
1. iPSC Microglia Survival Assay ($EC_{50}$ Experiments)
i. Antibody Coating For coating of 384 well plates (Cell Carrier Ultra, Perkin Elmer), stock solutions of 1 mg/mL of the N297G and LALAPG variants of h3.10C2.v1 and hPara.09.v2.N297G were prepared in cold DMEM/F12 (Gibco). Stock solutions were mixed and used for serial dilutions in 96 well reagent master blocks (Greiner Bio-One). Coating solutions were transferred to 384 well plates by repeat dispensing (n=4 to 6) of 25 μL/well using a pipetting robot (Assist Plus, Integra) equipped with an automatic multichannel pipette (Voyager 125 Integra). To minimize evaporation and edge effects, outer wells were filled with DPBS (Sigma-Aldrich). After brief centrifugation, plates were incubated over night at 37° C., 5% $CO_2$, and 95% humidity.

ii. iPSC Microglia Culture Media Preparation

Base media used was basal medium (BrainPhys Basal, StemCell Technologies) containing B27 supplement (Gibco), N2 supplement (Gibco), 1 mM Creatin (Sigma), 200 nM L-ascorbic acid 2-phosphate sesquimagnesium (Sigma), 20 ng/mL recombinant BDNF (Peprotech), 20 ng/mL recombinant human GDNF (Peprotech), 1 μg/mL laminin mouse protein (Gibco), 0.5 mM Glutamax™ (Gibco), 50 U/mL Penicillin-Streptomycin (Gibco), 0.1 mg/mL Normocin™ (InvivoGen), 5 ng/mL recombinant human TGF-β1 (Peprotech, HEK293 derived), 1.5 ng/mL ovine wool cholesterol (Avanti), 0.1 ng/mL oleic acid (Cayman Chemicals), 0.001 ng/mL 11(Z)-eicosenoic acid (Cayman Chemicals), 460 μM 1-Thioglycerol (Sigma-Aldrich), 10 μg/mL Insulin, 5.5 μg/mL Transferrin, 6.7 ng/mL sodium selenite (ITS-G, Gibco), 5.4 μg/mL human insulin solution (Sigma). BDNF, GDNF, TGF-β1, IL-34 and M-CSF were reconstituted in 0.1% BSA. Ovine wool cholesterol, oleic acid and 11(Z)-eicosenoic acid were freshly prepared in ethanol every month. To obtain complete microglia culture medium, reduced microglia medium was supplemented with 100 ng/mL recombinant humane IL-34 (Peprotech) and 25 ng/mL recombinant human M-CSF (Peprotech). For preparation of minimal microglia culture medium, base medium was supplemented with 25 ng/mL recombinant humane IL-34 (Peprotech) and 0.313 ng/mL recombinant human M-CSF (Peprotech).

iii. iPSC Microglia Cell Thawing, Seeding, and Culture

Human wild-type or TREM2KO iPSC-derived microglia (iCell Microglia, Fujifilm Cellular Dynamics, Inc.) were thawed in complete microglia medium. After counting, cells were centrifuged and resuspended in minimal microglia culture medium. For cell survival assays, coating solutions of previously coated 384 well plates (Cell Carrier Ultra, Perkin Elmer) were aspirated and cells were seeded with 8,000 cells/well in 50 μL of respective media. Plates were briefly centrifuged and cells were cultured for 3 days at 37° C., 5% $CO_2$, and 95% humidity.

iv. Collection of Supernatant and Fixation of Cells

After 3 days of culture, supernatants of cells were collected by a pipetting robot (Assist Plus, Integra) equipped with an automatic multichannel pipette (Voyager 125 μL, Integra). Aspiration speed was set to 2 μL/sec and pipetting height was kept at 1-1.2 mm above plate bottom to avoid disturbance of the cell layer. 30 μL/well was transferred to 384 deep well microplate (Greiner Bio-One). Right after supernatant collection, cells were fixed in 4% PFA (Electron Microscopy Science), 4% sucrose (Sigma-Aldrich) in DPBS (Sigma-Aldrich) for 1 hour at room temperature. After fixation, cells were washed twice with DPBS (Sigma-Aldrich).

2. Immunostaining

Prior to immunostaining, cells were incubated with blocking buffer containing 2% normal donkey serum (JacksounImmuno Research), 1% BSA (JacksonImmuno Research) and 0.1% Triton X-100 (Sigma-Aldrich) in DPBS (Sigma-Aldrich) for 1 hour at room temperature. Primary rabbit-anti-Iba1 polyclonal antibody (1:500, Wako) was diluted in blocking solution, incubated for 1 hour at room temperature and cells were washed three times with blocking buffer. Secondary Cy3 donkey-anti-rabbit (1:600, JacksonImmuno Research), Alexa Fluor™ 488 Phalloidin (1:1000, Invitrogen) and Hoechst 33342 (1:10000, Invitrogen) were prepared in blocking buffer and incubated for another hour at room temperature. After secondary staining, cells were washed 6 times by repeat addition and aspiration of DPBS (Sigma-Aldrich) and stored in the dark until imaging.

3. Imaging

Microplates containing stained microglia were imaged on automated high content imager (Opera Phenix® High Content Screening System, Perkin Elmer) equipped with a 20× water immersion objective. Tile scans (3×3 tiles) of all wells were acquired in spinning disk confocal mode (image size 1080×1080 pixels, pixel size 0.598 μm), resulting in an effective field of view of 2.88 $mm^2$ (~27% of each well). Each position was imaged in three fluorescent channels. Excitation of nuclear dye Hoechst 33342 was performed at 405 nm and the main emitted signal was detected at 456 nm. Actin was detected at 522 nm by excitation of Alexa Fluor™ 488 Phalloidin at 488 nm. Iba1 was visualized by excitation of Cy3 at 561 nm, mainly emitting at 599 nm.

4. iPSC Microglia Aβ Plaque Formation Assay

To test the effect of plate-bound anti-TREM2 antibodies in formation and compaction of an Aβ plaque, an in vitro human iPSC-MG plaque formation assay using synthetic Aβ oligomers to mimic the increased level of Aβ oligomers found in the AD brain was conducted. iPSC microglia were cultured as described in Section 1 of this example in the presence of control antibody (gD hIgG1 N297G), or anti-TREM2 antibodies at increasing concentration in the presence of Aβ oligomers, without IL-34 and CSF-1. Aβ oligomers were generated by incubating reconstituted Aβ monomer (1-42) (Anaspec) to 100 µM in BrainPhys™ basal media in 4° C. for 24 hours. Aβ oligomers were applied to cells right after plating at final concentration of 2.5 µM. Cells were incubated for 2 days and then fixed and stained for AP, Methoxy-X04 (amyloid plaque dye), and IBA1. Microplates containing stained microglia were imaged on automated high content imager (IN CELL 6000, General Electric) equipped with a 20× air objective. Tile scans (3×3 tiles) of all wells were acquired. Each position was taken in four fluorescent channels. Excitation of Aβ plaque binding dye Methoxy-X04 was performed at 405 nm and the main emitted signal was detected at 456 nm. Actin was detected at 522 nm by excitation of Alexa Fluor™ 488 Phalloidin at 488 nm. Iba1 was visualized by excitation of Cy3 at 561 nm, mainly emitting at 599 nm. Aβ was visualized by Anti-6E10 antibody using an excitation wavelength of 647 nM.

5. AlphaLISA® Assay 48 or 96 well cell culture microplates of different formats were coated with 200 µg/mL antibody in DMEM/F12 (Gibco). 96 well plates (Greiner Bio-One) were coated with 50 µL/well and 48 well plates (Greiner Bio-One) were coated with 150 µL/well and incubated over night at 37° C., 5% $CO_2$, 95% humidity. iPSC microglia were plated and culture as described in Section 1 of this example.

6. Lysate Preparation

After 3 days of culturing, samples for measurements of phosphorylation on Tyr525/526 and total levels of endogenous SYK were obtained by cell lysis with lysis buffer (lysis buffer ultra, Perkin Elmer). Used culture medium was removed and freshly prepared 1× lysis buffer was added to microplates (100 µL for 48 well, 60 µL for 96 well). Plates were agitated on a plate shaker (350 rpm) for 10 minutes at room temperature. Concentrated samples were generated by successive carryover of lysates to non-lysed replicate wells of the same culture condition (N=3 to 4, n=2 to 3). Plates were agitated again for 10 minutes at room temperature and concentrated lysates were transferred to 96 well deep well plate (Greiner Bio-One) and frozen at −80° C.

7. Luminex Assay

Multiplex protein quantification from collected microglia culture supernatants was performed using Luminex multianalyte profiling technology (Inflammation 20-Plex Human ProcartaPlex™ Panel). The assay kit was used according to manufacturer's protocol. To obtain sufficient sample volume, supernatants of multiple wells of the same conditions were pooled and pooled samples were analyzed in duplicates. Assay plates were read on Luminex™ MAGPIX™ Instrument System (Invitrogen).

8. SYK Phosphorylation Assay

To determine whether anti-TREM2 antibodies induced SYK phosphorylation, wild-type iPSC-MG were cultured in 48 well plates in culture media without IL-34 and CSF-1 and in the presence of plate-bound antibody: control (gD hIgG1 N297G), anti-TREM2 hPara.09.V2 hIgG1 N297G, or variant hPara.Q100P.V104L hIgG1 N297G antibody. Cells were plated for indicated time points (1 hour, 4 hours, 24 hours), then were lysed and analyzed with AlphaLISA® assay for pSYK and total SYK. The ratio was further normalized at each time point to the ratio measured using anti-gD control antibody. For each condition, there were n=4 wells. The ratio of phospho-SYK to total SYK in protein lysate from the treated cells was measured by ELISA.

B. Results

1. Anti-TREM2 Antibodies Promote Human iPSC-MG Survival

Figure 23A:
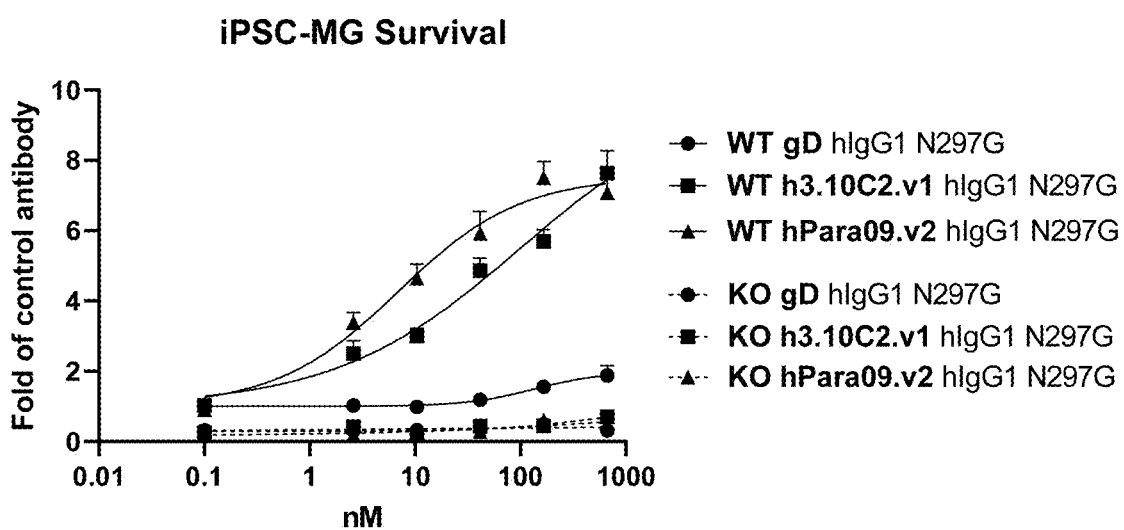
FIGS. 23A-E show that rat anti-human and humanized anti-TREM2 antibodies promote human induced pluripotent stem cell (iPSC) microglia survival.

We tested whether anti-TREM2 antibodies 3.10C2v1 and hPara09.v2 (in an IgG1 N297G background) promote human iPSC derived microglia (iPSC-MG) survival by culturing iPSC-MG without IL-34 and CSF-1, which are normally required for microglia survival, compared to control anti-gD antibody. (FIG. 23A). With the control antibody, most microglia died after 3 days of culture without IL-34 and CSF-1. In contrast, 3.10C2v1 and hPara09.v2 promoted iPSC-MG survival in a dose-dependent manner. To validate that the survival effect is mediated through TREM2 signaling, antibodies were also tested in TREM2 knock-out (KO) iPSC microglia. Antibodies 3.10C2v1 and hPara09.v2 did not promote TREM2-KO iPSC microglia survival. Therefore, anti-TREM2 agonist antibodies 3.10C2v1 and hPara09.v2 promoted iPSC-MG survival in a TREM2 dependent manner.

Figure 23B:
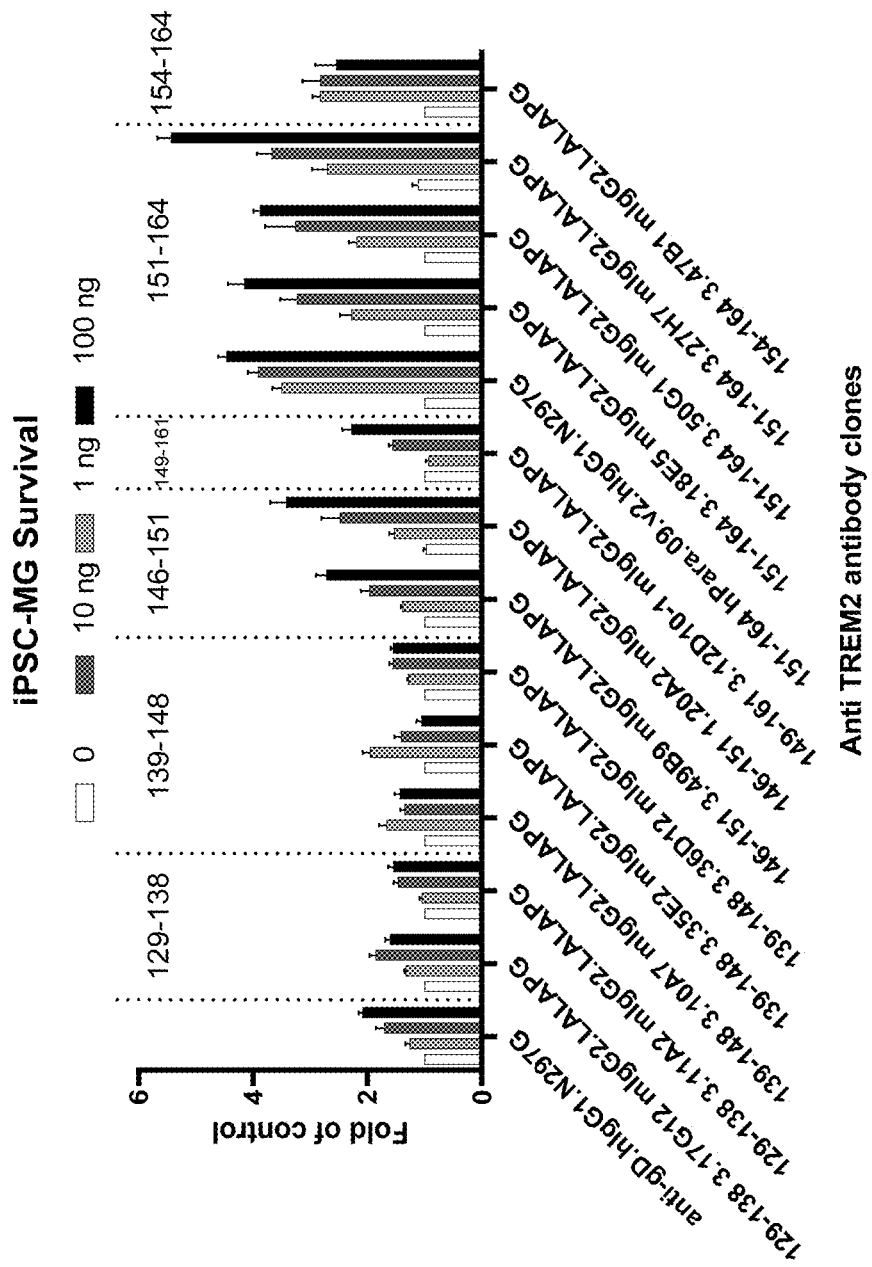

The human iPSC-MG survival assay was used to screen anti-TREM2 antibodies from the screens of Example 1 that showed binding to different regions of hTREM2, using 2-4 antibody clones with the highest affinity from each of 6 epitope bins (FIG. 23B). Antibodies in the epitope bin corresponding to the 3.10C2 group showed the highest survival activity even at 1 ng and 10 ng. Thus, 3.10C2 group antibodies showed the highest agonist activity in promoting iPSC-MG microglia survival.

2. Anti-TREM2 Antibodies Induce pSYK-Dependent Survival in iPSC-MG

Figure 23C:
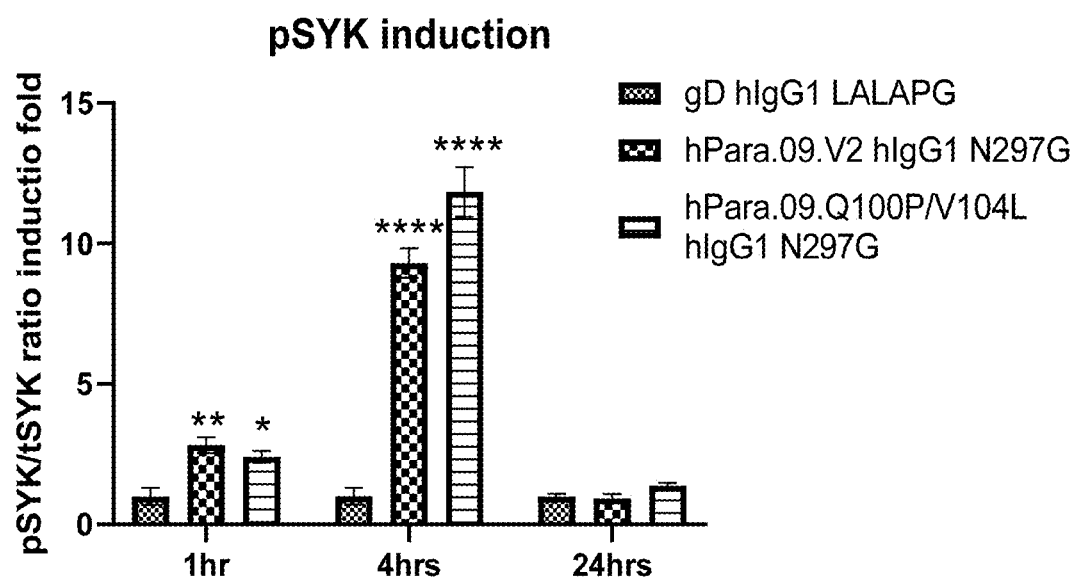

TREM2 signals through its association with DAP12, which recruits SYK through its cytosolic immunoreceptor tyrosine-based activation motifs (ITAMs). SYK, therefore is a downstream effector of TREM2 signaling. As shown in FIG. 23C, compared to the control anti-gD antibody, both hPara.09.V2 hIgG1 N297G and variant hPara.Q100P.V104L hIgG1 N297G antibodies showed a 2-fold elevation of phospho-SYK at 1 hour of incubation, and more than 10-fold induction at 4 hours (Error bar+/−SEM. * $P<0.05$,  $P<0.01$, **$<0.0001$, using a 2 way ANOVA). Phospho-SYK levels returned to control level at 24 hours. Consistent with results shown above for human MDM cells, both antibodies elicited increased TREM2 signaling via SYK kinase in iPSC-derived microglia.

Figure 23D:
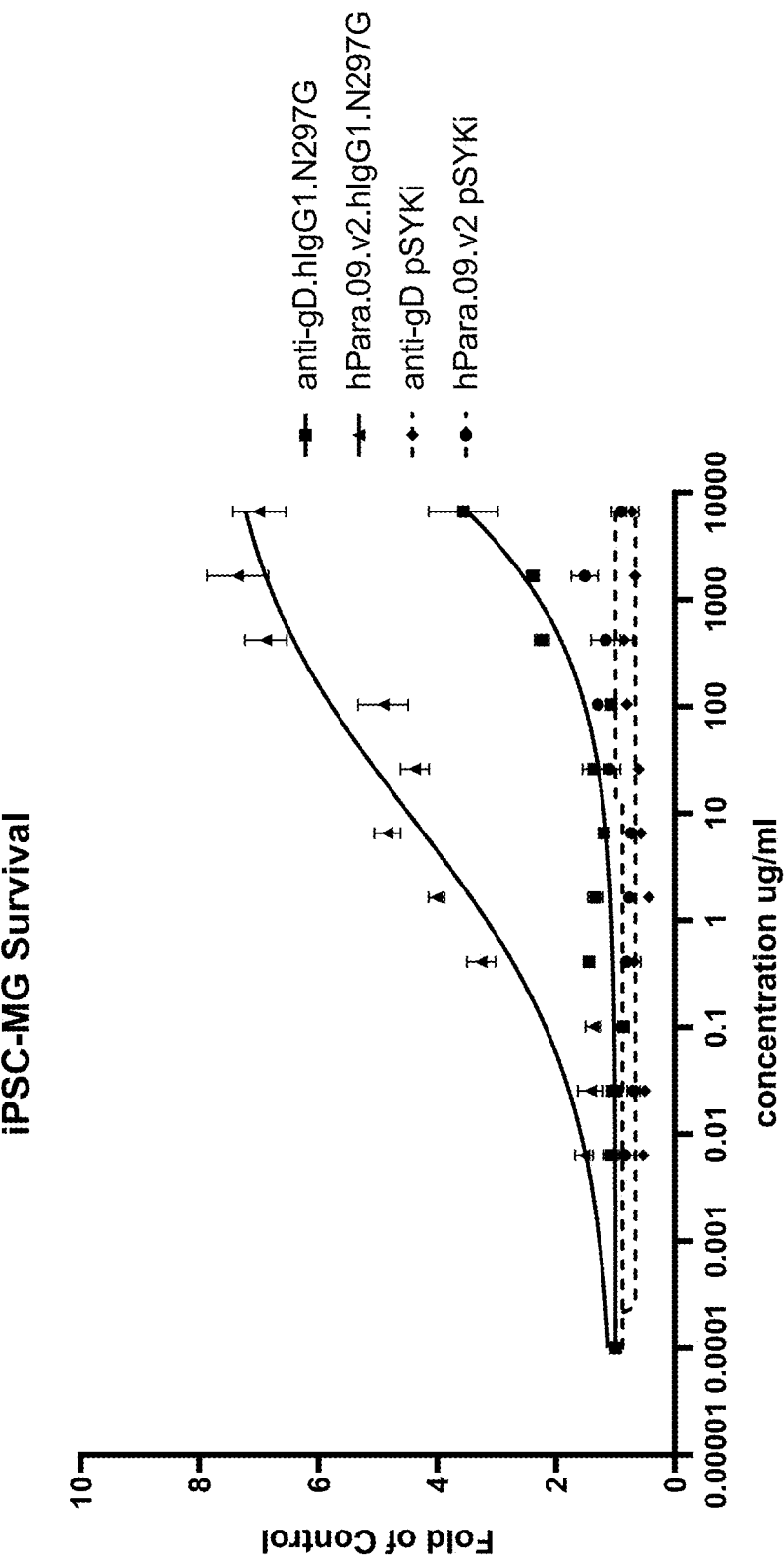

To test if TREM2 activation mediated survival requires SYK kinase activity, human iPSC-MG were incubated with anti-TREM2 antibody hPara.09.V2 hIgG1 N297G in the presence of a SYK inhibitor PRT-060318 (PRT318) at 250 nM (FIG. 23D). In the presence of the SYK inhibitor, hPara.09.V2 hIgG1 N297G did not promote iPSC-MG survival, indicating that the TREM2 mediated survival function requires SYK activity.

Figure 23E:
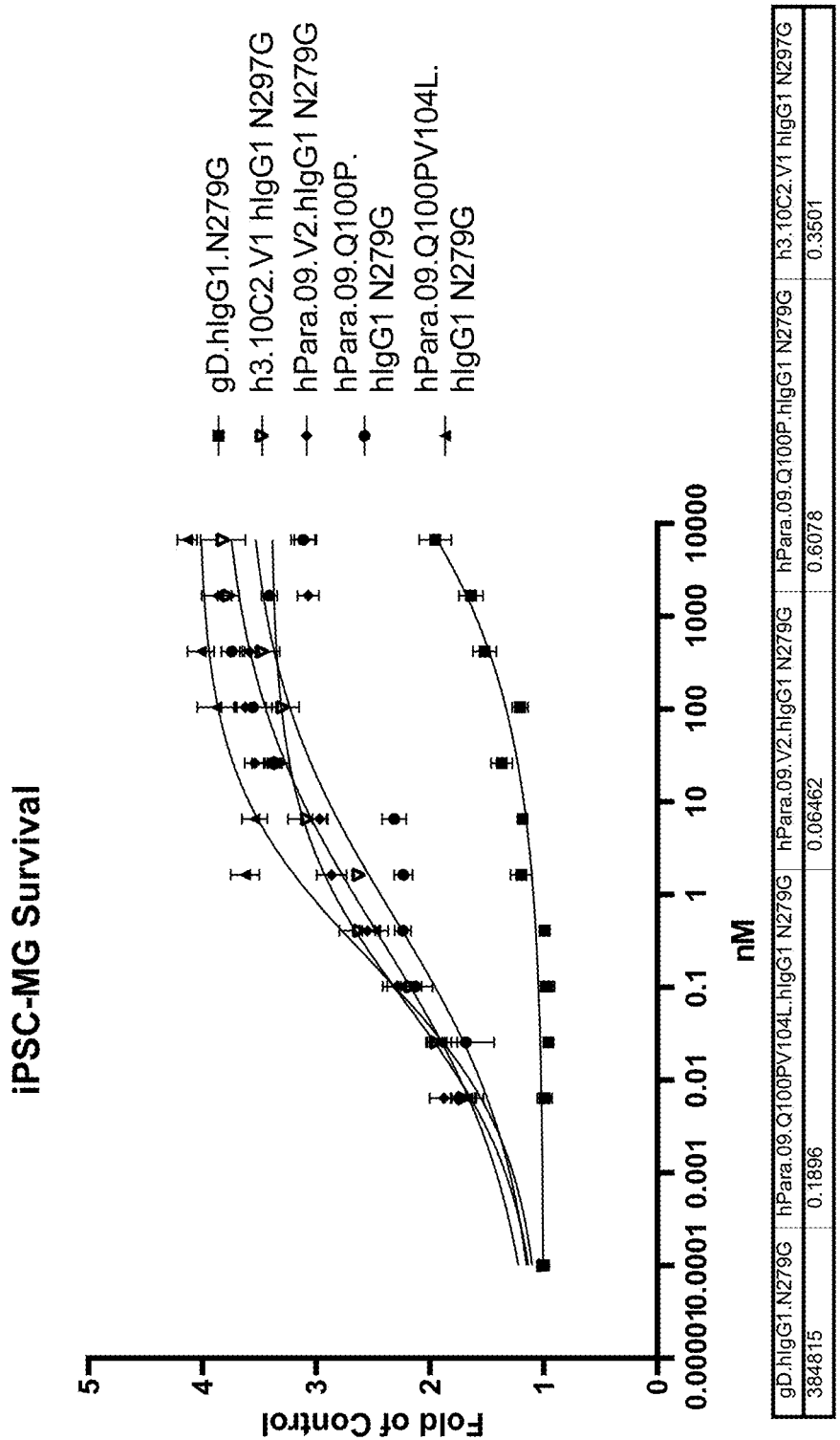

The iPSC-MG assay was further used to determine the $EC_{50}$ of anti-TREM2 antibody clones. As shown in FIG. 23E, the tested anti-TREM2 antibodies promoted iPSC-MG survival in the sub-nanomolar range.

These data further confirmed that the antibodies potently activate TREM2 signaling through phosphorylation of SYK in macrophage and microglia models.

3. Anti-TREM2 Antibodies and TREM2's Neuroprotective Function Against Alzheimer's Disease Several prior studies have indicated that TREM2 activity regulates microglial packing of Aβ into a dense plaque, and this may confer an important neuroprotective activity in Alzheimer's disease (AD). (Ulrich et al., *ACS Chem Neurosci* doi: 10.1021/acschemneuro.5b00313 (2016); Yeh F L et al., *Trends Mol Med* doi: 10.1016/j.molmed.2017.03.008 (2017); Bohlen C J et al., *Ann Rev Genet* doi: 10.1146/annurev-genet-112618-043515 (2019); Wang Y et al., *J Exp Med* doi: 10.1084/jem.20151948 (2016); Meilandt W J et al., *J Neurosci* doi: 10.1523/JNEUROSCI.1871-19.2019 (2020).)

Figure 24A:
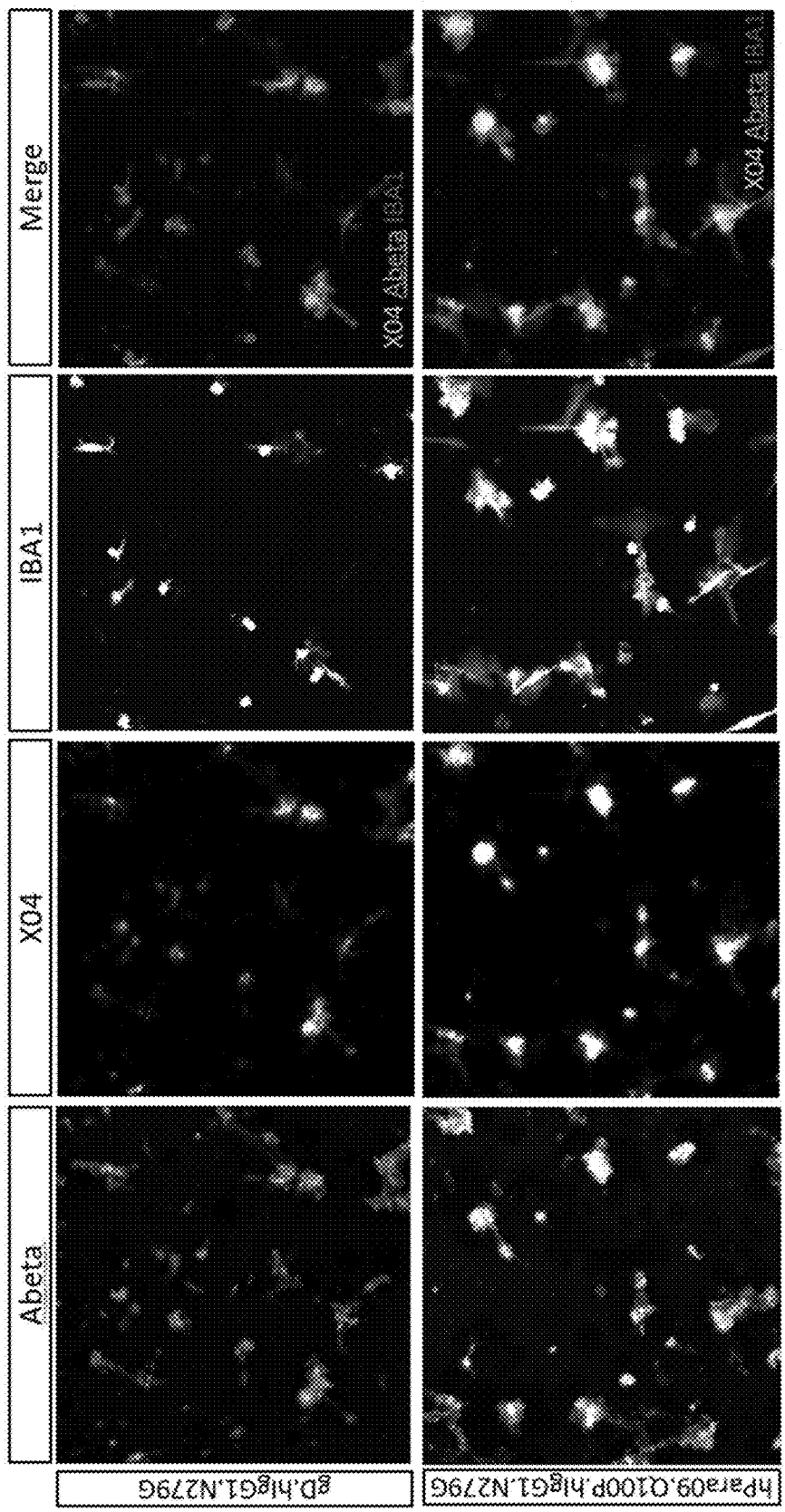
FIG. 24A-C show that humanized anti-TREM2 antibodies increase iPSC-MG amyloid beta plaque formation and compaction.
Figure 24B:
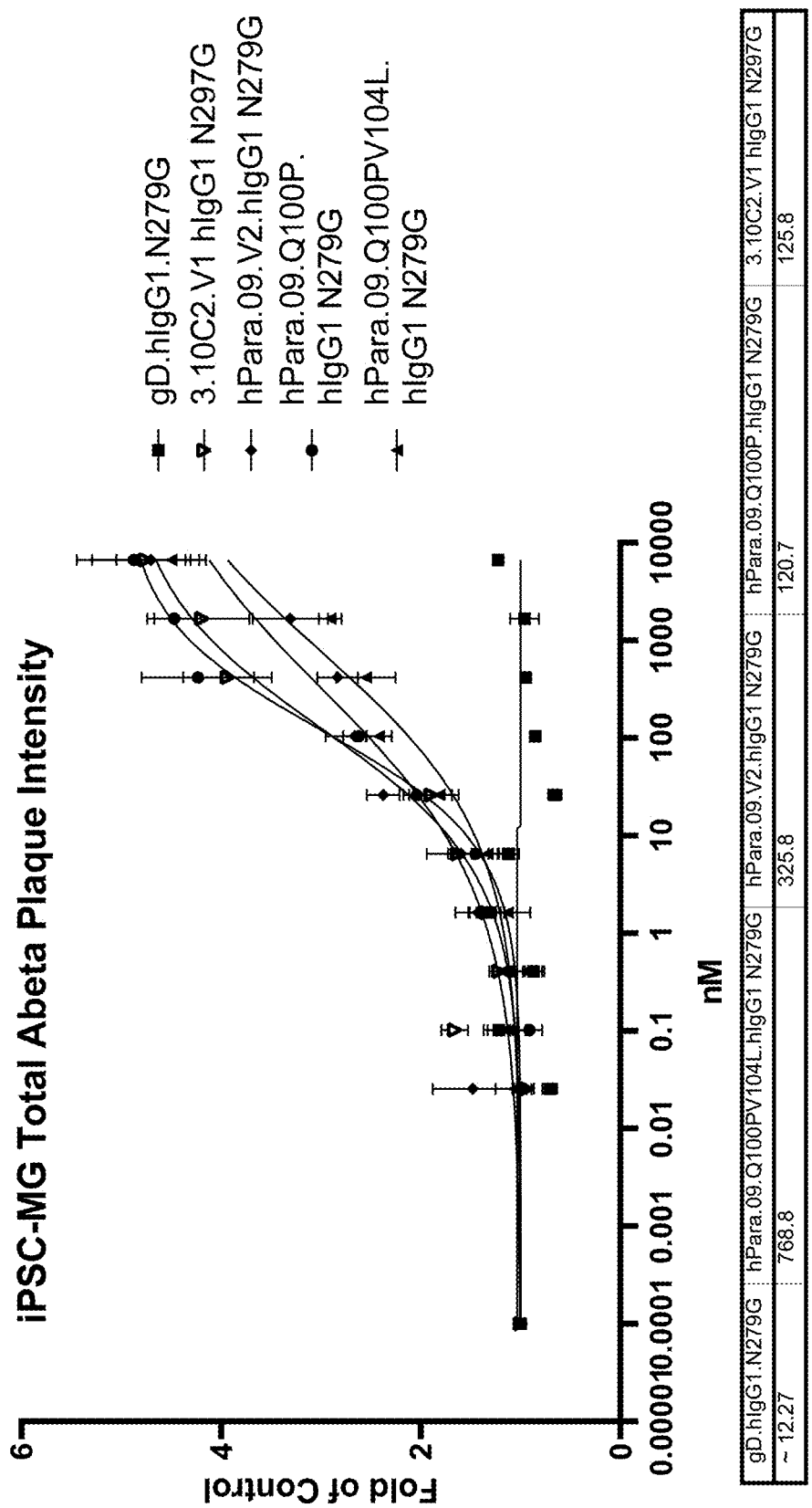
Figure 24C:
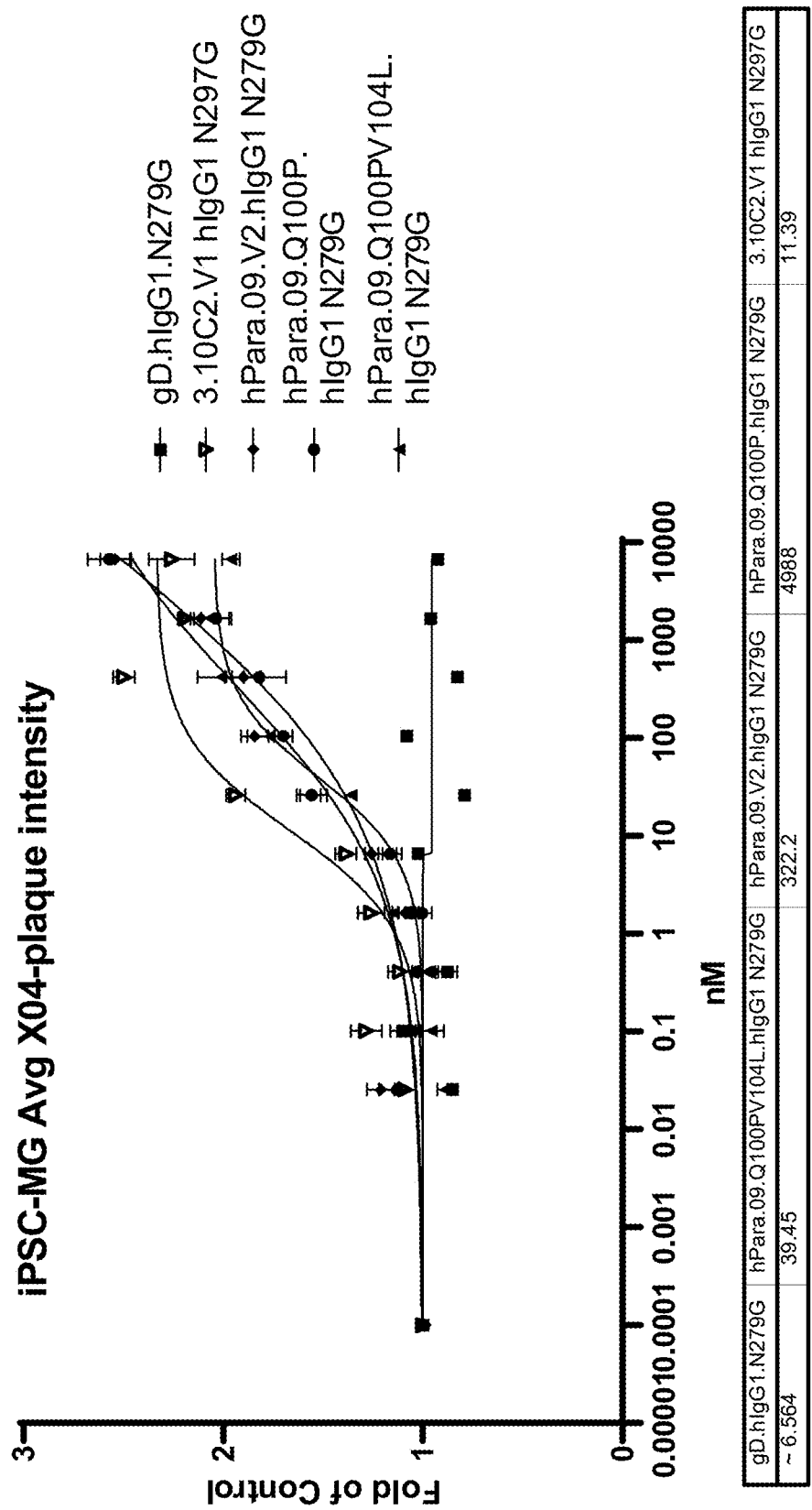

FIG. 24A shows staining of cells treated with either control anti-gD antibody or hPara09.Q100P with markers for Aβ (Abeta), amyloid plaques ($X_{O4}$), and 113A1 individually, and in combination (merged). Adding Aβ oligomers to human iPSC derived microglia culture for 2 days led to robust Aβ plaque-like structure formation and formation of Aβ aggregates (FIG. 24A Aβ panel at left). The amyloid specific binding dye Methoxy-$X_{O4}$ binds to a specific confirmation of Aβ peptide found in the amyloid plaques (Klunk W E et al., *Neutopathol Exp Neurol* doi: 10.1093/jnen/61.9.797 (2002)). X04 staining was used to confirm that observed aggregates were amyloid plaques formed by the microglia. (FIG. 24A, X04 panel at center.) The IBA1 marker labels microglia. In FIG. 24A, the IBA1 panel at right shows more intense IBA1 staining in the presence of the hPara09.Q100P hIgG1 N279G antibody.

Increases in Aβ and X04 staining intensity each reflect the formation and compaction of amyloid plaques. Compared to control antibody, hPara09.Q100P hIgG1 N279G enhanced the formation of Aβ aggregates in human iPSC microglia (FIG. 24A). Aβ aggregates in cells treated with the control antibodies were more diffuse, whereas the Aβ aggregates formed in the presence of the anti-TREM2 hPara09.Q100P hIgG1 N279G antibody were brighter and much more compacted and round (FIG. 24A, Aβ panel). The increased Aβ staining indicated that there are more Aβ peptides compacted into the same area of Aβ aggregates in response to anti-TREM2 hPara09.Q100P hIgG1 N279G antibody. Consistent with the Aβ staining, there was also more intense X04 staining in the Aβ aggregates in the presence of anti-TREM2, indicating more dye was bound to the specific amyloid plaque-like structures (FIG. 24A, X04 panel). More microglia were detected surrounding the amyloid plaques in the presence of anti-TREM2 compared to control (FIG. 24A, Merged panel).

Several humanized anti-TREM2 antibodies were tested in this assay in addition to hPara09.Q100P hIgG1 N279G. To quantify total amyloid plaque formation, total X04 intensity was measured and normalized to a no antibody control. N=4 wells per condition. Error bar+/−SEM. There was up to a 5-fold increase of amyloid plaque-like structures in the presence of the anti-TREM2 antibodies. (FIG. 24B). To measure amyloid plaque compaction, the average intensity of plaque dye X04 staining within each of the Aβ aggregate area was measured. FIG. 24C shows average X04 iPSC-MG plaque intensity at increasing antibody concentrations. $EC_{50}$ values are provided in nM for each antibody in the table below the curve. As shown in FIG. 24C, anti-TREM2 antibodies increased the average X04 intensity up to 3-fold.

Thus, treatment with anti-TREM2 antibodies of the present disclosure demonstrated up to 10-fold increase of phospho-SYK ratio, indicative of TREM2 signal activation, and led to a 5-8 fold increase of microglia survival in the absence of the required microglial growth factors IL-34 and CSF-1. In the presence of Aβ oligomers modeling the AD pathological brain environment, the anti-TREM2 antibodies also increased Aβ plaque formation and compaction by 3-5 fold, as measured by increases in total Aβ plaque intensity and average X04 plaque intensity. This increased microglia survival might allow more microglia to act on Aβ oligomers and package them into amyloid plaques. Therefore, the antibodies may offer neuroprotection in vivo by activating TREM2 signaling in human microglia, functionally increasing microglia survival, and promoting Aβ compaction into amyloid plaques.

Example 18A: Systemic Administration of 3.10C2 and Para.09 in Mice Decreased in Vivo Soluble TREM2 Levels A. Materials and Methods Transgenic mice expressing human TREM2 in a PS2APP mouse TREM2 knock-out (KO) background were dosed with 3.10C2, Para.09 (rat Para.09-LC 3.27H7), or a control gp120 IgG antibody by intraperitoneal (i.p.) administration. Each antibody comprised a mIgG2a LALAPG backbone. The doses administered were 20 mg/kg and 80 mg/kg on day 0, and plasma and brain samples were collected on day 3.

The mice were 7 to 8 months old. Mice were anesthetized with Avertin and blood was collected by cardiac puncture. Mouse brains were perfused with cold phosphate buffer saline (PBS), removed and split down the midline. One hemisphere was drop fixed in 4% PFA for 48 hours then transferred to PBS then 30% sucrose for cryopreservation. Coronal sections (35 μm) were made on a sliding microtome. From the other hemibrain, the hippocampus and cortex were isolated and quickly frozen. Cortical tissue was homogenized in 10 volumes of TBS (50 mm Tris pH 7.5, 150 mm NaCl) containing protease inhibitor cocktail (Roche Catalog No. 4693159001) and PhosSTOP™ (Roche Catalog No. 4906837001); 1 ml lysis buffer was used for every 100 mg tissue. Subsequently, one 3-mm stainless steel bead (Qiagen) was added into each tube and samples were homogenized with the Qiagen TissueLyser™ II at 30 Hz for 3 min. The homogenized samples were then cleared by centrifugation at 20,000×-g for 20 min at 4° C. Supernatants were transferred to new tubes and stored at −80° C.

The Human TREM2 ELISA assay by R&D Systems (Catalog No. DY1828-05) was used to test for sTREM2 in plasma and brain lysates. The human sTREM2 capture antibody (AF1828) that was provided in the assay kit was diluted in PBS and immobilized in 96 well plates. After blocking and washing the plate diluted sample and standards were added and incubated for 2 hours at room temperature. After washing, the human sTREM2 detection antibody was diluted and incubated for another 2 hrs. The plate was once again washed and incubated with Streptavidin-HRP for 20 min followed by a substrate solution incubation of 20 min at room temperature. After stopping the reaction, the plate was read using two filters, 450 nm for detection and 570 nm for background. Concentrations were determined on a standard curve obtained by plotting optical density versus concentration.

B. Results

Administration of the 3.10C2.mIgG2a LALAPG and Para.09. mIgG2a LALAPG antibodies caused a dose-dependent decrease in soluble TREM2 levels in both plasma (FIG. 25A) and brain homogenate (FIG. 25B) samples, relative to levels of soluble TREM2 measured after administration of a control antibody (gp120). A decrease in sTREM2 may indicate that the antibodies block shedding or alternatively that they may induce internalization of the receptor upon activation. The decrease in sTREM2 suggests that the therapeutic antibodies can engage with the target in vivo in the periphery and in the brain.

Example 18B: Para09 Administration Results in a Decrease in In Vivo Plasma Soluble TREM2 Levels, Contrary to the Effect Seen with a Comparator Anti-TREM2 Antibody A. Materials and Methods Transgenic mice (5-6 months old) expressing human TREM2 in a PS2APP mouse TREM2 knock-out (KO) background were dosed with Para.09 (rat Para.09-LC 3.27H7), a comparator antibody AL2p58, or a control gp120 IgG antibody by i.p. administration. Each antibody comprised a mIgG2a LALAPG backbone. The doses administered were: Para09-100 mg/kg, 200 mg/kg; A12p58-20 mg/kg, 100 mg/kg, 200 mg/kg; gp120 isotype control—200 mg/kg. Terminal plasma was collected on day 3 or day 7.

Animal handling, tissue collection and processing, and human TREM2 ELISA assay by R&D Systems were performed as described in Example 18A. Mice were anesthetized with Avertin and blood was collected by cardiac puncture. The Human TREM2 ELISA assay by R&D Systems (Catalog No. DY1828-05) was used to test for sTREM2 in plasma lysates. The human sTREM2 capture antibody that was provided in the assay kit was diluted in PBS and immobilized in 96 well plates. After blocking and washing the plate diluted sample and standards were added and incubated for 2 hours at room temperature. After washing, the human sTREM2 detection antibody was diluted and incubated for another 2 hrs. The plate was once again washed and incubated with Streptavidin-HRP for 20 min followed by a substrate solution incubation of 20 min at room temperature. After stopping the reaction, the plate was read using two filters, 450 nm for detection and 570 nm for background. Concentrations were determined on a standard curve obtained by plotting optical density versus concentration.

B. Results

Administration of Para.09 mIgG2a LALAPG antibodies caused a substantial and dose-dependent decrease of 70%-85% in soluble TREM2 levels in plasma (FIG. 25C) samples. In contrast, the comparator anti-TREM2 antibody, which has been described as binding to the stalk region of TREM2, AL2p58 (see WO2019028292), and is shown in earlier Examples to bind to sTREM2, showed a marked increase in plasma sTREM2 levels of more than 2 fold relative to sTREM2 levels seen with the control antibody. This increase in plasma sTREM2 levels in animals treated with AL2p58 persisted for at least 7 days post-treatment, as shown in FIG. 25C. Thus, administration of Para09 reduced sTREM2 levels in plasma whereas administration of the comparator antibody had the opposite effect of causing a prolonged and substantial increase in plasma sTREM2 levels in vivo, which may be an undesirable side effect of binding to sTREM2.

Experiment 18C: Single Dose Intravenous Injection of h3.10C2.v1 and hPara.09.v2 Antibodies in Cynomolgus Monkeys Decreased Soluble TREM2 Levels In Vivo A. Materials and Methods Native female cynomolgus monkeys approximately 2-3 years old were dosed intravenously with h3.10C2.v1.huIgG1.N297G, hPara.09.v2.hIgG.N297G, or a control antibody (anti-gD.hIgG1.N297G) at 50 or 200 mg/kg on day 1. Cynomolgus monkeys were surgically implanted with an intrathecal catheter in the lumbar spine for CSF sample collection. Blood samples were collected from conscious animals via a peripheral vein. Animals were euthanized and gross necropsy performed to collect brain samples. Brain punctures at 30-50 mg were collected from the cerebellum, cerebral cortex, and hippocampus. CSF and plasma samples were collected on day −7, 0, 1 and 2 for the cohorts that had a duration of 2 days post dose and on day −7, 0, 1, 2, 4, 7, 10, 14, 21, and 28 for the cohorts that had a duration of 28 days post dose. The samples collected on day −7 and 0 prior to treatment were averaged to determine baseline soluble TREM2 (sTREM2) concentration. Brain samples were collected from animals euthanized on study days 3 and 29.

A commercial human TREM2 ELISA kit (Origene EA102484) was used to determine soluble TREM2 levels in cynomolgus CSF, plasma, and brain lysate. The 96-well plates were precoated with anti-TREM2 capture antibody. 100 µL of standard, controls or samples were added to each well and incubated at 37° C. for 90 minutes. The contents of the wells were removed by aspiration and 100 µL of diluted biotinylated detection antibody was added into each well. After 1 hr incubation at 37° C., the plates were washed 3 times with wash buffer. 100 µL/well of avidin-peroxidase secondary detection reagent was added to the plates and plates were further incubated at 37° C. for 30 minutes. After washing the plates 5 times, 90 µL/well of color developing reagent was added and the plates were incubated for 15-25 minutes. 100 µL/well of stop solution was added to stop the color development. Absorbance was measured at 450 nm against a reference wavelength of 650 nm. The concentration of the samples was extrapolated from a 4-parameter fit of the standard curve. The reportable assay range is 0.0313-2.0 ng/mL with a lower limit quantification of 156 pg/mL for CSF, 313 pg/mL for plasma, and 94 pg/mL for brain lysate.

B. Results

Figure 26A:
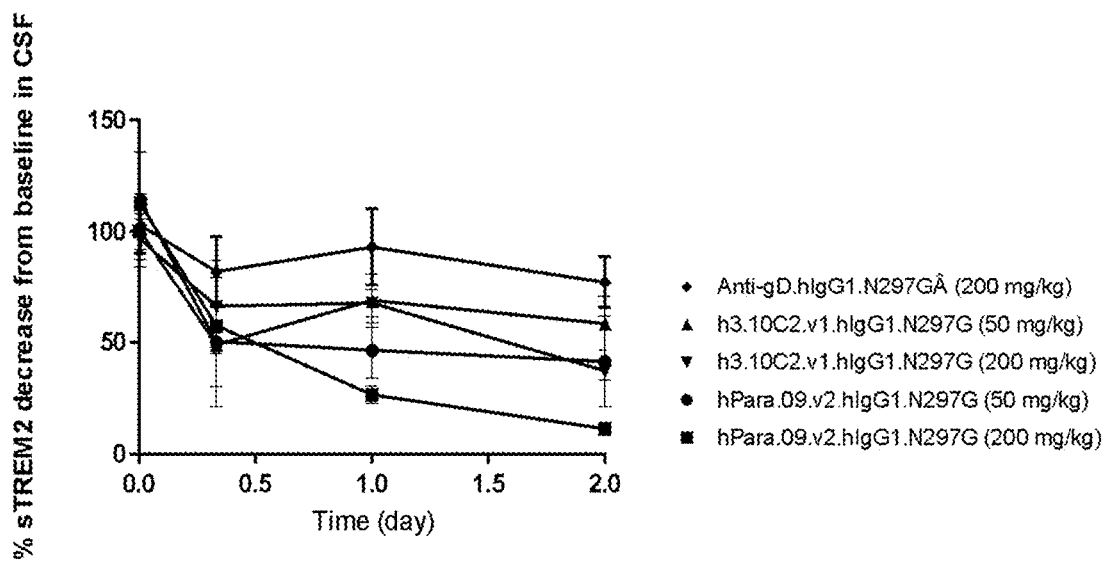
FIGS. 26A-F show sTREM2 levels over time in CSF, plasma, and brain lysate samples from cynomolgus monkeys dosed with h3.10C2.v1.hIgG1.N297G, hPara.09.v2.hIgG1.N297G or anti-gD.hIgG1.N297G control antibody.
Figure 26B:
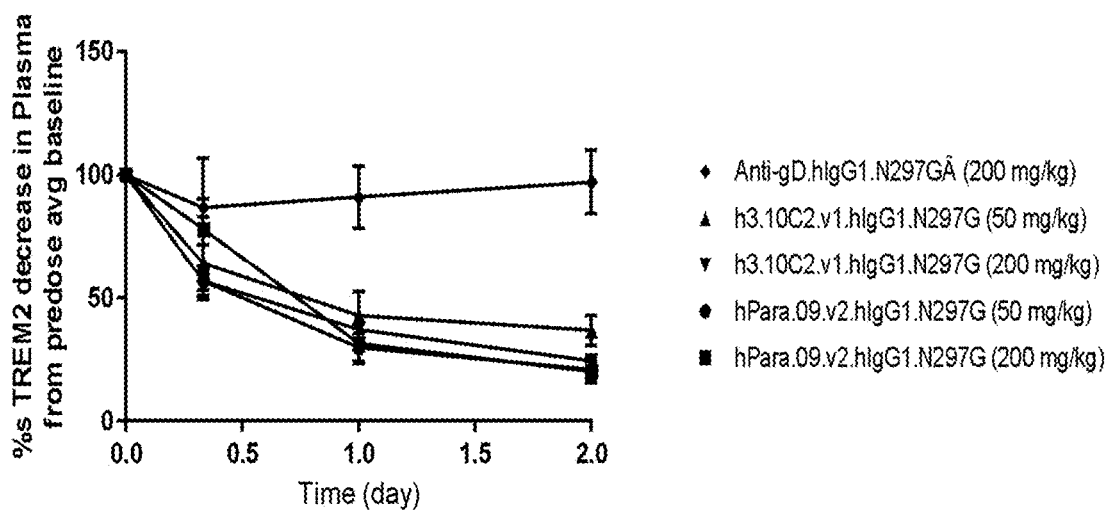
Figure 26C:
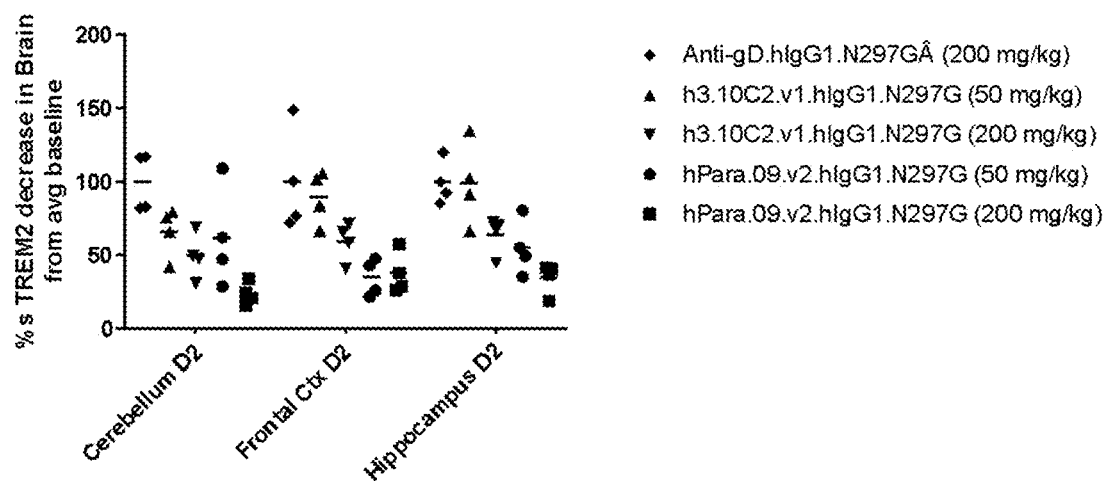
Figure 26D:
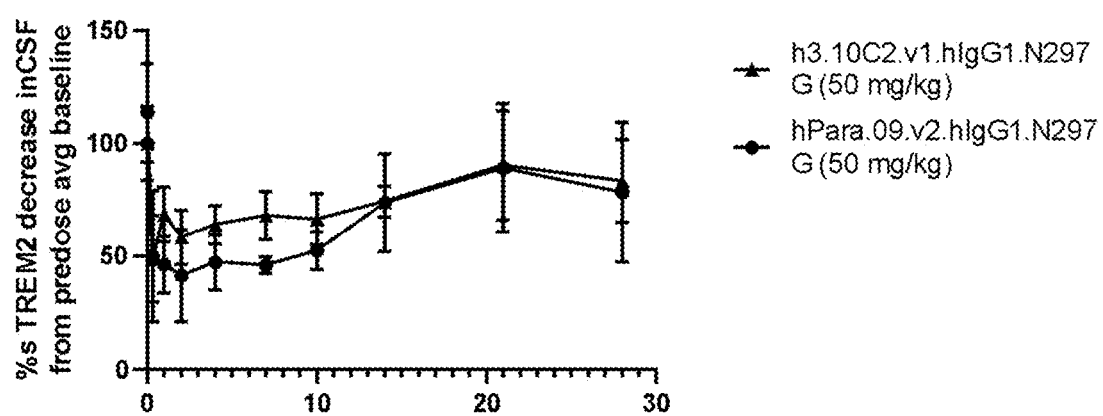
Figure 26E:
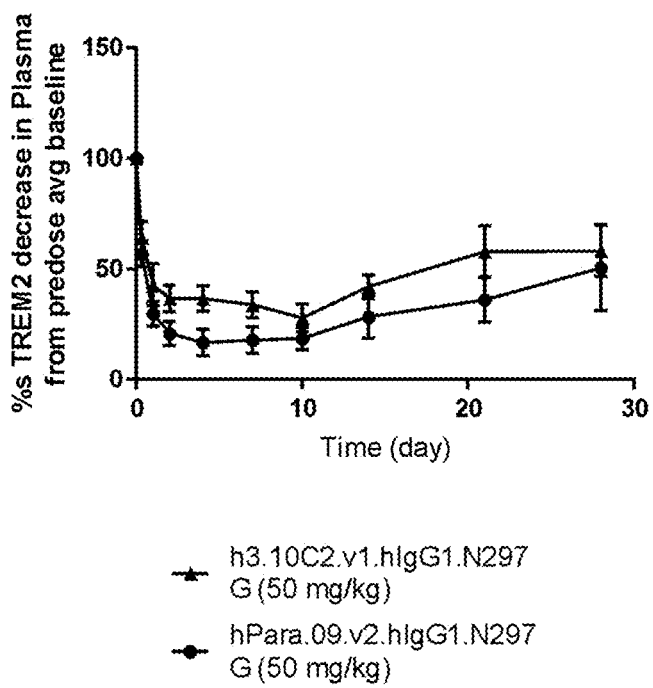
Figure 26F:
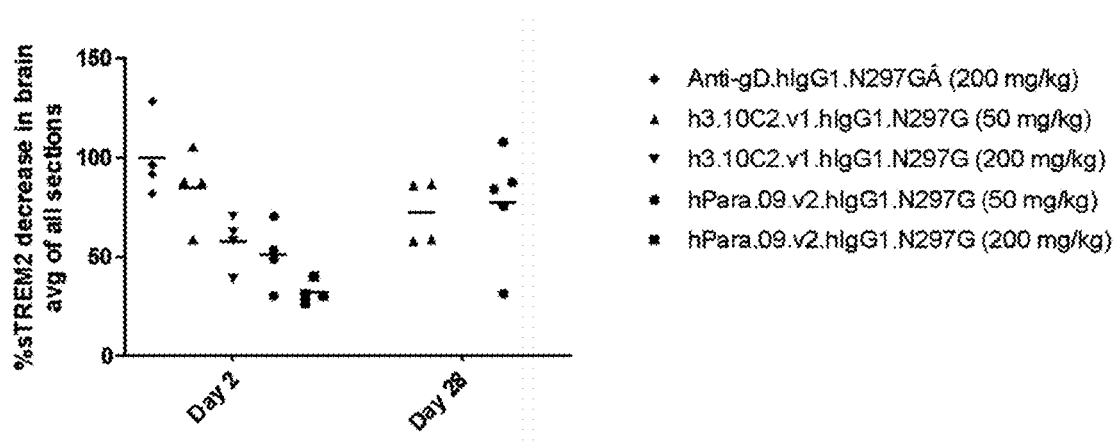

A general trend of decreased sTREM2 was observed for most samples in h3.10C2.v1.huIgG1.N297G and hPara.09.v2.hIgG.N297G groups compared to the control group (FIGS. 26A-26C). The greatest decrease was observed in plasma (4=50% for treatment groups relative to control group), then CSF, then brain. Treatment with h3.10C2.v1.huIgG1.N297G or hPara.09.v2.hIgG.N297G appeared to show a dose dependent response in CSF and brain. hPara.09.v2.hIgG.N297G showed the largest decrease in brain and CSF sTREM2 compared to h3.10C2.v1.huIgG1.N297G. For the 50 mg/kg groups that ran for 28 days, decrease in sTREM2 was observed in brain, CSF, and plasma especially at ten days (FIGS. 26D-26F).

The decrease of sTREM2 suggests that the therapeutic antibodies can engage with the intact TREM2 target in vivo in the brain and CSF, and also lead to prolonged reduction of sTREM2 in the periphery.

Example 19: TREM2 Activating Antibodies Increase Cell Proliferation In Vivo

A. Material and methods

Free floating coronal sections (35 µm, two per animal) were washed in PBS twice for 5 minutes followed by PBS-Triton X100 (0.1%) twice for 10 minutes. Sections were then incubated in Dako Target Retrieval Solution (Roche Catalog No. S236784-2) for 10 minutes at 105C, washed in PBS then blocked in 5% bovine serum albumin (BSA) 0.3% Triton X100 in PBS for 2 to 3 hours at room temperature. Primary antibody (mouse monoclonal Ki67; BD Pharmigen Catalog No. 556003) was diluted 1:100 and incubated at 4° C. overnight, donkey anti-mouse Alexa555 secondary antibody was incubated at RT for 2 hours. Sections were mounted onto Superfrost™ plus (Fisherbrand) glass slides and cover-slipped with Prolong™ Gold plus DAPI antifade mounting media. Image acquisition of immunofluorescent slides was performed at 200× magnification using the NanoZoomer® S60 or XR (Hamamatsu Corp, San Jose, CA) digital whole slide scanner. Ideal exposure for each channel was determined based on samples with the brightest intensity and set for the whole set of slides to run as a batch.

Brain sections from mice treated with 3.10C2, Para09, or control gp120 IgG antibody (each antibody comprised a mIgG2a LALAPG backbone) were stained for the proliferation marker Ki67, and number of Ki67+/DAPI+ cells were calculated. Cells positive for Ki67 and DAPI were counted and averaged from two sections per animal.

B. Results

Figure 27:
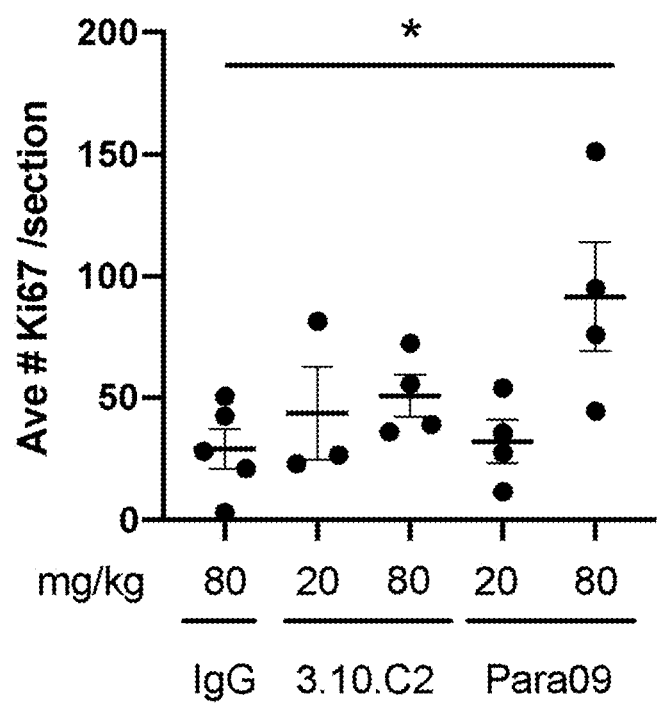
FIG. 27 shows brain sections from mice treated with 3.10C2, Para.09, or a control antibody that were stained for the proliferation marker Ki67. Cell proliferation is represented as the average number of Ki67+ cells per number of 4',6-diamidino-2-phenylindole (DAPI)-positive cells.

As shown in FIG. 27, Para.09 (at 80 mg/kg) significantly increased the number of Ki67+ cells three days post a single injection compared with isotype control-treated mice. A one-way ANOVA of Ki67+ cells found a significant treatment effect ($F_{(4, 15)} = 3.477$ $P = 0.0336$) with a significant difference between Para.09 (80 mg/kg) and control isotype (gp120, 80 mg/kg) by Tukey's post-hoc multiple comparison ($p < 0.05$). This data confirms that Para.09 induces TREM2 pathway activation and increases cell proliferation in vivo.

Example 20: Effects of Anti-TREM2 Antibodies on Amyloid and Tau Pathology in a Murine Model for Human Alzheimer's Disease Pathological hallmarks of Alzheimer's Disease (AD) include extracellular deposits of beta-amyloid peptides that form amyloid plaques and intracellular deposits of aggregated hyperphosphorylated tau called neurofibrillary tangles. These pathologies are followed by an increase in brain inflammation, including activated astrocytes and microglia, and neurodegeneration. Transgenic mice expressing human mutations in presenilin 2 and amyloid precursor protein, which cause familial forms of AD, (PS2APP mice) show similar age-dependent increases in Abeta pathology as seen in AD patients. PS2APP mice crossed to Tau mutant P301L mice (TauPS2APP mice) show additional hallmarks of AD pathology, including hyperphosphorylated Tau and neurodegeneration. Human TREM2 (hTREM2 BAC) expressing mice, in a mouse Trem2 knockout background, are bred to TauPS2APP mice in order to test whether activating human Trem2 using anti-TREM2 antibody enhances microglia activity and facilitates the removal of toxic amyloid-beta peptides, by engulfment or compaction into less toxic amyloid plaques. In this study, groups of 14-16 TauPS2APP-hTrem2 mice receive weekly or monthly (every 4 week) systemic injections of a low or high dose of anti-TREM2 antibody or a control IgG antibody for 16 weeks starting at 34 weeks of age. Changes in brain atrophy by volumetric MIll are monitored by imaging mice at the beginning and end of treatment.

At the completion of dosing, plasma and brain samples are collected to measure antibody exposures by ELISA, one hemibrain is fixed in paraformaldehyde for immunohistochemical staining, and cortical and hippocampal tissue are collected for biochemical analysis. Histological staining for plaque formation is performed using an amyloid stain, such as methoxy-X04. Microglial clustering around plaques and changes in morphology are assessed by staining with a microglial marker such as Iba1 and Methoxy-X04. To determine if treatment alters the development of plaque-associated neurodegeneration (neuritic dystrophy), sections are co-stained for plaques, with methoxy-X04 and a lysosomal protein marker, e.g., LAMP1, which accumulates in the neuritic dystrophy surrounding the plaque.

The effect of anti-TREM2 antibody treatment on histological measures of pTau and neurodegeneration in the hippocampus is measured by staining for various forms of phosphorylated and aggregated tau (e.g, with AT8, PHF1, MC1, and p212/214 antibodies). Neurodegeneration is assessed by staining sections with an amino-cupric silver stain that detects degenerating axons and processes. Neurofilament light chain (NfL), a soluble marker of degenerating axons, is also measured by ELISA from the plasma and CSF.

Example 21: Effects of Anti-TREM2 Antibodies in a Multiple Sclerosis Model

Multiple sclerosis (MS) is a disease characterized by an autoimmune related demyelination in the CNS. In patients, the disease presents in episodes of symptoms such as ataxia, limb weakness, and optic neuritis among other neurological effects. Whether activation of the TREM2 pathway by anti-TREM2 antibodies accelerates remyelination is tested in a cuprizone-induced demyelination model of MS. Cuprizone is a toxic copper chelating agent that when introduced into rodent chow (0.2 to 0.25%) reliably targets oligodendrocytes causing a demyelinating lesion along white matter tracts in the brain, which mimics the demyelination observed in human MS patients. Mice are typically treated for 4 weeks, at which time lesions of the corpus callosum are detectable by MM. After removal from cuprizone chow, normal wild-type mice show an accumulation of degraded myelin (measured by staining for dMBP) 3 days post-cuprizone treatment, decreased intact myelin (measured by Solochrome cyanine staining) and astrocytic (GFAP) and microglial (Iba1) infiltration into the lesion site. Increased precursor and mature oligodendrocytes (Olig2) in wild-type mice typically become elevated by day 3, supporting remyelination, which is typically complete by 14 days post-cuprizone treatment. Electron microscopy may also be used to quantify levels of remyelination in the white matter tracts.

The impact of anti-TREM2 antibody treatment on remyelination events is tested using hTREM2-BAC transgenic mice exposed to cuprizone chow for four weeks, to induce a lesion, and then treated with either an anti-TREM2 antibody or an isotype control antibody such as gp120, while the cuprizone chow is removed. Typically, each group comprises 5-10 mice. Groups include mice on control chow or cuprizone chow for 4 weeks, with the groups of mice on cuprizone chow for 4 weeks then placed on control chow for 3, 7, or 14 days. Mice receive a single high dose of anti-TREM2 or control antibody after the 4 weeks of cuprizone chow and brain and plasma samples are collected either 3, 7, or 14 days after the antibody injection. Stained sections of the corpus callosum lesions (e.g., 6-18 sections per subject) are quantified using high resolution imaging and automated analysis software (MATLAB). Samples from the 14 day post-antibody injection are measured for remyelination by electron microscopy.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

Sequence Table

The following table provides certain sequences described or cited in the text and figures herein. In SEQ ID Nos: 90, 92-93, and 95-101, TREM2 residues H157 and S158, the location of the cleavage site in the protein, are underlined.

| Seq Id. No. | Description | Sequence |
|---|---|---|
| 1 | 3.10C2.v1 heavy chain CDR1 | NVWMH |
| 2 | 3.10C2.v1 heavy chain CDR2 | HIKAKSDNYATYYAESVKG |
| 3 | 3.10C2.v1 heavy chain CDR3 | LDY |
| 4 | 3.10C2.v1 light chain CDR1 | RSSRSLLTSKGITSLY |
| 5 | 3.10C2.v1 light chain CDR2 | RMSNLAS |
| 6 | 3.10C2.v1 light chain CDR3 | AQFLVYPYT |
| 7 | h3.10C2.v1 heavy chain variable region | EVQLVESGGGLVQPGGSLKLSCATSGFPFSNVWMHWVRQASGKGLEWIAHIKAKSDNYATYYAESVKGRFTISRDDSKTTIYLQMNSLKTEDTAVYYCTGLDYWGQGTTVTVSS |
| 8 | h3.10C2.v1 light chain variable region | DVVMTQSPLSLPVTPGEPASISCRSSRSLLTSKGITSLYWYLQKPGQSPQLLIYRMSNLASGVPDRFSGSGSGTDFTLKISRVEAEDVGVYYCAQFLVYPYTFGQGTKVEIK |
| 9 | 3.10C2.v1 heavy chain CDR1 (Chothia) | GFPFSNV |
| 10 | 3.10C2.v1 heavy chain CDR2 (Chothia) | KAKSDNYA |
| 11 | PARA.09.v2 heavy chain CDR1 | NVWLH |
| 12 | PARA.09 and PARA.09.v2 heavy chain CDR2 | HIKAKSDNYATYYAESVKG |
| 13 | PARA.09 and PARA.09.v2 heavy chain CDR3 | ILEY |
| 14 | PARA.09 and PARA.09.v2 light chain CDR1 | RSSRSLLTSKGITSLY |

-continued

Sequence Table
The following table provides certain sequences described or cited in the text and figures herein. In SEQ ID Nos: 90, 92-93, and 95-101, TREM2 residues H157 and S158, the location of the cleavage site in the protein, are underlined.

| Seq Id. No. | Description | Sequence |
|---|---|---|
| 15 | PARA.09 and PARA.09.v2 light chain CDR2 | RMSNLAS |
| 16 | PARA.09 and PARA.09.v2 light chain CDR3 | AQFLVYPYT |
| 17 | hPARA.09.V2 heavy chain variable region | EVQLVESGGGLVQPGGSLKLSCATSGFPFSNVWLHWVRQASGKGPEWVAHIK AKSDNYATYYAESVKGRFTISRDDSKNTVYLQMNSLKTEDTAVYYCTDILEY WGQGTLVTVSS |
| 18 | hPARA.09.V2 light chain variable region | DVVMTQSPLSLPVTPGEPASISCRSSRSLLTSKGITSLYWYLQKPGQSPQLL IYRMSNLASGIPDRFSGSGSGTDFTLKISRVEAEDVGVYYCAQFLVYPYTFG QGTKVEIK |
| 19 | PARA.09 and PARA.09v2 heavy chain CDR1 (Chothia) | GFPFSNV |
| 20 | PARA.09 and PARA.09.v2 heavy chain CDR2 (Chothia) | KAKSDNYA |
| 21 | Human TREM2 NP_061838.1 (including signal sequence) | MEPLRLLILL FVTELSGAHN TTVFQGVAGQ SLQVSCPYDS MKHWGRRKAW CRQLGEKGPC QRVVSTHNLW LLSFLRRWNG STAITDDTLG GTLTITLRNL QPHDAGLYQC QSLHGSEADT LRKVLVEVLA DPLDHRDAGD LWFPGESESF EDAHVEHSIS RSLLEGEIPF PPTSILLLLA CIFLIKILAA SALWAAAWHG QKPGTHPPSE LDCGHDPGYQ LQTLPGLRDT |
| 22 | Human TREM2 (without signal sequence) | HN TTVFQGVAGQ SLQVSCPYDS MKHWGRRKAW CRQLGEKGPC QRVVSTHNLW LLSFLRRWNG STAITDDTLG GTLTITLRNL QPHDAGLYQC QSLHGSEADT LRKVLVEVLA DPLDHRDAGD LWFPGESESF EDAHVEHSIS RSLLEGEIPF PPTSILLLLA CIFLIKILAA SALWAAAWHG QKPGTHPPSE LDCGHDPGYQ LQTLPGLRDT |
| 23 | Soluble human TREM2 (TREM2 ectodomain) | HN TTVFQGVAGQ SLQVSCPYDS MKHWGRRKAW CRQLGEKGPC QRVVSTHNLW LLSFLRRWNG STAITDDTLG GTLTITLRNL QPHDAGLYQC QSLHGSEADT LRKVLVEVLA DPLDHRDAGD LWFPGESESF EDAHVEH |
| 24 | 3.10C2 heavy chain CDR1 | NVWMH |
| 25 | 3.10C2 heavy chain CDR2 | HIKAKSDNYATYYAESVKG |
| 26 | 3.10C2 heavy chain CDR3 | LDY |
| 27 | 3.10C2 light chain CDR1 | RSSKSLLGVRDITSLY |

-continued

Sequence Table
The following table provides certain sequences described or cited in the text and figures herein. In SEQ ID Nos: 90, 92-93, and 95-101, TREM2 residues H157 and S158, the location of the cleavage site in the protein, are underlined.

| Seq Id. No. | Description | Sequence |
|---|---|---|
| 28 | 3.10C2 light chain CDR2 | RMSNLAS |
| 29 | 3.10C2 light chain CDR3 | AQFLRYPYT |
| 30 | 3.10C2 heavy chain variable region | EVQLVETGGSLVQPGKSLKLTCATSGFPFSNVWMHWVRQSPEKQLEWIAHIKAKSDNYATYYAESVKGRFTISRDDSKTSIYLQMNSLKEDDTAIYYCTGLDYWGQGVMVTVSS |
| 31 | 3.10C2 light chain variable region | DTVLTQAPLSLSVTPGESASISCRSSKSLLGVRDITSLYWYLQKPGKSPQLLIYRMSNLASGVPDRFSGSGSETDFTLKISEVETEDVGVYYCAQFLRYPYTFGPGTKLELK |
| 32 | 3.10C2 heavy chain CDR1 (Chothia) | GFPFSNV |
| 33 | 3.10C2 heavy chain CDR2 (Chothia) | KAKSDNYA |
| 34 | 3.50G1 heavy chain CDR1 | NVWMH |
| 35 | 3.50G1 heavy chain CDR2 | HIKAKSDNYATYYAESVKG |
| 36 | 3.50G1 heavy chain CDR3 | LDY |
| 37 | 3.50G1 light chain CDR1 | RSNKSLLGIRDITSLY |
| 38 | 3.50G1 light chain CDR2 | RMSNLAS |
| 39 | 3.50G1 light chain CDR3 | AQFLRYPYT |
| 40 | 3.50G1 heavy chain variable region | EVQLVETGGSLVQPGKSLKLTCATSGFPFSNVWMHWVRQSPEKQLEWIAHIKAKSDNYATYYAESVKGRFTISRDDSKTSIYLQMNSLKDDDTAIYYCTGLDYWGQGVMVTVSS |
| 41 | 3.50G1 light chain variable region | DTVLTQAPLSVSVTPGESASISCRSNKSLLGIRDITSLYWFLQKPGKSPQLLIYRMSNLASGVPDRFSGSGSETDFTLKISEVETEDVGVYYCAQFLRYPYTFGPGTKLELQ |
| 42 | 3.50G1 heavy chain CDR1 (Chothia) | GFPFSNV |

-continued

Sequence Table
The following table provides certain sequences described or cited in the text and figures herein. In SEQ ID Nos: 90, 92-93, and 95-101, TREM2 residues H157 and S158, the location of the cleavage site in the protein, are underlined.

| Seq Id. No. | Description | Sequence |
|---|---|---|
| 43 | 3.50G1 heavy chain CDR2 (Chothia) | KAKSDNYA |
| 44 | 3.18E5 heavy chain CDR1 | NVWMH |
| 45 | 3.18E5 heavy chain CDR2 | HIKAKSDNYATYYAESVKG |
| 46 | 3.18E5 heavy chain CDR3 | LDY |
| 47 | 3.18E5 light chain CDR1 | RSNKSLLGIRDITSLY |
| 48 | 3.18E5 light chain CDR2 | RMSNLAS |
| 49 | 3.18E5 light chain CDR3 | AQFLRYPYT |
| 50 | 3.18E5 heavy chain variable region | EVQLVETGGSLVQPGKSLKLTCATSGFPFSNVWMHWVRQSPEKQLEWIAHIKAKSDNYATYYAESVKGRFTISRDDSKTTIYLQMNSLKEADTAIYYCTGLDYWGQGVMVTVSS |
| 51 | 3.18E5 light chain variable region | DTVLTQAPLSVSVTPGESASISCRSNKSLLGIRDITSLYWYLQKPGKSPQLLIYRMSNLASGVPDRFSGSGSETDFTLKISEVETEDVGVYYCAQFLRYPYTFGPGTKLELK |
| 52 | 3.18E5 heavy chain CDR1 (Chothia) | GFPFSNV |
| 53 | 3.18E5 heavy chain CDR2 (Chothia) | KAKSDNYA |
| 54 | 3.36F5 heavy chain CDR1 | NVWMH |
| 55 | 3.36F5 heavy chain CDR2 | QIKGKSDNYATYYAESLQG |
| 56 | 3.36F5 heavy chain CDR3 | LDY |
| 57 | 3.36F5 light chain CDR1 | RSNKSLLSSKGITSLY |
| 58 | 3.36F5 light chain CDR2 | RMSNLAS |

Sequence Table

The following table provides certain sequences described or cited in the text and figures herein. In SEQ ID Nos: 90, 92-93, and 95-101, TREM2 residues H157 and S158, the location of the cleavage site in the protein, are underlined.

| Seq Id. No. | Description | Sequence |
|---|---|---|
| 59 | 3.36F5 light chain CDR3 | AQFLQYPYT |
| 60 | 3.36F5 heavy chain variable region | [sequence provided in FIG. 3B] |
| 61 | 3.36F5 light chain variable region | [sequence provided in FIG. 3A] |
| 62 | 3.36F5 heavy chain CDR1 (Chothia) | GFTFTNV |
| 63 | 3.36F5 heavy chain CDR2 (Chothia) | KGKSDNYA |
| 64 | 3.27H7 heavy chain CDR1 | NVWLH |
| 65 | 3.27H7 heavy chain CDR2 | QIKARSDNYATYYAESVKG |
| 66 | 3.27H7 heavy chain CDR3 | LDY |
| 67 | 3.27H7 light chain CDR1 | RSSRSLLTSKGITSLY |
| 68 | 3.27H7 light chain CDR2 | RMSNLAS |
| 69 | 3.27H7 light chain CDR3 | AQFLVYPYT |
| 70 | 3.27H7 heavy chain variable region | EVQLVETGGSLVQPGGSLKLTCATSGFPFSNVWLHWIRRSPEKQLEWVAQIKARSDNYATYYAESVKGRFIVSRDDSKTTIYLQMNNLKEEDTAIYYCTGLDYWGQGVMVTVSS |
| 71 | 3.27H7 light chain variable region | DVVLTQAPLSVSVTPGESASISCRSSRSLLTSKGITSLYWYLQKPGMSPHLLIYRMSNLASGIPDRFSGSGSETDFTLKISEVEPEDVGVYYCAQFLVYPYTFGAGTKLELK |
| 72 | 3.27H7 heavy chain CDR1 (Chothia) | GFPFSNV |
| 73 | 3.27H7 heavy chain CDR2 (Chothia) | KARSDNYA |

Sequence Table

The following table provides certain sequences described or cited in the text and figures herein. In SEQ ID Nos: 90, 92-93, and 95-101, TREM2 residues H157 and S158, the location of the cleavage site in the protein, are underlined.

| Seq Id. No. | Description | Sequence |
|---|---|---|
| 74 | IGHV3-73*01 germline heavy chain | EVQLVESGGGLVQPGGSLKLSCAASGFTFSGSAMHWVRQASGKGLEWVGRIR SKANSYATAYAASVKGRFTISRDDSKNTAYLQMNSLKTEDTAVYYCTRMDVW GQGTTVTVSS |
| 75 | IGKV2-28*01 germline light chain | DIVMTQSPLSLPVTPGEPASISCRSSQSLLHSNGYNYLDWYLQKPGQSPQLL IYLGSNRASGVPDRFSGSGSGTDFTLKISRVEAEDVGVYYCMQALQTPYTFG QGTKLEIK |
| 76 | 3.10C2-H1 heavy chain variable region | EVQLVETGGSLVQPGKSLKLTCATSGFPFSNVWMHWVRQSPEKQLEWIAHIK AKSDNYATYYAESVKGRFTISRDDSKTSIYLQMNSLKEDDTAIYYCTGLDYW GQGVMVTVSS |
| 77 | 3.10C2-H3 heavy chain variable region | EVQLVETGGSLVQPGKSLKLTCATSGFPFSNVWMHWVRQSPEKQLEWIAHIK AKSDNYATYYAESVKGRFTISRDDSKTSIYLQMNSLKEDDTAIYYCTGLDYW GQGVMVTVSS |
| 78 | 3.10C2-H5 heavy chain variable region | EVQLVETGGSLVQPGKSLKLTCATSGFPFSNVWMHWVRQSPEKQLEWIAHIK AKSDNYATYYAESVKGRFTISRDDSKTSIYLQMNSLKEDDTAIYYCTGLDYW GQGVMVTVSS |
| 79 | 3.10C2-L1 light chain variable region | DTVLTQAPLSLSVTPGESASISCRSSKSLLGVRDITSLYWYLQKPGKSPQLL IYRMSNLASGVPDRFSGSGSETDFTLKISEVETEDVGVYYCAQFLRYPYTFG PGTKLELK |
| 80 | 3.10C2-L5 light chain variable region | DTVLTQAPLSLSVTPGESASISCRSSKSLLGVRDITSLYWYLQKPGKSPQLL IYRMSNLASGVPDRFSGSGSETDFTLKISEVETEDVGVYYCAQFLRYPYTFG PGTKLELK |
| 81 | Para.09-H1 heavy chain variable region | EVQLVETGGSLVQPGKSLRLTCATSGFPFSNVWLHWVRQSPEKHPEWVAHIK AKSDNYATYYAESVKGRFTISRDDSKSSVFLQMNSLKEEDTAIYYCTDILEY WGQGTLVTVSS |
| 82 | Para.09-H5 heavy chain variable region | EVQLVETGGSLVQPGKSLRLTCATSGFPFSNVWLHWVRQSPEKHPEWVAHIK AKSDNYATYYAESVKGRFTISRDDSKSSVFLQMNSLKEEDTAIYYCTDILEY WGQGTLVTVSS |
| 83 | Para.09-H7 heavy chain variable region | EVQLVETGGSLVQPGKSLRLTCATSGFPFSNVWLHWVRQSPEKHPEWVAHIK AKSDNYATYYAESVKGRFTISRDDSKSSVFLQMNSLKEEDTAIYYCTDILEY WGQGTLVTVSS |
| 84 | 3.27H7-L1 light chain variable region | DVVLTQAPLSVSVTPGESASISCRSSRSLLTSKGITSLYWYLQKPGMSPHLL IYRMSNLASGIPDRFSGSGSETDFTLKISEVEPEDVGVYYCAQFLVYPYTFG AGTKLELK |
| 85 | 3.27H7-L6 light chain variable region | DVVLTQAPLSVSVTPGESASISCRSSRSLLTSKGITSLYWYLQKPGMSPHLL IYRMSNLASGIPDRFSGSGSETDFTLKISEVEPEDVGVYYCAQFLVYPYTFG AGTKLELK |
| 86 | Human IgG1 Fc region | EPKSCDKTHTCPPCPAPELLGGPSVFLFPPKPKDTLMISRTPEVTCVVVDVS HEDPEVKFNWYVDGVEVHNAKTKPREEQYNSTYRVVSVLTVLHQDWLNGKEY KCKVSNKALPAPIEKTISKAKGQPREPQVYTLPPSRDELTKNQVSLTCLVKG FYPSDIAVEWESNGQPENNYKTTPPVLDSDGSFFLYSKLTVDKSRWQQGNVF SCSVMHEALHNHYTQKSLSLSPGK |
| 87 | Human IgG1 N297G Fc region | EPKSCDKTHTCPPCPAPELLGGPSVFLFPPKPKDTLMISRTPEVTCVVVDVS HEDPEVKFNWYVDGVEVHNAKTKPREEQYG̲STYRVVSVLTVLHQDWLNGKEY KCKVSNKALPAPIEKTISKAKGQPREPQVYTLPPSRDELTKNQVSLTCLVKG FYPSDIAVEWESNGQPENNYKTTPPVLDSDGSFFLYSKLTVDKSRWQQGNVF SCSVMHEALHNHYTQKSLSLSPGK |

Sequence Table

The following table provides certain sequences described or cited in the text and figures herein. In SEQ ID Nos: 90, 92-93, and 95-101, TREM2 residues H157 and S158, the location of the cleavage site in the protein, are underlined.

| Seq Id. No. | Description | Sequence |
| --- | --- | --- |
| 88 | Murine IgG2 Fc region | AKTTAPSVYPLAPVCGDTTGSSVTLGCLVKGYFPEPVTLTWNSGSLSSGVHT FPAVLQSDLYTLSSSVTVTSSTWPSQSITCNVAHPASSTKVDKKIEPRGPTI KPCPPCKCPAPNLLGGPSVFIFPPKIKDVLMISLSPIVTCVVVDVSEDDPDV QISWFVNNVEVHTAQTQTHREDYNSTLRVVSALPIQHQDWMSGKEFKCKVNN KDLPAPIERTISKPKGSVRAPQVYVLPPPEEEMTKKQVTLTCMVTDFMPEDI YVEWTNNGKTELNYKNTEPVLDSDGSYFMYSKLRVEKKNWVERNSYSCSVVH EGLHNHHTTKSFSRTPGK |
| 89 | Murine IgG2 LALAPG Fc region | AKTTAPSVYPLAPVCGDTTGSSVTLGCLVKGYFPEPVTLTWNSGSLSSGVHT FPAVLQSDLYTLSSSVTVTSSTWPSQSITCNVAHPASSTKVDKKIEPRGPTI KPCPPCKCPAPNAAGGPSVFIFPPKIKDVLMISLSPIVTCVVVDVSEDDPDV QISWFVNNVEVHTAQTQTHREDYNSTLRVVSALPIQHQDWMSGKEFKCKVNN KDLGAPIERTISKPKGSVRAPQVYVLPPPEEEMTKKQVTLTCMVTDFMPEDI YVEWTNNGKTELNYKNTEPVLDSDGSYFMYSKLRVEKKNWVERNSYSCSVVH EGLHNHHTTKSFSRTPGK |
| 90 | hTREM2 stalk 129-174 | LADPLDHRDAGDLWFPGESESFEDAHVEHSISRSLLEGEIPFPPTS |
| 91 | hTREM2 stalk 129-148 | LADPLDHRDAGDLWFPGESE |
| 92 | hTREM2 stalk 139-158 | GDLWFPGESESFEDAHVEHS |
| 93 | hTREM2 stalk 149-168 | SFEDAHVEHSISRSLLEGEI |
| 94 | hTREM2 stalk 159-175 | ISRSLLEGEIPFPPTSI |
| 95 | hTREM2 stalk 146-169 | ESESFEDAHVEHSISRSLLEGEIP |
| 96 | hTREM2 stalk 146-161 | ESESFEDAHVEHSISR |
| 97 | hTREM2 stalk 151-165 | EDAHVEHSISRSLLE |
| 98 | hTREM2 stalk 155-169 | VEHSISRSLLEGEIP |
| 99 | hTREM2 stalk 152-161 | DAHVEHSISR |
| 100 | hTREM2 stalk 154-164 | HVEHSISRSLL |
| 101 | hTREM2 stalk 151-161 | EDAHVEHSISR |
| 102 | 3.10C2 HC CDR3 (IMGT) | TGLDY |
| 103 | Para.01 HC CDR3 (IMGT) | ILAYS |

-continued

Sequence Table
The following table provides certain sequences described or cited in the text and figures herein. In SEQ ID Nos: 90, 92-93, and 95-101, TREM2 residues H157 and S158, the location of the cleavage site in the protein, are underlined.

| Seq Id. No. | Description | Sequence |
| --- | --- | --- |
| 104 | Para.02 HC CDR3 (IMGT) | TLGAY |
| 105 | Para.03 HC CDR3 (IMGT) | TPGVY |
| 106 | Para.04 HC CDR3 (IMGT) | TRFDY |
| 107 | Para.05 HC CDR3 (IMGT) | REGFDY |
| 108 | Para.06 HC CDR3 (IMGT) | RGRLVD |
| 109 | Para.07 HC CDR3 (IMGT) | RNYFDY |
| 110 | Para.08 HC CDR3 (IMGT) | RSGPSY |
| 111 | Para.09 HC CDR3 (IMGT) | TDILEY |
| 112 | Para.10 HC CDR3 (IMGT) | TGLGDY |
| 113 | Para.11 HC CDR3 (IMGT) | TPAFDY |
| 114 | Para.12 HC CDR3 (IMGT) | TRLGDY |
| 115 | Para.13 HC CDR3 (IMGT) | TRQLGG |
| 116 | Para.14 HC CDR3 (IMGT) | TSGSLY |
| 117 | Para.15 HC CDR3 (IMGT) | TSPPDY |
| 118 | Para.16 HC CDR3 (IMGT) | LPKGFAY |
| 119 | Para.17 HC CDR3 (IMGT) | PRDLGDY |
| 120 | Para.18 HC CDR3 (IMGT) | SLFFNYH |
| 121 | Para.19 HC CDR3 (IMGT) | SPRGFAY |
| 122 | Para.20 HC CDR3 (IMGT) | STAPFAY |
| 123 | Para.21 HC CDR3 (IMGT) | TFNNFDS |
| 124 | Para.22 HC CDR3 (IMGT) | TGSYFDY |
| 125 | Para.23 HC CDR3 (IMGT) | TLFFNYH |
| 126 | Para.24 HC CDR3 (IMGT) | TLGGYNY |

-continued

Sequence Table
The following table provides certain sequences described or cited in the text and figures herein. In SEQ ID Nos: 90, 92-93, and 95-101, TREM2 residues H157 and S158, the location of the cleavage site in the protein, are underlined.

| Seq Id. No. | Description | Sequence |
|---|---|---|
| 127 | Para.25 HC CDR3 (IMGT) | TPGNFNY |
| 128 | Para.26 HC CDR3 (IMGT) | TSGGFDY |
| 129 | Para.27 HC CDR3 (IMGT) | TSGYFDY |
| 130 | Para.28 HC CDR3 (IMGT) | TVTLGAY |
| 131 | Para.29 HC CDR3 (IMGT) | TYRGFDF |
| 132 | hPara.09.v2 Q100P Light Chain Variable Region | DVVMTQSPLSLPVTPGEPASISCRSSRSLLTSKGITSLYWYLQKPGQSPQLLIYRMSNLASGIPDRFSGSGSGTDFTLKISRVEAEDVGVYYCAQFLVYPYTFGPGTKVEIK |
| 133 | hPara.09.v2 Q100P Heavy Chain Variable Region | EVQLVESGGGLVQPGGSLKLSCATSGFPFSNVWLHWVRQASGKGPEWVAHIKAKSDNYATYYAESVKGRFTISRDDSKNTVYLQMNSLKTEDTAVYYCTDILEYWGQGTLVTVSS |
| 134 | hPara.09.v2 I58V/Q100P Light Chain Variable Region | DVVMTQSPLSLPVTPGEPASISCRSSRSLLTSKGITSLYWYLQKPGQSPQLLIYRMSNLASGVPDRFSGSGSGTDFTLKISRVEAEDVGVYYCAQFLVYPYTFGPGTKVEIK |
| 135 | hPara.09.v2 I58V/Q100P Heavy Chain Variable Region | EVQLVESGGGLVQPGGSLKLSCATSGFPFSNVWLHWVRQASGKGPEWVAHIKAKSDNYATYYAESVKGRFTISRDDSKNTVYLQMNSLKTEDTAVYYCTDILEYWGQGTLVTVSS |
| 136 | hPara.09.v2 Q100P/V104L Light Chain Variable Region | DVVMTQSPLSLPVTPGEPASISCRSSRSLLTSKGITSLYWYLQKPGQSPQLLIYRMSNLASGIPDRFSGSGSGTDFTLKISRVEAEDVGVYYCAQFLVYPYTFGPGTKLEIK |
| 137 | hPara.09.v2 Q100P/V104L Heavy Chain Variable Region | EVQLVESGGGLVQPGGSLKLSCATSGFPFSNVWLHWVRQASGKGPEWVAHIKAKSDNYATYYAESVKGRFTISRDDSKNTVYLQMNSLKTEDTAVYYCTDILEYWGQGTLVTVSS |
| 138 | hPara.09.H5-3.10C2.L10 Light Chain Variable Region | DTVMTQSPLSLPVTPGEPASISCRSSKSLLGVRDITSLYWYLQKPGQSPQLLIYRMSNLASGVPDRFSGSGSGTDFTLKISRVEAEDVGVYYCAQFLRYPYTFGPGTKVEIK |
| 139 | hPara.09.H5-3.10C2.L10 Heavy Chain Variable Region | EVQLVESGGGLVQPGGSLKLSCATSGFPFSNVWLHWVRQASGKGPEWVAHIKAKSDNYATYYAESVKGRFTISRDDSKNTVYLQMNSLKTEDTAVYYCTDILEYWGQGTLVTVSS |
| 140 | Alt-R CRISPR-Cas9 crRNA 1 | TTGTAGATTCCGCAGCGTAA |
| 141 | Alt-R CRISPR-Cas9 crRNA 2 | AATGGTGAGAGTGCCACCCA |

-continued

Sequence Table
The following table provides certain sequences described or cited in the text and figures herein. In SEQ ID Nos: 90, 92-93, and 95-101, TREM2 residues H157 and S158, the location of the cleavage site in the protein, are underlined.

| Seq Id. No. | Description | Sequence |
|---|---|---|
| 142 | Alt-R CRISPR-Cas9 crRNA 3 | TACCAGTGCCAGAGCCTCCA |
| 143 | H3.10C2.H1.hIgG1.N297G | EVQLVESGGGLVQPGGSLKLSCATSGFPFSNVWMHWVRQASGKGLEWIAHIK AKSDNYATYYAESVKGRFTISRDDSKTTIYLQMNSLKTEDTAVYYCTGLDYW GQGTTVTVSSASTKGPSVFPLAPSSKSTSGGTAALGCLVKDYFPEPVTVSWN SGALTSGVHTFPAVLQSSGLYSLSSVVTVPSSSLGTQTYICNVNHKPSNTKV DKKVEPKSCDKTHTCPPCPAPELLGGPSVFLFPPKPKDTLMISRTPEVTCVV VDVSHEDPEVKFNWYVDGVEVHNAKTKPREEQYGSTYRVVSVLTVLHQDWLN GKEYKCKVSNKALPAPIEKTISKAKGQPREPQVYTLPPSREEMTKNQVSLTC LVKGFYPSDIAVEWESNGQPENNYKTTPPVLDSDGSFFLYSKLTVDKSRWQQ GNVFSCSVMHEALHNHYTQKSLSLSPGK |
| 144 | hPara.09.H5. hIgG1.N297G (also called hPara.09.v2. hIgG1.N297G) | EVQLVESGGGLVQPGGSLKLSCATSGFPFSNVWLHWVRQASGKGPEWVAHIK AKSDNYATYYAESVKGRFTISRDDSKNTVYLQMNSLKTEDTAVYYCTDILEY WGQGTLVTVSSASTKGPSVFPLAPSSKSTSGGTAALGCLVKDYFPEPVTVSW NSGALTSGVHTFPAVLQSSGLYSLSSVVTVPSSSLGTQTYICNVNHKPSNTK VDKKVEPKSCDKTHTCPPCPAPELLGGPSVFLFPPKPKDTLMISRTPEVTCV VVDVSHEDPEVKFNWYVDGVEVHNAKTKPREEQYGSTYRVVSVLTVLHQDWL NGKEYKCKVSNKALPAPIEKTISKAKGQPREPQVYTLPPSREEMTKNQVSLT CLVKGFYPSDIAVEWESNGQPENNYKTTPPVLDSDGSFFLYSKLTVDKSRWQ QGNVFSCSVMHEALHNHYTQKSLSLSPGK |
| 145 | h3.10C2.v1 Q100P Light Chain Variable Region | DVVMTQSPLSLPVTPGEPASISCRSSRSLLTSKGITSLYWYLQKPGQSPQLL IYRMSNLASGIPDRFSGSGSGTDFTLKISRVEAEDVGVYYCAQFLVYPYTFG PGTKVEIK |
| 146 | h3.10C2.v1 Q100P Heavy Chain Variable Region | EVQLVESGGGLVQPGGSLKLSCATSGFPFSNVWMHWVRQASGKGLEWIAHIK AKSDNYATYYAESVKGRFTISRDDSKTTIYLQMNSLKTEDTAVYYCTGLDYW GQGTTVTVSS |
| 147 | h3.10C2.v1 I58V/Q100P Light Chain Variable Region | DVVMTQSPLSLPVTPGEPASISCRSSRSLLTSKGITSLYWYLQKPGQSPQLL IYRMSNLASGVPDRFSGSGSGTDFTLKISRVEAEDVGVYYCAQFLVYPYTFG PGTKVEIK |
| 148 | h3.10C2.v1 I58V/Q100P Heavy Chain Variable Region | EVQLVESGGGLVQPGGSLKLSCATSGFPFSNVWMHWVRQASGKGLEWIAHIK AKSDNYATYYAESVKGRFTISRDDSKTTIYLQMNSLKTEDTAVYYCTGLDYW GQGTTVTVSS |
| 149 | h3.10C2.v1 Q100P/V104L Light Chain Variable Region | DVVMTQSPLSLPVTPGEPASISCRSSRSLLTSKGITSLYWYLQKPGQSPQLL IYRMSNLASGIPDRFSGSGSGTDFTLKISRVEAEDVGVYYCAQFLVYPYTFG PGTKLEIK |
| 150 | h3.10C2.v1 Q100P/V104L Heavy Chain Variable Region | EVQLVESGGGLVQPGGSLKLSCATSGFPFSNVWMHWVRQASGKGLEWIAHIK AKSDNYATYYAESVKGRFTISRDDSKTTIYLQMNSLKTEDTAVYYCTGLDYW GQGTTVTVSS |
| 151 | h3.10C2.H1-3.10C2.L10 Light Chain Variable Region | DTVMTQSPLSLPVTPGEPASISCRSSKSLLGVRDITSLYWYLQKPGQSPQLL IYRMSNLASGVPDRFSGSGSGTDFTLKISRVEAEDVGVYYCAQFLRYPYTFG PGTKVEIK |
| 152 | h3.10C2.H1-3.10C2.L10 Heavy Chain | EVQLVESGGGLVQPGGSLKLSCATSGFPFSNVWMHWVRQASGKGLEWIAHIK AKSDNYATYYAESVKGRFTISRDDSKTTIYLQMNSLKTEDTAVYYCTGLDYW GQGTTVTVSS |

-continued

Sequence Table
The following table provides certain sequences described or cited in the text and figures herein. In SEQ ID Nos: 90, 92-93, and 95-101, TREM2 residues H157 and S158, the location of the cleavage site in the protein, are underlined.

| Seq Id. No. | Description | Sequence |
|---|---|---|
| | Variable Region | |
| 153 | hPara.09.H5-3.10C2.L10 CDR L1 | RSSKSLLGVRDITSLY |
| 154 | hPara.09.H5-3.10C2.L10 CDR L2 | RMSNLAS |
| 155 | hPara.09.H5-3.10C2.L10 CDR L3 | AQFLRYPYT |
| 156 | hPara.09.H5-3.10C2.L10 CDR H1 | NVWLH |
| 157 | hPara.09.H5-3.10C2.L10 CDR H2 | HIKAKSDNYATYYAESVKG |
| 158 | hPara.09.H5-3.10C2.L10 CDR H3 | ILEY |
| 159 | h3.10C2.H1-3.10C2.L10 light chain CDR1 | RSSKSLLGVRDITSLY |
| 160 | h3.10C2.H1-3.10C2.L10 light chain CDR2 | RMSNLAS |
| 161 | h3.10C2.H1-3.10C2.L10 light chain CDR 3 | AQFLRYPYT |
| 162 | h3.10C2.H1-3.10C2.L10 heavy chain CDR1 | NVWMH |
| 163 | h3.10C2.H1-3.10C2.L10 heavy chain CDR2 | HIKAKSDNYATYYAESVKG |
| 164 | h3.10C2.H1-3.10C2.L10 heavy chain CDR3 | LDY |
| 165 | Human IgG1 Fc LALAPG | EPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALGAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 166 | Human IgG4 Fc | ESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCK |

-continued

Sequence Table
The following table provides certain sequences described or cited in the text and figures herein. In SEQ ID Nos: 90, 92-93, and 95-101, TREM2 residues H157 and S158, the location of the cleavage site in the protein, are underlined.

| Seq Id. No. | Description | Sequence |
|---|---|---|
|  |  | VSNKGLPSSIEKTISKAKGQPREPQVYTLPPSQEEMTKNQVSLTCLVKGFYP SDIAVEWESNGQPENNYKTTPPVLDSDGSFFLYSRLTVDKSRWQEGNVFSCS VMHEALHNHYTQKSLSLSLGK |
| 167 | Human IgG4 Fc S228P | ESKYGPPCPPCPAPEFLGGPSVFLFPPKPKDTLMISRTPEVTCVVVDVSQED PEVQFNWYVDGVEVHNAKTKPREEQFNSTYRVVSVLTVLHQDWLNGKEYKCK VSNKGLPSSIEKTISKAKGQPREPQVYTLPPSQEEMTKNQVSLTCLVKGFYP SDIAVEWESNGQPENNYKTTPPVLDSDGSFFLYSRLTVDKSRWQEGNVFSCS VMHEALHNHYTQKSLSLSLGK |
| 168 | 3.17A9 light chain | DIQMTQSPSFLSASVGDRVTINCKVSQNVDRNLNWYQQNLGEPPKPLINFAN SLQTGVPSRFSGSGSGTDFTLTISSLQPEDVATYFCLQHNSWPLTFGSGTKL EIKRADAAPTVSIFPPSSEQLTSGGASVVCFLNNFYPKDINVKWKIDGSERQ NGVLNSWTDQDSKDSTYSMSSTLTLTKDEYERHNSYTCEATHKTSTSPIVKS FNRNEC |
| 169 | 3.17A9 heavy chain | EVQLQQSGAELGKPGTSIKLSCKVSGFNIRSTFMHWVNQRPGKGLEWIGRID PANGNTVYGEKFKNKATLTADTSSNTAYMQLSQLKSDDTAIYFCALEFGVSW FEYWGQGTLVTVSSAKTTAPSVYPLAPVCGDTTGSSVTLGCLVKGYFPEPVT LTWNSGSLSSGVHTFPAVLQSDLYTLSSSVTVTSSTWPSQSITCNVAHPASS TKVDKKIEPRGPTIKPCPPCKCPAPNLLGGPSVFIFPPKIKDVLMISLSPIV TCVVVDVSEDDPDVQISWFVNNVEVHTAQTQTHREDYNSTLRVVSALPIQHQ DWMSGKEFKCKVNNKDLPAPIERTISKPKGSVRAPQVYVLPPPEEEMTKKQV TLTCMVTDFMPEDIYVEWTNNGKTELNYKNTEPVLDSDGSYFMYSKLRVEKK NWVERNSYSCSVVHEGLHNHHTTKSFSRTPGK |
| 170 | 1.16B8 light chain | DIQMTQTPSSMPASLGERVTISCRASQGISNYLNWYQQKPDGTIKPLIYYTS NLQSGVPSRFSGSGSGTDYSLTISSLEPEDFAMYYCQQYDSSPWTFGGGTKL EIKRADAAPTVSIFPPSSEQLTSGGASVVCFLNNFYPKDINVKWKIDGSERQ NGVLNSWTDQDSKDSTYSMSSTLTLTKDEYERHNSYTCEATHKTSTSPIVKS FNRNEC |
| 171 | 1.16B8 heavy chain | EVQLVESGGGLVQPGRSLKLSCAASGFTFSDSAMAWVRQAPKKGLEWVATII YDTSSTYYRDSVKGRFTISRDNAKSTLYLQMDSLRSEDTATYYCALFGVDVM DAWGQGASVTVSSAKTTAPSVYPLAPVCGDTTGSSVTLGCLVKGYFPEPVTL TWNSGSLSSGVHTFPAVLQSDLYTLSSSVTVTSSTWPSQSITCNVAHPASST KVDKKIEPRGPTIKPCPPCKCPAPNAAGGPSVFIFPPKIKDVLMISLSPIVT CVVVDVSEDDPDVQISWFVNNVEVHTAQTQTHREDYNSTLRVVSALPIQHQD WMSGKEFKCKVNNKDLGAPIERTISKPKGSVRAPQVYVLPPPEEEMTKKQVT LTCMVTDFMPEDIYVEWTNNGKTELNYKNTEPVLDSDGSYFMYSKLRVEKKN WVERNSYSCSVVHEGLHNHHTTKSFSRTPGK |
| 172 | Murine Kappa (light chain) constant region | RADAAPTVSIFPPSSEQLTSGGASVVCFLNNFYPKDINVKWKIDGSERQNGV LNSWTDQDSKDSTYSMSSTLTLTKDEYERHNSYTCEATHKTSTSPIVKSFNR NEC |
| 173 | Sequence for Alt-R CRISPR-Cas9 crRNA | TTGTAGATTCCGCAGCGTAA |
| 174 | Sequence for Alt-R CRISPR-Cas9 crRNA | AATGGTGAGAGTGCCACCCA |
| 175 | Sequence for Alt-R CRISPR-Cas9 crRNA | TACCAGTGCCAGAGCCTCCA |
| 176 | hPara.09v2 light chain | DVVMTQSPLSLPVTPGEPASISCRSSRSLLTSKGITSLYWYLQKPGQSPQLL IYRMSNLASGIPDRFSGSGSGTDFTLKISRVEAEDVGVYYCAQFLVYPYTFG QGTKVEIKRTVAAPSVFIFPPSDEQLKSGTASVVCLLNNFYPREAKVQWKVD NALQSGNSQESVTEQDSKDSTYSLSSTLTLSKADYEKHKVYACEVTHQGLSS PVTKSFNRGEC |

Sequence Table
The following table provides certain sequences described or cited in the text and figures herein. In SEQ ID Nos: 90, 92-93, and 95-101, TREM2 residues H157 and S158, the location of the cleavage site in the protein, are underlined.

| Seq Id. No. | Description | Sequence |
|---|---|---|
| 177 | hTREM2 stalk domain comprising peptide residues 129-175 (FIG. 2A) | LADPLDHRDAGDLWFPGESESFEDAHVEHSISRSLLEGEIPFPPTS |

What is claimed is:

1. An isolated antibody that specifically binds to triggering receptor expressed on myeloid cells-2 (TREM2), wherein the antibody comprises:
a heavy chain variable region (VH) comprising a heavy chain complementary determining region 1 (CDR-H1) comprising the amino acid sequence of SEQ ID NO: 11 or 19, a CDR-H2 comprising the amino acid sequence of SEQ ID NO: 12 or 20, and a CDR-H3 comprising the amino acid sequence of SEQ ID NO: 13; and a light chain variable region (VL) comprising a CDR-L1 comprising the amino acid sequence of SEQ ID NO: 14, a CDR-L2 comprising the amino acid sequence of SEQ ID NO: 15, and a CDR-L3 comprising the amino acid sequence of SEQ ID NO: 16.

2. The antibody of claim 1, wherein the antibody comprises a VH that is at least 90%, at least 95%, at least 97%, or at least 99% identical to the amino acid sequence of SEQ ID NO: 17 and/or wherein the antibody comprises a VL that is at least 90%, at least 95%, at least 97%, or at least 99% identical to the amino acid sequence of SEQ ID NO: 18.

3. The antibody of claim 1, wherein the antibody comprises a VH comprising the amino acid sequence of SEQ ID NO: 17.

4. The antibody of claim 1, wherein the antibody comprises a VL comprising the amino acid sequence of SEQ ID NO: 18.

5. The isolated antibody of claim 1, wherein the antibody has one or more of the following properties:
(a) specifically binds to the stalk domain of TREM2;
(b) does not bind to soluble TREM2 (sTREM2);
(c) specifically binds to a TREM2 polypeptide consisting of amino acids 146-161 (SEQ ID NO: 96) or 151-165 (SEQ ID NO: 97) with higher affinity than to a TREM2 polypeptide consisting of amino acids 139-158 (SEQ ID NO: 92) and/or 159-175 (SEQ ID NO: 94);
(d) specifically binds to a TREM2 epitope spanning the H157-S158 cleavage site;
(e) shows reduced binding affinity to a TREM2 stalk domain polypeptide comprising D152A, H157A, and I159A substitutions compared to a wild-type TREM2 stalk domain polypeptide as measured by bilayer interferometry;
(f) specifically binds to human and cynomolgus TREM2 with a $K_D$ of less than 1 nM, less than 0.7 nM, less than 0.6 nM, less than 0.5 nM, less than 0.4 nM, or less than 0.3 nM, or 100-500 pM or 100-200 pM at 37° C. by surface plasmon resonance (SPR); and/or
(g) specifically binds to human and cynomolgus TREM2 with a $K_D$ of less than 100 pM, less than 50 pM, less than 10 pM, less than 7 pM, less than 5 pM, less than 4 pM, less than 3 pM, or less than 2 pM, or 10-50 pM or 10-25 pM at 37° C. by surface plasmon resonance (SPR).

6. The antibody of claim 1, wherein the antibody has one or more of the following characteristics:
   a. induces luciferase reporter activity in Jurkat-NFAT luciferase reporter cells expressing human TREM2;
   b. decreases levels of sTREM2 in vivo in plasma;
   c. inhibits shedding of sTREM2 in Jurkat-NFAT luciferase reporter cells expressing human TREM2;
   d. induces tyrosine phosphorylation in human MDM cells;
   e. induces SYK phosphorylation in human MDM cells;
   f. enhances survival of human iPSC-derived microglia in absence of IL-34 and CSF-1;
   g. inhibits shedding of sTREM2 in human iPSC-derived microglia;
   h. induces SYK phosphorylation in human iPSC-derived microglia; and/or
   i. increases total Aβ plaque intensity and/or average X04 plaque intensity in presence of Aβ oligomers in human iPSC-derived microglia.

7. The antibody of claim 1, wherein the antibody has an off-target binding score of <1 in an off-target binding assay.

8. The antibody of claim 1, which is an antibody fragment, such as an Fv, single-chain Fv (scFv), Fab, Fab', or (Fab')$_2$.

9. The antibody of claim 1, which is an IgG antibody, such as an IgG1, IgG2, IgG3, or IgG4 antibody.

10. The antibody of claim 9, wherein the antibody comprises a wild-type, human IgG1 or wild-type human IgG4 Fc region.

11. The antibody of claim 9, wherein the antibody comprises a human IgG1 Fc region comprising (a) an N297G substitution, (b) L234A, L235A, and P329G substitutions (LALAPG substitutions), or (c) N297G, M428L, and N434S substitutions.

12. The antibody of claim 9, wherein the antibody has reduced effector function, is effectorless, or does not bind to FcγR.

13. The antibody of claim 9, wherein the antibody comprises a human IgG1 Fc region comprising an N297G substitution.

14. The antibody of claim 9, wherein the antibody comprises a human IgG4 Fc region comprising an S228P substitution or comprising S228P, M252Y, S254T, and T256E substitutions.

15. The antibody of claim 1, which is a multispecific antibody.

16. The antibody of claim 1, which is conjugated covalently or noncovalently to at least one other molecule.

17. The antibody of claim 1, which is a full length antibody.

18. The antibody of claim 1, which is an IgG antibody lacking a C-terminal lysine in the heavy chain constant region.

19. The antibody of claim 1, which is a bispecific antibody.

20. The antibody of claim 16, wherein the at least one other molecule comprises a detection label and/or a drug.

21. A pharmaceutical composition comprising an antibody of claim 1 and a pharmaceutically acceptable carrier.

22. An isolated nucleic acid or set of two or more nucleic acids encoding the antibody of claim 1.

23. An isolated host cell comprising the nucleic acid of claim 22 or a vector comprising the nucleic acid.

24. An isolated vector comprising one or more nucleic acids encoding the heavy chain and the light chain of the antibody of claim 1.

25. A method of producing an antibody that specifically binds to TREM2 comprising culturing the host cell of claim 24 under conditions suitable for the expression of the antibody, wherein the method optionally further comprises recovering the antibody from the host cell.

26. A method of treating a condition associated with TREM2 loss of function in a subject in need thereof, comprising administering the antibody of claim 1 to the subject.

27. The method of claim 26, wherein the condition is, or wherein the subject suffers from, a neuroinflammatory or neurodegenerative disease.

28. The method of claim 27, wherein the neuroinflammatory or neurodegenerative disease is Alzheimer's disease, Parkinson's disease, frontotemporal dementia, dementia, multiple sclerosis (MS), amyotrophic lateral sclerosis (ALS), Nasu-Hakola disease, Guillain-Barré Syndrome (GBS), lysosomal storage disease, sphingomyelinlipidosis (Neimann-Pick C), mucopolysaccharidosis II/IIIB, metachromatic leukodystrophy, multifocal motor neuropathy, neuro-Behcet's disease, neuromyelitis optica (NMO), optic neuritis, polymyositis, dermatomyositis, stroke, transverse myelitis, traumatic brain injury, or spinal cord injury.

29. The method of claim 28, wherein the disease is Alzheimer's disease.

30. The method of claim 28, wherein the disease is MS.

31. A method of reducing levels of sTREM2 in a subject in need thereof, comprising administering the antibody of claim 1 to the subject.

32. An isolated antibody that specifically binds to triggering receptor expressed on myeloid cells-2 (TREM2), wherein the antibody comprises a heavy chain comprising the amino acid sequence of SEQ ID NO: 17 and a light chain comprising the amino acid sequence of SEQ ID NO: 18.

33. The isolated antibody of claim 32, wherein the antibody specifically binds to the TREM2 stalk domain and does not bind to soluble TREM2 (sTREM2), and wherein the antibody specifically binds to a TREM2 epitope spanning the H157-S158 cleavage site and/or specifically binds to a TREM2 polypeptide consisting of amino acids 146-161 (SEQ ID NO: 96) or 151-165 (SEQ ID NO: 97) with higher affinity than to a TREM2 polypeptide consisting of amino acids 139-158 (SEQ ID NO: 92) and/or 159-175 (SEQ ID NO: 94).

34. The isolated antibody of claim 32, wherein the antibody specifically binds to the TREM2 stalk domain and does not bind to soluble TREM2 (STREM2), and wherein the antibody is a TREM2 agonist.

35. The isolated antibody of claim 32, wherein the antibody shows reduced binding affinity to a TREM2 stalk domain polypeptide comprising D152A, H157A, and I159A substitutions compared to a wild-type TREM2 stalk domain polypeptide as measured by bilayer interferometry and/or specifically binds to human and cynomolgus TREM2 with a $K_D$ of less than 100 pM, less than 50 pM, less than 10 pM, less than 7 pM, less than 5 pM, less than 4 pM, less than 3 pM, or less than 2 pM, or 10-50 pM or 10-25 pM at 37° C. by surface plasmon resonance (SPR).

36. The isolated antibody of claim 32, wherein the antibody has one or more of the following characteristics:
   a. induces luciferase reporter activity in Jurkat-NFAT luciferase reporter cells expressing human TREM2;
   b. decreases levels of sTREM2 in vivo in plasma;
   c. inhibits shedding of sTREM2 in Jurkat-NFAT luciferase reporter cells expressing human TREM2;
   d. induces tyrosine phosphorylation in human MDM cells;
   e. induces SYK phosphorylation in human MDM cells;

f. enhances survival of human iPSC-derived microglia in absence of IL-34 and CSF-1;
g. inhibits shedding of sTREM2 in human iPSC-derived microglia;
h. induces SYK phosphorylation in human iPSC-derived microglia; and/or
i. increases total Aβ plaque intensity and/or average X04 plaque intensity in presence of Aβ oligomers in human iPSC-derived microglia.

37. The antibody of claim 32, wherein the antibody has an off-target binding score of <1 in an off-target binding assay.

38. The antibody of claim 32, wherein the antibody comprises a human IgG1 Fc region comprising (a) an N297G substitution, (b) L234A, L235A, and P329G substitutions (LALAPG substitutions), or (c) N297G, M428L, and N434S substitutions.

39. The antibody of claim 32, wherein the antibody has reduced effector function, is effectorless, or does not bind to FcγR.

40. An isolated antibody that specifically binds to triggering receptor expressed on myeloid cells-2 (TREM2), wherein the antibody comprises a heavy chain comprising the amino acid sequence of SEQ ID NO: 144 and a light chain comprising the amino acid sequence of SEQ ID NO: 176.

41. An isolated antibody that specifically binds to triggering receptor expressed on myeloid cells-2 (TREM2), wherein the antibody comprises a heavy chain comprising the amino acid sequence of SEQ ID NO: 144 but lacking the C-terminal lysine of SEQ ID NO: 144 or lacking the C-terminal glycine and lysine of SEQ ID NO: 144 and a light chain comprising the amino acid sequence of SEQ ID NO: 176.

42. An isolated antibody that specifically binds to triggering receptor expressed on myeloid cells-2 (TREM2), wherein the antibody comprises a heavy chain consisting of the amino acid sequence of SEQ ID NO: 144 and a light chain consisting of the amino acid sequence of SEQ ID NO: 176.

* * * * *